United States Patent
Claffey et al.

(10) Patent No.: US 8,183,238 B2
(45) Date of Patent: May 22, 2012

(54) BICYCLIC AND TRICYCLIC COMPOUNDS AS KAT II INHIBITORS

(75) Inventors: Michelle M. Claffey, Stonington, CT (US); Amy B. Dounay, Ledyard, CT (US); Matthew M. Hayward, Old Lyme, CT (US); Suobao Rong, Groton, CT (US); Patrick R. Verhoest, Old Lyme, CT (US); Jamison B. Tuttle, Westbrook, CT (US); Xinmin Gan, Groton, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 12/816,612

(22) Filed: Jun. 16, 2010

(65) Prior Publication Data

US 2010/0324043 A1 Dec. 23, 2010

Related U.S. Application Data

(60) Provisional application No. 61/334,389, filed on May 13, 2010, provisional application No. 61/218,149, filed on Jun. 18, 2009.

(51) Int. Cl.
| | |
|---|---|
| A61K 31/52 | (2006.01) |
| A61K 31/519 | (2006.01) |
| A61K 31/5377 | (2006.01) |
| A61K 31/4375 | (2006.01) |
| A61K 31/473 | (2006.01) |
| A61K 31/4741 | (2006.01) |
| A61K 31/506 | (2006.01) |
| A61K 31/501 | (2006.01) |
| A61K 31/517 | (2006.01) |
| C07D 473/30 | (2006.01) |
| C07D 473/20 | (2006.01) |
| C07D 413/12 | (2006.01) |
| C07D 405/10 | (2006.01) |
| C07D 401/10 | (2006.01) |
| C07D 401/04 | (2006.01) |
| C07D 471/04 | (2006.01) |
| C07D 215/58 | (2006.01) |
| C07D 221/10 | (2006.01) |
| C07D 413/10 | (2006.01) |
| C07D 491/048 | (2006.01) |
| C07D 487/04 | (2006.01) |

(52) U.S. Cl. ........... 514/235.2; 514/252.04; 514/259.31; 514/262.1; 514/263.22; 514/265.1; 514/266.21; 514/269; 514/275; 514/290; 514/300; 514/312; 544/128; 544/238; 544/263; 544/276; 544/280; 544/281; 544/284; 544/319; 544/331; 546/110; 546/122; 546/155; 546/89

(58) Field of Classification Search .................. None
See application file for complete search history.

(56) References Cited

U.S. PATENT DOCUMENTS

2005/0009870 A1 1/2005 Sher et al. ............... 514/312

FOREIGN PATENT DOCUMENTS

WO WO2009064836 5/2009

OTHER PUBLICATIONS

McAllister et al., caplus an 2011:452651.*
Weichert, caplus an 1963:403821.*
McCord, T. J., et al., "A comparative study of the rearrangement of some 6- and 7-halo-substituted 3-amino-3,4-dihydro-1-hydroxycarbostyrils in concentrated hydrohalic acids", Journal of Heterocyclic Chemistry, Mar.-Apr. 1982, pp. 401-406, 19(2). XP-002601715.
Davis, A. L., et al., "Synthesis and antibacterial activities of some chloro analogs of 3-amino-3, 4-dihydro-1-hydroxycarbostyril", Journal of Medicinal Chemistry, Jul. 1975, pp. 752-755, 18(7). XP-002601716.
Davis, A.L., et al., "Synthesis of the 3-methyl and 4-methyl derivatives of 3-amino-3,4-dihydro-1-hydroxycarbostyril and related compounds", Journal of Heterocyclic Chemistry, 1980, pp. 1405-1408, 17(7). XP-002601717.
Davis, A. L., et al., "Synthesis and microbiological properties of some substituted derivatives of 3-amino-3,4-dihydrocarbostyril", Journal of Medicinal Chemistry, May 1970, pp. 549-550, 13(3). XP-002601718.
Davis, A. L., et al., "Synthesis and microbiological properties of 3-amino-3,4-dihydro-1-hydroxycarbostyril", Journal of Medicinal Chemistry, Sep. 1964, pp. 632-634, 7(5). XP-002601719.
McCord, T. J., et al., "The synthesis, configuration, and conformation of cis- and trans-3-amino-3,4-dihydro-1-hydroxy-4-methylcarbostyrils and other configurationally related compounds", Journal of Heterocyclic Chemistry, Aug. 1981, pp. 1035-1039, 18(5). XP-002601720.

(Continued)

Primary Examiner — Sun Jae Loewe
(74) Attorney, Agent, or Firm — Feng Shao

(57) ABSTRACT

Compounds of Formula X:

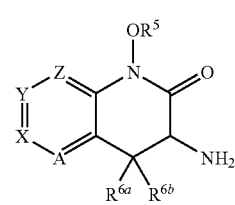

wherein A, X, Y, Z, $R^5$, $R^{6a}$, and $R^{6b}$ are as defined herein, and pharmaceutically acceptable salts thereof, are described as useful for the treatment of cognitive deficits associated with schizophrenia and other neurodegenerative and/or neurological disorders in mammals, including humans.

13 Claims, 2 Drawing Sheets

OTHER PUBLICATIONS

Schwarcz, R., et al., "Kynurenic Acid: A Potential Pathogen in Brain Disorders", Annals of The New York Academy of Science, May 1992, pp. 140-153, vol. 648.

Okuno, E., et al., "Measurement of Rat Brain Kynurenine Aminotransferase at Physiological Kynurenine Concentrations", Journal of Neurochemistry, 1991, pp. 533-540, 57(2).

Kessler, M., et al., "A Glycine Site Associated with N-Methyl-D-Aspartic Acid Receptors: Characterization and Identification of a New Class of Antagonists", 1989, Journal of Neurochemistry, pp. 1319-1328, 52(4).

Davis, A.L., et al., "Preparation and Antimicrobial Properties of D and L Forms of 3-Amino-3,4-dihydro-1-hydroxycarbostyril", Journal of Medicinal Chemistry, 1972, pp. 325-327, 15(3).

McCord, T., et al., "The Rearrangement of 3-Amino-3,4-dihydro-1-hydroxycarbostyril in Acidic Media (1)", J. Heterocyclic Chemistry, Feb. 1972, pp. 119-122, vol. 9.

* cited by examiner

BICYCLIC AND TRICYCLIC COMPOUNDS AS KAT II INHIBITORS

CROSS REFERENCE TO RELATED APPLICATIONS

This application claims benefit of U.S. Ser. No. 61/218,149, filed 18 Jun. 2009 and U.S. Ser. No. 61/334,389, filed 13 May 2010, both of which are incorporated herein in their entirety by reference.

FIELD OF THE INVENTION

The present invention relates to the treatment of cognitive deficits associated with schizophrenia and other neurodegenerative and/or neurological disorders in mammals, including humans. More particularly, this invention relates to bicyclic and tricyclic inhibitors of the KAT II enzyme, useful for the treatment of such disorders.

BACKGROUND OF THE INVENTION

KAT (kynurenine aminotransferase) II is a primary enzyme in the brain for catalyzing the transamination of kynurenine to KYNA (kynurenic acid). *J. Neurochem.*, 57, 533-540, 1991. KYNA is an effective excitatory amino acid (EAA) receptor antagonist with affinity for the glycine modulatory site of the N-methyl-D-aspartate (NMDA) receptor complex (M. Kessler et al., *J. Neurochem.*, vol. 52, pp. 1319-1328, 1989). As a naturally occurring brain metabolite, KYNA probably serves as a negative endogenous modulator of cerebral glutamatergic function (R. Schwarcz et al., *Ann. N.Y. Acad. Sci.*, vol. 648, pp. 140-153, 1992).

EAA receptors and in particular NMDA receptors are known to play a central role in the function of the mammalian brain (J. C. Watkins and G. L. Collingridge, Eds., *The NMDA Receptor*, Oxford University Press, Oxford, 1989, p. 242). For example, NMDA receptor activation is essential for cognitive processes, such as, for example, learning and memory (Watkins and Collingridge, supra, pp. 137-151). Therefore, reducing KYNA synthesis by inhibition of its synthetic enzyme may enhance EAA signaling and improve cognitive processes, especially in disease states where NMDA hypofunction is anticipated. Thus, there is a need for compounds which act as KAT II inhibitors to reduce KYNA synthesis within the brain to improve cognitive dysfunction in human disease states.

SUMMARY OF THE INVENTION

The present invention is directed to compounds of Formula X:

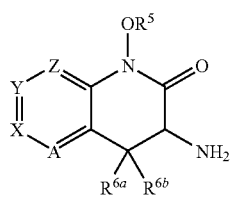

wherein:
A, X, Y, and Z are defined as follows:
(i) A is N or $CR^1$, X is N or $CR^2$, Y is N or $CR^3$, and Z is N or $CR^4$, provided that no more than two of A, X, Y, and Z are N;

(ii) A and X together form a 5- or 6-membered aromatic, N-containing heteroaromatic, or O-containing heterocycloalkyl ring fused to the ring containing A and X, Y is N or $CR^3$, and Z is N or $CR^4$, wherein the 5- or 6-membered aromatic, N-containing heteroaromatic, or O-containing heterocycloalkyl ring is substituted by $R^1$ and $R^2$;

(iii) X and Y together form a 5- or 6-membered aromatic, N-containing heteroaromatic, or O-containing heterocycloalkyl ring fused to the ring containing X and Y, A is N or $CR^1$, and Z is N or $CR^4$, wherein the 5- or 6-membered aromatic, N-containing heteroaromatic, or O-containing heterocycloalkyl ring is substituted by $R^2$ and $R^3$; or (iv) Y and Z together form a 5- or 6-membered aromatic, N-containing heteroaromatic, or O-containing heterocycloalkyl ring fused to the ring containing Y and Z, A is N or $CR^1$, and X is N or $CR^2$, wherein the 5- or 6-membered aromatic, N-containing heteroaromatic, or O-containing heterocycloalkyl ring is substituted by $R^3$ and $R^4$;

$R^1$ is H, halo, alkyl, alkoxy, or cyclopropyl;

$R^2$, $R^3$, and $R^4$ are independently H, halo, alkyl, aryl, aralkyl, heteroaryl, alkoxy, cycloalkyloxy, alkoxyaryl, aryloxy, aralkyloxy, heterocycloalkyloxy, heteroaryloxy, cycloalkyl, alkylaryloxy, alkylheterocycloalkyl, alkylheteroaryloxy, heterocycloalkyl, CN, $CH_2NR^7R^8$, $NR^7R^8$, $C(=O)NR^7R^8$, $SO_2NR^7R^8$, $SO_2R^{7a}$, $NR^7SO_2R^{7a}$, and $NR^7C(=O)R^{7a}$, wherein each said alkyl, aryl, aralkyl, heteroaryl, alkoxy, cycloalkyloxy, alkoxyaryl, aryloxy, aralkyloxy, heterocycloalkyloxy, heteroaryloxy, cycloalkyl, alkylaryloxy, alkylheterocycloalkyl, alkylheteroaryloxy, heterocycloalkyl may be substituted with one or more substituents selected from hydroxy, amino, halo, alkyl, haloalkyl, CN, alkoxy, haloalkoxy, alkylamino, and aminoalkyl;

$R^5$ is H, $C(=O)R^9$, $C(=O)OR^9$, $C(=O)NR^{9a}R^{9b}$, or $(CH_2)R^{10}$;

$R^{6a}$ and $R^{6b}$ are independently H, methyl, halomethyl, fluoro, or methoxy;

each $R^7$ and $R^8$ is independently H, alkyl, haloalkyl, aryl, or heteroaryl;

each $R^{7a}$ is independently alkyl, haloalkyl, aryl, or heteroaryl;

$R^9$ is alkyl, aryl, heteroaryl, or cycloalkyl, wherein each said alkyl, aryl, heteroaryl, and cycloalkyl may be substituted with one or more substituents selected from hydroxy, amino, halo, alkoxy, and aminoalkyl;

each $R^{9a}$ and $R^{9b}$ is independently H, alkyl, aryl, heteroaryl, or cycloalkyl, wherein each said alkyl, aryl, heteroaryl, and cycloalkyl may be substituted with one or more substituents selected from hydroxy, amino, halo, alkoxy, and aminoalkyl, or, when $R^5$ is $C(=O)NR^{9a}R^{9b}$, $R^{9a}$ and $R^{9b}$, together with the nitrogen atom to which they are attached, form a 5- or 6-membered N-containing heterocyclic ring;

$R^{10}$ is

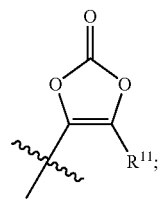

$R^{11}$ is H, alkyl, aryl, heteroaryl, or cycloalkyl, wherein each said alkyl, aryl, heteroaryl, and cycloalkyl may be substituted with one or more substituents selected from hydroxy, amino, halo, alkoxy, and aminoalkyl;

and pharmaceutically acceptable salts thereof;

provided that the compound of Formula X is not (3S)-3-amino-7-bromo-1-hydroxy-3,4-dihydroquinolin-2(1H)-one; (3R)-3-amino-7-bromo-1-hydroxy-3,4-dihydroquinolin-2(1H)-one; rac-3-amino-7-bromo-1-hydroxy-3,4-dihydroquinolin-2(1H)-one; rac-3-amino-8-chloro-1-hydroxy-3,4-dihydroquinolin-2(1H)-one; rac-3-amino-7-chloro-1-hydroxy-3,4-dihydroquinolin-2(1H)-one; rac-3-amino-7-fluoro-1-hydroxy-3,4-dihydroquinolin-2(1H)-one; rac-3-amino-6-chloro-1-hydroxy-3,4-dihydroquinolin-2(1H)-one; rac-3-amino-5-chloro-1-hydroxy-3,4-dihydroquinolin-2(1H)-one; rac-3-amino-6-bromo-1-hydroxy-3,4-dihydroquinolin-2(1H)-one; rac-3-amino-6-fluoro-1-hydroxy-3,4-dihydroquinolin-2(1H)-one; rac-3-amino-1-hydroxy-4-methyl-3,4-dihydroquinolin-2(1H)-one; (3S)-3-amino-1-hydroxy-3,4-dihydroquinolin-2(1H)-one; or (3R)-3-amino-1-hydroxy-3,4-dihydroquinolin-2(1H)-one.

This invention also includes pharmaceutically acceptable salts, hydrates, solvates, isomers, crystalline and non-crystalline forms, isomorphs, polymorphs, and metabolites of compounds of Formula X. This invention also includes all tautomers and stereochemical isomers of these compounds.

This invention also is directed, in part, to a method for treating a KAT II mediated disorder in a mammal. Such disorders include cognitive deficits associated with schizophrenia and other neurodegenerative and/or neurological disorders. The method comprises administering a compound of Formula X or a pharmaceutically acceptable salt thereof, to the mammal in an amount that is therapeutically effective to treat the condition.

DETAILED DESCRIPTION OF THE INVENTION

Figure 1:
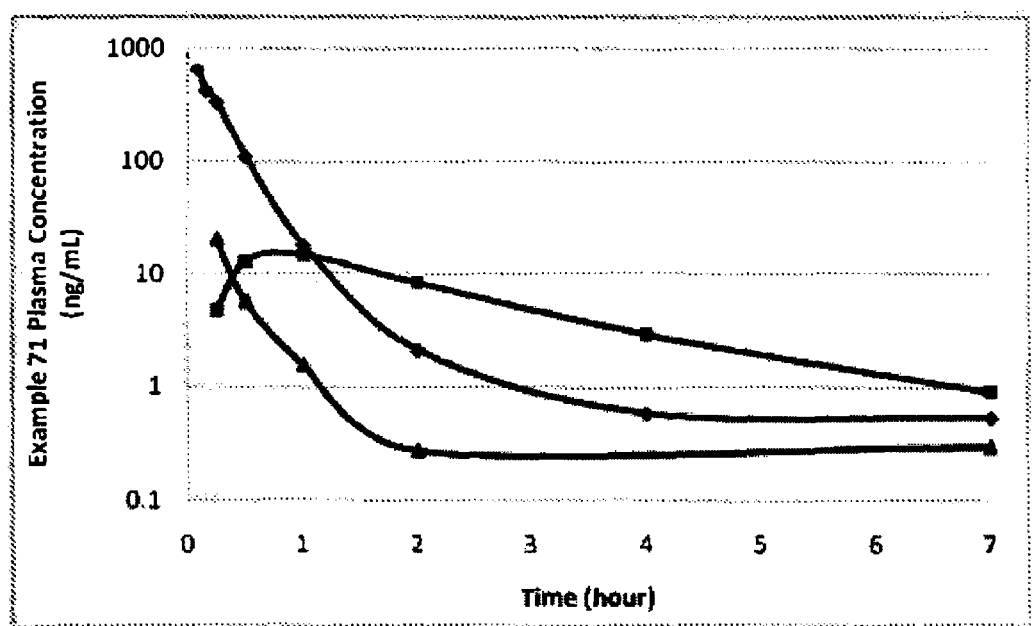
FIG. 1 describes in vivo plasma exposure of Example 71 in dogs following dosing of Example 71 (IV or PO) or Example 72 (PO). The line indicated by "-♦-" represents plasma exposure of Example 71 following intraveneous administration of Example 71 at 0.5 mg/kg. The line indicated by "-▲-" represents plasma exposure of Example 71 following administration of Example 71 by oral gavage at 2 mg/kg. The line indicated by "-■-" represents plasma exposure of Example 71 following administration of Example 72 by oral gavage at a dose equivalent to 1 mg/kg of Example 71.

One embodiment of the present invention is a compound of Formula X as described above.

Another embodiment of the present invention is a compound of Formula XA or Formula XB:

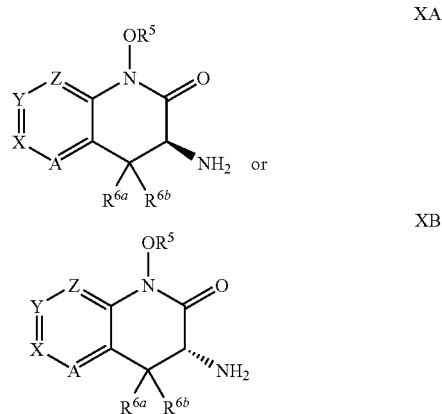

wherein A, X, Y, Z, $R^5$, $R^{6a}$, and $R^{6b}$ are as defined herein for Formula X.

Another embodiment of the present invention is a compound of Formula XI or Formula XIA that is a compound of Formula X or Formula XA, respectively, wherein:

A, X, Y, and Z are defined as follows:
 (i) A is N or $CR^1$, X is N or $CR^2$, Y is N or $CR^3$, and Z is N or $CR^4$, provided that no more than two of A, X, Y, and Z are N;
 (ii) A and X together form a 5- or 6-membered aromatic or N-containing heteroaromatic ring fused to the ring containing A and X, Y is N or $CR^3$, and Z is N or $CR^4$, wherein the 5- or 6-membered aromatic or N-containing heteroaromatic ring is substituted by $R^1$ and $R^2$; or
 (iii) Y and Z together form a 5- or 6-membered aromatic, N-containing heteroaromatic, or O-containing heterocycloalkyl ring fused to the ring containing Y and Z, A is N or $CR^1$, and X is N or $CR^2$, wherein the 5- or 6-membered aromatic or N-containing heteroaromatic ring is substituted by $R^3$ and $R^4$;

$R^1$, $R^2$, $R^3$, and $R^4$ are independently H, halo, alkyl, aryl, aralkyl, heteroaryl, alkoxy, aryloxy, aralkyloxy, heterocycloalkyloxy, heteroaryloxy, cycloalkyl, alkylheterocycloalkyl, heterocycloalkyl, $CH_2NR^7R^8$, and $SO_2R^{7a}$, wherein each said aryl, aralkyl, heteroaryl, alkoxy, aryloxy, aralkyloxy, heterocycloalkyloxy, heteroaryloxy, cycloalkyl, alkylheterocycloalkyl, and heterocycloalkyl, may be substituted with one or more substituents selected from halo, alkyl, haloalkyl, CN, alkoxy, haloalkoxy, and alkylamino;

$R^5$ is H;

$R^{6a}$ and $R^{6b}$ are independently H or methyl;

each $R^7$ and $R^8$ is independently alkyl or aryl;

each $R^{7a}$ is independently alkyl, haloalkyl, aryl, or heteroaryl; and pharmaceutically acceptable salts.

Another embodiment of the present invention is a compound of Formula XI or Formula XIA, where A, X, Y, Z, $R^{6a}$, $R^{6b}$, $R^7$, $R^{7a}$, and $R^8$ have any definition described herein and $R^1$ is H, halo, alkyl, alkoxy, or cyclopropyl, or $R^1$ is H, halo, or alkoxy.

Another embodiment of the present invention is a compound of Formula XI or Formula XIA wherein $R^1$ is H, halo, $C_{1-3}$ alkyl, $C_{1-3}$ alkoxy, or cyclopropyl.

Another embodiment of the present invention is a compound of Formula XI or Formula XIA wherein $R^1$ is H, halo, $C_{1-3}$ alkyl, $C_{1-3}$ alkoxy, or cyclopropyl; $R^4$ is H, halo, $C_{1-6}$ alkyl, $C_{1-6}$ alkoxy, $C_{3-6}$ cycloalkyl, 4-6-membered heterocycloalkyl, CN, $NR^7R^8$, $C(=O)NR^7R^8$, $SO_2NR^7R^8$, $NR^7SO_2R^8$, and $NR^7C(=O)R^{7a}$, wherein each said alkyl, alkoxy, aryloxy, heterocycloalkyloxy, heteroaryloxy, cycloalkyl, and heterocycloalkyl may be substituted with one or more substituents selected from hydroxy, amino, halo, alkoxy, and aminoalkyl; each $R^7$ and $R^8$ is independently H, alkyl, or haloalkyl; and each $R^{7a}$ is alkyl or haloalkyl.

Another embodiment of the present invention is a compound of Formula XI or Formula XIA wherein $R^1$ is H, halo, $C_{1-3}$ alkyl, $C_{1-3}$ alkoxy, or cyclopropyl; $R^4$ is H, halo, $C_{1-6}$ alkyl, $C_{1-6}$ alkoxy, $C_{3-6}$ cycloalkyl, 4-6-membered heterocycloalkyl, CN, $C(=O)NR^7R^8$, or $SO_2NR^7R^8$, wherein each said alkyl, alkoxy, aryloxy, heteroaryloxy, cycloalkyl, and heterocycloalkyl may be substituted with one or more substituents selected from hydroxy, amino, halo, alkoxy, and aminoalkyl; and each $R^7$ and $R^8$ is independently H, alkyl, or haloalkyl.

Another embodiment of the present invention is a compound of Formula XII or Formula XIIA that is a compound of Formula X or Formula XA, respectively:

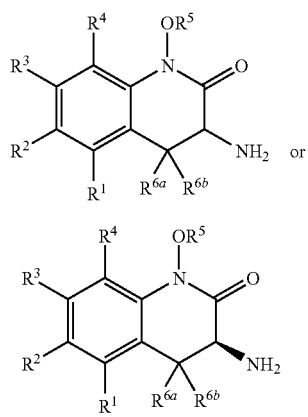

wherein $R^1$ is H, halo, $C_{1-3}$ alkyl, $C_{1-3}$ alkoxy, or cyclopropyl; $R^2$, $R^3$, $R^4$, and $R^5$ are as defined above for Formula X; and one of $R^{6a}$ and $R^{6b}$ is H and the other is H, methyl, fluoromethyl, fluoro, or methoxy.

Another embodiment of the present invention is a compound of Formula XII or Formula XIIA wherein $R^1$, $R^2$, $R^3$, and $R^4$ are independently H, F, Cl, Br, $CH_3$, or $CF_3$; and one of $R^{6a}$ and $R^{6b}$ is H and the other is H or $CH_3$.

Another embodiment of the present invention is a compound of Formula XII or Formula XIIA wherein $R^1$ is H; $R^2$ is H, Cl, or $CH_3$; $R^3$ is H or $CH_3$; and $R^4$ is H, F, $CH_3$, or $CF_3$.

Another embodiment of the present invention is a compound of Formula XII' or Formula XIIA' that is a compound of Formula XII or Formula XIIA, respectively, wherein $R^1$ is H; $R^2$ is H, arylalkyl that is benzyl, aryloxy that is phenoxy, or heteroaryloxy, wherein said aryl or heteroaryl may be substituted with one or more substituents selected from hydroxy, amino, halo, alkyl, haloalkyl, CN, alkoxy, haloalkoxy, alkylamino, and aminoalkyl; $R^3$ is H or alkoxy, wherein said alkoxy may be substituted with one or more halo; and $R^4$ is H.

Another embodiment of the present invention is a compound of Formula XII' or Formula XIIA' wherein $R^2$ is H or benzyl.

Another embodiment of the present invention is a compound of Formula XII' or Formula XIIA' wherein $R^3$ is H.

Another embodiment of the present invention is a compound of Formula XIII or Formula XIIIA that is a compound of Formula X or Formula XA, respectively:

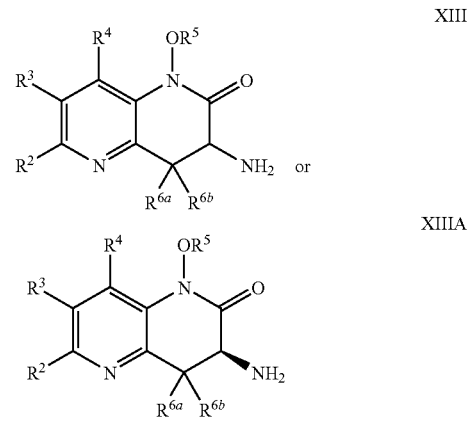

wherein $R^2$, $R^3$, $R^4$, and $R^5$ are as defined herein for Formula X or Formula XA; and one of $R^{6a}$ and $R^{6b}$ is H and the other is H, methyl, fluoromethyl, fluoro, or methoxy.

Another embodiment of the present invention is a compound of Formula XIII or Formula XIIIA wherein $R^2$, $R^3$, and $R^4$ are independently H, F, Cl, Br, $CH_3$, or $CF_3$; and one of $R^{6a}$ and $R^{6b}$ is H and the other is H or $CH_3$.

Another embodiment of the present invention is a compound of Formula XIII or Formula XIIIA wherein $R^2$, $R^3$, $R^4$, $R^{6a}$, and $R^{6b}$ are H.

Another embodiment of the present invention is a compound selected from Examples 1-71, 74-120, and 124-171; and pharmaceutically acceptable salts thereof.

Another embodiment of the present invention is a compound selected from the compounds shown in Table X, below, and pharmaceutically acceptable salts thereof.

Another embodiment of the present invention is a method for the treatment or prevention in a mammal of a condition selected from the group consisting of acute neurological and psychiatric disorders; stroke; cerebral ischemia; spinal cord trauma; cognitive impairment, including mild cognitive impairment; head trauma; perinatal hypoxia; cardiac arrest; hypoglycemic neuronal damage; dementia; Alzheimer's disease; Huntington's Chorea; amyotrophic lateral sclerosis; ocular damage; retinopathy; cognitive disorders; idiopathic and drug-induced Parkinson's disease; muscular spasms and disorders associated with muscular spasticity including tremors; epilepsy; convulsions; migraine; urinary incontinence; substance tolerance; substance withdrawal; psychosis; schizophrenia; negative symptoms associated with schizophrenia; autism, including autism spectrum disorders; bipolar disorder; depression, including but not limited to Major Depressive Disorder and treatment-resistant depression; cognitive impairment associated with depression; cognitive impairment associated with cancer therapy; anxiety; mood disorders; inflammatory disorders; sepsis; cirrhosis; cancer and/or tumors associated with immune response escape; trigeminal neuralgia; hearing loss; tinnitus; macular degeneration of the eye; emesis; brain edema; pain; tardive dyskinesia; sleep disorders; attention deficit/hyperactivity disorder; attention deficit disorder; disorders that comprise as a symptom a deficiency in attention and/or cognition; and conduct disorder; comprising administering a compound selected from (3S)-3-amino-7-bromo-1-hydroxy-3,4-dihydroquinolin-2(1H)-one, (3R)-3-amino-7-bromo-1-hydroxy-3,4-dihydroquinolin-2(1H)-one, rac-3-amino-7-bromo-1-hydroxy-3,4-dihydroquinolin-2(1H)-one, rac-3-amino-8-chloro-1-hydroxy-3,4-dihydroquinolin-2(1H)-one, rac-3-amino-7-chloro-1-hydroxy-3,4-dihydroquinolin-2(1H)-one, rac-3-amino-7-fluoro-1-hydroxy-3,4-dihydroquinolin-2(1H)-one, rac-3-amino-6-chloro-1-hydroxy-3,4-dihydroquinolin-2(1H)-one, rac-3-amino-5-chloro-1-hydroxy-3,4-dihydroquinolin-2(1H)-one, rac-3-amino-6-bromo-1-hydroxy-3,4-dihydroquinolin-2(1H)-one, rac-3-amino-6-fluoro-1-hydroxy-3,4-dihydroquinolin-2(1H)-one, rac-3-amino-1-hydroxy-4-methyl-3,4-dihydroquinolin-2(1H)-one, (3S)-3-amino-1-hydroxy-3,4-dihydroquinolin-2(1H)-one, or (3R)-3-amino-1-hydroxy-3,4-dihydroquinolin-2(1H)-one, or a compound of Formula X.

Another embodiment of the present invention is a method for the treatment or prevention in a mammal of a condition selected from the group consisting of dementia; cognitive deficit symptoms of Alzheimer's disease; attention deficit symptoms of Alzheimer's disease; multi-infarct dementia, alcoholic dementia or other drug-related dementia, dementia associated with intracranial tumors or cerebral trauma, dementia associated with Huntington's disease or Parkinson's disease, or AIDS-related dementia; delirium; amnestic disorder; post-traumatic stress disorder; mental retardation; a learning disorder (e.g., reading disorder, mathematics disorder, or a disorder of written expression); attention-deficit/hyperactivity disorder; age-related cognitive decline; cognitive deficits associated with psychoses; or cognitive deficits associated with schizophrenia, comprising administering a compound selected from (3S)-3-amino-7-bromo-1-hydroxy-3,4-dihydroquinolin-2(1H)-one, (3R)-3-amino-7-bromo-1-hydroxy-3,4-dihydroquinolin-2(1H)-one, rac-3-amino-7-bromo-1-hydroxy-3,4-dihydroquinolin-2(1H)-one, rac-3-amino-8-chloro-1-hydroxy-3,4-dihydroquinolin-2(1H)-one, rac-3-amino-7-chloro-1-hydroxy-3,4-dihydroquinolin-2(1H)-one, rac-3-amino-7-fluoro-1-hydroxy-3,4-dihydroquinolin-2(1H)-one, rac-3-amino-6-chloro-1-hydroxy-3,4-dihydroquinolin-2(1H)-one, rac-3-amino-5-chloro-1-hydroxy-3,4-dihydroquinolin-2(1H)-one, rac-3-amino-6-bromo-1-hydroxy-3,4-dihydroquinolin-2(1H)-one, rac-3-amino-6-fluoro-1-hydroxy-3,4-dihydroquinolin-2(1H)-one, rac-3-amino-1-hydroxy-4-methyl-3,4-dihydroquinolin-2(1H)-one, (3S)-3-amino-1-hydroxy-3,4-dihydroquinolin-2(1H)-one, or (3R)-3-amino-1-hydroxy-3,4-dihydroquinolin-2(1H)-one, or a compound of Formula X.

Another embodiment of the present invention is a method for the treatment or prevention in a mammal of a condition selected from the group consisting of acute neurological and psychiatric disorders; stroke; cerebral ischemia; spinal cord trauma; cognitive impairment, including mild cognitive impairment; head trauma; perinatal hypoxia; cardiac arrest; hypoglycemic neuronal damage; dementia; Alzheimer's disease; Huntington's Chorea; amyotrophic lateral sclerosis; ocular damage; retinopathy; cognitive disorders; idiopathic and drug-induced Parkinson's disease; muscular spasms and disorders associated with muscular spasticity including tremors; epilepsy; convulsions; migraine; urinary incontinence; substance tolerance; substance withdrawal; psychosis; schizophrenia; negative symptoms associated with schizophrenia; autism, including autism spectrum disorders; bipolar disorder; depression, including but not limited to Major Depressive Disorder and treatment-resistant depression; cognitive impairment associated with depression; cognitive impairment associated with cancer therapy; anxiety; mood disorders; inflammatory disorders; sepsis; cirrhosis; cancer and/or tumors associated with immune response escape; trigeminal neuralgia; hearing loss; tinnitus; macular degeneration of the eye; emesis; brain edema; pain; tardive dyskinesia; sleep disorders; attention deficit/hyperactivity disorder; attention deficit disorder; disorders that comprise as a symptom a deficiency in attention and/or cognition; and conduct disorder; comprising administering a compound of Formula X.

Another embodiment of the present invention is a method for the treatment or prevention in a mammal of a condition selected from the group consisting of dementia; cognitive deficit symptoms of Alzheimer's disease; attention deficit symptoms of Alzheimer's disease; multi-infarct dementia, alcoholic dementia or other drug-related dementia, dementia associated with intracranial tumors or cerebral trauma, dementia associated with Huntington's disease or Parkinson's disease, or AIDS-related dementia; delirium; amnestic disorder; post-traumatic stress disorder; mental retardation; a learning disorder (e.g., reading disorder, mathematics disorder, or a disorder of written expression); attention-deficit/hyperactivity disorder; age-related cognitive decline; cognitive deficits associated with psychoses; or cognitive deficits associated with schizophrenia, comprising administering a compound of Formula X.

Another embodiment of the present invention is a compound of Formula XIV or Formula XIVA that is a compound of Formula X or Formula XA, respectively:

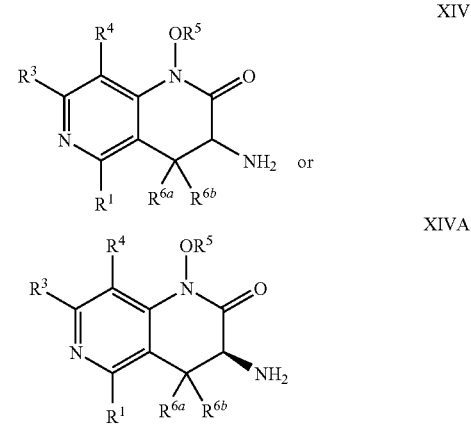

wherein $R^1$ is H, halo, $C_{1-3}$ alkyl, $C_{1-3}$ alkoxy, or cyclopropyl; one of $R^{6a}$ and $R^{6b}$ is H and the other is H, methyl, fluoromethyl, fluoro, or methoxy; and $R^3$, $R^4$, and $R^5$ are as defined above for Formula X or Formula XA.

Another embodiment of the present invention is a compound of Formula XV or Formula XVA that is a compound of Formula X or Formula XA, respectively:

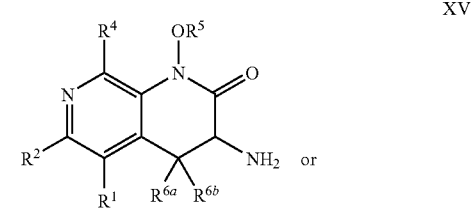

-continued

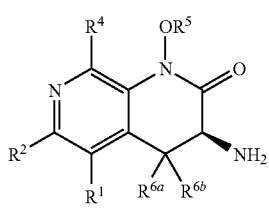
XVA wherein R¹ is H, halo, C₁₋₃ alkyl, C₁₋₃ alkoxy, or cyclopropyl; one of R^{6a} and R^{6b} is H and the other is H, methyl, fluoromethyl, fluoro, or methoxy; and R², R⁴, and R⁵ are as defined above for Formula X or Formula XA.

Another embodiment of the present invention is a compound of Formula XV or Formula XVA wherein R¹ is H, halo, C₁₋₃ alkyl, C₁₋₃ alkoxy, or cyclopropyl; one of R^{6a} and R^{6b} is H and the other is H, methyl, fluoromethyl, fluoro, or methoxy; and R², R⁴, and R⁵ are as defined above for Formula X or Formula XA.

Another embodiment of the present invention is a compound of Formula XV or Formula XVA, wherein R¹ and R⁴ are H; R² is arylalkyl that is benzyl, aryloxy that is phenoxy, or heteroaryloxy, wherein said aryl or heteroaryl may be substituted with one or more substituents selected from hydroxy, amino, halo, alkyl, haloalkyl, CN, alkoxy, haloalkoxy, alkylamino, and aminoalkyl.

Another embodiment of the present invention is a compound of Formula XVI or Formula XVIA that is a compound of Formula X or Formula XA, respectively:

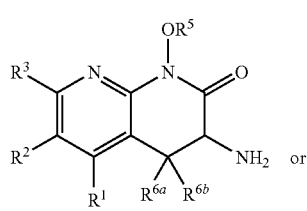
XVI

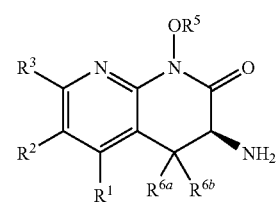
XVIA wherein R¹ is H, halo, C₁₋₃ alkyl, C₁₋₃ alkoxy, or cyclopropyl; one of R^{6a} and R^{6b} is H and the other is H, methyl, fluoromethyl, fluoro, or methoxy; and wherein R², R³, and R⁵ are as defined above for Formula X or Formula XA.

Another embodiment of the present invention is a compound of Formula XVI or Formula XVIA wherein R¹ is H, halo, C₁₋₃ alkyl, C₁₋₃ alkoxy, or cyclopropyl; one of R^{6a} and R^{6b} is H and the other is H, methyl, fluoromethyl, fluoro, or methoxy; and wherein R², R³, and R⁵ are as defined above for Formula X or Formula XA.

Another embodiment of the present invention is a compound of Formula XVI or Formula XVIA wherein R² is arylalkyl that is benzyl or aryloxy, wherein said aryl may be substituted with one or more substituents selected from hydroxy, amino, halo, alkyl, haloalkyl, CN, alkoxy, haloalkoxy, alkylamino, and aminoalkyl; and R³ is H or alkyl.

Another embodiment of the present invention is a compound of Formula XVI or Formula XVIA wherein R² is arylalkyl that is benzyl or aryloxy that is phenoxy, wherein said aryl may be substituted with one or more substituents selected from hydroxy, amino, halo, alkyl, haloalkyl, CN, alkoxy, haloalkoxy, alkylamino, and aminoalkyl; and R³ is H or methyl.

Another embodiment of the present invention is a compound of Formula XVII or Formula XVIIA that is a compound of Formula X or Formula XA, respectively:

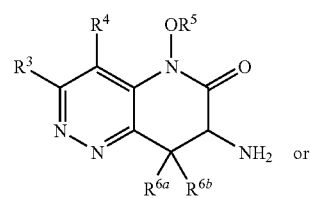
XVII

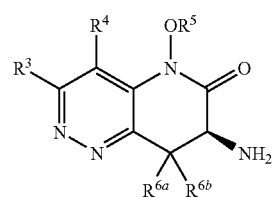
XVIIA wherein one of R^{6a} and R^{6b} is H and the other is H, methyl, fluoromethyl, fluoro, or methoxy; and R³, R⁴, and R⁵ are as defined above for Formula X or Formula XA.

Another embodiment of the present invention is a compound of Formula XVIII or Formula XVIIIA that is a compound of Formula X or Formula XA, respectively:

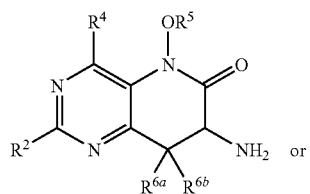
XVIII

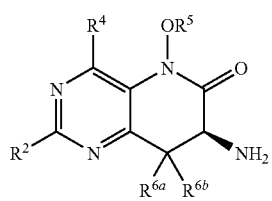
XVIIIA wherein one of R^{6a} and R^{6b} is H and the other is H, methyl, fluoromethyl, fluoro, or methoxy; and R², R⁴, and R⁵ are as defined above for Formula X or Formula XA.

Another embodiment of the present invention is a compound of Formula XIX or Formula XIXA that is a compound of Formula X or Formula XA, respectively:

XIX

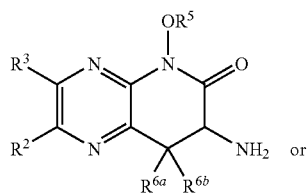

XIXA

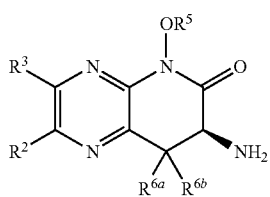

wherein one of $R^{6a}$ and $R^{6b}$ is H and the other is H, methyl, fluoromethyl, fluoro, or methoxy; and $R^2$, $R^3$, and $R^5$ are as defined above for Formula X or Formula XA.

Another embodiment of the present invention is a compound of Formula XX or Formula XXA that is a compound of Formula X or Formula XA, respectively:

XX

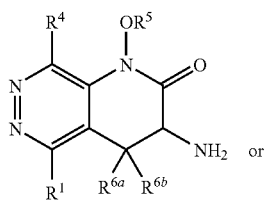

XXA

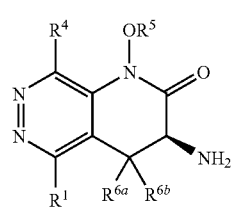

wherein $R^1$ is H, $C_{1-3}$ alkyl, $C_{1-3}$ alkoxy, or cyclopropyl; one of $R^{6a}$ and $R^{6b}$ is H and the other is H, methyl, fluoromethyl, fluoro, or methoxy; and $R^4$ and $R^5$ are as defined above for Formula X or Formula XA.

Another embodiment of the present invention is a compound of Formula XXI or Formula XXIA that is a compound of Formula X or XA, respectively:

XXI

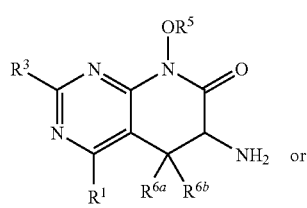

XXIA

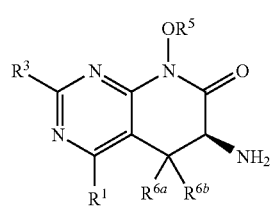

wherein $R^1$ is H, $C_{1-3}$ alkyl, $C_{1-3}$ alkoxy, or cyclopropyl; one of $R^{6a}$ and $R^{6b}$ is H and the other is H, methyl, fluoromethyl, fluoro, or methoxy; and $R^3$ and $R^5$ are as defined above for Formula X or Formula XA.

Another embodiment of the present invention is a compound of Formula XXII or Formula XXIIA that is a compound of Formula X or Formula XA, respectively:

XXII

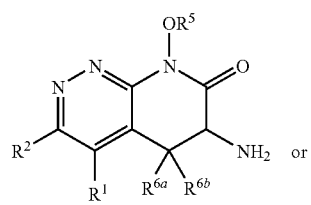

XXIIA

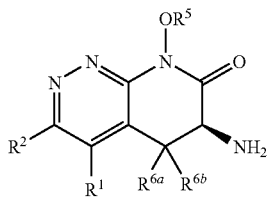

wherein $R^1$ is H, halo, $C_{1-3}$ alkyl, $C_{1-3}$ alkoxy, or cyclopropyl; one of $R^{6a}$ and $R^{6b}$ is H and the other is H, methyl, fluoromethyl, fluoro, or methoxy; and $R^2$ and $R^5$ are as defined above for Formula X or Formula XA.

Another embodiment of the present invention is a compound of Formula XXIII or Formula XXIIIA that is a compound of Formula X or XA, respectively:

XXIII

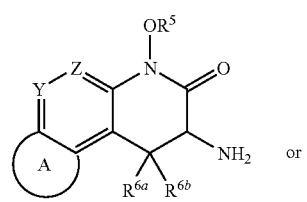

XXIIIA

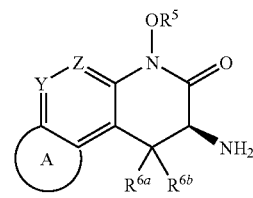

wherein the ring substituent A is a 5- or 6-membered aromatic, N-containing heteroaromatic, or O-containing heterocycloalkyl ring substituent substituted by $R^1$ and $R^2$; $R^1$ is H, halo, $C_{1-3}$ alkyl, $C_{1-3}$ alkoxy, or cyclopropyl; and $R^2$, Y, Z, $R^5$, $R^{6a}$, and $R^{6b}$ are as defined above for Formula X or Formula XA.

Another embodiment of the present invention is a compound of Formula XXIII or Formula XXIIIA wherein the ring substituent A is selected from the group of substituents shown in Table A, below; wherein A is substituted by $R^1$ and $R^2$; and wherein $R^1$ and $R^2$ are as defined for Formula XXIII or Formula XXIIIA, respectively.

TABLE A

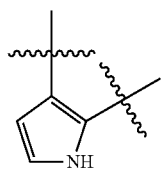

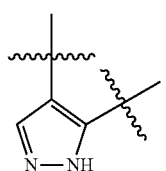

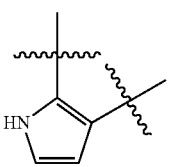

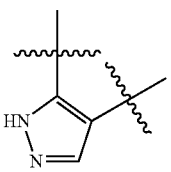

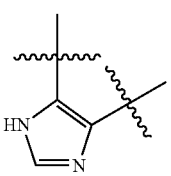

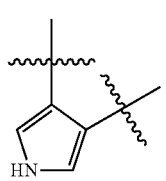

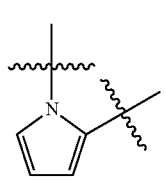

TABLE A-continued

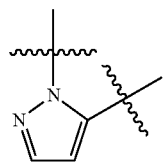

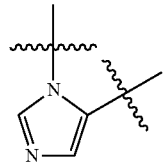

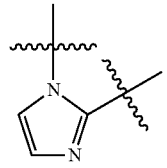

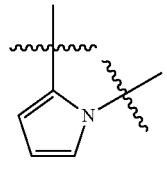

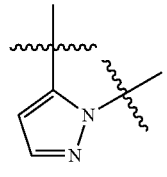

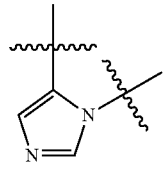

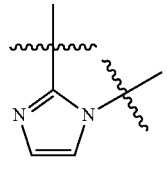

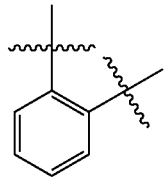

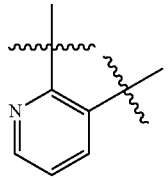

TABLE A-continued

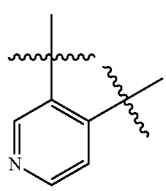

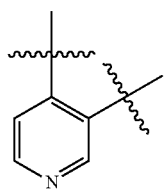

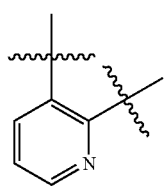

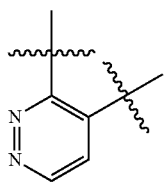

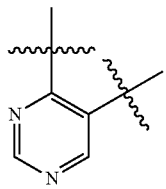

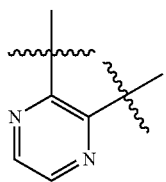

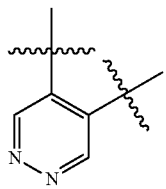

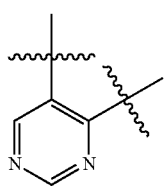

TABLE A-continued

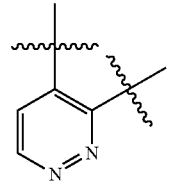

Another embodiment of the present invention is a compound of Formula XXIV or Formula XXIVA that is a compound of Formula X or Formula XA, respectively:

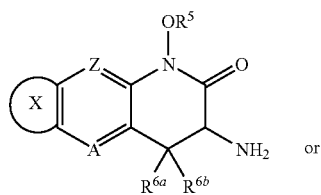

XXIV

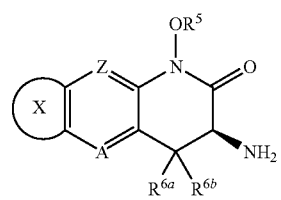

XXIVA wherein the ring substituent X is a 5- or 6-membered aromatic, N-containing heteroaromatic, or O-containing heterocycloalkyl ring substituent substituted by $R^2$ and $R^3$; $R^1$ (i.e., when A is $CR^1$) is H, halo, $C_{1-3}$ alkyl, $C_{1-3}$ alkoxy, or cyclopropyl; and $R^2$, $R^3$, A, Z, $R^5$, $R^{6a}$, and $R^{6b}$ are as defined above for Formula X or Formula XA.

Another embodiment of the present invention is a compound of Formula XXIV or Formula XXIVA wherein the ring substituent X is selected from the group of substituents shown in Table A, above; wherein the ring substituent X is substituted by $R^2$ and $R^3$; and wherein $R^2$ and $R^3$ are as defined for Formula XXIV.

Another embodiment of the present invention is a compound of Formula XXV or Formula XXVA that is a compound of Formula X or Formula XA, respectively:

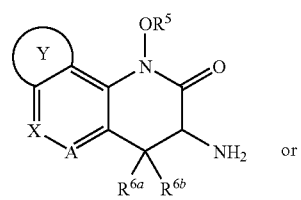

XXV

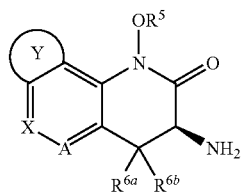

XXVA wherein the ring substituent Y is a 5- or 6-membered aromatic, N-containing heteroaromatic, or O-containing heterocycloalkyl ring substituent substituted by $R^3$ and $R^4$; $R^1$ (i.e., when A is $CR^1$) is H, halo, $C_{1-3}$ alkyl, $C_{1-3}$ alkoxy, or cyclopropyl; and $R^3$, $R^4$, A, X, $R^5$, $R^{6a}$, and $R^{6b}$ are as defined above for Formula X or Formula XA.

Another embodiment of the present invention is a compound of Formula XXV or Formula XXVA wherein the ring substituent Y is selected from the group of substituents shown in Table A, above; wherein said ring substituent Y is substituted by $R^3$ and $R^4$; and wherein $R^3$ and $R^4$ are as defined for Formula XXV.

Compounds of Formula X or compounds related thereto when $R^5$ is H can form a Schiff base with pyridoxal-5-phosphate (also called PLP and/or vitamin B6) in the KAT II enzyme, to inhibit formation of kynurenic acid. Literature reports of other PLP-dependent enzymes (R. B. Silverman et al, *J. Am. Chem. Soc.* 1998, 120, 2256) also demonstrate that an initially formed inhibitor-PLP Schiff base can undergo base-induced tautomerization to an isomeric ketimine, which can further isomerize to an aromatized inhibitor-PLP adduct. Another embodiment of the present invention is a Schiff base, or the product of base-promoted isomerization thereof, formed between a compound of Formula X, as defined herein, and pyridoxal-5-phosphate.

Another embodiment of the present invention is a Schiff base, or the product of base-promoted isomerization thereof, formed between a compound of Formula X, as defined herein, and pyridoxal-5-phosphate, wherein said Schiff base is formed in vivo.

Prodrugs that have little or no pharmacological activity themselves can, when administered into or onto the body, be converted into compounds of Formula X having the desired activity.

Another embodiment of the present invention is a compound of Formula X or Formula XA wherein $R^1$ is H, halo, $C_{1-3}$ alkyl, $C_{1-3}$ alkoxy, or cyclopropyl; $R^5$ is $C(=O)R^9$, $C(=O)OR^9$, $C(=O)NR^{9a}R^{9b}$, or $(CH_2)R^{10}$; and $R^{11}$ is methyl.

Another embodiment of the present invention is a compound of Formula X or Formula XA wherein $R^5$ is $C(=O)NR^{9a}R^{9b}$.

Another embodiment of the present invention is a compound of Formula X or Formula XA wherein $R^5$ is

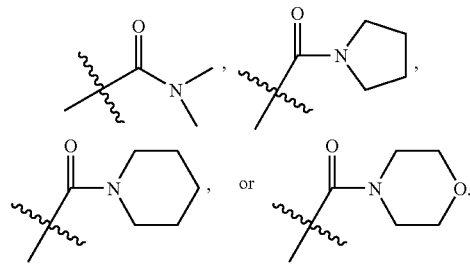

Another embodiment of the present invention is a compound selected from Examples 72, 73, and 121-123; and pharmaceutically acceptable salts thereof.

Another embodiment of the present invention is (3S)-3-amino-1-[(dimethylcarbamoyl)oxy]-3,4-dihydroquinolin-2(1H)-one (see Example 73), and pharmaceutically acceptable salts thereof.

Another embodiment of the present invention is a compound selected from the compounds shown in Table Y, below, and pharmaceutically acceptable salts thereof.

Another embodiment of the present invention is a compound selected from the compounds shown in Table Z, below, and pharmaceutically acceptable salts thereof.

Another embodiment of the present invention is a compound of Formula XIB, Formula XIIB, Formula XIIIB, Formula XIVB, Formula XVB, Formula XVIB, Formula XVIIB, Formula XVIIIB, Formula XXIB, Formula XXIIB, Formula XXIIIB, Formula XXIVB, or Formula XXVB, that is a compound of Formula XIA, Formula XIIA, Formula XIIIA, Formula XIVA, Formula XVA, Formula XVIA, Formula XVIIA, Formula XVIIIA, Formula XXIA, Formula XXI IA, Formula XXIIIA, Formula XXIVA, or Formula XXVA, respectively, wherein the right side of the molecule has the following stereochemistry:

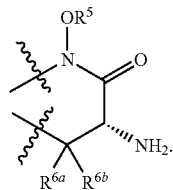

Unless otherwise specified, for the sake of brevity, any reference herein to compounds of Formula X shall include reference to any compounds of the invention, including any compounds of Formulas X, XA, XI, XIA, XII, XIIA, XIII, XIIIA, XIV, XIVA, XV, XVA, XVI, XVIA, XVII, XVIIA, XVIII, XVIIIA, XXI, XXIA, XXII, XXIIA, XXIII, XXIIIA, XXIV, XXIVA, XXV, or XXVA, without specific reference to each Formula.

Unless otherwise specified, any variable not mentioned in Formulas X, XA, XI, XIA, XII, XIIA, XII', XIIA', XIII, XIIIA, XIV, XIVA, XV, XVA, XVI, XVIA, XVII, XVIIA, XVIII, XVIIIA, XIX, XIXA, XX, XXA, XXI, XXIA, XXII, XXIIA, XXIII, XXIIIA, XXIV, XXIVA, XXV, or XXVA will have the definition as provided in Formula X. Furthermore, unless otherwise specified, reference to a compound of any Formula disclosed herein shall also include pharmaceutically acceptable salts thereof.

Abbreviations and Definitions

The term "alkyl" refers to a linear or branched-chain saturated hydrocarbyl substituent (i.e., a substituent obtained from a hydrocarbon by removal of a hydrogen) containing from one to twenty carbon atoms; in one embodiment from one to twelve carbon atoms; in another embodiment, from one to ten carbon atoms; in another embodiment, from one to six carbon atoms; and in another embodiment, from one to four carbon atoms. Examples of such substituents include methyl, ethyl, propyl (including n-propyl and isopropyl), butyl (including n-butyl, isobutyl, sec-butyl and tert-butyl), pentyl, isoamyl, hexyl and the like.

"Alkenyl" refers to an aliphatic hydrocarbon having at least one carbon-carbon double bond, including straight chain, branched chain or cyclic groups having at least one carbon-carbon double bond. In one embodiment, the alkenyl group has 2 to 20 carbon atoms (whenever a numerical range; e.g., "2-20", is stated herein, it means that the group, in this case the alkenyl group, may contain 2 carbon atoms, 3 carbon atoms, etc. up to and including 20 carbon atoms). In another embodiment, it is a medium size alkenyl having 2 to 10 carbon atoms. For example, as used herein, the term "($C_2$-$C_6$) alkenyl" means straight or branched chain unsaturated radicals of 2 to 6 carbon atoms, including, but not limited to ethenyl, 1-propenyl, 2-propenyl (allyl), iso-propenyl, 2-methyl-1-propenyl, 1-butenyl, 2-butenyl, and the like; optionally substituted by 1 to 5 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$ alkyl. When the compounds of the invention contain a $(C_2-C_6)$alkenyl group, the compound may exist as the pure E (entgegen) form, the pure Z (zusammen) form, or any mixture thereof.

"Alkynyl" refers to an aliphatic hydrocarbon having at least one carbon-carbon triple bond, including straight chain, branched chain or cyclic groups having at least one carbon-carbon triple bond. In one embodiment, the alkynyl group has 2 to 20 carbon atoms (whenever a numerical range; e.g., "2-20", is stated herein, it means that the group, in this case the alkynyl group, may contain 2 carbon atoms, 3 carbon atoms, etc. up to and including 20 carbon atoms). In another embodiment, it is a medium size alkynyl having 2 to 10 carbon atoms. In another embodiment, it is a lower alkynyl having 2 to 6 carbon atoms. For example, as used herein, the term "$(C_2-C_6)$alkynyl" is used herein to mean straight or branched hydrocarbon chain alkynyl radical as defined above having 2 to 6 carbon atoms and one triple bond.

The term "cycloalkyl" refers to a carbocyclic substituent obtained by removing a hydrogen from a saturated carbocyclic molecule and having three to fourteen carbon atoms. In one embodiment, a cycloalkyl substituent has three to ten carbon atoms. Examples of cycloalkyl include cyclopropyl, cyclobutyl, cyclopentyl and cyclohexyl.

The term "cycloalkyl" also includes substituents that are fused to a $C_6-C_{10}$ aromatic ring or to a 5-10-membered heteroaromatic ring, wherein a group having such a fused cycloalkyl group as a substituent is bound to a carbon atom of the cycloalkyl group. When such a fused cycloalkyl group is substituted with one or more substituents, the one or more substituents, unless otherwise specified, are each bound to a carbon atom of the cycloalkyl group. The fused $C_6-C_{10}$ aromatic ring or 5-10-membered heteroaromatic ring may be optionally substituted with halogen, $C_1-C_6$ alkyl, $C_3-C_{10}$ cycloalkyl, or =O. A cycloalkyl may be a single ring, which typically contains from 3 to 6 ring atoms. Examples include cyclopropyl, cyclobutyl, cyclopentyl, and cyclohexyl. Alternatively, 2 or 3 rings may be fused together, such as bicyclodecanyl and decalinyl.

The term "aryl" refers to an aromatic substituent containing one ring or two or three fused rings. The aryl substituent may have six to eighteen carbon atoms. As an example, the aryl substituent may have six to fourteen carbon atoms. The term "aryl" may refer to substituents such as phenyl, naphthyl and anthracenyl. The term "aryl" also includes substituents such as phenyl, naphthyl and anthracenyl that are fused to a $C_4-C_{10}$ carbocyclic ring, such as a $C_5$- or a $C_6$-carbocyclic ring, or to a 4-10-membered heterocyclic ring, wherein a group having such a fused aryl group as a substituent is bound to an aromatic carbon of the aryl group. When such a fused aryl group is substituted with one or more substituents, the one or more substituents, unless otherwise specified, are each bound to an aromatic carbon of the fused aryl group. The fused $C_4-C_{10}$ carbocyclic or 4-10-membered heterocyclic ring may be optionally substituted with halogen, $C_1-C_6$ alkyl, $C_3-C_{10}$ cycloalkyl, or =O. Examples of aryl groups include accordingly phenyl, naphthalenyl, tetrahydronaphthalenyl (also known as "tetralinyl"), indenyl, isoindenyl, indanyl, anthracenyl, phenanthrenyl, and benzonaphthenyl (also known as "phenalenyl").

The term "aralkyl" or "arylalkyl" refers to an alkyl substituent, as defined herein, substituted by an aryl substituent, as defined herein. Aralkyl substituents may have from seven to 24 carbon atoms. Examples of aralkyl groups include benzyl (i.e., phenylmethyl), phenylethyl, indenylmethyl, and naththalenylethyl.

In some instances, the number of carbon atoms in a hydrocarbyl substituent (i.e., alkyl, alkenyl, cycloalkyl, cycloalkenyl, aryl, etc.) is indicated by the prefix "$C_x$-$C_y$," or "$C_{x-y}$," wherein x is the minimum and y is the maximum number of carbon atoms in the substituent. Thus, for example, "$C_1$-$C_6$ alkyl and "$C_{1-6}$ alkyl" both refer to an alkyl substituent containing from 1 to 6 carbon atoms. Illustrating further, $C_3$-$C_6$ cycloalkyl and $C_{3-6}$ cycloalkyl refer to saturated cycloalkyl containing from 3 to 6 carbon ring atoms.

In some instances, the number of atoms in a cyclic substituent containing one or more heteroatoms (i.e., heteroaryl or heterocycloalkyl) is indicated by the prefix "X—Y-membered", wherein x is the minimum and y is the maximum number of atoms forming the cyclic moiety of the substituent. Thus, for example, 5-8-membered heterocycloalkyl refers to a heterocycloalkyl containing from 5 to 8 atoms, including one or more heteroatoms, in the cyclic moiety of the heterocycloalkyl.

The term "hydroxy" or "hydroxyl" refers to —OH. When used in combination with another term(s), the prefix "hydroxy" indicates that the substituent to which the prefix is attached is substituted with one or more hydroxy substituents. Compounds bearing a carbon to which one or more hydroxy substituents are attached include, for example, alcohols, enols and phenol.

The term "hydroxyalkyl" refers to an alkyl that is substituted with at least one hydroxy substituent. Examples of hydroxyalkyl include hydroxymethyl, hydroxyethyl, hydroxypropyl and hydroxybutyl.

The term "cyano" (also referred to as "nitrile") means CN.

The term "carbonyl" means C(O) or C=O.

The term "amino" refers to $NH_2$.

The term "alkylamino" refers to an amino group, wherein at least one alkyl chain is bonded to the amino nitrogen in place of a hydrogen atom. Examples of alkylamino substituents include monoalkylamino such as methylamino (exemplified by the formula $NH(CH_3)$), and dialkylamino such as dimethylamino (exemplified by the formula —$N(CH_3)_2$).

The term "halogen" refers to fluorine (which may be depicted as F), chlorine (which may be depicted as Cl), bromine (which may be depicted as Br), or iodine (which may be depicted as I). In one embodiment, the halogen is chlorine. In another embodiment, the halogen is fluorine. In another embodiment, the halogen is bromine.

The prefix "halo" indicates that the substituent to which the prefix is attached is substituted with one or more independently selected halogen substituents. For example, haloalkyl refers to an alkyl that is substituted with at least one halogen substituent. Where more than one hydrogen is replaced with halogens, the halogens may be identical or different. Examples of haloalkyls include chloromethyl, dichloromethyl, difluorochloromethyl, dichlorofluoromethyl, trichloromethyl, 1-bromoethyl, fluoromethyl, difluoromethyl, trifluoromethyl, 2,2,2-trifluoroethyl, difluoroethyl, pentafluoroethyl, difluoropropyl, dichloropropyl, and heptafluoropropyl. Illustrating further, "haloalkoxy" refers to an alkoxy that is substituted with at least one halogen substituent. Examples of haloalkoxy substituents include chloromethoxy, 1-bromoethoxy, fluoromethoxy, difluoromethoxy, trifluoromethoxy (also known as "perfluoromethyloxy"), and 2,2,2-trifluoroethoxy. It should be recognized that if a substituent is substituted by more than one halogen substituent, those halogen substituents may be identical or different (unless otherwise stated).

The term "oxo" refers to =O.

The term "alkoxy" refers to an alkyl linked to an oxygen, which may also be represented as —OR, wherein the R represents the alkyl group. Examples of alkoxy include methoxy, ethoxy, propoxy and butoxy.

The term "cycloalkyloxy" refers to a cycloalkyl linked to an oxygen, which may also be represented as —OR, wherein the R represents the cycloalkyl group. Examples of cycloalkyloxy include cyclopropyloxy, cyclobutyloxy, and cyclopentyloxy.

The term "heterocycloalkyl" refers to a substituent obtained by removing a hydrogen from a saturated or partially saturated ring structure containing a total of 4 to 14 ring atoms. At least one of the ring atoms is a heteroatom usually selected from oxygen, nitrogen, or sulfur. A heterocycloalkyl alternatively may comprise 2 or 3 rings fused together, wherein at least one such ring contains a heteroatom as a ring atom (i.e., nitrogen, oxygen, or sulfur). In a group that has a heterocycloalkyl substituent, the ring atom of the heterocycloalkyl substituent that is bound to the group may be the at least one heteroatom, or it may be a ring carbon atom, where the ring carbon atom may be in the same ring as the at least one heteroatom or where the ring carbon atom may be in a different ring from the at least one heteroatom. Similarly, if the heterocycloalkyl substituent is in turn substituted with a group or substituent, the group or substituent may be bound to the at least one heteroatom, or it may be bound to a ring carbon atom, where the ring carbon atom may be in the same ring as the at least one heteroatom or where the ring carbon atom may be in a different ring from the at least one heteroatom.

The term "heterocycloalkyl" also includes substituents that are fused to a $C_6$-$C_{10}$ aromatic ring or to a 5-10-membered heteroaromatic ring, wherein a group having such a fused heterocycloalkyl group as a substituent is bound to a heteroatom of the heterocycloalkyl group or to a carbon atom of the heterocycloalkyl group. When such a fused heterocycloalkyl group is substituted with one or more substituents, the one or more substituents, unless otherwise specified, are each bound to a heteroatom of the heterocycloalkyl group or to a carbon atom of the heterocycloalkyl group. The fused $C_6$-$C_{10}$ aromatic ring or 5-10-membered heteroaromatic ring may be optionally substituted with halogen, $C_1$-$C_6$ alkyl, $C_3$-$C_{10}$ cycloalkyl, $C_1$-$C_6$ alkoxy, or =O.

The term "heterocycloalkyloxy" refers to a heterocycloalkyl linked to an oxygen, which may also be represented as —OR, wherein the R represents the heterocycloalkyl group. Examples of heterocycloalkyloxy include oxetanyloxy (such as oxetan-3-yloxy), tetrahydrofuranyloxy (such as tetrahydrofuran-3-yloxy), and tetrahydropyranyloxy (such as tetrahydro-2H-pyran-4-yloxy or tetrahydro-2H-pyran-3-yloxy).

The term "heteroaryl" refers to an aromatic ring structure containing from 5 to 14 ring atoms in which at least one of the ring atoms is a heteroatom (i.e., oxygen, nitrogen, or sulfur), with the remaining ring atoms being independently selected from the group consisting of carbon, oxygen, nitrogen, and sulfur. A heteroaryl may be a single ring or 2 or 3 fused rings. Examples of heteroaryl substituents include 6-membered ring substituents such as pyridyl, pyrazyl, pyrimidinyl, and pyridazinyl; 5-membered ring substituents such as triazolyl, imidazolyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6-/5-membered fused ring substituents such as benzothiofuranyl, isobenzothiofuranyl, benzisoxazolyl, benzoxazolyl and purinyl; and 6-/6-membered fused rings such as quinolinyl, isoquinolinyl, cinnolinyl, quinazolinyl, and 1,4-benzoxazinyl. In a group that has a heteroaryl substituent, the ring atom of the heteroaryl substituent that is bound to the group may be the at least one heteroatom, or it may be a ring carbon atom, where the ring carbon atom may be in the same ring as the at least one heteroatom or where the ring carbon atom may be in a different ring from the at least one heteroatom. Similarly, if the heteroaryl substituent is in turn substituted with a group or substituent, the group or substituent may be bound to the at least one heteroatom, or it may be bound to a ring carbon atom, where the ring carbon atom may be in the same ring as the at least one heteroatom or where the ring carbon atom may be in a different ring from the at least one heteroatom. The term "heteroaryl" also includes pyridyl N-oxides and groups containing a pyridine N-oxide ring.

Examples of single ring heteroaryls include furanyl, thiophenyl (also known as "thiofuranyl"), pyrrolyl, imidazolyl, pyrazolyl, triazolyl, tetrazolyl, oxazolyl, isoxazolyl, thiazolyl, isothiazolyl, thiadiazolyl, oxadiazolyl [including 1,2,4-oxadiazolyl (also known as "azoximyl"), 1,2,5-oxadiazolyl (also known as "furazanyl"), or 1,3,4-oxadiazolyl], oxatriazolyl (including 1,2,3,4-oxatriazolyl or 1,2,3,5-oxatriazolyl), pyridinyl (also known as "azinyl"), diazinyl [including pyridazinyl (also known as "1,2-diazinyl"), pyrimidinyl (also known as "1,3-diazinyl" or "pyrimidyl"), or pyrazinyl (also known as "1,4-diazinyl")], and triazinyl [including s-triazinyl (also known as "1,3,5-triazinyl"), as-triazinyl (also known 1,2,4-triazinyl), and v-triazinyl (also known as "1,2,3-triazinyl")].

Examples of 2-fused-ring heteroaryls include indolizinyl, pyrindinyl, purinyl, naphthyridinyl, pyridopyridinyl (including pyrido[3,4-b]-pyridinyl, pyrido[3,2-b]pyridinyl, or pyrido[4,3-b]pyridinyl), and pteridinyl, indolyl, isoindolyl, isoindazolyl, phthalazinyl, quinoxalinyl, quinazolinyl, benzoxazolyl, indoxazinyl, anthranilyl, benzoxadiazolyl, benzofuranyl, isobenzofuranyl, benzothienyl, isobenzothienyl, benzothiazolyl, benzothiadiazolyl, benzimidazolyl, benzotriazolyl, benzoxazinyl, and benzisoxazinyl.

Examples of 3-fused-ring heteroaryls or heterocycloalkyls include 5,6-dihydro-4H-imidazo[4,5,1-ij]quinoline, 4,5-dihydroimidazo[4,5,1-hi]indole, 4,5,6,7-tetrahydroimidazo[4,5,1-jk][1]benzazepine, and dibenzofuranyl.

Other examples of fused ring heteroaryls include benzo-fused heteroaryls such as indolyl, isoindolyl (also known as "isobenzazolyl" or "pseudoisoindolyl"), benzazinyl [including quinolinyl (also known as "1-benzazinyl") or isoquinolinyl (also known as "2-benzazinyl")], phthalazinyl, quinoxalinyl, quinazolinyl, benzodiazinyl [including cinnolinyl (also known as "1,2-benzodiazinyl") or quinazolinyl (also known as "1,3-benzodiazinyl")], benzoxazolyl, indoxazinyl (also known as "benzisoxazolyl"), benzoxadiazolyl, benzofuranyl (also known as "coumaronyl"), isobenzofuranyl, benzothienyl (also known as "benzothiophenyl," "thionaphthenyl," or "benzothiofuranyl"), isobenzothienyl (also known as "isobenzothiophenyl," "isothianaphthenyl," or "isobenzothiofuranyl"), benzothiazolyl, benzothiadiazolyl, benzimidazolyl, benzotriazolyl, benzoxazinyl, benzisoxazinyl (including 1,2-benzisoxazinyl or 1,4-benzisoxazinyl), carbazolyl, and acridinyl.

The term "heteroaryl" also includes substituents such as pyridyl and quinolinyl that are fused to a $C_4$-$C_{10}$ carbocyclic ring, such as a $C_5$ or a $C_6$ carbocyclic ring, or to a 4-10-membered heterocyclic ring, wherein a group having such a fused aryl group as a substituent is bound to an aromatic carbon of the heteroaryl group or to a heteroatom of the heteroaryl group. When such a fused heteroaryl group is substituted with one or more substituents, the one or more substituents, unless otherwise specified, are each bound to an aromatic carbon of the heteroaryl group or to a heteroatom of the heteroaryl group. The fused $C_4$-$C_{10}$ carbocyclic or 4-10-membered heterocyclic ring may be optionally substituted with halogen, $C_1$-$C_6$ alkyl, $C_3$-$C_{10}$ cycloalkyl, or =O.

Additional examples of heteroaryls and heterocycloalkyls include: 3-1H-benzimidazol-2-one, (1-substituted)-2-oxo-benzimidazol-3-yl, 2-tetrahydrofuranyl, 3-tetrahydrofuranyl, 2-tetrahydropyranyl, 3 tetrahydropyranyl, 4-tetrahydropyranyl, [1,3]-dioxalanyl, [1,3]-dithiolanyl, [1,3]-dioxanyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, 2H-imidazol-2-one, 1-phthalimidinyl, benzoxanyl, benzo[1,3]dioxine, benzo[1,4]dioxine, benzopyrrolidinyl, benzopiperidinyl, benzoxolanyl, benzothiolanyl, 4,5,6,7-tetrahydropyrazol[1,5-a]pyridine, benzothianyl, pyrrolidinyl, dihydrofuranyl, tetrahydrothienyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, quinolizinyl, pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-2-yl (C-attached).

If a substituent is described as being "substituted," a non-hydrogen substituent is in the place of a hydrogen attached to a carbon, oxygen, sulfur or nitrogen of the substituent. Thus, for example, a substituted alkyl substituent is an alkyl substituent wherein at least one non-hydrogen substituent is in the place of a hydrogen substituent on the alkyl substituent. To illustrate, monofluoroalkyl is alkyl substituted with a fluoro substituent, and difluoroalkyl is alkyl substituted with two fluoro substituents. It should be recognized that if there is more than one substitution on a substituent, each non-hydrogen substituent may be identical or different (unless otherwise stated).

If a substituent is described as being "optionally substituted," the substituent may be either substituted or not substituted. If a carbon of a substituent is described as being optionally substituted with one or more of a list of substituents, one or more of the hydrogens on the carbon (to the extent there are any) may separately and/or together be replaced with an independently selected optional substituent. If a nitrogen of a substituent is described as being optionally substituted with one or more of a list of substituents, one or more of the hydrogens on the nitrogen (to the extent there are any) may each be replaced with an independently selected optional substituent. One exemplary substituent may be depicted as —NR'R", wherein R' and R" together with the nitrogen atom to which they are attached, may form a heterocyclic ring. The heterocyclic ring formed from R' and R" together with the nitrogen atom to which they are attached may be partially or fully saturated. In one embodiment, the heterocyclic ring consists of 4 to 7 atoms. In another embodiment, the heterocyclic ring is selected from the group consisting of pyrrolyl, imidazolyl, pyrazolyl, triazolyl, tetrazolyl, isoxazolyl, and thiazolyl.

If a group of substituents are collectively described as being optionally substituted by one or more of a list of substituents, the group may include: (1) unsubstitutable substituents, (2) substitutable substituents that are not substituted by the optional substituents, and/or (3) substitutable substituents that are substituted by one or more of the optional substituents.

If a substituent is described as being optionally substituted with up to a particular number of non-hydrogen substituents, that substituent may be either (1) not substituted; or (2) substituted by up to that particular number of non-hydrogen substituents or by up to the maximum number of substitutable positions on the substituent, whichever is less. Thus, for example, if a substituent is described as a heteroaryl optionally substituted with up to 3 non-hydrogen substituents, then any heteroaryl with less than 3 substitutable positions would be optionally substituted by up to only as many non-hydrogen substituents as the heteroaryl has substitutable positions. To illustrate, tetrazolyl (which has only one substitutable position) would be optionally substituted with up to one non-hydrogen substituent. To illustrate further, if an amino nitrogen is described as being optionally substituted with up to 2 non-hydrogen substituents, then the nitrogen will be optionally substituted with up to 2 non-hydrogen substituents if the amino nitrogen is a primary nitrogen, whereas the amino nitrogen will be optionally substituted with up to only 1 non-hydrogen substituent if the amino nitrogen is a secondary nitrogen.

A prefix attached to a multi-moiety substituent only applies to the first moiety. To illustrate, the term "alkylcycloalkyl" contains two moieties: alkyl and cycloalkyl. Thus, a $C_1$-$C_6$ prefix on $C_1$-$C_6$ alkylcycloalkyl means that the alkyl moiety of the alkylcycloalkyl contains from 1 to 6 carbon atoms; the $C_1$-$C_6$ prefix does not describe the cycloalkyl moiety. To illustrate further, the prefix "halo" on haloalkoxyalkyl indicates that only the alkoxy moiety of the alkoxyalkyl substituent is substituted with one or more halogen substituents. If the halogen substitution may only occur on the alkyl moiety, the substituent would be described as "alkoxyhaloalkyl." If the halogen substitution may occur on both the alkyl moiety and the alkoxy moiety, the substituent would be described as "haloalkoxyhaloalkyl."

If substituents are described as being "independently selected" from a group, each substituent is selected independent of the other. Each substituent therefore may be identical to or different from the other substituent(s).

As used herein the term "Formula X" may be referred to as "a compound of the invention" or as "compounds of the invention." Such terms are also defined to include all forms of the compound of Formula X, including hydrates, solvates, isomers, crystalline and non-crystalline forms, isomorphs, polymorphs, and metabolites thereof.

The following abbreviations are used herein:

| | |
|---|---|
| AIBN: | 2,2'-Azobisisobutyronitrile |
| APCI: | Atmospheric pressure chemical ionization |
| BOC: | tert-Butoxycarbonyl |
| BOC$_2$O: | Di-tert-butyl dicarbonate |

| | |
|---|---|
| br: | Broad |
| CD₃OD: | Deuterated methanol |
| CDCl₃: | Deuterated chloroform |
| d: | Doublet |
| DCM: | Dichloromethane |
| dd: | Doublet of doublets |
| DMF: | N,N-Dimethylformamide |
| DMSO: | Dimethyl sulfoxide |
| DMSO-d₆: | Deuterated dimethyl sulfoxide |
| Et₂O: | Diethyl ether |
| EtOAc: | Ethyl acetate |
| EtOH: | Ethanol |
| g: | Gram |
| h: | Hours |
| HPLC: | High performance liquid chromatography |
| J: | Coupling constant |
| LCMS: | Liquid chromatography-mass spectrometry |
| m: | Multiplet |
| M: | Molar |
| mCPBA: | meta-Chloroperoxybenzoic acid |
| MeCN: | Acetonitrile |
| MeOH: | Methanol |
| mEq: | Milliequivalent |
| mg: | Milligram |
| MHz: | Megahertz |
| min: | Minutes |
| mL: | Milliliter |
| µL: | Microliter |
| mmol: | Millimole |
| MS: | Mass spectrometry |
| N: | Normal |
| NaOEt: | Sodium ethoxide |
| NBS: | N-Bromosuccinimide |
| NCS: | N-Chlorosuccinimide |
| NEt₃: | Triethylamine |
| NMR: | Nuclear magnetic resonance |
| Pd(II)(OAc)₂: | Palladium (II) acetate |
| ppm: | Parts per million |
| psi: | Pounds per square inch |
| Pt/C: | Platinum on carbon |
| q: | Quartet |
| RT: | room temperature |
| s: | Singlet |
| t: | Triplet |
| —OTf: | CF₃SO₃— |
| TFA: | Trifluoroacetic acid |
| THF: | Tetrahydrofuran |
| TLC: | Thin layer chromatography |

Isomers

When an asymmetric center is present in a compound of Formula X, hereinafter referred to as the compound of the invention, the compound may exist in the form of optical isomers (enantiomers). In one embodiment, the present invention comprises enantiomers and mixtures, including racemic mixtures of the compounds of Formula X. In another embodiment, for compounds of Formula X that contain more than one asymmetric center, the present invention comprises diastereomeric forms (individual diastereomers and mixtures thereof) of compounds. When a compound of Formula X contains an alkenyl group or moiety, geometric isomers may arise.

Tautomeric Forms

The present invention comprises the tautomeric forms of compounds of Formula X. Where structural isomers are interconvertible via a low energy barrier, tautomeric isomerism ('tautomerism') can occur. This can take the form of proton tautomerism in compounds of Formula X containing, for example, an imino, keto, or oxime group, or so-called valence tautomerism in compounds which contain an aromatic moiety. It follows that a single compound may exhibit more than one type of isomerism. The various ratios of the tautomers in solid and liquid form is dependent on the various substituents on the molecule as well as the particular crystallization technique used to isolate a compound.

Salts

The compounds of this invention may be used in the form of salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient (as opposed to, for example, being used in an in vitro context), the salt preferably is pharmaceutically acceptable. The term "pharmaceutically acceptable salt" refers to a salt prepared by combining a compound of Formula X with an acid whose anion, or a base whose cation, is generally considered suitable for human consumption. Pharmaceutically acceptable salts are particularly useful as products of the methods of the present invention because of their greater aqueous solubility relative to the parent compound. For use in medicine, the salts of the compounds of this invention are non-toxic "pharmaceutically acceptable salts." Salts encompassed within the term "pharmaceutically acceptable salts" refer to non-toxic salts of the compounds of this invention which are generally prepared by reacting the free base with a suitable organic or inorganic acid.

Suitable pharmaceutically acceptable acid addition salts of the compounds of the present invention when possible include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include, for example, aliphatic, cycloaliphatic, aromatic, araliphatic, heterocyclylic, carboxylic, and sulfonic classes of organic acids.

Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sulfanilate, cyclohexylaminosulfonate, algenic acid, β-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, tosylate, and undecanoate.

Furthermore, where the compounds of the invention carry an acidic moiety, suitable pharmaceutically acceptable salts thereof may include alkali metal salts, i.e., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diethanolamine, glycine, lysine, meglumine, ethanolamine, tromethamine and zinc salts.

Organic salts may be made from secondary, tertiary or quaternary amine salts, such as tromethamine, diethylamine, N,N'-benzylethylenediamine, chloroprocaine, choline, diethanolamine, ethylenediamine, meglumine (N-methylglucamine), and procaine. Basic nitrogen-containing groups may be quaternized with agents such as lower alkyl ($C_1$-$C_6$) halides (e.g., methyl, ethyl, propyl, and butyl chlorides, bromides, and iodides), dialkyl sulfates (i.e., dimethyl, diethyl, dibutyl, and diamyl sulfates), long chain halides (i.e., decyl, lauryl, myristyl, and stearyl chlorides, bromides, and iodides), arylalkyl halides (i.e., benzyl and phenethyl bromides), and others.

In one embodiment, hemisalts of acids and bases may also be formed, for example, hemisulphate and hemicalcium salts.

Isotopes

The present invention also includes isotopically labeled compounds, which are identical to those recited in Formula X, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorous, sulfur, fluorine and chlorine, such as $^2H$, $^3H$, $^{13}C$, $^{11}C$, $^{14}C$, $^{15}N$, $^{18}O$, $^{17}O$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of Formula X of this invention and prodrugs thereof can generally be prepared by carrying out the procedures disclosed in the Schemes and/or in the Examples and Preparations below, by substituting a readily available isotopically labeled reagent for a non-isotopically labeled reagent.

The invention also relates to prodrugs of the compounds of Formula X. Thus certain derivatives of compounds of Formula X which may have little or no pharmacological activity themselves can, when administered into or onto the body, be converted into compounds of Formula X having the desired activity, for example, by hydrolytic cleavage. Such derivatives are referred to as "prodrugs". Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (Ed. E. B. Roche, American Pharmaceutical Association).

Prodrugs in accordance with the invention can, for example, be produced by replacing appropriate functionalities present in the compounds of Formula X with certain moieties known to those skilled in the art as 'pro-moieties' as described, for example, in Design of Prodrugs by H. Bundgaard (Elsevier, 1985).

Some non-limiting examples of prodrugs in accordance with the invention include:
(i) where the compound of Formula X contains a carboxylic acid functionality which is functionalized into a suitably metabolically labile group (esters, carbamates, etc.) on the compound of Formula X;
(ii) where the compound of Formula X contains an alcohol functionality which is functionalized into a suitably metabolically labile group (esters, carbonates, carbamates, acetals, ketals, etc.) on the compound of Formula X; and
(iii) where the compound of Formula X contains a primary or secondary amino functionality, or an amide which is functionalized into a suitably metabolically labile group, e.g., a hydrolyzable group (amides, carbamates, ureas, phosphonates, sulfonates, etc.) on the compound of Formula X.

Further examples of replacement groups in accordance with the foregoing examples and examples of other prodrug types may be found in the aforementioned references.

Moreover, certain compounds of Formula X may themselves act as prodrugs of other compounds of Formula X.

Administration and Dosing

Typically, a compound of the invention is administered in an amount effective to treat a condition as described herein. The compounds of the invention are administered by any suitable route in the form of a pharmaceutical composition adapted to such a route, and in a dose effective for the treatment intended. Therapeutically effective doses of the compounds required to treat the progress of the medical condition are readily ascertained by one of ordinary skill in the art using preclinical and clinical approaches familiar to the medicinal arts.

The compounds of the invention may be administered orally. Oral administration may involve swallowing, so that the compound enters the gastrointestinal tract, or buccal or sublingual administration may be employed by which the compound enters the blood stream directly from the mouth.

In another embodiment, the compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the compounds of the invention may also be administered topically to the skin or mucosa, that is, dermally or transdermally. In another embodiment, the compounds of the invention can also be administered intranasally or by inhalation. In another embodiment, the compounds of the invention may be administered rectally or vaginally. In another embodiment, the compounds of the invention may also be administered directly to the eye or ear.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions. In one embodiment, the total daily dose of a compound of the invention (administered in single or divided doses) is typically from about 0.01 to about 100 mg/kg. In another embodiment, total daily dose of the compound of the invention is from about 0.1 to about 50 mg/kg, and in another embodiment, from about 0.5 to about 30 mg/kg (i.e., mg compound of the invention per kg body weight). In one embodiment, dosing is from 0.01 to 10 mg/kg/day. In another embodiment, dosing is from 0.1 to 1.0 mg/kg/day. Dosage unit compositions may contain such amounts or submultiples thereof to make up the daily dose. In many instances, the administration of the compound will be repeated a plurality of times in a day (typically no greater than 4 times). Multiple doses per day typically may be used to increase the total daily dose, if desired.

For oral administration, the compositions may be provided in the form of tablets containing 0.01, 0.05, 0.1, 0.5, 1.0, 2.5, 5.0, 10.0, 15.0, 25.0, 50.0, 75.0, 100, 125, 150, 175, 200, 250 and 500 milligrams of the active ingredient for the symptomatic adjustment of the dosage to the patient. A medicament typically contains from about 0.01 mg to about 500 mg of the active ingredient, or in another embodiment, from about 1 mg to about 100 mg of active ingredient. Intravenously, doses may range from about 0.01 to about 10 mg/kg/minute during a constant rate infusion.

Suitable subjects according to the present invention include mammalian subjects. Mammals according to the present invention include, but are not limited to, canine, feline, bovine, caprine, equine, ovine, porcine, rodents, lagomorphs, primates, and the like, and encompass mammals in utero. In one embodiment, humans are suitable subjects. Human subjects may be of either gender and at any stage of development.

Use in the Preparation of a Medicament

In another embodiment, the invention comprises the use of one or more compounds of the invention for the preparation of a medicament for the treatment of the conditions recited herein.

Pharmaceutical Compositions

For the treatment of the conditions referred to herein, the compound of the invention can be administered as compound per se. Alternatively, pharmaceutically acceptable salts are suitable for medical applications because of their greater aqueous solubility relative to the parent compound.

In another embodiment, the present invention comprises pharmaceutical compositions. Such pharmaceutical compositions comprise a compound of the invention presented with a pharmaceutically acceptable carrier. The carrier can be a solid, a liquid, or both, and may be formulated with the compound as a unit-dose composition, for example, a tablet, which can contain from 0.05% to 95% by weight of the active compounds. A compound of the invention may be coupled with suitable polymers as targetable drug carriers. Other pharmacologically active substances can also be present.

The compounds of the present invention may be administered by any suitable route, preferably in the form of a pharmaceutical composition adapted to such a route, and in a dose effective for the treatment intended. The active compounds and compositions, for example, may be administered orally, rectally, parenterally, or topically.

Oral administration of a solid dose form may be, for example, presented in discrete units, such as hard or soft capsules, pills, cachets, lozenges, or tablets, each containing a predetermined amount of at least one compound of the present invention. In another embodiment, the oral administration may be in a powder or granule form. In another embodiment, the oral dose form is sub-lingual, such as, for example, a lozenge. In such solid dosage forms, the compounds of Formula X are ordinarily combined with one or more adjuvants. Such capsules or tablets may contain a controlled-release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (i.e., water). Such compositions also may comprise adjuvants, such as wetting, emulsifying, suspending, flavoring (e.g., sweetening), and/or perfuming agents.

In another embodiment, the present invention comprises a parenteral dose form. "Parenteral administration" includes, for example, subcutaneous injections, intravenous injections, intraperitoneally, intramuscular injections, intrasternal injections, and infusion. Injectable preparations (i.e., sterile injectable aqueous or oleaginous suspensions) may be formulated according to the known art using suitable dispersing, wetting agents, and/or suspending agents.

In another embodiment, the present invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound which enhances absorption or penetration of the active ingredient through the skin or other affected areas. When the compounds of this invention are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Formulations suitable for topical administration to the eye include, for example, eye drops wherein the compound of this invention is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (i.e., absorbable gel sponges, collagen) and non-biodegradable (i.e., silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

In another embodiment, the present invention comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman et al., Eds., Pharmaceutical Dosage Forms, Marcel Decker, New York, N.Y., 1980; and Kibbe et al., Eds., Handbook of Pharmaceutical Excipients (3rd Ed.), American Pharmaceutical Association, Washington, 1999.

Co-Administration

The compounds of the present invention can be used, alone or in combination with other therapeutic agents, in the treatment of various conditions or disease states. The compound(s) of the present invention and other therapeutic agent(s) may be may be administered simultaneously (either in the same dosage form or in separate dosage forms) or sequentially. An exemplary therapeutic agent may be, for example, a metabotropic glutamate receptor agonist.

The administration of two or more compounds "in combination" means that the two compounds are administered closely enough in time that the presence of one alters the biological effects of the other. The two or more compounds may be administered simultaneously, concurrently or sequentially. Additionally, simultaneous administration may be carried out by mixing the compounds prior to administration or by administering the compounds at the same point in time but at different anatomic sites or using different routes of administration.

The phrases "concurrent administration," "co-administration," "simultaneous administration," and "administered simultaneously" mean that the compounds are administered in combination.

In one embodiment, the compounds of this invention are administered as adjunctive therapy with known anti-psychotics such as Ziprasidone (Geodon), Clozapine, Molindone, Loxapine, Pimozide, Risperidone, Olanzapine, Remoxipride, Sertindole, Amisulpride, Quetiapine, Prochlorperazine, Fluphenazine, Trifluoroperazine, Thioridazine, Haloperidol, Chlorpromazine, Flupentixol and Pipotiazine.

In another embodiment, the compounds of the present invention may also be used in combination with CNS agents such as antidepressants (such as sertraline), anti-Parkinsonian drugs (such as deprenyl, L-dopa, Requip, Mirapex, MAOB inhibitors such as selegiline and rasagiline, comT inhibitors such as Tasmar, A-2 inhibitors, dopamine reuptake inhibitors, NMDA antagonists, Nicotine agonists, Dopamine agonists and inhibitors of neuronal nitric oxide synthase), anti-Alzheimer's drugs such as donepezil, tacrine, alpha2delta inhibitors, COX-2 inhibitors, gaba pentenoids, propentofylline or metrifonate, and antipsychotics such as PDE10 inhibitors, 5HT2C agonists, alpha 7 nicotinic receptor agonists, CB1 antagonists and compounds having activity antagonizing dopamine D2 receptors.

Kits

The present invention further comprises kits that are suitable for use in performing the methods of treatment described above. In one embodiment, the kit contains a first dosage form comprising one or more of the compounds of the present invention and a container for the dosage, in quantities sufficient to carry out the methods of the present invention.

In another embodiment, the kit of the present invention comprises one or more compounds of the invention.

Intermediates

In another embodiment, the invention relates to the novel intermediates useful for preparing the compounds of the invention.

General Synthetic Schemes

The compounds of Formula X may be prepared by the methods described below, together with synthetic methods known in the art of organic chemistry, or modifications and derivatizations that are familiar to those of ordinary skill in the art. The starting materials used herein are commercially available or may be prepared by routine methods known in the art (such as those methods disclosed in standard reference books such as the COMPENDIUM OF ORGANIC SYNTHETIC METHODS, Vol. I-XII (published by Wiley-Interscience)). Preferred methods include, but are not limited to, those described below.

During any of the following synthetic sequences it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991, and T. W. Greene and P. G. M. Wuts, Protective Groups in Organic Chemistry, John Wiley & Sons, 1999, which are hereby incorporated by reference.

Compounds of Formula X, or their pharmaceutically acceptable salts, can be prepared according to the reaction Schemes discussed herein below. Unless otherwise indicated, the substituents in the Schemes are defined as above. Isolation and purification of the products is accomplished by standard procedures, which are known to a chemist of ordinary skill.

It will be understood by one skilled in the art that the various symbols, superscripts and subscripts used in the schemes, methods and examples are used for convenience of representation and/or to reflect the order in which they are introduced in the schemes, and are not intended to necessarily correspond to the symbols, superscripts or subscripts in the appended claims. The schemes are representative of methods useful in synthesizing the compounds of the present invention. They are not to constrain the scope of the invention in any way.

Scheme 1 depicts one method of preparation of the precursor of the 3-amino-1-hydroxy-3,4-dihydroquinolin-2(1H)-one series of compounds of this invention. Nitration of a substituted aromatic ring gives the desired nitro compound (II). In cases where the required aniline or aminoheterocycle (III) is commercially available or known in the literature, it can be oxidized with hydrogen peroxide in sulfuric acid, by a modification of the procedure described by W. S. Wilson et al., *J. Org. Chem.* 1986, 51, 3261, or with meta-chloroperoxybenzoic acid in toluene at reflux as described by M. C. Pirrung et al., *J. Am. Chem. Soc.* 2005, 127, 4609. The oxidation can also be carried out by a modification of the procedure described in US 2006/0009509 using sodium perborate in glacial acetic acid. The resulting ortho-methyl-, nitro-substituted aromatic compound (IV) can be brominated according to standard procedures, for instance with N-bromosuccinimide and 2,2'-azobisisobutyronitrile in carbon tetrachloride. If the corresponding alcohol is available, it can be converted to bromide V with, for example, phosphorus tribromide (either from a commercial source or formed in situ), as described by R. M. Rzasa et al., *Bioorg. Med. Chem.* 2007, 15, 6574.

Scheme 1

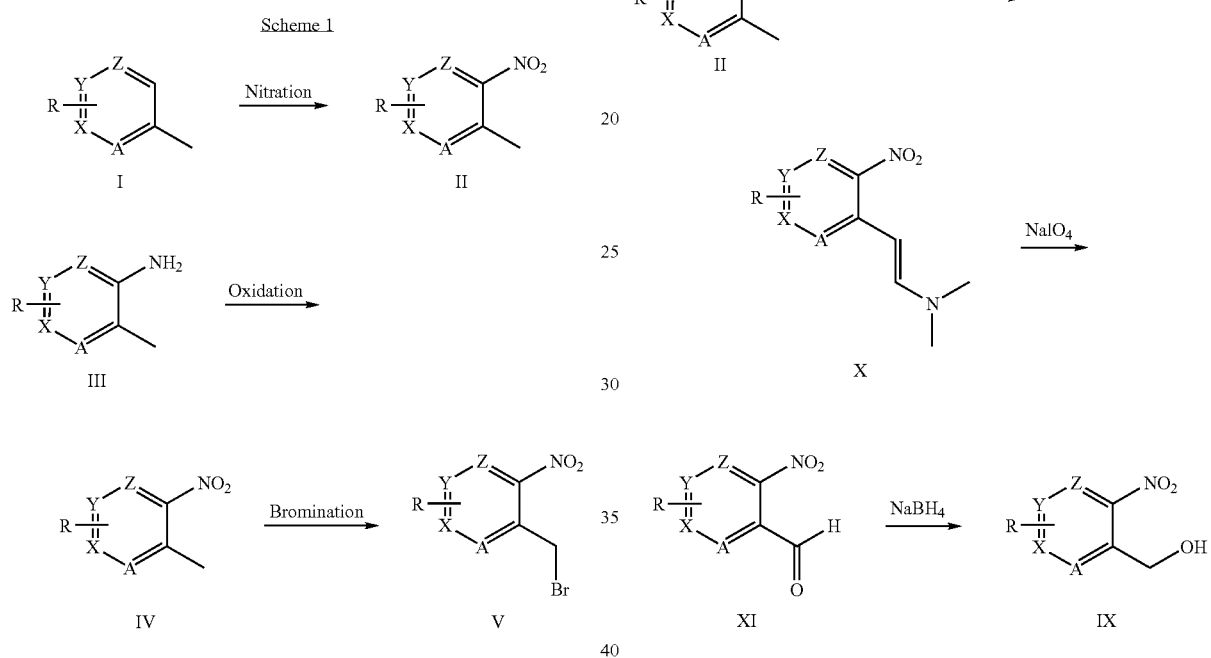

In some cases, the desired aromatic ring is available more effectively via the route shown in Scheme 2. Following the procedure of A. Ashimori et al., *Chem. Pharm. Bull.,* 38, 1990, 2446, a nitropyridine such as VI can be oxidized with meta-chloroperoxybenzoic acid, followed by the addition of acetic anhydride and hydrolysis to the alcohol (IXa) with potassium carbonate in methanol. Alternatively, the desired alcohol can be obtained via the procedure described by R. R. Tidwell et al., *J. Med. Chem.* 2007, 50, 2468 wherein the initial ortho-methyl, nitro-substituted aromatic compound II is converted to the dimethylaminoethylene derivative (X) with N,N-dimethylformamide dimethyl acetal (DMF-DMA), then to the aldehyde (XI) with sodium periodate, and is finally reduced to the alcohol (IX) with sodium borohydride.

In some instances, an aromatic starting material bearing the desired R substituent is not commercially available. The R group can be introduced into compounds of type XII, by employing a Suzuki reaction (see Scheme 3), for instance by using a modification of the procedure from D. J. Wallace and C.-y. Chen, *Tetrahedron Lett.,* 2002, 43, 6987. The resulting acid or ester (XV or XIII) can then be reduced by standard reduction conditions such as lithium borohydride or sodium borohydride, activated with zinc chloride if necessary, giving in both cases compound IX. In cases where the reduction of a carbonyl-containing functional group provides an alcohol, it can be converted to a mesylate in situ, for instance with methanesulfonyl chloride and triethylamine in dichloromethane.

Scheme 2

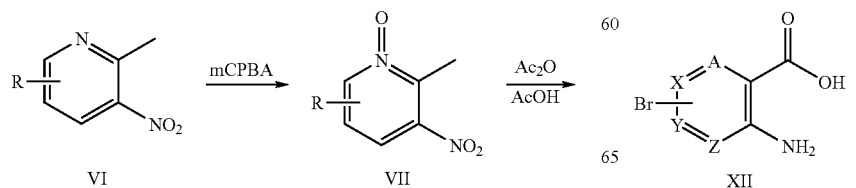

Scheme 3

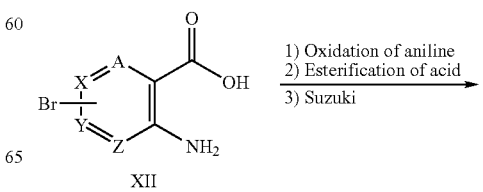

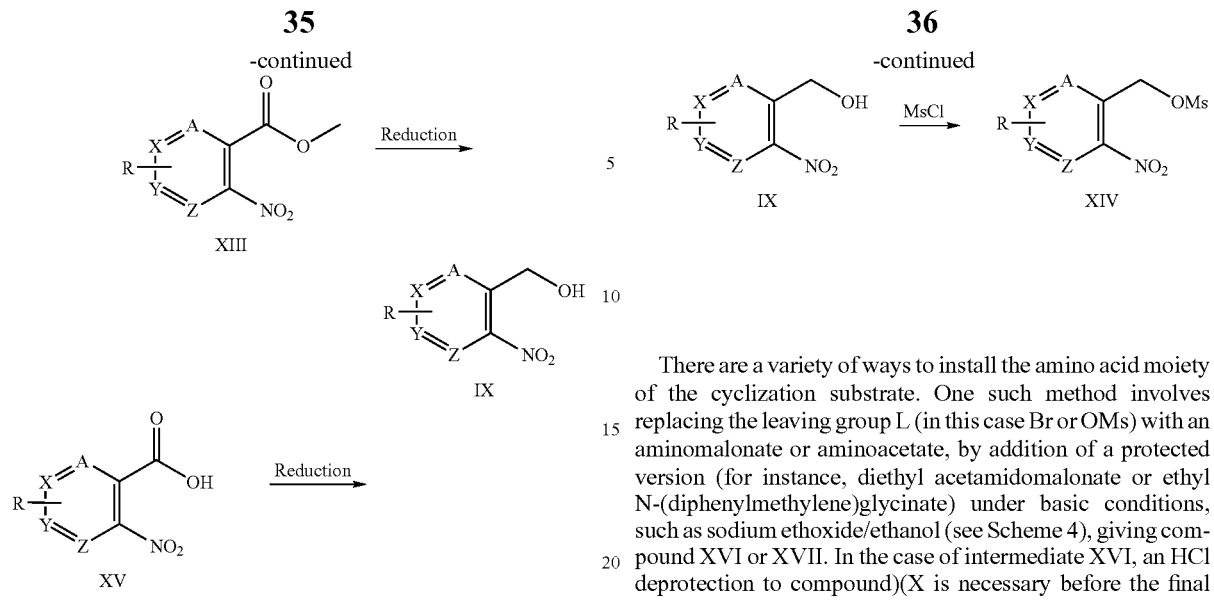

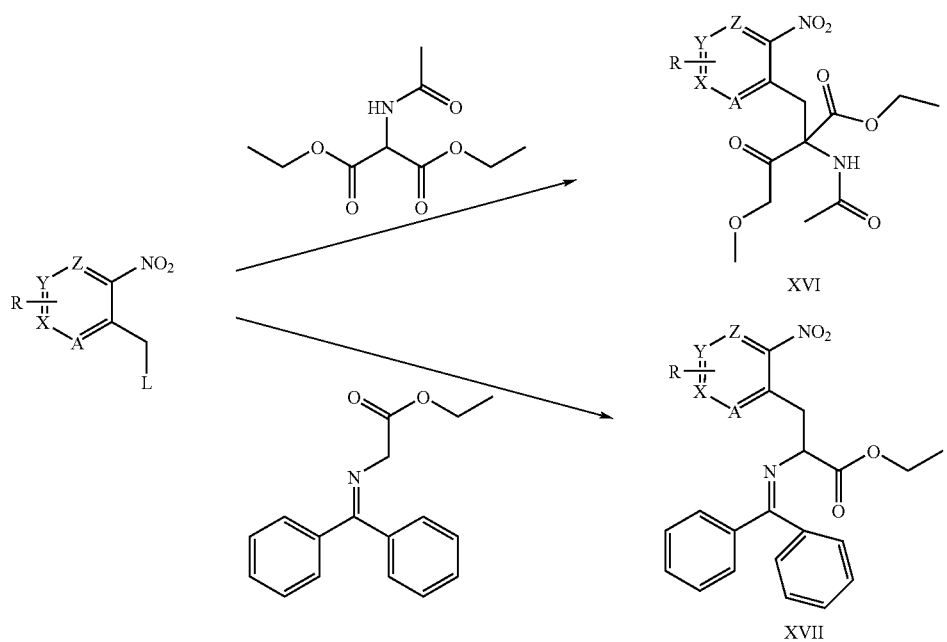

There are a variety of ways to install the amino acid moiety of the cyclization substrate. One such method involves replacing the leaving group L (in this case Br or OMs) with an aminomalonate or aminoacetate, by addition of a protected version (for instance, diethyl acetamidomalonate or ethyl N-(diphenylmethylene)glycinate) under basic conditions, such as sodium ethoxide/ethanol (see Scheme 4), giving compound XVI or XVII. In the case of intermediate XVI, an HCl deprotection to compound)(X is necessary before the final nitro reduction is carried out.

Scheme 4

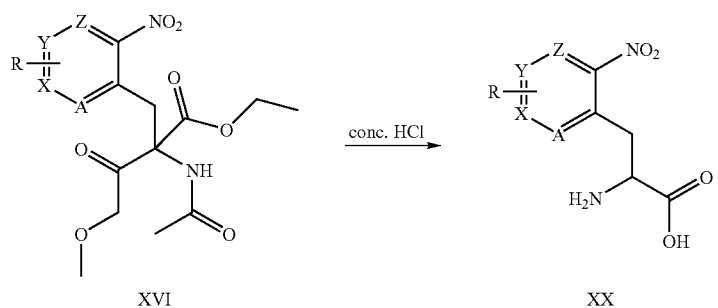

The amino acid portion can also be added stereoselectively, using the methods shown in Scheme 5 and Scheme 6.
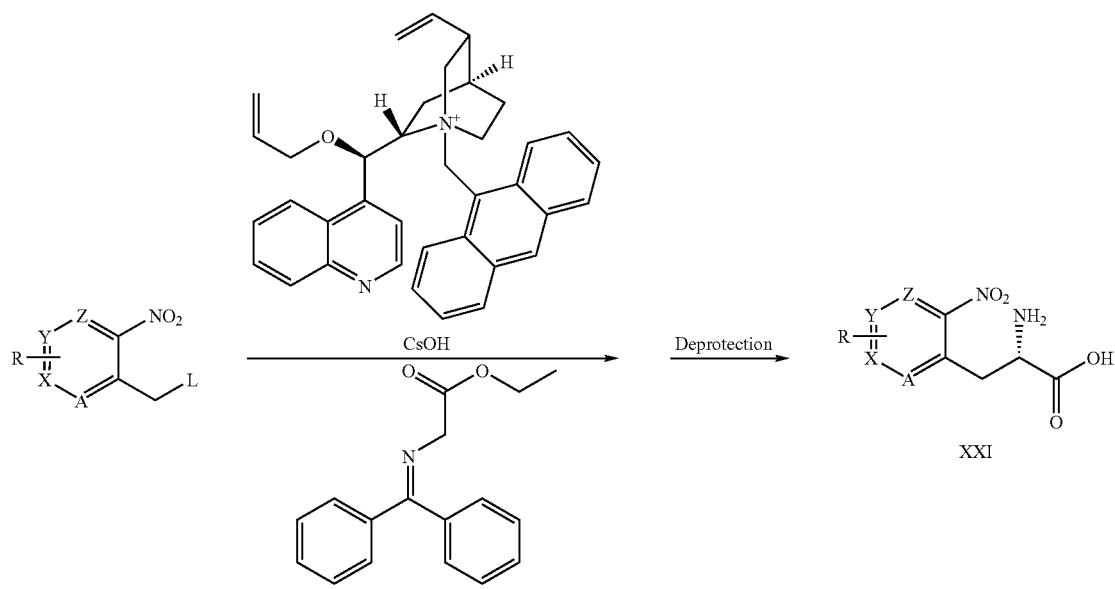
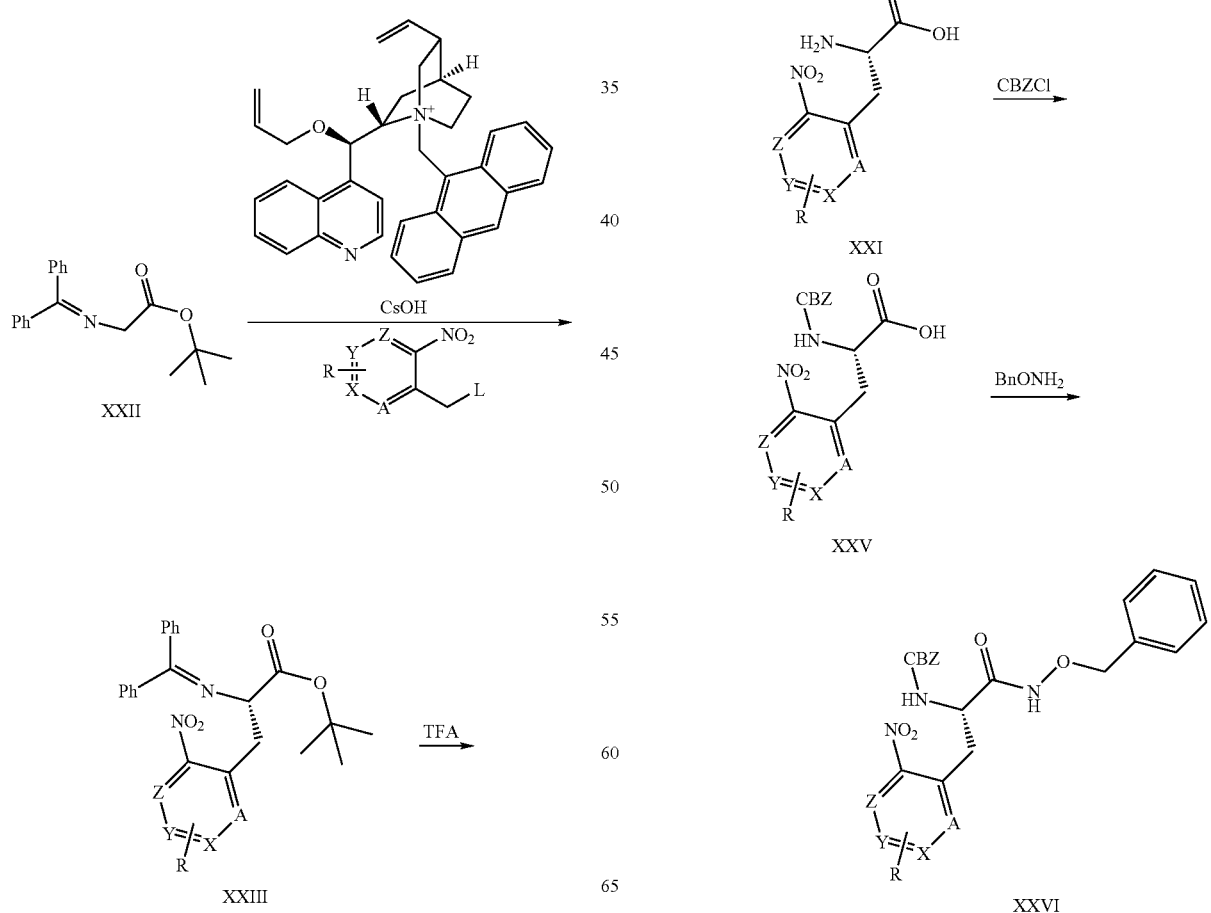

The enantioselective route is inspired by the work of S. Kumar and U. Ramachandran, *Tetrahedron Asymmetry* 2003, 14, 2539. The desired aromatic group can be installed using a chiral catalyst (see E. J. Corey et al., *J. Am. Chem. Soc.* 1997, 119, 12414-12415), to give, after further manipulation, intermediate XXI or XXVI. Once the intermediate is in hand, cyclization can be effected by the routes shown in Scheme 7 or Scheme 8.

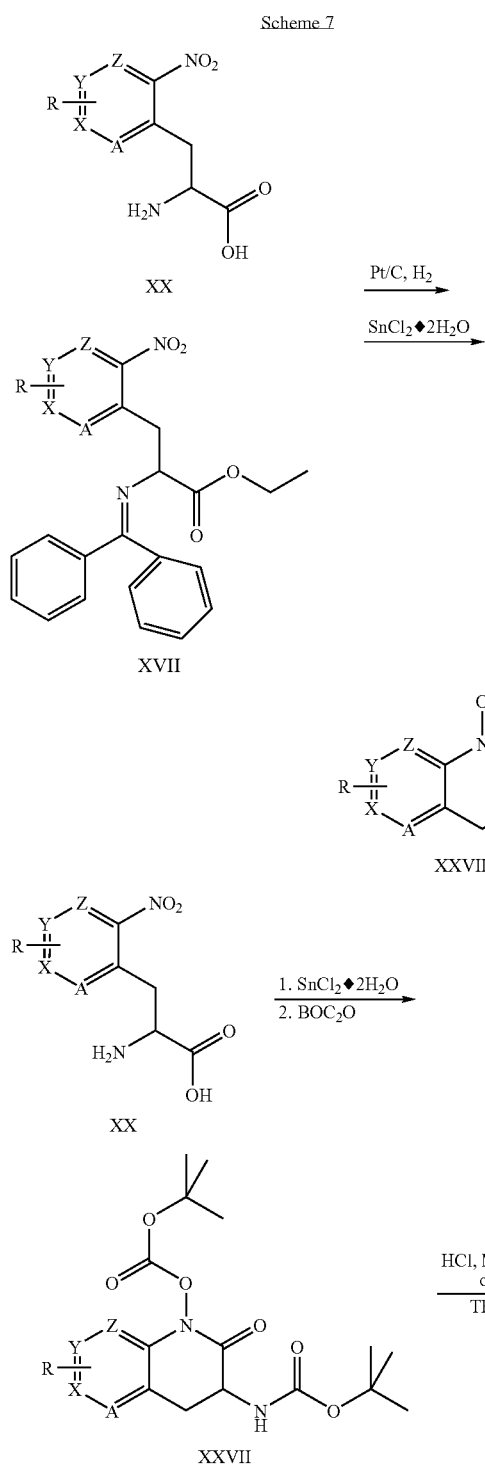

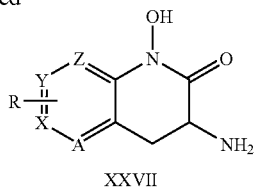

The nitro group can be reduced via hydrogenation, through an adaptation of the work of T. J. McCord et al., *J. Heterocyclic Chem.* 1972, 9, 119. Alternatively, a tin(II) chloride reduction can be used, according to the procedure of D. Shi et al., *Synthesis,* 2008, 2000. A modification of the tin(II) chloride approach which uses sodium acetate, from the work of D. Kuzmich and C. Mulrooney, *Synthesis* 2003, 1671, can also be employed. Cyclization occurs in situ (see Scheme 7). Most final products can be isolated after cyclization, but some analogues may need to be protected (either in situ during the cyclization or after the reaction) in order to facilitate purification. The protection can be done according to standard procedures, using di-tert-butyl dicarbonate; either HCl or trifluoroacetic acid can be utilized for subsequent deprotection.

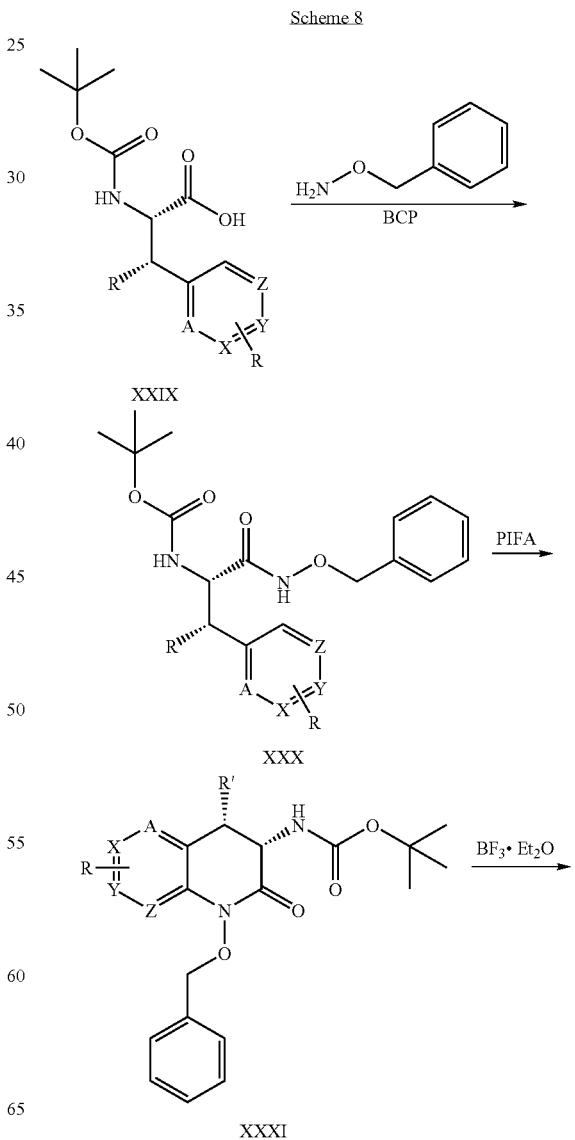

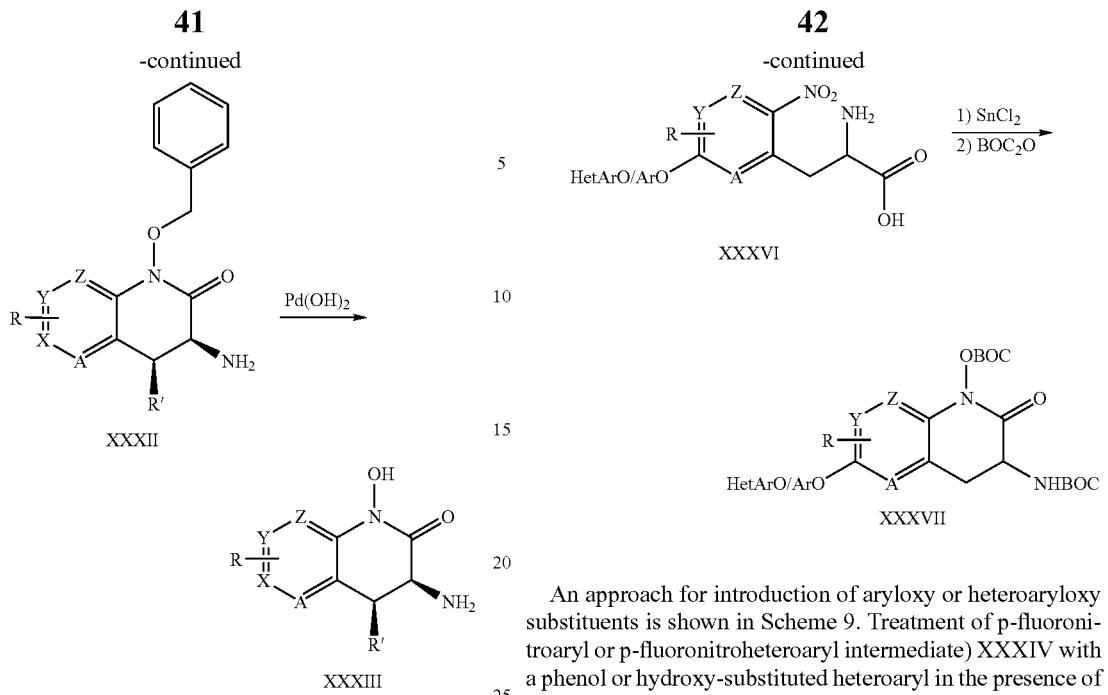

Scheme 8 describes an alternative route to the desired analogues. Compound XXX can be synthesized starting with the appropriate substituted N-BOC amino acid, which is first coupled with O-benzyl hydroxylamine, for example, by reaction with BOP [(benzotriazol-1-yloxy)-tris(dimethylamino) phosphonium hexafluorophosphate] and triethylamine in dichloromethane. The cyclization to XXXI can be carried out using PIFA [phenyliodine(III) bis(trifluoroacetate)] in dichloromethane. The BOC group can be removed using boron trifluoride etherate in tetrahydrofuran at reflux, and the benzyl group can be reductively removed, for instance with palladium hydroxide in ethanol at reflux with 1-methyl-cyclohexadiene, to give the final product XXXIII.

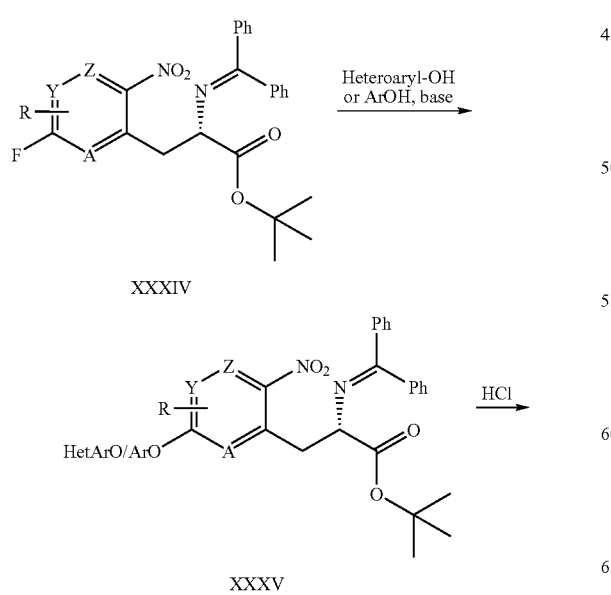

An approach for introduction of aryloxy or heteroaryloxy substituents is shown in Scheme 9. Treatment of p-fluoronitroaryl or p-fluoronitroheteroaryl intermediate) XXXIV with a phenol or hydroxy-substituted heteroaryl in the presence of a base, such as $Cs_2CO_3$, can provide intermediate XXXV. (Racemization of the α-stereocenter has been observed under these reaction conditions.) Deprotection under acidic conditions followed by reductive cyclization and in situ BOC protection can provide intermediate XXXVII.

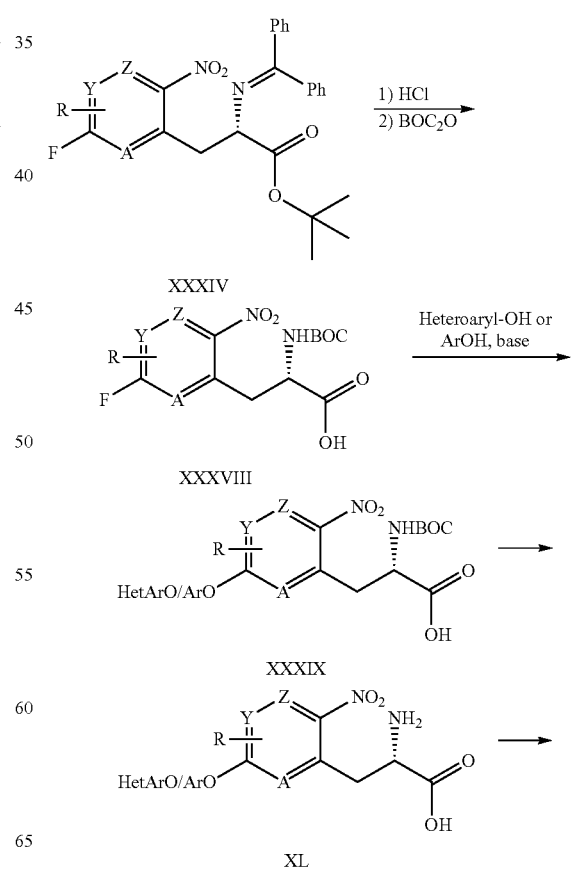

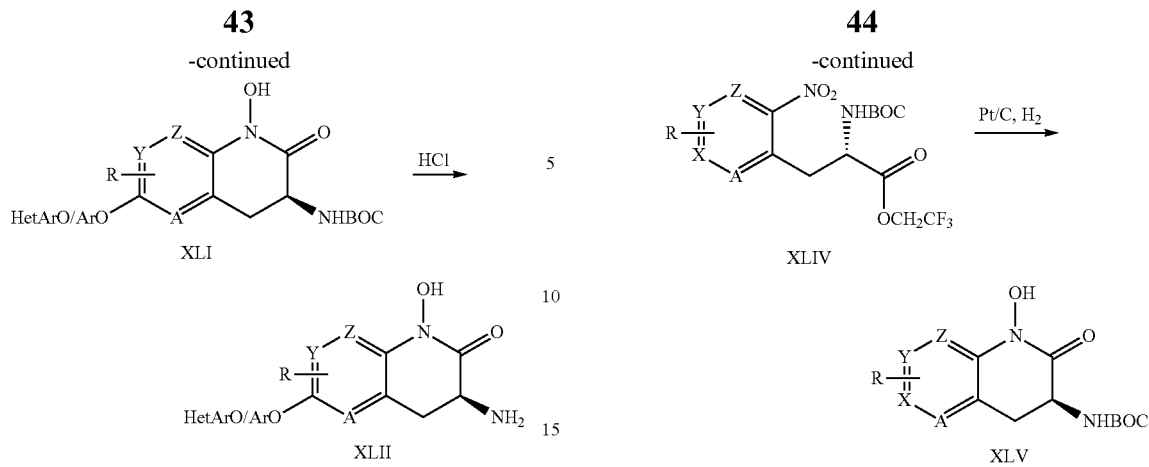

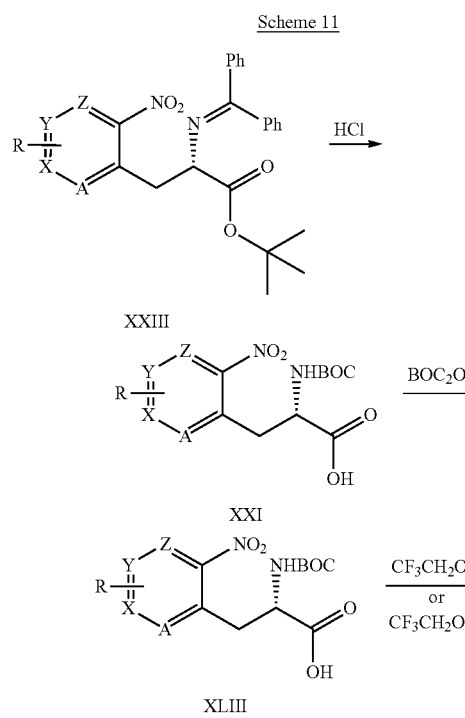

Scheme 10 outlines an alternate approach for introduction of aryloxy or heteroaryloxy substituents. Acid-promoted deprotection of XXXIV followed by BOC protection of the amino group can provide p-fluoronitroaryl or p-fluoronitroheteroaryl intermediate XXXVIII. The aryloxy or heteroaryloxy group can be installed under basic conditions to generate intermediate XXXIX without racemization of the stereocenter. Deprotection under acidic conditions provides intermediate XL. Cyclization of XL or XXXIX under reductive conditions can be effected in a variety of ways, such as treatment with tin(II) chloride, or via platinum- or palladium-catalyzed hydrogenation. Optional protection of the amino group as a BOC derivative can be carried out in situ by reaction with $BOC_2O$ after cyclization of XL, to provide XLI. The cyclization can also be carried out without amino group protection, to generate XLII directly. If a BOC group is employed, acid-mediated deprotection of XLI generates compound XLII.

In some cases, the reductive cyclization of an activated ester, such as a trifluoroethyl ester, provides improved access to cyclic hydroxamic acid derivatives (XLV). Referring to Scheme 11, acid-promoted deprotection of XXIII provides α-amino acid XXI, which can be converted to carbamate XLIII. Subsequent treatment of XLIII with 2,2,2-trifluoroethanol, using a coupling reagent such as HBTU, in DMF can provide the corresponding 2,2,2-trifluoroethyl ester XLIV, which can undergo reductive cyclization to yield hydroxamic acid derivative XLV. Alternatively, 2,2,2-trifluoroethyl ester XLIV can be formed by reaction of intermediate XLIII with 2,2,2-trifluoroethyl trifluoromethanesulfonate in the presence of a base such as triethylamine.

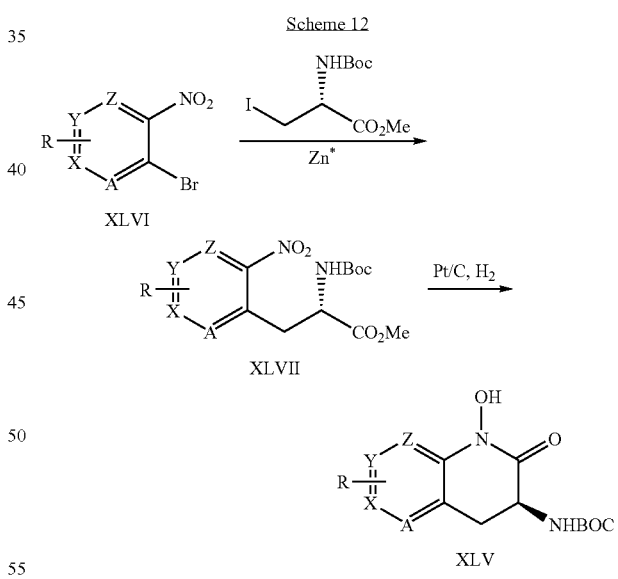

The amino acid moiety can also be installed using a serine-derived zinc reagent, as shown in Scheme 12. This approach involves modification of a published protocol for $sp^2$-$sp^3$ couplings of this type (see E. Moreno et al., *Org. Biomol. Chem.* 2006, 4, 3639-3647). Thus, o-bromonitroaryls or o-bromonitroheteroaryls XLVI can be converted to the corresponding BOC-protected-aminoesters XLVII. Intermediates XLVII can be subjected to reductive conditions, such as catalytic hydrogenation using Pt/C in pyridine, to afford cyclic hydroxamic acid derivatives XLV.

Scheme 13

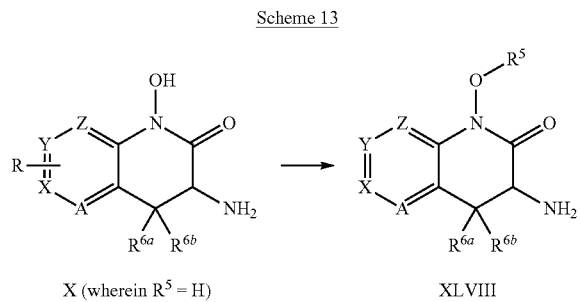

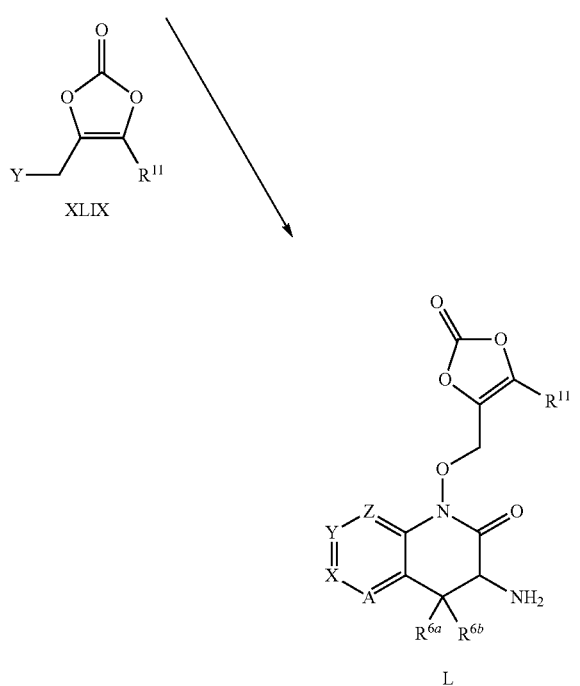

The compound of Formula X wherein R⁵ is H can be converted to a carbamate prodrug (XLVIII, where R⁵ is C(=O)NR$^{9a}$R$^{9b}$) by reaction with the appropriate carbamoyl chloride in the presence of a base such as pyridine. It may be advantageous to temporarily protect the free primary amine group prior to this transformation. Similarly, use of an acyl chloride [ClC(=O)R⁹] or acyl anhydride {[R⁹C(=O)]₂O} provides the corresponding ester prodrug [XLVIII, where R⁵ is C(=O)R⁹], while a chloroformate reactant [ClC(=O)OR⁹] can be used to prepare the carbonate prodrug [XLVIII, where R⁵ is C(=O)OR⁹]. Prodrugs of formula L, wherein R¹¹ is as defined above, can be prepared via alkylation of the compound of Formula X or Formula XA with a derivative XLIX (Y=MsO, Cl, Br) in the presence of a base such as potassium carbonate.

EXPERIMENTAL PROCEDURES AND WORKING EXAMPLES

The following illustrate the synthesis of various compounds of the present invention. Additional compounds within the scope of this invention may be prepared using the methods illustrated in these Examples, either alone or in combination with techniques generally known in the art.

Experiments were generally carried out under inert atmosphere (nitrogen or argon), particularly in cases where oxygen- or moisture-sensitive reagents or intermediates were employed. Commercial solvents and reagents were generally used without further purification, including anhydrous solvents where appropriate (generally Sure-Seal™ products from the Aldrich Chemical Company, Milwaukee, Wis.). Mass spectrometry data is reported from either liquid chromatography-mass spectrometry (LCMS), atmospheric pressure chemical ionization (APCI), or gas chromatography-mass spectrometry (GCMS). Chemical shifts for nuclear magnetic resonance (NMR) data are expressed in parts per million (ppm, δ) referenced to residual peaks from the deuterated solvents employed.

For syntheses referencing procedures in other Examples, reaction conditions (length of reaction and temperature) may vary. In general, reactions were followed by thin layer chromatography or mass spectrometry, and subjected to work-up when appropriate. Purifications may vary between experiments: in general, solvents and the solvent ratios used for eluants/gradients were chosen to provide appropriate R$_f$s or retention times.

Example 1

Synthesis of 3-amino-1-hydroxy-3,4-dihydro-1,8-naphthyridin-2(1H)-one, trifluoroacetate salt (8)

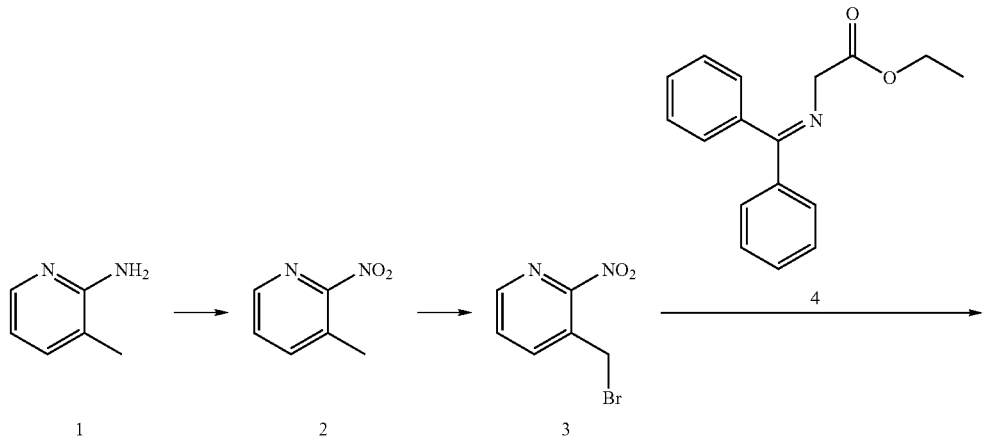

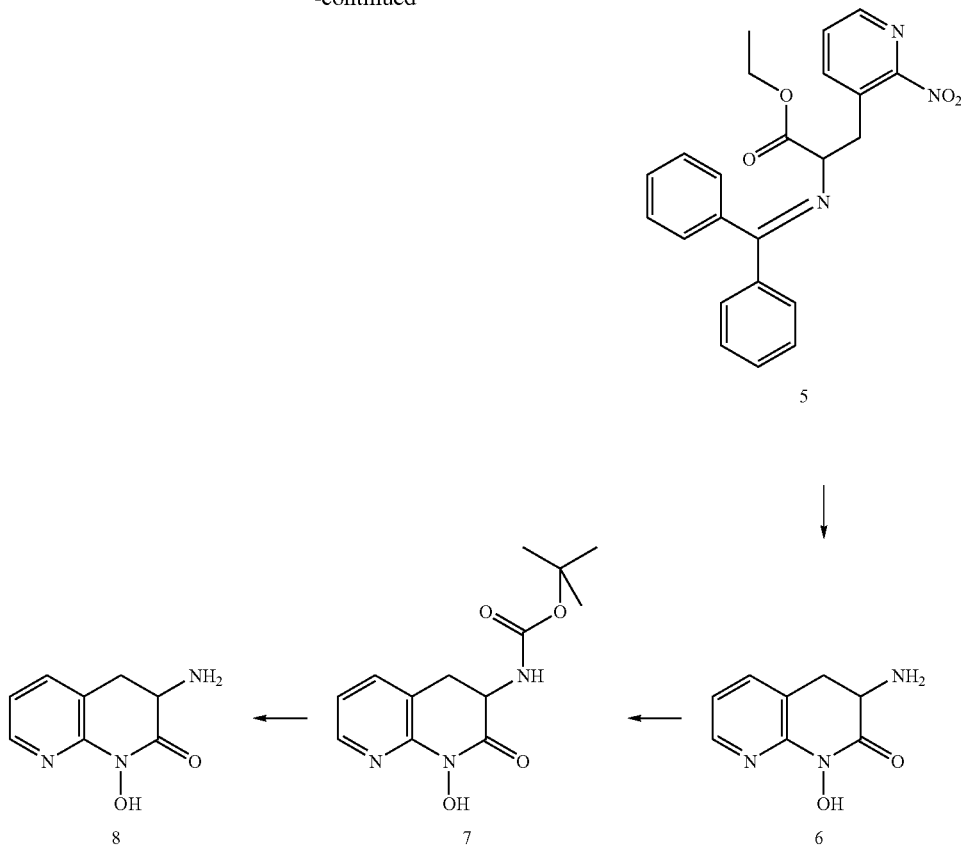

3-Methyl-2-nitropyridine (2) To a solution of H$_2$O$_2$ (120 g, 1.1 mol) in fuming sulfuric acid (250 mL) was added a solution of 3-methylpyridin-2-amine (1) (16 g, 0.15 mol) in concentrated sulfuric acid (50 mL) drop-wise, while keeping the reaction temperature at 0° C. After stirring for 3 h at 10-25° C., the reaction mixture was brought to pH=11-12 by adding an aqueous 40% NaOH solution at 0-5° C. The resulting mixture was extracted with ethyl acetate (3×500 mL). The combined organic layers were washed with saturated aqueous sodium chloride solution, dried over Na$_2$SO$_4$ and filtered. The solvent was removed in vacuo to give the desired compound (18.2 g, 89%) as a yellow oil.

3-(Bromomethyl)-2-nitropyridine (3) A solution of 3-methyl-2-nitropyridine (2) (12.4 g, 90.0 mmol), NBS (16.0 g, 90.4 mmol) and AIBN (0.5 g, 3.0 mmol) in CCl$_4$ (50 mL) was refluxed overnight. TLC (Eluant: 20:1 petroleum ether/EtOAc) showed that most of the starting material had been consumed. The precipitate was filtered off and the filtrate was concentrated under reduced pressure to give a residue (12.6 g), which was used in the next step without purification.

Ethyl 2-(diphenylmethyleneamino)-3-(2-nitropyridin-3-yl)propanoate (5) NaH (0.9 g, 65% dispersion in mineral oil, 22 mmol) was added to DMF (100 mL) at 0° C. After 10 min, ethyl N-(diphenylmethylene)glycinate (4) (5.5 g, 20.6 mmol) was added at 0° C. After 1 h, a solution of 3-(bromomethyl)-2-nitropyridine (3) (4.0 g, 18.5 mmol) in DMF (10 mL) was added drop-wise at 0° C. After stirring for 30 min, TLC (Eluant: 3:1 petroleum ether/EtOAc) indicated that the starting material had been completely consumed. The reaction was diluted with water and extracted with EtOAc (3×100 mL). The combined organic layers were washed with saturated aqueous sodium chloride solution, dried over Na$_2$SO$_4$ and filtered, and the filtrate was concentrated under reduced pressure. The residue was purified by silica gel chromatography (Eluant: 3:1 petroleum ether/EtOAc) to give the product (4.2 g, 58%); LCMS m/z 404.4 (M+1). $^1$H NMR (400 MHz, CDCl$_3$) δ 1.26 (t, J=7.2 Hz, 3H), 3.39 (dd, J=13.4, 9.2 Hz, 1H), 3.59 (dd, J=13.6, 4.2 Hz, 1H), 4.19 (m, 2H), 4.49 (dd, J=9.0, 4.2 Hz, 1H), 6.68 (br d, J=6.6 Hz, 2H), 7.31-7.43 (m, 6H), 7.46 (dd, J=7.7, 4.6 Hz, 1H), 7.58 (m, 2H), 7.88 (br d, J=7.5 Hz, 1H), 8.43 (dd, J=4.5, 1.5 Hz, 1H).

3-Amino-1-hydroxy-3,4-dihydro-1,8-naphthyridin-2(1H)-one (6) To a solution of ethyl 2-(diphenylmethyleneamino)-3-(2-nitropyridin-3-yl)propanoate (5) (1.8 g, 4.4 mmol) in anhydrous EtOH (20 mL) was added tin(II) chloride dihydrate (2.0 g, 9.6 mmol) at RT. After stirring for 1 h, TLC (Eluant: 1:1 petroleum ether/EtOAc) showed complete consumption of starting material. The solvent was removed under reduced pressure, and the residue was washed with Et$_2$O (3×50 mL) to give the crude product (2.5 g), which was used in the next step without purification.

tert-Butyl (1-hydroxy-2-oxo-1,2,3,4-tetrahydro-1,8-naphthyridin-3-yl)carbamate (7) To a suspension of 3-amino-1-hydroxy-3,4-dihydro-1,8-naphthyridin-2(1H)-one (6) (2.5 g, 54.4 mmol) in anhydrous EtOH (100 mL) was added NEt$_3$ (5 mL) at RT. After 10 min, BOC$_2$O (3.0 g, 13.8 mmol) was added and the reaction was stirred overnight. The solvent was removed under reduced pressure, and the residue was purified by preparative TLC to give the product (0.20 g, 5%).

3-Amino-1-hydroxy-3,4-dihydro-1,8-naphthyridin-2(1H)-one, trifluoroacetate salt (8) A solution of tert-butyl(1-hydroxy-2-oxo-1,2,3,4-tetrahydro-1,8-naphthyridin-3-yl)carbamate (7) (0.20 g, 0.72 mmol) and TFA (0.6 mL) in DCM (4 mL) was stirred at 0-5° C. for 3 hr. The solvent was removed under reduced pressure, and the residue was washed with Et$_2$O to give compound 8 (120 mg, 68%) as a solid. LCMS m/z 180.0 (M+1). $^1$H NMR (400 MHz, DMSO-d$_6$) δ 3.07 (dd, J=15, 14.5 Hz, 1H), 3.18 (dd, J=15.1, 6.5 Hz, 1H), 4.50 (dd, J=14.2, 6.7 Hz, 1H), 7.15 (dd, J=7.3, 5.0 Hz, 1H), 7.79 (br d, J=7.0 Hz, 1H), 8.32 (br d, J=4.8 Hz, 1H), 8.61 (br s, 3H), 10.60 (br s, 1H); HPLC purity: 99.02%, Column: Waters XTerra, 5 μm; Mobile phase: 70% hexane (0.5% NEt$_3$) in EtOH.

Example 2

Synthesis of 3-amino-6-fluoro-1-hydroxy-3,4-dihydroquinolin-2(1H)-one, hydrochloride salt (15)

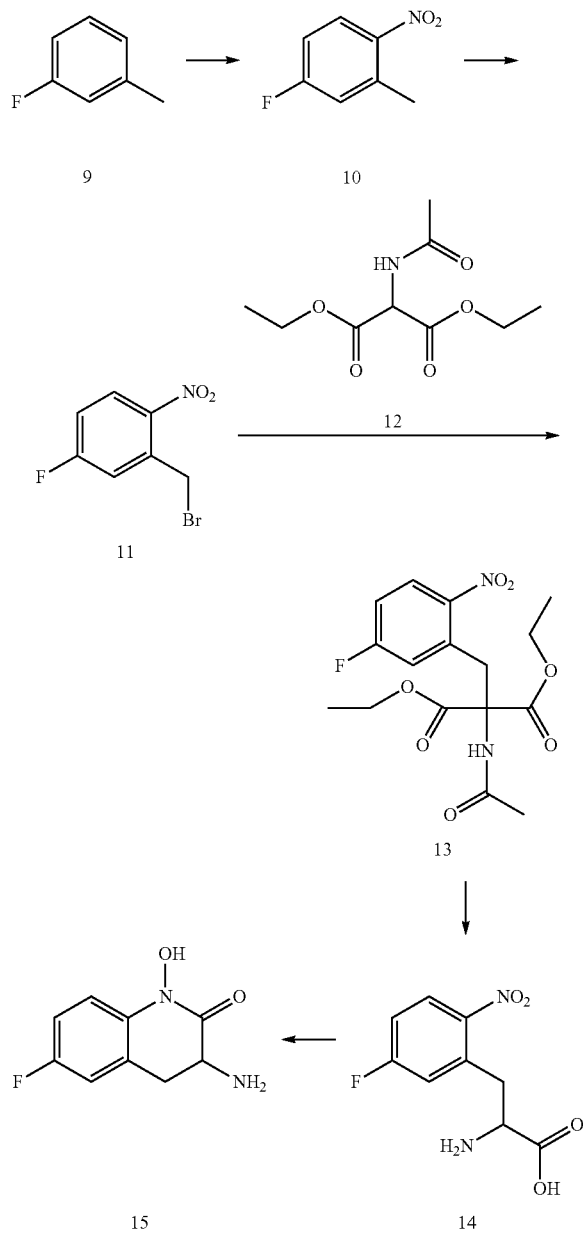

4-Fluoro-2-methyl-1-nitrobenzene (10) To a stirred solution of aqueous nitric acid (90%, 100 mL) was added 1-fluoro-3-methylbenzene (9) (30 g, 273 mmol) drop-wise at 0-5° C. The resulting mixture was stirred for 0.5 h then poured onto ice-water. The aqueous layer was extracted with DCM (3×50 mL) and the combined organic layers were washed with saturated aqueous NaHCO$_3$ (100 mL), dried over anhydrous Na$_2$SO$_4$, filtered and concentrated in vacuo. The residue was purified by silica gel chromatography (Gradient: 0.5% to 3.3% EtOAc in petroleum ether) to afford the product as a yellow oil (16 g, 38%). $^1$H NMR (400 MHz, CDCl$_3$) δ 2.64 (s, 3H), 7.01-7.06 (m, 2H), 8.07 (m, 1H).

2-(Bromomethyl)-4-fluoro-1-nitrobenzene (11) To a stirred solution of 4-fluoro-2-methyl-1-nitrobenzene (10) (16 g, 103 mmol) in CCl$_4$ (180 mL) was added NBS (22 g, 123 mmol) and AIBN (2 g, 12 mmol) at RT. The mixture was stirred under reflux overnight, and the solvent was then removed in vacuo. The residue was purified by chromatography on silica gel (Gradient: 1% to 20% ethyl acetate in petroleum ether) to afford the product as a green oil (12 g, 50%). $^1$H NMR (400 MHz, CDCl$_3$) δ 4.83 (s, 2H), 7.18 (m, 1H), 7.32 (m, 1H), 8.15 (dd, J=9.0, 5.0 Hz, 1H).

Diethyl acetamido(5-fluoro-2-nitrobenzyl)malonate (13) To a stirred solution of NaOEt (3.5 g, 51.0 mmol) in EtOH (120 mL) was added diethyl acetamidomalonate (12) (11 g, 51 mmol) at 70° C. After 0.5 hour, 2-(bromomethyl)-4-fluoro-1-nitrobenzene (11) (10 g, 43 mmol) was added, and the resulting mixture was stirred for 3 hours. The reaction was quenched by adding water (100 mL), and the mixture was extracted with DCM (3×100 mL). The combined organic layers were concentrated under reduced pressure. The residue was purified by silica gel chromatography (Gradient: 2% to 33% EtOAc in petroleum ether) to afford the product as a white solid (3.4 g, 21%). $^1$H NMR (400 MHz, CDCl$_3$) δ 1.28 (t, J=7.1 Hz, 6H), 1.99 (s, 3H), 4.08 (s, 2H), 4.18-4.32 (m, 4H), 6.51 (br s, 1H), 6.99 (dd, J=9.0, 2.8 Hz, 1H), 7.09 (m, 1H), 7.92 (dd, J=9.0, 5.2 Hz, 1H).

2-Amino-3-(5-fluoro-2-nitrophenyl)propanoic acid, hydrochloride salt (14) A stirred solution of diethyl acetamido(5-fluoro-2-nitrobenzyl)malonate (13) (3.4 g, 9.2 mmol) in aqueous HCl (6M, 50 mL) was stirred under reflux overnight. The solvent was removed in vacuo to afford the crude product, which was washed with Et$_2$O (3×20 mL) to provide the product as a white solid (1.7 g, 81%). $^1$H NMR (400 MHz, CD$_3$OD) δ 2.15 (dd, J=14.1, 7.6 Hz, 1H), 2.41 (dd, J=14.1, 7.2 Hz, 1H), 3.10 (dd, J=7.5, 7.3 Hz, 1H), 6.04-6.10 (m, 2H), 6.97 (m, 1H).

3-Amino-6-fluoro-1-hydroxy-3,4-dihydroquinolin-2 (1H)-one, hydrochloride salt (15) A stirred suspension of 2-amino-3-(5-fluoro-2-nitrophenyl)propanoic acid, hydrochloride salt (14) (1.50 g, 6.57 mmol), Pt/C (5%, 0.2 g) and concentrated HCl (1.5 mL) in MeOH (200 mL) was hydrogenated under H$_2$ (30 psi) at RT for 3 h. After filtration of the catalyst, the solvent was removed in vacuo to afford the crude product. The solid was recrystallized from MeOH (10 mL) to obtain the product as a white solid (700 mg, 58%). LCMS m/z 197.2 (M+1). $^1$H NMR (400 MHz, CD$_3$OD) δ 3.17 (dd, J=15, 14 Hz, 1H), 3.28 (dd, J=14.9, 6.5 Hz, 1H), 4.36 (dd, J=14.6, 6.5 Hz, 1H), 7.11-7.16 (m, 2H), 7.40 (dd, J=9.6, 4.8 Hz, 1H); HPLC purity: 96.67%, Column: Waters HILIC, 5 μm; Gradient: water (0.1% TFA) to 60% MeCN (0.1% TFA) in water (0.1% TFA).

Example 3

Synthesis of 3-amino-1-hydroxy-8-(trifluoromethyl)-3,4-dihydroquinolin-2(1H)-one (19)

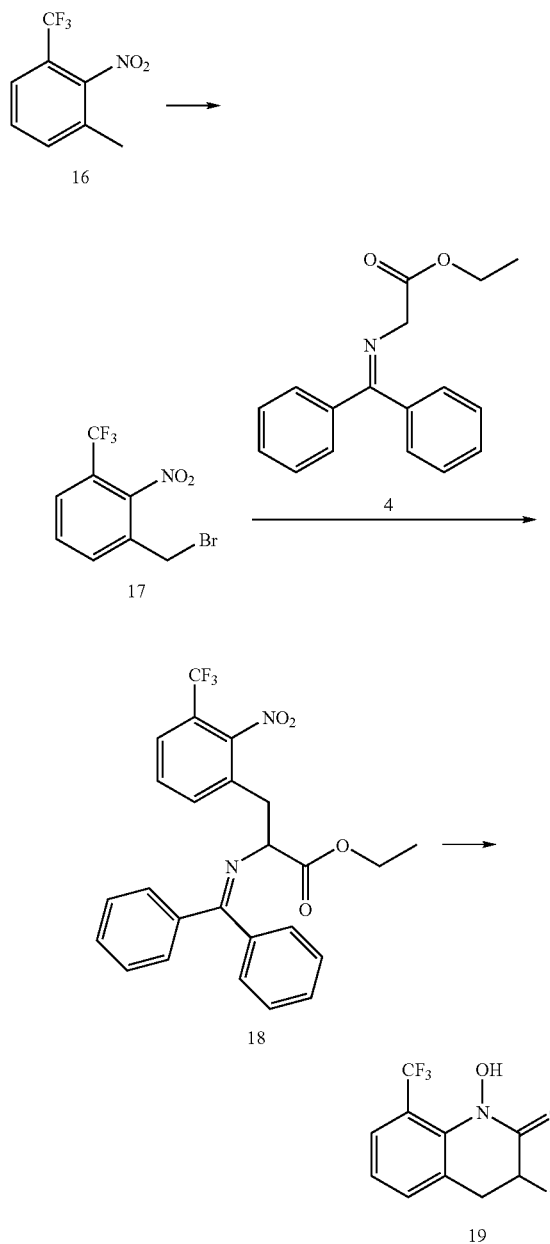

1-(Bromomethyl)-2-nitro-3-(trifluoromethyl)benzene (17) A mixture of 1-methyl-2-nitro-3-(trifluoromethyl)benzene (16) (5.0 g, 24 mmol), NBS (4.3 g, 24 mmol) and AIBN (0.3 g, 1.9 mmol) in CCl$_4$ (50 mL) was heated under reflux overnight. The precipitate was removed via filtration and the filtrate was concentrated under reduced pressure to give the crude product (8 g), which was used in the next step without further purification. $^1$H NMR (400 MHz, CDCl$_3$) δ 4.45 (s, 2H), 7.66 (dd, J=8, 7.5 Hz, 1H), 7.76 (br d, J=7.5 Hz, 1H), 7.81 (br d, J=8 Hz, 1H).

Ethyl 2-(diphenylmethyleneamino)-3-[2-nitro-3-(trifluoromethyl)phenyl]propanoate (18) Ethyl 2-(diphenylmethyleneamino)-3-[2-nitro-3-(trifluoromethyl)phenyl]propanoate (18) was prepared according to the general procedure for the synthesis of ethyl 2-(diphenylmethyleneamino)-3-(2-nitropyridin-3-yl)propanoate (5) in Example 1, except that 1-(bromomethyl)-2-nitro-3-(trifluoromethyl)benzene (17) from the previous step was used in place of 3-(bromomethyl)-2-nitropyridine (3) (Yield: 3.2 g, 28% over 2 steps).

3-Amino-1-hydroxy-8-(trifluoromethyl)-3,4-dihydroquinolin-2(1H)-one (19) A solution of ethyl 2-(diphenylmethyleneamino)-3-[2-nitro-3-(trifluoromethyl)phenyl]propanoate (18) (1.8 g, 3.8 mmol) and tin(II) chloride dihydrate (1.8 g, 7.7 mmol) in anhydrous EtOH (30 mL) was heated at reflux for 5 h. The solvent was removed under reduced pressure. The residue was washed with Et$_2$O (3×50 mL) to give crude material, which was purified by recrystallization from EtOAc to afford the product as a solid (0.21 g, 23%). LCMS m/z 247.3 (M+1). $^1$H NMR (400 MHz, DMSO-d$_6$) δ 1.98 (br s, 2H), 2.78 (J=15, 14 Hz, 1H), 3.00 (dd, J=15.4, 5.4 Hz, 1H), 3.59 (dd, J=13.6, 5.6 Hz, 1H), 7.21 (dd, J=7.8, 7.6 Hz, 1H), 7.53 (d, J=7.5 Hz, 1H), 7.63 (d, J=8.2 Hz, 1H), 10.55 (br s, 1H); HPLC purity: 97.52%, Column: Waters XTerra, 5 μm; Gradient: 0% to 60% MeCN (0.1% TFA) in water (0.1% TFA).

Example 4

Synthesis of (3S)-3-amino-1-hydroxy-3,4-dihydroquinolin-2(1H)-one (21)

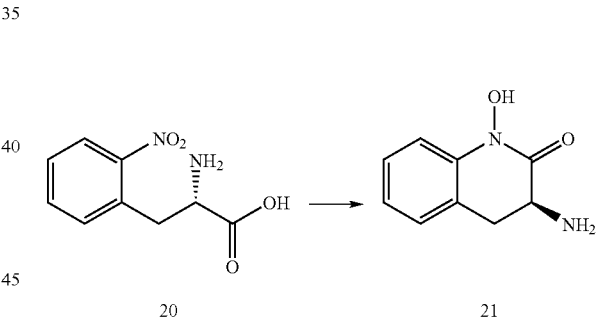

L-2-Nitrophenylalanine (20) (419.6 mg, 2.0 mmol) was dissolved in MeOH (23.8 mL) and water (240 μL). Concentrated HCl (2-4 drops) was added to aid solubility. Pt/C (42 mg) was added and the reaction was hydrogenated on a Parr shaker at 10 psi for 1 h, whereupon the reaction was filtered through Celite. The catalyst was washed with a 1N solution of NH$_4$OH in MeOH and then with MeOH. The filtrate was concentrated to provide a crude product, which was subsequently dry packed with a minimum amount of silica, using a MeOH/DCM solution to dissolve the material. Purification using silica gel chromatography (Gradient: 0% to 20% MeOH (containing 1% NH$_4$OH) in DCM) provided the product as a solid (207 mg, 58%). APCI m/z 179.1 (M+1). $^1$H NMR (400 MHz, CD$_3$OD) δ 2.88 (dd, J=14, 15 Hz, 1H), 3.09 (dd, J=15.3, 6.2 Hz, 1H), 3.67 (dd, J=13.6, 6.1 Hz, 1H,) 7.06 (ddd, J=7.2, 7.2, 1.7 Hz, 1H), 7.23 (br d, J=7.5 Hz, 1H), 7.27-7.34 (m, 2H).

Example 5

Synthesis of (3R)-3-amino-7-bromo-1-hydroxy-3,4-dihydroquinolin-2(1H)-one (29)

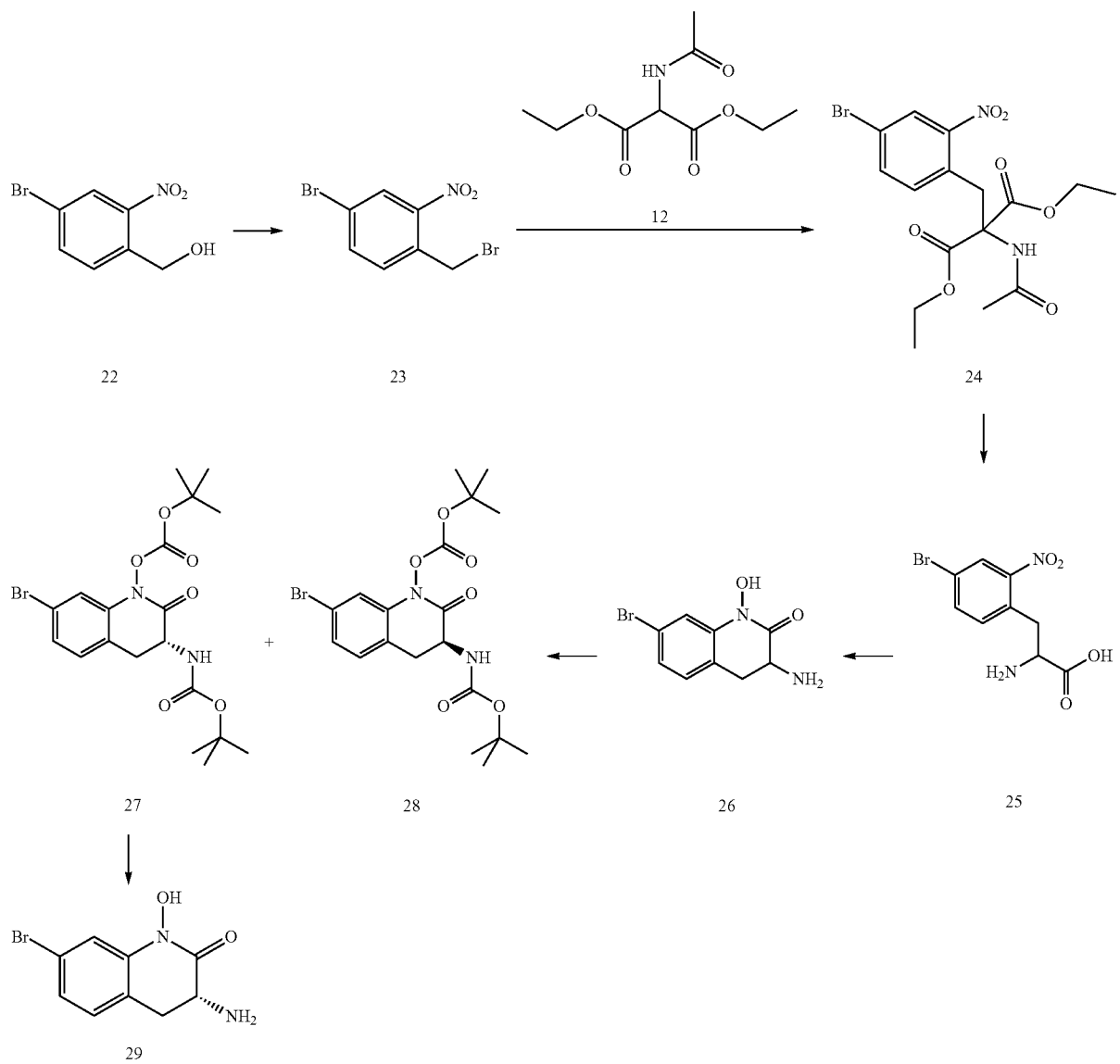

4-Bromo-1-(bromomethyl)-2-nitrobenzene (23) To a stirred solution of (4-bromo-2-nitrophenyl)methanol (22) (1.00 g, 4.31 mmol) in DMF (40 mL) was added NBS (1.6 g, 9.0 mmol) and triphenylphosphine (2.4 g, 9.2 mmol). After two minutes, the reaction mixture was concentrated in vacuo. The residue was partitioned between water and DCM, and the aqueous layer was extracted with additional DCM. The combined organic layers were concentrated and the residue was purified by silica gel chromatography (Gradient: 0% to 20% EtOAc in heptane) to provide the product (880 mg, 69%). $^1$H NMR (400 MHz, CDCl$_3$) δ 4.78 (s, 2H), 7.47 (d, J=8.2 Hz, 1H), 7.75 (dd, J=8.2, 2.1 Hz, 1H), 8.20 (d, J=2.1 Hz, 1H).

Diethyl acetamido(4-bromo-2-nitrobenzyl)malonate (24) NaOEt (95%, 182 mg, 2.54 mmol) was added to a solution of diethyl acetamidomalonate (12) (98%, 563 mg, 2.54 mmol) in EtOH. The resulting mixture was stirred for 30 min at RT and then treated with a solution of 4-bromo-1-(bromomethyl)-2-nitrobenzene (23) (500 mg, 1.7 mmol) in EtOH. After stirring overnight, the reaction was concentrated in vacuo. The residue was dissolved in EtOAc, washed with water and saturated aqueous sodium chloride solution, dried over sodium sulfate, filtered and concentrated under reduced pressure. Purification by silica gel chromatography (Gradient: 0% to 80% EtOAc in heptane) afforded the product as a white solid (540 mg, 74%). LCMS m/z 432.8 (M+1). $^1$H NMR (500 MHz, CDCl$_3$) δ 1.28 (t, J=7.1 Hz, 6H), 1.97 (s, 3H), 4.03 (s, 2H), 4.18-4.30 (m, 4H), 6.48 (s, 1H), 7.16 (d, J=8.3 Hz, 1H), 7.62 (dd, J=8.3, 2.0 Hz, 1H), 7.98 (d, J=1.8 Hz, 1H).

2-Amino-3-(4-bromo-2-nitrophenyl)propanoic acid, hydrochloride salt (25) A mixture of diethyl acetamido(4-bromo-2-nitrobenzyl)malonate (24) (5.5 g, 13 mmol) in concentrated aqueous HCl containing roughly 10% dioxane was stirred under reflux until the reaction was shown to be complete by LCMS. The reaction mixture was concentrated to dryness under reduced pressure, and the residue was triturated with Et$_2$O to give the product as a solid (2.8 g, 66%). LCMS m/z 290.8 (M+1).

3-Amino-7-bromo-1-hydroxy-3,4-dihydroquinolin-2 (1H)-one (26) To a solution of 2-amino-3-(4-bromo-2-nitrophenyl)propanoic acid, hydrochloride salt (25) (343 mg, 1.06 mmol) in EtOH (10 mL) was added tin(II) chloride dihydrate (541 mg, 2.40 mmol), and the reaction was stirred at RT overnight. It was then quenched with aqueous ammonium hydroxide (1.5 mL), and the resulting precipitate was removed via filtration and washed with MeOH. The combined filtrates were concentrated in vacuo, and the residue was purified by chromatography on silica gel to provide the title product as a white powder (161 mg, 58%). LCMS m/z 258.9 (M+1). $^1$H NMR (500 MHz, DMSO-d$_6$) δ 2.71 (dd, J=15.4, 12.9 Hz, 1H) 2.99 (dd, J=15.6, 6.1 Hz, 1H), 3.56 (dd, J=12.8, 6.0 Hz, 1H) 7.17-7.21 (m, 2H), 7.28 (d, J=1.7 Hz, 1H).

tert-Butyl {(3R)-7-bromo-1-[(tert-butoxycarbonyl)oxy]-2-oxo-1,2,3,4-tetrahydroquinolin-3-yl}carbamate (27) and tert-butyl {(3S)-7-bromo-1-[(tert-butoxycarbonyl)oxy]-2-oxo-1,2,3,4-tetrahydroquinolin-3-yl}carbamate (28) 3-Amino-7-bromo-1-hydroxy-3,4-dihydroquinolin-2(1H)-one (26) (130.3 mg, 0.51 mmol) was suspended in DCM (2.5 mL). After addition of NaHCO$_3$ (94 mg, 1.12 mmol) and BOC$_2$O (215 mg, 0.99 mmol), the reaction was heated to reflux overnight. The mixture was filtered and the filtrate was concentrated under reduced pressure to give a racemic mixture of the products as an off-white glassy foam (197 mg). APCI m/z 402.5 [(M-tert-Bu)+1]. Separation of enantiomers was carried out via chiral chromatography (Column: ChiralPAK AD-H, 250×10.0 mm, 5 μm; Flow rate: 10 mL/min; Eluant: 80:20 CO$_2$/propanol). tert-Butyl {(3R)-7-bromo-1-[(tert-butoxycarbonyl)oxy]-2-oxo-1,2,3,4-tetrahydroquinolin-3-yl}carbamate (27), which eluted first, was obtained as a white glassy foam (58.8 mg, 25%), and its enantiomer tert-butyl {(3S)-7-bromo-1-[(tert-butoxycarbonyl)oxy]-2-oxo-1,2,3,4-tetrahydroquinolin-3-yl}carbamate (28) as a yellow glassy foam (67.6 mg, 29%). The absolute configurations of these two compounds were assigned based on the relative potency of the derived Examples 5 and 6, in accordance with the relative activity of Examples 4 and 14, which were prepared from enantiomerically pure starting materials.

(3R)-3-Amino-7-bromo-1-hydroxy-3,4-dihydroquinolin-2(1H)-one (29) tert-Butyl {(3R)-7-bromo-1-[(tert-butoxycarbonyl)oxy]-2-oxo-1,2,3,4-tetrahydroquinolin-3-yl}carbamate (27) (57.5 mg, 0.13 mmol) was dissolved in DCM (2.0 mL) in a sealed vial, TFA (0.141 mL) was added and the reaction mixture was shaken at 50° C. overnight. The solvent was removed under reduced pressure, and the residue was azeotroped three times with MeOH, then purified by silica gel chromatography (Gradient: 0% to 20% MeOH in DCM) to give the title product as a white powder (13.2 mg, 40%). LCMS m/z 258.9 (M+1). $^1$H NMR (500 MHz, DMSO-d$_6$) δ 2.70 (dd, J=15.5, 12.7 Hz, 1H), 3.00 (dd, J=15.6, 6.0 Hz, 1H), 3.54 (dd, J=12.7, 6.0 Hz, 1H), 7.17-7.21 (m, 2H), 7.29 (d, J=1.5 Hz, 1H).

Example 6

Synthesis of (3S)-3-amino-7-bromo-1-hydroxy-3,4-dihydroquinolin-2(1H)-one (30)

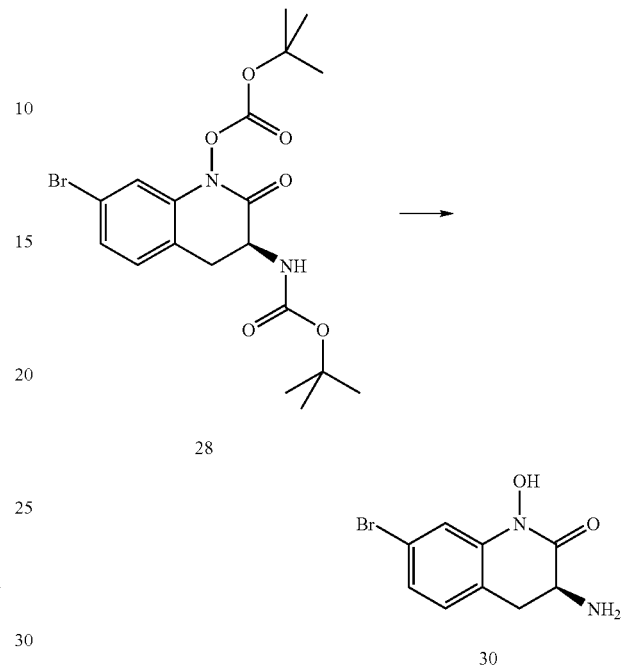

Following the procedure for the preparation of (3R)-3-amino-7-bromo-1-hydroxy-3,4-dihydroquinolin-2(1H)-one (29) in Example 5 but using tert-butyl {(3S)-7-bromo-1-[(tert-butoxycarbonyl)oxy]-2-oxo-1,2,3,4-tetrahydroquinolin-3-yl}carbamate (28) as starting material, the title product was obtained as a white powder (23 mg, 62%). LCMS m/z 258.9 (M+1). $^1$H NMR (500 MHz, DMSO-d$_6$) δ 2.70 (br dd, J=15.6, 12.7 Hz, 1H) 2.99 (dd, J=15.6, 6.1 Hz, 1H), 3.52 (dd, J=12.7, 6.0 Hz, 1H), 7.16-7.20 (m, 2H), 7.28 (d, J=1.6 Hz, 1H).

Example 7

Synthesis of (3S,4S)-3-amino-1-hydroxy-4-methyl-3,4-dihydroquinolin-2(1H)-one, hydrochloride salt (35)

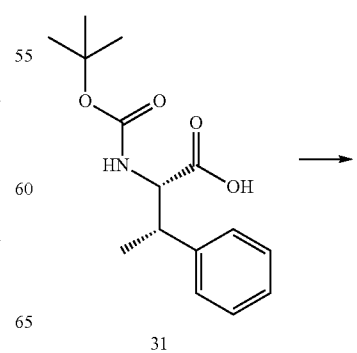

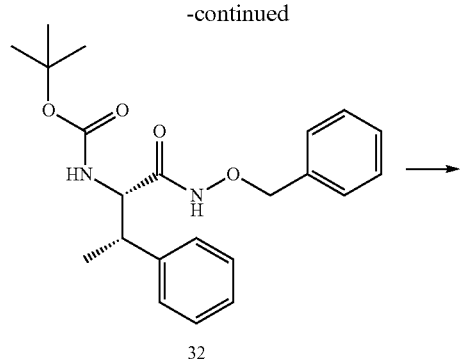

32

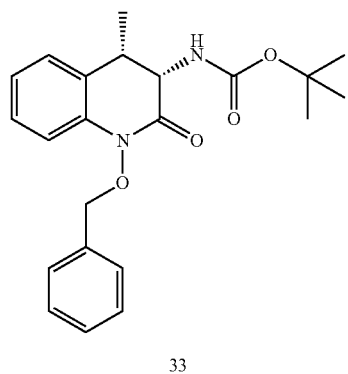

33

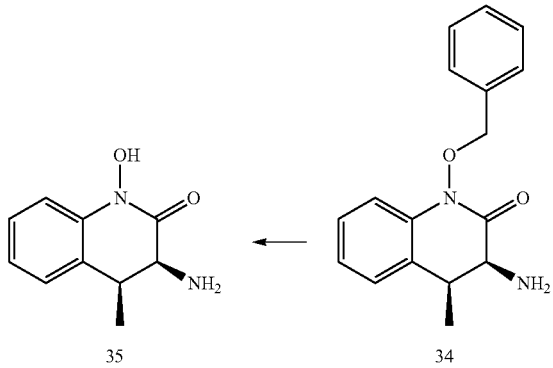

35    34 tert-Butyl (2S,3S)-1-(benzyloxyamino)-1-oxo-3-phenylbutan-2-ylcarbamate (32) (2S,3S)-2-[(tert-Butoxycarbonyl)amino]-3-phenylbutanoic acid (31) (1.0 g, 3.6 mmol) and O-benzyl hydroxylamine (0.69 mg, 4.3 mmol) were combined in DCM (25 mL), and NEt$_3$ (5 mL, 29 mmol) and benzotriazol-1-yloxy-tris(dimethylamino)phosphonium hexafluorophosphate (BOP, 1.58 g, 3.6 mmol) were added. The reaction was stirred for 48 hours at RT, whereupon the solvent was removed under reduced pressure. The residue was diluted with EtOAc, washed with water (3×20 mL), washed with saturated aqueous sodium chloride solution, dried over magnesium sulfate, filtered and concentrated in vacuo. The residue was purified via silica gel chromatography (Eluant: 30% EtOAc in hexane). The residue was crystallized by trituration of the oil with Et$_2$O to give the product as a white solid (1.30 g, 94%). LCMS m/z 385.0 (M+1). $^1$H NMR (400 MHz, CDCl$_3$) δ 1.28 (br d, J=6.8 Hz, 3H), 1.34 (s, 9H), 3.36 (m, 1H), 4.12 (dd, J=8.2, 8.2 Hz, 1H), 4.87 (s, 2H), 4.95 (br d, J=8.4 Hz, 1H), 5.40 (br s, 1H), 7.20-7.38 (m, 10H).

tert-Butyl (3S,4S)-1-(benzyloxy)-4-methyl-2-oxo-1,2,3,4-tetrahydroquinolin-3-ylcarbamate (33) tert-Butyl (2S,3S)-1-(benzyloxyamino)-1-oxo-3-phenylbutan-2-ylcarbamate (32) (0.50 g, 1.3 mmol) was dissolved in DCM (10 mL), in an ice-cooled flask. Phenyliodine(III) bis(trifluoroacetate) (PIFA, 0.84 g, 1.9 mmol) was added in one portion and the reaction was stirred at 0° C. to RT overnight. The reaction mixture was diluted with DCM (20 mL) and washed with a saturated aqueous NaHCO$_3$ solution, then with saturated aqueous sodium chloride solution, dried over magnesium sulfate, filtered and concentrated in vacuo. The resulting yellow oil was purified by silica gel chromatography (Eluant: 30% EtOAc in hexane) to give the product as a yellow oil still containing impurities (0.50 g). APCI m/z 283.3 [(M-BOC)+1].

(3S,4S)-3-Amino-1-(benzyloxy)-4-methyl-3,4-dihydroquinolin-2(1H)-one (34) tert-Butyl (3S,4S)-1-(benzyloxy)-4-methyl-2-oxo-1,2,3,4-tetrahydroquinolin-3-ylcarbamate (33) from the previous step (0.50 g, <1.3 mmol) was dissolved in THF (10 mL), and BF$_3$.Et$_2$O (0.235 mL, 1.87 mmol) was added drop-wise at RT. The reaction was refluxed for three hours. The solvent was removed in vacuo, and the residue was dissolved in EtOAc. The solution was basified using a 10% aqueous NaOH solution, and the organic layer was washed with water, washed with saturated aqueous sodium chloride solution, dried over magnesium sulfate, filtered and concentrated in vacuo. The residue was purified by silica gel chromatography (Eluant: 30% EtOAc in hexane) to give the product, still containing impurities (100 mg). LCMS m/z 283.1 (M+1). $^1$H NMR (400 MHz, CDCl$_3$) δ 1.14 (d, J=7.2 Hz, 3H), 3.12 (qd, J=7.1, 5.5 Hz, 1H), 3.81 (d, J=5.4 Hz, 1H), 5.01 (d, J=9.2 Hz, 1H), 5.17 (d, J=9.2 Hz, 1H), 7.09 (m, 1H), 7.20-7.43 (m, 6H), 7.53-7.56 (m, 2H).

(3S,4S)-3-Amino-1-hydroxy-4-methyl-3,4-dihydroquinolin-2(1H)-one, hydrochloride salt (35) (3S,4S)-3-Amino-1-(benzyloxy)-4-methyl-3,4-dihydroquinolin-2(1H)-one (34) from the previous reaction (100 mg, <0.35 mmol) was dissolved in EtOH (4 mL) and 1-methyl-1,4-cyclohexadiene (1 mL), and treated with Pd(OH)$_2$ (10 mg, 035 mol). The reaction was refluxed for 1 h, then filtered through a Celite pad, which was subsequently washed with EtOAc. Concentration of the filtrate in vacuo provided a solid, which was purified by silica gel chromatography (Eluant: 30% MeOH in EtOAc) to afford the free base of the product. R$_f$=0.3 (20% MeOH in EtOAc). A 1N solution of HCl in Et$_2$O was used to make the hydrochloride salt (15 mg, 6% over three steps). LCMS m/z 193.1 (M+1). $^1$H NMR (400 MHz, CD$_3$OD) δ 1.13 (d, J=7.0 Hz, 3H), 3.18 (m, 1H), 4.01 (d, J=5.5 Hz, 1H), 7.10 (ddd, J=7.2, 7.2, 1.2 Hz, 1H), 7.22-7.37 (m, 3H).

Example 8

Synthesis of 3-amino-6-chloro-1-hydroxy-8-methyl-3,4-dihydroquinolin-2(1H)-one (42)

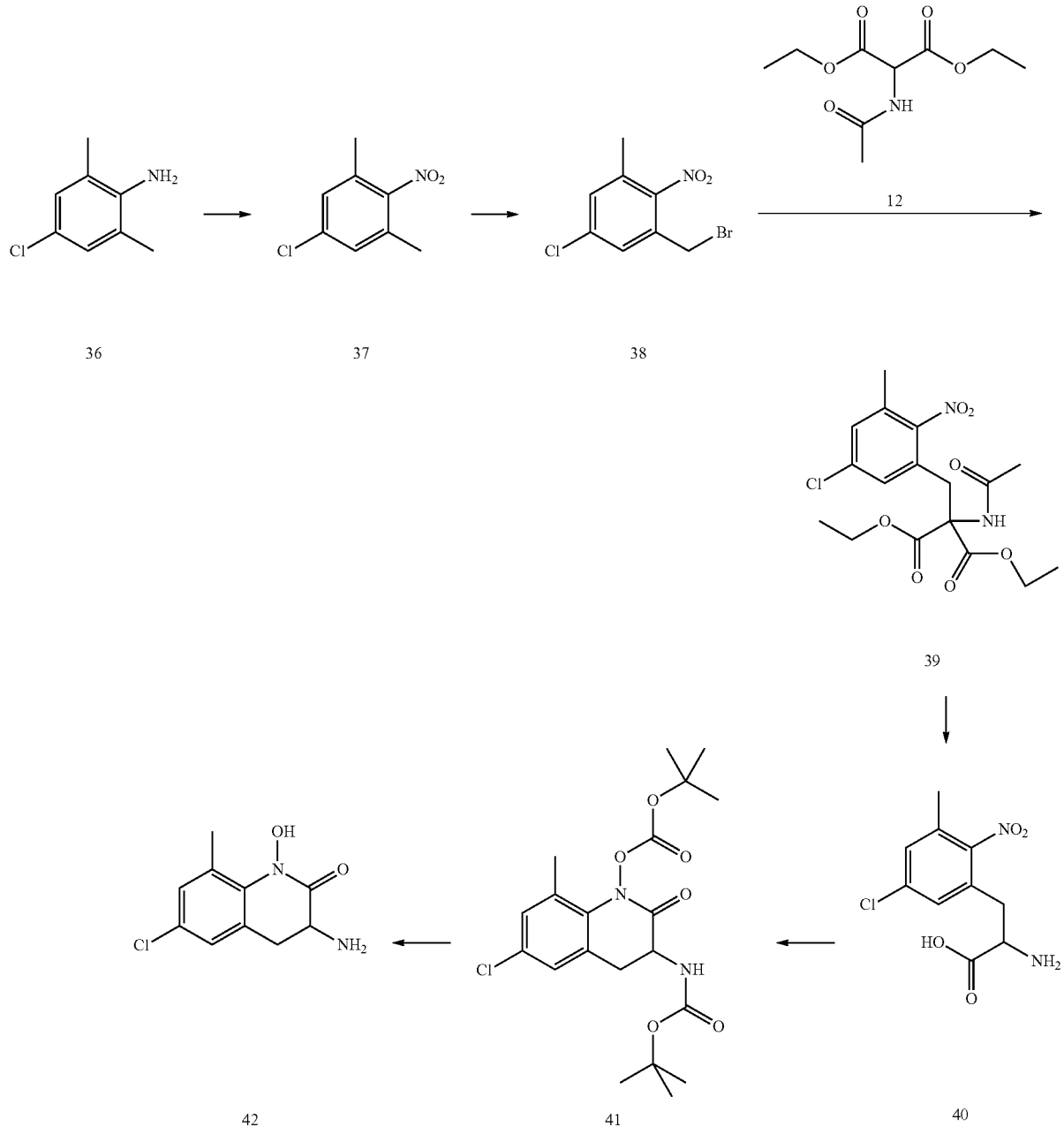

5-Chloro-1,3-dimethyl-2-nitrobenzene (37) To a solution of 4-chloro-2,6-dimethylbenzenamine (36) (6.14 g, 39.5 mmol) in toluene (200 mL) was added mCPBA (44.2 g, 197 mmol). The reaction was heated at reflux overnight, then allowed to cool at RT, washed with aqueous 1N NaOH, dried over magnesium sulfate, filtered and concentrated in vacuo. The crude material was adsorbed onto silica and purified by silica gel chromatography (Gradient: 0% to 50% EtOAc in heptane) to provide the product (2.84 g, 39%). $^1$H NMR (400 MHz, CDCl$_3$) δ 2.31 (m, 6H), 7.14 (m, 2H).

1-(Bromomethyl)-5-chloro-3-methyl-2-nitrobenzene (38) Following the procedure for the preparation of 1-(bromomethyl)-2-nitro-3-(trifluoromethyl)benzene (17) in Example 3, reaction of 5-chloro-1,3-dimethyl-2-nitrobenzene (37) provided the title compound as a solid (50%). $^1$H NMR (400 MHz, CDCl$_3$) δ 2.36 (m, 3H), 4.43 (s, 2H), 7.28 (m, 1H), 7.37 (m, 1H).

Diethyl acetamido(5-chloro-3-methyl-2-nitrobenzyl)malonate (39) Following the procedure for the preparation of diethyl acetamido(4-bromo-2-nitrobenzyl)malonate (24) in Example 5,1-(bromomethyl)-5-chloro-3-methyl-2-nitrobenzene (38) was converted to the title product, which was obtained as a solid (65%). LCMS m/z 401.0 (M+1). $^1$H NMR (400 MHz, DMSO-d$_6$) δ 1.15 (t, J=7.1 Hz, 6H), 1.90 (s, 3H), 2.24 (br s, 3H), 3.53 (s, 2H), 4.10-4.17 (m, 4H), 7.05 (br d, J=2.2 Hz, 1H), 7.56 (apparent dd, J=2.3, 0.7 Hz, 1H), 8.31 (br s, 1H).

2-Amino-3-(5-chloro-3-methyl-2-nitrophenyl)propanoic acid, hydrochloride salt (40) Following the procedure for the preparation of 2-amino-3-(4-bromo-2-nitrophenyl)propanoic acid, hydrochloride salt (25) in Example 5, diethyl acetamido(5-chloro-3-methyl-2-nitrobenzyl)malonate (39) was converted to the title product, which was obtained as a solid (assumed quantitative); LCMS m/z 259.0 (M+1).

tert-Butyl {1-[(tert-butoxycarbonyl)oxy]-6-chloro-8-methyl-2-oxo-1,2,3,4-tetrahydroquinolin-3-yl}carbamate (41) To a solution of 2-amino-3-(5-chloro-3-methyl-2-nitropheallowed to stir at RT for 30 minutes. The solvent was removed in vacuo, and the residue was adsorbed onto silica and purified by silica gel chromatography (Gradient: 0% to 45% [NH$_4$OH(1): MeOH(9): DCM (90)] in DCM) to provide the product (5.8 mg, 27%). LCMS m/z 226.9 (M+1). $^1$H NMR (400 MHz, CD$_3$OD) δ 2.46 (s, 3H), 2.84 (m, 1H), 2.93 (dd, J=15.3, 5.8 Hz, 1H), 3.62 (dd, J=13.9, 5.7 Hz, 1H), 7.09-7.13 (m, 2H).

Example 9

Synthesis of 3-amino-1-hydroxy-3,4-dihydro-1,5-naphthyridin-2(1H)-one, dihydrochloride salt (50)

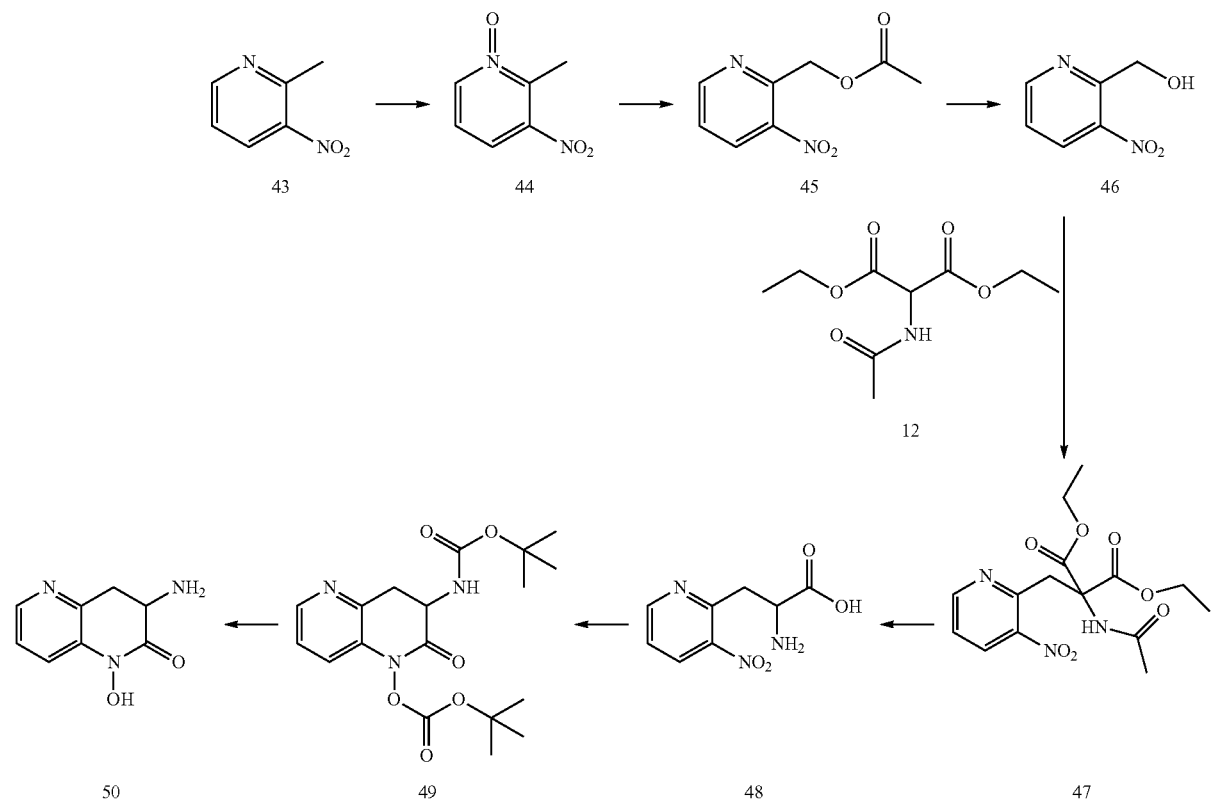

nyl)propanoic acid, hydrochloride salt (40) (0.11 g, 0.42 mmol) in EtOH (5 mL) was added tin(II) chloride dihydrate (0.20 g, 0.85 mmol). The reaction was heated to 60° C. for 5 h, then cooled to RT. Diisopropylethylamine (0.73 mL, 4.25 mmol) and BOC$_2$O (0.19 g, 0.85 mmol) were added and the reaction was allowed to stir at RT overnight. The reaction mixture was concentrated in vacuo, then partitioned between EtOAc and water. The aqueous layer was extracted with EtOAc, and the combined organic layers were dried over magnesium sulfate, filtered and concentrated under reduced pressure. The residue was purified by silica gel chromatography (Gradient: 0% to 60% EtOAc in heptane), to afford the product (40 mg, 22%), which was used directly in the next step.

3-Amino-6-chloro-1-hydroxy-8-methyl-3,4-dihydroquinolin-2(1H)-one (42) To a solution of tert-butyl{1-[(tert-butoxycarbonyl)oxy]-6-chloro-8-methyl-2-oxo-1,2,3,4-tetrahydroquinolin-3-yl}carbamate (41) (40 mg, 0.094 mmol) in DCM (3 mL) was added TFA (3 mL). The reaction was then 2-Methyl-3-nitropyridine 1-oxide (44) To a solution of 2-methyl-3-nitropyridine (43) (0.86 g, 6.23 mmol) in DCM (30 mL) was added mCPBA (2.8 g, 12.5 mmol). The reaction was then allowed to stir at RT for 6 h. Sodium thiosulfate (900 mg) was added and the mixture was allowed to stir overnight. The reaction mixture was diluted with additional DCM and washed with a saturated aqueous NaHCO$_3$ solution. The organic layer was dried over magnesium sulfate, filtered and concentrated in vacuo. The residue was purified by chromatography on silica gel (Gradient: 0% to 20% MeOH in DCM) to afford the product (782 mg, 81%). LCMS m/z 155.0 (M+1). $^1$H NMR (400 MHz, CDCl$_3$) δ 2.73 (m, 3H), 7.30 (br dd, J=8.1, 6.8 Hz, 1H), 7.72 (dq, J=8.4, 0.5 Hz, 1H), 8.48 (dq, J=6.6, 0.6 Hz, 1H).

(3-Nitropyridin-2-yl)methyl acetate (45) To a solution of 2-methyl-3-nitropyridine 1-oxide (44) (0.78 g, 5.07 mmol) in acetic acid at 90° C. was added acetic anhydride (0.72 mL, 7.61 mmol), and the reaction was heated at 110° C. overnight. The mixture was cooled, concentrated in vacuo and adsorbed onto silica. The crude residue was then purified by chromatography on silica gel (Gradient: EtOAc in heptane) to provide the product (572 mg, 57%). LCMS m/z 196.9 (M+1). $^1$H NMR (400 MHz, CDCl$_3$) δ 2.20 (s, 3H), 5.63 (s, 2H), 7.49 (br dd, J=8.2, 4.7 Hz, 1H), 8.41 (dd, J=8.3, 1.5 Hz, 1H), 8.84 (dd, J=4.7, 1.6 Hz, 1H).

(3-Nitropyridin-2-yl)methanol (46) To a solution of (3-nitropyridin-2-yl)methyl acetate (45) (5.72 g, 2.92 mmol) in MeOH (10 mL) and water (20 mL) was added potassium carbonate (2.0 g, 14.6 mmol). The reaction was then allowed to stir at RT overnight. The reaction mixture was concentrated in vacuo to remove most of the MeOH, and the resulting mixture was diluted with EtOAc and water. The aqueous layer was extracted several times with EtOAc, and the combined organic layers were dried over magnesium sulfate, filtered and concentrated under reduced pressure to give an orange oil. The yield was assumed to be quantitative. LCMS m/z 155.0 (M+1). $^1$H NMR (400 MHz, CDCl$_3$) δ 4.70 (br s, 1H), 5.17 (s, 2H), 7.54 (ddt, J=8.2, 4.7, 0.8 Hz, 1H), 8.55 (dd, J=8.2, 1.5 Hz, 1H), 8.89 (dd, J=4.8, 1.5 Hz, 1H).

Diethyl acetamido[(3-nitropyridin-2-yl)methyl]malonate (47) To a solution of (3-nitropyridin-2-yl)methanol (46) (1.45 g, 9.41 mmol) in DCM (80 mL) and EtOH (80 mL) at 0° C. was added NEt$_3$ (3.93 mL, 28.2 mmol) and methanesulfonyl chloride (98%, 0.829 mL, 10.3 mmol). The reaction was allowed to stir at RT for 50 minutes, then was washed with aqueous NaHCO$_3$ solution, dried over magnesium sulfate, filtered and concentrated in vacuo. In a separate flask, a solution of diethyl acetamidomalonate (12) (2.25 g, 10.3 mmol) in EtOH (50 mL) was treated with NaOEt (3.08 M solution in EtOH, 4.58 mL, 14.1 mmol), and the reaction was allowed to stir for 5 min. The mesylate residue was dissolved in DMF (10 mL) and added to the solution of diethyl acetamidomalonate anion. After 2 hours, the reaction mixture was concentrated in vacuo to remove as much EtOH as possible. The mixture was then diluted with EtOAc and water; the organic layer was separated and washed with water, dried over magnesium sulfate, filtered and concentrated in vacuo. Purification was carried out via silica gel chromatography (Gradient: 0% to 100% EtOAc in heptane) to afford the product (2.24 g, 67%). LCMS m/z 354.0 (M+1). $^1$H NMR (400 MHz, CDCl$_3$) δ 1.25 (t, J=7.1 Hz, 6H), 1.93 (s, 3H), 4.22-4.30 (m, 4H), 4.32 (s, 2H), 6.81 (br s, 1H), 7.37 (dd, J=8.2, 4.7 Hz, 1H), 8.21 (dd, J=8.2, 1.6 Hz, 1H), 8.65 (dd, J=4.7, 1.6 Hz, 1H).

2-Amino-3-(3-nitropyridin-2-yl)propanoic acid, hydrochloride salt (48) Diethyl acetamido[(3-nitropyridin-2-yl)methyl]malonate (47) was subjected to conditions similar to those used for preparation of 2-amino-3-(4-bromo-2-nitrophenyl)propanoic acid, hydrochloride salt (25) in Example 5, to provide the product as a solid (94%). LCMS m/z 211.9 (M+1). $^1$H NMR (400 MHz, CD$_3$OD) δ 3.87 (dd, half of ABX system, J=18.2, 7.0 Hz, 1H), 3.94 (dd, half of ABX system, J=18.2, 4.3 Hz, 1H), 4.64 (dd, J=6.9, 4.3 Hz, 1H), 7.65 (dd, J=8.3, 4.8 Hz, 1H), 8.55 (dd, J=8.3, 1.5 Hz, 1H), 8.84 (dd, J=4.8, 1.5 Hz, 1H).

tert-Butyl {1-[(tert-butoxycarbonyl)oxy]-2-oxo-1,2,3,4-tetrahydro-1,5-naphthyridin-3-yl}carbamate (49) To a solution of 2-amino-3-(3-nitropyridin-2-yl)propanoic acid, hydrochloride salt (48) (0.11 g, 0.37 mmol) in THF (10 mL) and MeOH (10 mL) at 0° C. was added sodium acetate trihydrate (0.35 mL, 3.73 mmol) and tin(II) chloride dihydrate (0.43 g, 1.86 mmol). The reaction was then allowed to stir at 0° C. for 6 h. NEt$_3$ (0.52 mL, 3.73 mmol) and BOC$_2$O (0.16 g, 0.75 mmol) were added to the reaction and the mixture was allowed to stir overnight. The reaction mixture was diluted with water and EtOAc, and the aqueous layer was extracted further with EtOAc. The combined organic layers were dried over magnesium sulfate, filtered and concentrated under reduced pressure. The crude reaction mixture was purified by silica gel chromatography (Gradient: 0% to 100% EtOAc in heptane) to provide the product (78 mg, 55%). LCMS m/z 380.0 (M+1).

3-Amino-1-hydroxy-3,4-dihydro-1,5-naphthyridin-2(1H)-one, dihydrochloride salt (50) To a solution of tert-butyl {1-[(tert-butoxycarbonyl)oxy]-2-oxo-1,2,3,4-tetrahydro-1,5-naphthyridin-3-yl}carbamate (49) (41 mg, 0.11 mmol) in MeOH (3 mL) was added concentrated HCl (1 mL). The reaction was allowed to stir at 40° C. overnight. The mixture was concentrated in vacuo to give the product as an orange solid (26 mg, 94%). LCMS m/z 180.0 (M+1). $^1$H NMR (400 MHz, DMSO-d$_6$) δ 3.41 (dd, half of ABX system, J=15, 14 Hz, 1H), 3.50 (dd, half of ABX system, J=15.6, 6.9 Hz, 1H), 4.62 (m, 1H), 7.49 (dd, J=8.1, 5.0 Hz, 1H), 7.73 (br d, J=8 Hz, 1H), 8.28 (dd, J=5.1, 1.2 Hz, 1H), 8.86 (br s, 3H).

Example 10

Synthesis of 3-amino-1-hydroxy-6-(trifluoromethyl)-3,4-dihydroquinolin-2(1H)-one, hydrochloride salt (53)

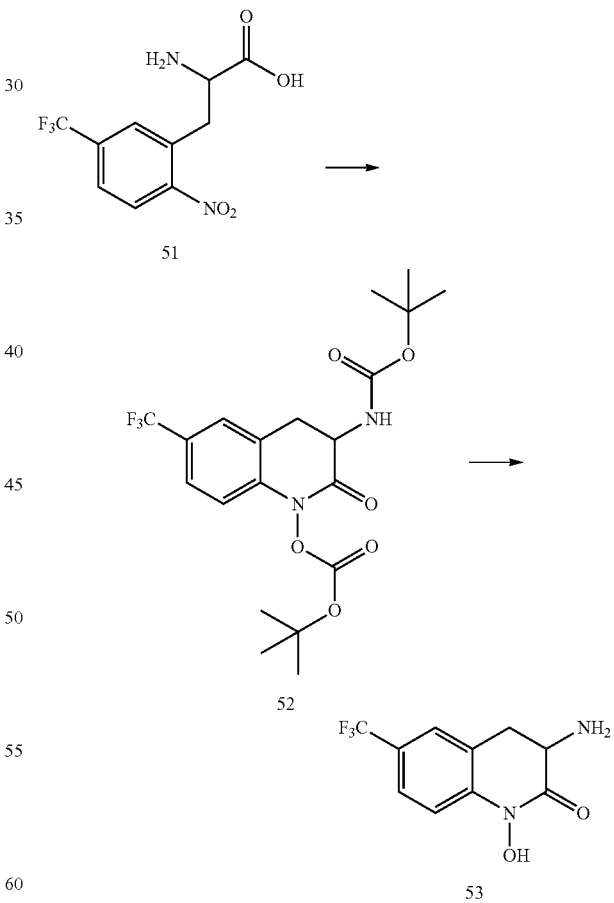

tert-Butyl {1-[(tert-butoxycarbonyl)oxy]-2-oxo-6-(trifluoromethyl)-1,2,3,4-tetrahydroquinolin-3-yl}carbamate (52) To an ice-cooled solution of 2-amino-3-[2-nitro-5-(trifluoromethyl)phenyl]propanoic acid, hydrochloride salt (51, prepared in similar manner to 2-amino-3-(5-fluoro-2-nitrophenyl)propanoic acid, hydrochloride salt (14) in Example 2, but beginning with 2-methyl-1-nitro-4-(trifluoromethyl)benzene) (178 mg, 0.566 mmol) in THF (10 mL) and MeOH (10 mL) was added sodium acetate trihydrate (0.778 g, 5.66 mmol) and tin(II) chloride dihydrate (0.658 g, 2.8 mmol). The reaction was allowed to stir at 0° C. for 4.5 h. NEt$_3$ (0.789 mL, 5.66 mmol) and BOC$_2$O (0.247 g, 1.13 mmol) were added, and the reaction was allowed to stir at RT overnight. The mixture was concentrated in vacuo, and the residue was partitioned between EtOAc and water. The aqueous layer was extracted with EtOAc, and the combined organic layers were dried over magnesium sulfate, filtered and concentrated under reduced pressure. Purification via silica gel chromatography (Gradient: 0% to 100% EtOAc in heptane) provided the product (63 mg, 25%). LCMS m/z 446.9 (M+1).

3-Amino-1-hydroxy-6-(trifluoromethyl)-3,4-dihydroquinolin-2(1H)-one, hydrochloride salt (53) To a solution of tert-butyl {1-[(tert-butoxycarbonyl)oxy]-2-oxo-6-(trifluoromethyl)-1,2,3,4-tetrahydroquinolin-3-yl}carbamate (52) (63 mg, 0.14 mmol) in MeOH (10 mL) was added concentrated HCl (3 mL). The reaction was heated at 40° C. until it was judged complete via LCMS analysis. The mixture was concentrated in vacuo to provide the title compound as a solid (35 mg, 88%). LCMS m/z 246.9 (M+1). $^1$H NMR (400 MHz, DMSO-d$_6$) δ 3.17 (m, 1H), 3.35 (dd, J=15.4, 6.3 Hz, 1H), 4.50 (m, H), 7.44 (d, J=8.5 Hz, 1H), 7.72 (br d, J=8.6 Hz, 1H), 7.79 (br s, 1H) 8.71 (br s, 2H), 11.12 (s, 1H).

Example 11

Synthesis of 2-amino-4-hydroxy-1,2-dihydrobenzo[f]quinolin-3(4H)-one (55)

Benzyl[4-(benzyloxy)-3-oxo-1,2,3,4-tetrahydrobenzo[t]quinolin-2-yl]carbamate (54, prepared from 2-amino-3-(1-naphthyl)propanoic acid according to the general procedure for synthesis of tert-butyl (3S,4S)-1-(benzyloxy)-4-methyl-2-oxo-1,2,3,4-tetrahydroquinolin-3-ylcarbamate (33) in Example 7) (35 mg, 0.077 mmol) was dissolved in a solution of boron trichloride in DCM (1.0 M, 5.00 mL, 5.00 mmol), and the reaction was heated at 50° C. for 1 h. After being quenched with MeOH (10 mL), the reaction was stirred for 15 min, then treated with silica gel impregnated with p-toluenesulfonic acid (0.68 mEq/g, 2 g, 1.36 mmol). After 1.5 hours, the silica was filtered off and rinsed with MeOH; the silica was then slurried with a 2N solution of ammonia in MeOH for 20 minutes, and filtered. The solids were rinsed with MeOH and the combined filtrates were concentrated in vacuo to afford a solid, which was triturated with Et$_2$O to provide the product as a solid (2 mg, 10%). LCMS m/z 229.0 (M+1). $^1$H NMR (400 MHz, CD$_3$OD) δ 3.07 (dd, J=15, 15 Hz, 1H), 3.82 (dd, J=16, 6.5 Hz, 1H), 4.00 (dd, J=14, 6 Hz, 1H), 7.45 (dd, J=7, 7 Hz, 1H), 7.58 (dd, J=8, 8 Hz, 1H), 7.67 (d, J=9 Hz, 1H), 7.88 (m, 2H), 8.01 (d, J=9 Hz, 1H).

Example 12

Synthesis of (3S)-3-amino-1-hydroxy-5-methoxy-3,4-dihydroquinolin-2(1H)-one, hydrochloride salt (60)

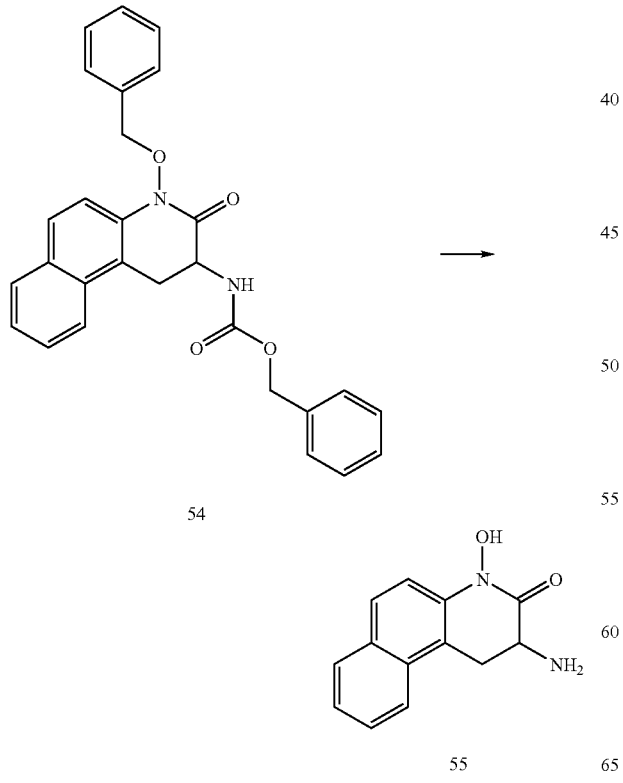

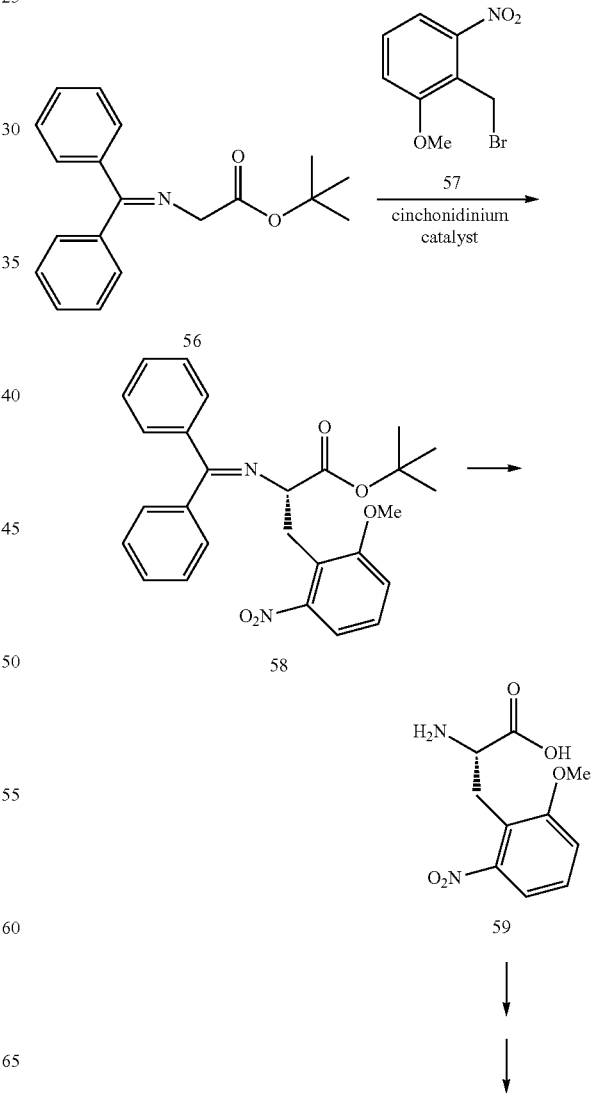

67
-continued

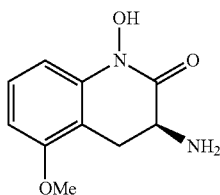
60 tert-Butyl N-(diphenylmethylene)-2-methoxy-6-nitro-L-phenylalaninate (58) To a solution of tert-butyl N-(diphenylmethylene)glycinate (56) (1.2 g, 4.2 mmol), 2-(bromomethyl)-1-methoxy-3-nitrobenzene (57) (0.86 g, 3.3 mmol) and O-allyl-N-(9-anthracenylmethyl)cinchonidinium bromide (0.21 g, 0.33 mmol) in DCM (10 mL) cooled at −30° C., was added CsOH (0.84 g, 5.0 mmol). (See E. J. Corey et al., *Journal of the American Chemical Society* 1997, 119, 12414-12415.) The reaction was stirred at −30° C. overnight. The mixture was warmed to 0° C., quenched with saturated aqueous ammonium chloride solution (5 mL) and diluted with DCM (5 mL). The aqueous layer was extracted with DCM (3×5 mL), and the combined organic layers were washed with water, dried over $Na_2SO_4$, filtered and concentrated under reduced pressure. The residue was purified by chromatography on silica gel (Gradient: 0% to 20% EtOAc in heptane) to give the title compound as a yellow solid (1.32 g, 87%). APCI m/z 461.2 (M+1). $^1$H NMR (400 MHz, $CDCl_3$) δ 1.41 (s, 9H), 3.49 (dd, J=13.5, 4.3 Hz, 1H), 3.55 (s, 3H), 3.63 (dd, J=13.6, 9.6 Hz, 1H), 4.29 (dd, J=9.6, 4.3 Hz, 1H), 6.64 (br d, J=6.4 Hz, 2H), 6.88 (m, 1H), 7.20-7.34 (m, 8H), 7.51-7.54 (m, 2H).

2-Methoxy-6-nitro-L-phenylalanine, hydrochloride salt (59) tert-Butyl N-(diphenylmethylene)-2-methoxy-6-nitro-L-phenylalaninate (58) (1.28 g, 2.78 mmol) was taken up in THF (8 mL) and water (8 mL), and treated with concentrated aqueous HCl solution (8 mL). After stirring overnight, the reaction was diluted with EtOAc (15 mL), and the organic layer was extracted with water (3×10 mL). The combined aqueous layers were concentrated in vacuo to provide the product as an off-white solid (750 mg, 97%). LCMS m/z 241.2 (M+1). $^1$H NMR (400 MHz, DMSO-$d_6$) δ 3.23 (dd, J=13.5, 6.3 Hz, 1H), 3.33 (dd, J=13.4, 9.4 Hz, 1H), 3.87 (s, 3H), 4.00 (br m, 1H), 7.40 (m, 1H), 7.50-7.55 (m, 2H), 8.56 (br s, 3H), 13.6 (v br s, 1H); e.e. 94.8%.

(3S)-3-Amino-1-hydroxy-5-methoxy-3,4-dihydroquinolin-2(1H)-one, hydrochloride salt (60) 2-Methoxy-6-nitro-L-phenylalanine, hydrochloride salt (59) was converted to the title product following the general procedure outlined for synthesis of 3-amino-1-hydroxy-6-(trifluoromethyl)-3,4-dihydroquinolin-2(1H)-one, hydrochloride salt (53) in Example 10. The product was obtained as an off-white solid (119 mg, 87%). LCMS m/z 209.0 (M+1). $^1$H NMR (400 MHz, DMSO-$d_6$) δ 2.72 (dd, J=15, 15 Hz, 1H), 3.46 (dd, J=15.5, 6.9 Hz, 1H), 3.83 (s, 3H), 4.34 (dd, J=14.4, 6.8 Hz, 1H), 6.82 (d, J=8.2 Hz, 1H), 6.92 (d, J=8.1 Hz, 1H), 7.31 (dd, J=8.3, 8.3 Hz, 1H), 8.66 (br s, 3H), 10.83 (br s, 1H).

68

Example 13

Synthesis of 3-amino-1-hydroxy-7-(3-methoxyphenyl)-3,4-dihydroquinolin-2(1H)-one, hydrochloride salt (62)

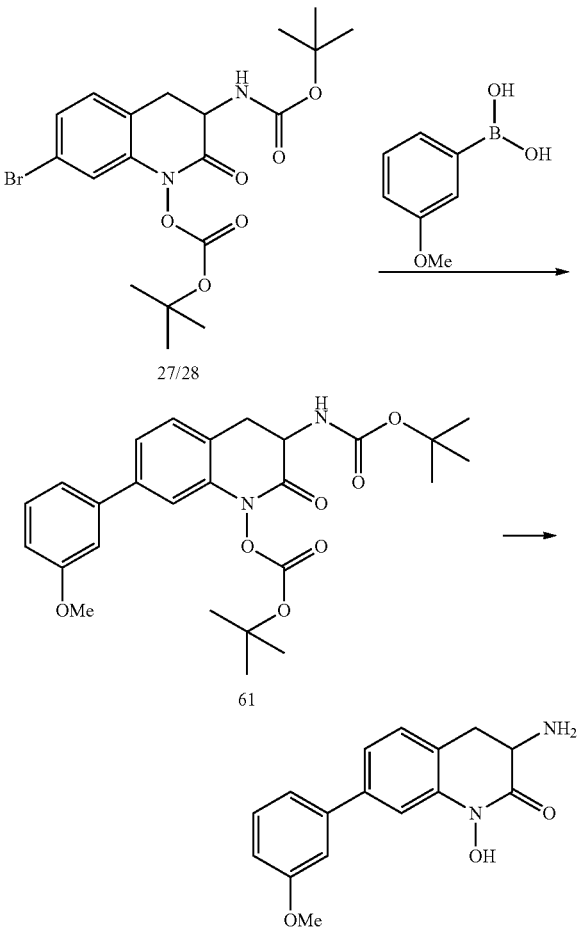

tert-Butyl 1-[(tert-butoxycarbonyl)oxy]-7-(3-methoxyphenyl)-2-oxo-1,2,3,4-tetrahydroquinolin-3-ylcarbamate (61) A sealable vial was charged with racemic tert-butyl {7-bromo-1-[(tert-butoxycarbonyl)oxy]-2-oxo-1,2,3,4-tetrahydroquinolin-3-yl}carbamate (27 and 28, from Example 5) (0.10 g, 0.22 mmol), biphenyl-2-yl(di-tert-butyl)phosphine (1.20 mg, 0.004 mmol), Pd(II)(OAc)$_2$ (0.4 mg, 0.002 mmol), KF (38 mg, 0.66 mmol) and (3-methoxyphenyl)boronic acid (50 mg, 0.33 mmol) under nitrogen. THF (3 mL) was added to the mixture and the reaction was heated at 60° C. for 20 h. The reaction mixture was diluted with EtOAc and the organic layer was washed with water, dried over magnesium sulfate, filtered and concentrated in vacuo. The residue was purified by chromatography on silica gel (Gradient: 0% to 60% EtOAc in heptane) to give the product as a gum (39 mg, 37%). LCMS m/z 485.1 (M+1). $^1$H NMR (400 MHz, $CDCl_3$) δ 1.49 (s, 9H), 1.57 (br s, 9H), 3.01 (br m, 1H), 3.51 (br m, 1H), 3.88 (s, 3H), 4.58 (br m, 1H), 5.60 (br s, 1H), 6.93 (ddd, J=8.3, 2.5, 0.8 Hz, 1H), 7.08 (m, 1H), 7.14 (br d, J=8 Hz, 1H), 7.28-7.33 (m, 2H), 7.37 (dd, J=8.0, 8.0 Hz, 1H).

3-Amino-1-hydroxy-7-(3-methoxyphenyl)-3,4-dihydroquinolin-2(1H)-one, hydrochloride salt (62) Reaction of tert-butyl 1-[(tert-butoxycarbonyl)oxy]-7-(3-methoxyphenyl)-2-oxo-1,2,3,4-tetrahydroquinolin-3-ylcarbamate (61) under the conditions described for deprotection of tert-butyl {1-[(tert-butoxycarbonyl)oxy]-2-oxo-1,2,3,4-tetrahydro-1,5-naphthyridin-3-yl}carbamate (49) in Example 9 provided the title compound as a solid (96%). LCMS m/z 285.3 (M+1). $^1$H NMR (400 MHz, DMSO-d$_6$) δ 3.13 (dd, J=14.9, 14.9 Hz, 1H), 3.25 (dd, J=15.0, 6.5 Hz, 1H), 3.82 (s, 3H), 4.44 (m, 1H), 6.98 (br dd, J=8.2, 2.5 Hz, 1H), 7.13 (m, 1H), 7.20 (br d, J=8 Hz, 1H), 7.38-7.43 (m, 3H), 7.50 (br d, J=1.5 Hz, 1H), 8.68 (br s, 3H), 10.97 (s, 1H).

Example 66

Synthesis of (3S)-3-amino-1-hydroxy-6-phenoxy-3,4-dihydro-1,8-naphthyridin-2(1H)-one (67)

added in one portion. After 5 min, the ice bath was removed, and an exotherm was observed, followed by evolution of SO$_2$ gas. The reaction mixture became a yellow solution, which was stirred at RT for 1 h. The reaction mixture was diluted with ice water, EtOAc (100 mL) was added and the water layer was made basic using aqueous NH$_4$OH solution. The organic layer was separated and dried over Mg$_2$SO$_4$, then filtered and concentrated in vacuo. Purification on silica gel (Eluant: 10% EtOAc in heptane) provided the product as a white solid (2.70 g, 40%). GCMS m/z 220 (M$^+$).

3-Bromo-2-nitro-5-phenoxypyridine (64) To a solution of 3-bromo-5-fluoro-2-nitropyridine (63) (1.0 g, 4.5 mmol) in MeCN (80 mL) was added phenol (478 mg, 5.08 mmol) and Cs$_2$CO$_3$ (326 mg, 5.43 mmol). The resulting mixture was stirred at 60° C. for 3 h. The reaction was diluted with EtOAc and washed with water. The organic layer was dried, filtered and concentrated under reduced pressure, and the residue was purified using silica gel chromatography (Eluant: 10% EtOAc in heptane) to provide the product as an oil (1.3 g, 98%). GCMS m/z 294 (M$^+$). $^1$H NMR (400 MHz, CDCl$_3$) δ

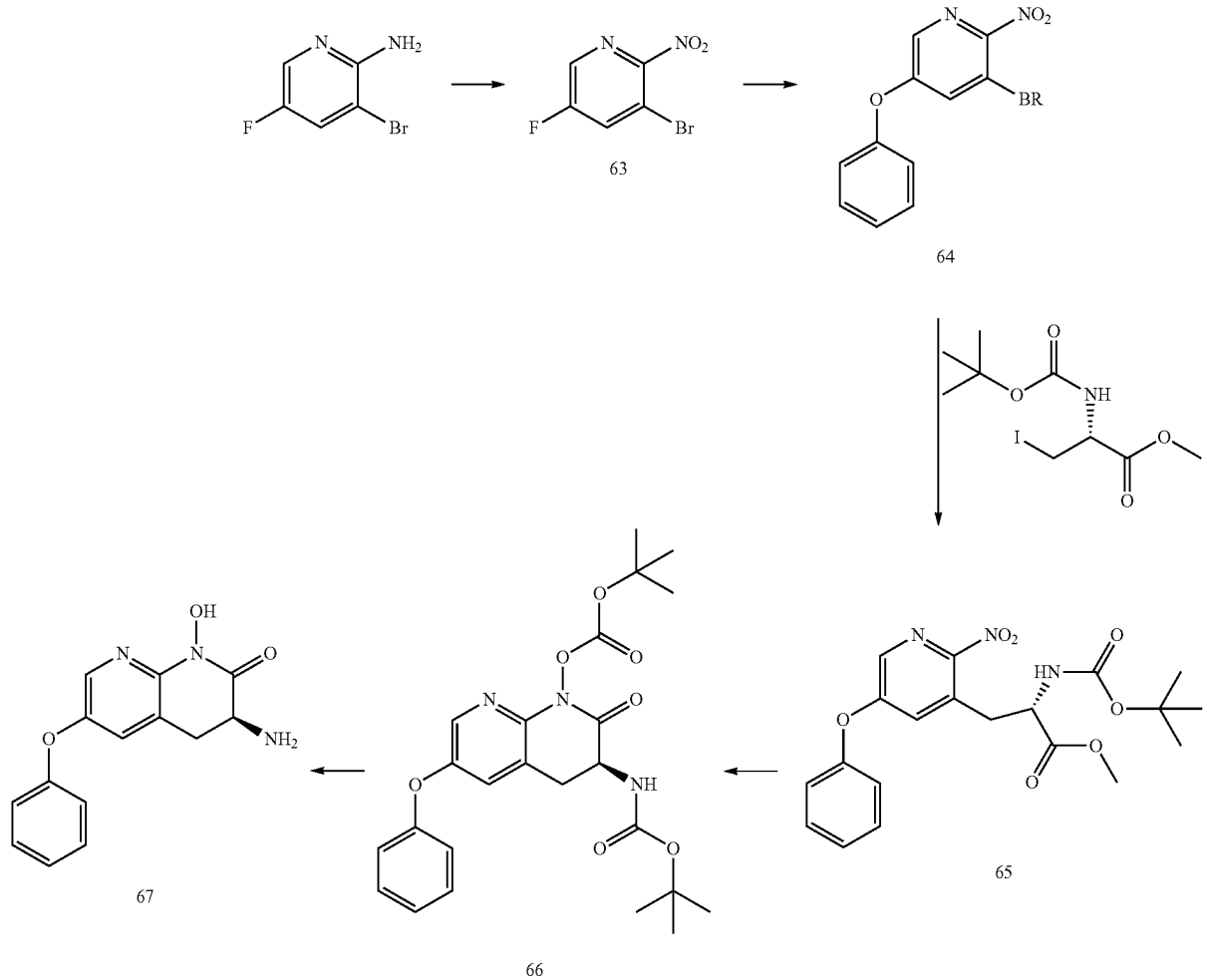

7.10-7.14 (m, 2H), 7.33 (br t, J=7.5 Hz, 1H), 7.49 (dd, J=8.5, 7.5 Hz, 2H), 7.58 (d, J=2.4 Hz, 1H), 8.18 (d, J=2.4 Hz, 1H).

3-Bromo-5-fluoro-2-nitropyridine (63) A flask was charged with concentrated H$_2$SO$_4$ (30 mL) and K$_2$S$_2$O$_8$ (28.3 g, 105 mmol) was added at RT and stirred for 5 min. The resulting viscous reaction mixture was cooled to 0° C. and then 3-bromo-5-fluoropyridin-2-amine (5 g, 30 mmol) was Methyl N-(tert-butoxycarbonyl)-3-(2-nitro-5-phenoxypyridin-3-yl)-L-alaninate (65) Trimethylsilyl chloride (0.348 ml, 2.74 mmol) was added to a stirring suspension of zinc dust (989 mg, 13.7 mmol) in dry DMF (1 mL) and the mixture was stirred for 30 min. The stirring was stopped, and the solids were allowed to settle for 10 min, at which time the supernatant was removed via syringe. The activated zinc was washed with DMF and the solvent was again removed with a syringe; the zinc was then dried under vacuum using a heat gun. A solution of methyl N-(tert-butoxycarbonyl)-3-iodo-L-alaninate (prepared according to S. van Zutphen et al., *Tetrahedron Lett.* 2007, 48, 2857-2859) (1.81 g, 5.49 mmol) in DMF (1.0 M) was added to the dry activated zinc, and the resulting suspension was stirred for 30 min at RT. The zincate solution was transferred via syringe into a dry flask under nitrogen. To this was sequentially added 3-bromo-2-nitro-5-phenoxypyridine (64) (1.35 g, 4.58 mmol), palladium(II) acetate (51.4 mg, 0.229 mmol) and then X-Phos (dicyclohexyl(2',4',6'-triisopropylbiphenyl-2-yl)phosphine, 218 mg, 0.458 mmol). The resulting solution was stirred at RT for 18 h. The reaction mixture was diluted with Et$_2$O (100 mL), washed with water (5×20 mL), dried over Mg$_2$SO$_4$, filtered and concentrated in vacuo. Purification via silica gel chromatography (Eluants: 10% EtOAc in heptane, then 15%, then 20%) afforded the product as a yellow oil (297 mg, 16% yield). LCMS m/z 418.1 (M+1). $^1$H NMR (400 MHz, CDCl$_3$) δ 1.38 (br s, 9H), 3.14-3.21 (m, 1H), 3.5 (m, 1H, assumed; obscured by residual Et$_2$O), 3.74 (s, 3H), 4.62-4.68 (m, 1H), 5.19 (br d, J=8 Hz, 1H), 7.09-7.13 (m, 2H), 7.27-7.32 (m, 2H), 7.47 (br dd, J=8, 8 Hz, 2H), 8.15 (br s, 1H).

tert-Butyl {(3S)-1-[(tert-butoxycarbonyl)oxy]-2-oxo-6-phenoxy-1,2,3,4-tetrahydro-1,8-naphthyridin-3-yl}carbamate (66) Methyl N-(tert-butoxycarbonyl)-3-(2-nitro-5-phenoxypyridin-3-yl)-L-alaninate (65) (217 mg, 0.52 mmol) was dissolved in THF (5 mL) and MeOH (5 mL), and the resulting solution was cooled to 0° C. with an ice-water bath. To this was added tin(II) chloride dihydrate (704 mg, 3.12 mmol) and sodium acetate trihydrate (778 mg, 5.72 mmol), and the reaction was allowed to stir at 0° C. for 10 min and then at RT for 2 h. At that time, NEt$_3$ (0.725 mL, 5.20 mmol) and BOC$_2$O (227 mg, 1.04 mmol) were added and the mixture was stirred at RT for 18 h. Solvents were removed in vacuo, and the remaining semi-solid was filtered through Celite and washed with EtOAc (3×20 mL). The combined EtOAc filtrates were washed with water (2×20 mL) and saturated aqueous NaHCO$_3$ solution (2×20 mL), dried over Mg$_2$SO$_4$, filtered and concentrated under reduced pressure. The crude residue was purified on silica gel (Eluant: 1:1 EtOAc/heptane) to provide the product as an oil (240 mg, 98%). LCMS m/z 472.1 (M+1). $^1$H NMR (400 MHz, CDCl$_3$) δ 1.47 (br s, 9H), 1.57 (s, 9H), 2.84-2.98 (m, 1H), 3.39-3.48 (m, 1H), 4.50-4.61 (m, 1H), 5.58-5.64 (m, 1H), 7.02 (d, J=8.0 Hz, 2H), 7.15-7.23 (m, 2H), 7.39 (br dd, J=8, 8 Hz, 2H), 8.08 (br s, 1H).

(3S)-3-Amino-1-hydroxy-6-phenoxy-3,4-dihydro-1,8-naphthyridin-2(1H)-one (67) tert-Butyl {(3S)-1-[(tert-butoxycarbonyl)oxy]-2-oxo-6-phenoxy-1,2,3,4-tetrahydro-1,8-naphthyridin-3-yl}carbamate (66) (240 mg, 0.509 mmol) was treated with a solution of HCl in Et$_2$O (2 M, 2 mL) and allowed to stir at RT for 66 h. The solvent was removed under reduced pressure, and the residue was dissolved in a solution of 1:4 (1:9 NH$_4$OH: CH$_3$OH): dichloromethane (0.5 mL). This solution was subjected to silica gel chromatography (Eluant: 1:4 (1:9 NH$_4$OH: CH$_3$OH): dichloromethane) to provide the product as a white solid (83 mg, 61%). LCMS m/z 272.0 (M+1). $^1$H NMR (400 MHz, CD$_3$OD) δ 2.98 (br dd, J=15, 14 Hz, 1H), 3.18 (dd, J=15.3, 6.2 Hz, 1H), 4.01 (dd, J=13.8, 6.1 Hz, 1H), 7.03-7.07 (m, 2H), 7.17 (br t, J=7.4 Hz, 1H), 7.40 (dd, J=8.5, 7.5 Hz, 2H), 7.44-7.46 (m, 1H), 8.00 (br d, J=2 Hz, 1H).

Example 67

Synthesis of (3S)-3-amino-1-hydroxy-6-(phenylsulfonyl)-3,4-dihydroquinolin-2(1H)-one, hydrochloride salt (72)

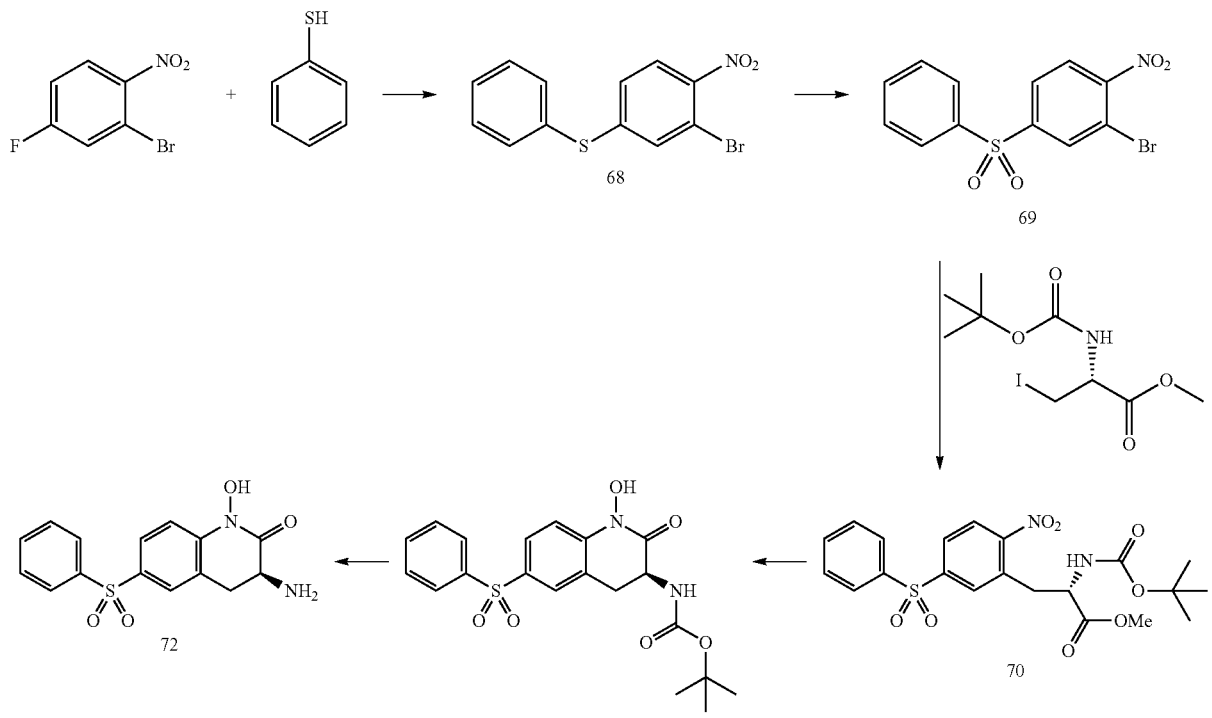

2-Bromo-1-nitro-4-(phenylthio)benzene (68) A mixture of 2-bromo-4-fluoro-1-nitrobenzene (4.3 g, 20 mmol) and K$_2$CO$_3$ (5.39 g, 39.0 mmol) in DMF (100 mL) was heated to 80° C. To the mixture was added benzenethiol (2.15 g, 19.5 mmol) and the mixture was stirred at 80° C. for 1 h. The reaction mixture was quenched by the addition of water (200 mL), and extracted with EtOAc (3×400 mL). The combined organic layers were washed with saturated aqueous sodium chloride solution, dried over Na$_2$SO$_4$, filtered and concentrated in vacuo to afford the product as a yellow solid (6 g, 99%), which was used for the next step without further purification.

2-Bromo-1-nitro-4-(phenylsulfonyl)benzene (69) A mixture of 2-bromo-1-nitro-4-(phenylthio)benzene (68) (5.8 g, 18.7 mmol) and mCPBA (11.3 g, 56.1 mmol) in DCM (120 mL) was stirred at 15° C. for 1 h. The reaction mixture was quenched by addition of saturated aqueous Na$_2$SO$_3$ solution (20 mL), and extracted with DCM (3×500 mL). The combined organic layers were washed with saturated aqueous sodium chloride solution, dried over Na$_2$SO$_4$, filtered and concentrated under reduced pressure. The residue was purified by column chromatography on silica gel (Eluant: 10:1 petroleum ether/EtOAc) to give material that was then crystallized from EtOH (100 mL). The product was obtained as a yellow solid (2 g, 30%). LCMS m/z 340.9, 342.9 (M+1). $^1$H NMR (400 MHz, CDCl$_3$) δ 7.56-7.62 (m, 2H), 7.65-7.70 (m, 1H), 7.88 (d, J=8.4 Hz, 1H), 7.94-8.03 (m, 3H), 8.31 (s, 1H).

Methyl N-(tert-butoxycarbonyl)-2-nitro-5-(phenylsulfonyl)-L-phenylalaninate (70) Compound 70 was prepared from 2-bromo-1-nitro-4-(phenylsulfonyl)benzene (69) according to the general procedure for the synthesis of methyl N-(tert-butoxycarbonyl)-3-(2-nitro-5-phenoxypyridin-3-yl)-L-alaninate (65) in Example 66. The product was obtained as an off-white foam (250 mg, 37%). LCMS m/z 463.1 (M−1).

tert-Butyl[(3S)-1-hydroxy-2-oxo-6-(phenylsulfonyl)-1,2,3,4-tetrahydroquinolin-3-yl]carbamate (71) Ammonium formate (84.8 mg, 1.34 mmol) was added to a solution of methyl N-(tert-butoxycarbonyl)-2-nitro-5-(phenylsulfonyl)-L-phenylalaninate (70) (125 mg, 0.269 mmol) in pyridine (2.7 mL), followed by platinum on carbon (5%, 4 mg). The black suspension was stirred at 60° C. for 18 h, then allowed to cool to RT and filtered through an Acrodisc® syringe filter (Pall Life Sciences). The filtrate was concentrated, and the residue was purified via chromatography on silica gel (Gradient: 0% to 60% EtOAc in heptane), to provide the product as a white solid (62 mg, 55%). LCMS m/z 417.0 (M−1). $^1$H NMR (500 MHz, CDCl$_3$) δ 1.43 (s, 9H), 2.94 (br dd, J=15, 14 Hz, 1H), 3.37-3.45 (m, 1H), 4.45-4.53 (m, 1H), 5.38 (br d, J=6 Hz, 1H), 7.44 (d, J=8.5 Hz, 1H), 7.51-7.55 (m, 2H), 7.57-7.61 (m, 1H), 7.75 (br s, 1H), 7.90-7.95 (m, 3H), 8.5-8.9 (v br s, 1H).

(3S)-3-Amino-1-hydroxy-6-(phenylsulfonyl)-3,4-dihydroquinolin-2(1H)-one, hydrochloride salt (72) Compound 72 was prepared from tert-butyl [(3S)-1-hydroxy-2-oxo-6-(phenylsulfonyl)-1,2,3,4-tetrahydroquinolin-3-yl]carbamate (71) according to the general procedure for the synthesis of (3S)-3-amino-1-hydroxy-6-phenoxy-3,4-dihydro-1,8-naphthyridin-2(1H)-one (67) in Example 66, except that the neutral product (15 mg, 34%) was converted to its hydrochloride salt by dissolution in DCM and treatment with 2 N HCl in Et$_2$O, followed by removal of solvent in vacuo. The product was obtained as a solid. Characterization data was obtained on the neutral form of the product. LCMS m/z 318.9 (M+1). $^1$H NMR (500 MHz, CDCl$_3$) δ 2.81-2.94 (m, 1H), 3.01-3.13 (m, 1H), 3.65-3.79 (br s, 1H), 4.3-5.1 (v br s, 3H), 7.28-7.35 (m, 1H), 7.49-7.54 (m, 2H), 7.55-7.60 (m, 1H), 7.67 (br s, 1H), 7.73-7.79 (m, 1H), 7.91 (br d, J=7.3 Hz, 2H).

Example 68

Synthesis of (3S)-3-amino-6-benzyl-1-hydroxy-3,4-dihydroquinolin-2(1H)-one, trifluoroacetic acid salt (82)

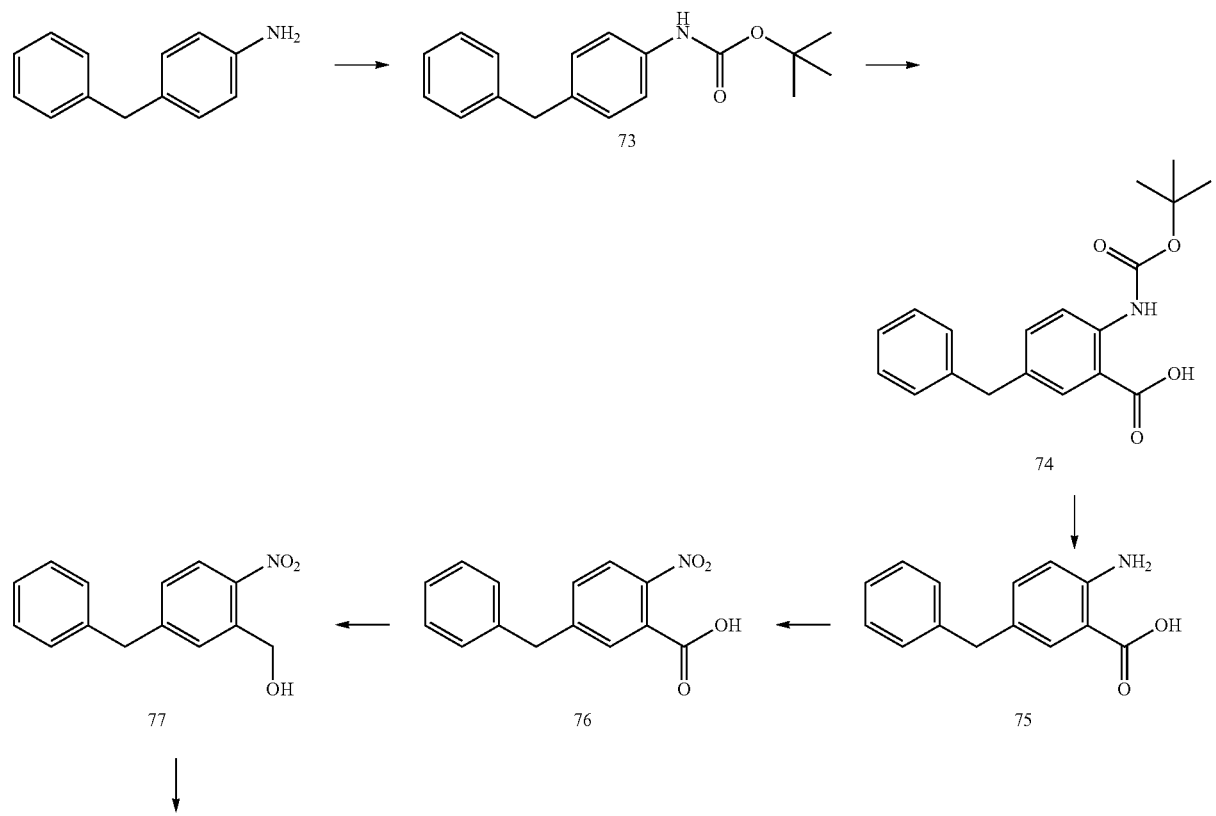

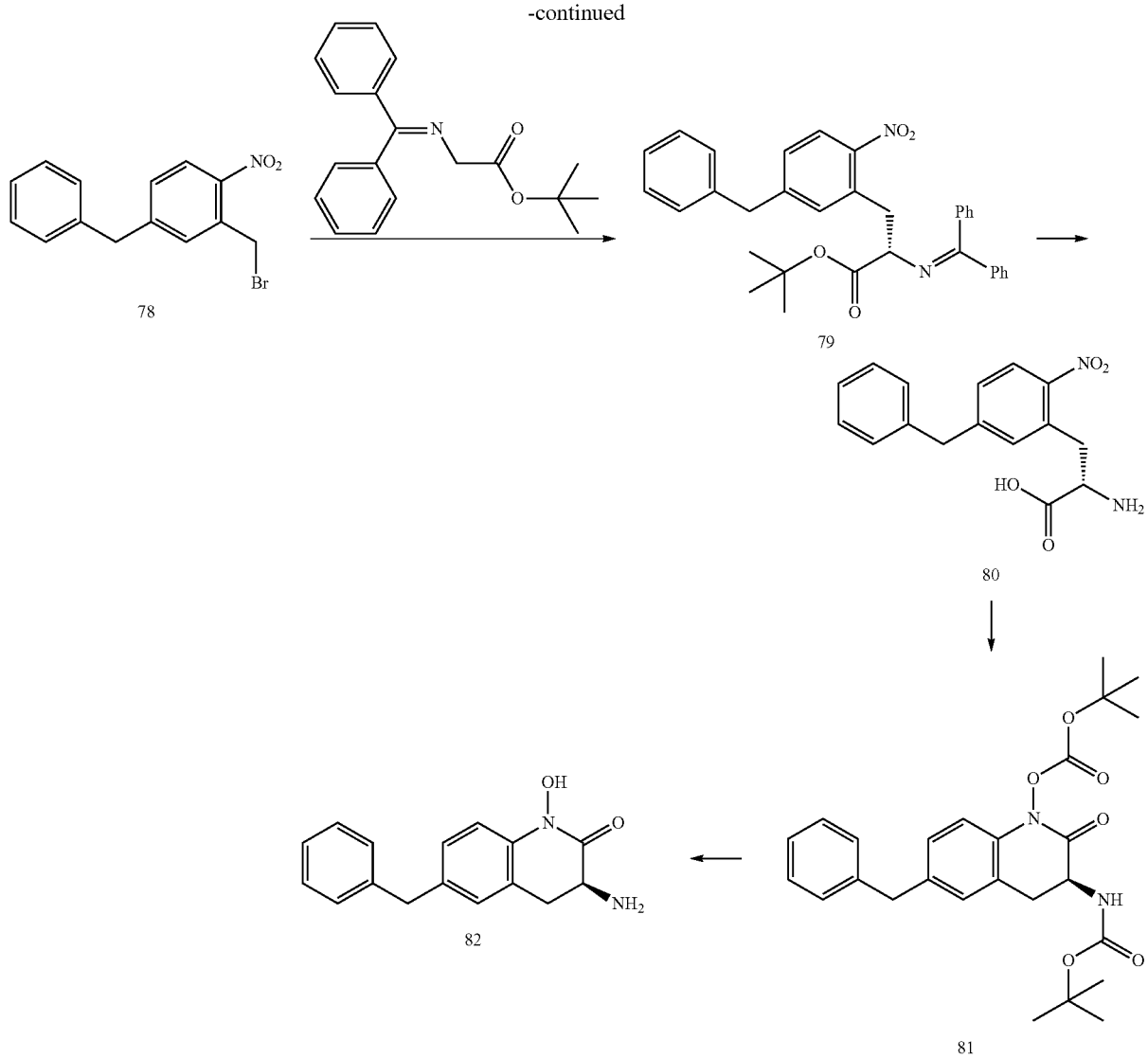

tert-Butyl (4-benzylphenyl)carbamate (73) To a solution of 4-benzylaniline (12.5 g, 68.2 mmol) in a 1:1 solution of dichloromethane and saturated aqueous $Na_2CO_3$ was added $(BOC)_2O$ (16.5 g, 75 mmol). The reaction was allowed to stir at RT for 18 h. The reaction mixture was extracted with dichloromethane (3×200 mL), washed with water, dried over sodium sulfate, filtered and concentrated under reduced pressure to provide the product as a solid (14.8 g, 77%). $^1$H NMR (500 MHz, $CDCl_3$) δ 1.51 (s, 9H), 3.93 (s, 2H), 6.41 (br s, 1H), 7.10-7.29 (m, 9H).

5-Benzyl-2-[(tert-butoxycarbonyl)amino]benzoic acid (74) tert-Butyllithium (1.7 M solution in pentane, 55.3 mL, 94.0 mmol) was added drop-wise to a −78° C. solution of tert-butyl (4-benzylphenyl)carbamate (73) (8.33 g, 29.4 mmol) in anhydrous THF. The resulting mixture was allowed to warm to −50° C. and stirred for 2 h. The reaction was carefully poured onto finely crushed dry ice (300 g); stirring was continued and the reaction was allowed to warm to RT. The reaction mixture was diluted with EtOAc (200 mL), washed with water (3×100 mL) and with aqueous HCl (1 N, 3×100 mL). The organic layers were combined, dried over sodium sulfate, filtered, and concentrated under reduced pressure to provide the product as a solid (9 g, 90%). This material was taken to the next step without purification. LCMS m/z 326.2 (M−1). $^1$H NMR (500 MHz, $CDCl_3$) δ 1.52 (s, 9H), 3.93 (s, 2H), 7.10-7.29 (m, 9H).

2-Amino-5-benzyl benzoic acid (75) 5-Benzyl-2-[(tert-butoxycarbonyl)amino]benzoic acid (74) (9 g, 30 mmol) was dissolved in a 1:1 mixture of TFA and dichloromethane at 0° C. and stirred at RT overnight. The reaction was concentrated under reduced pressure, taken up in EtOAc (150 mL), and washed with water (3×200 mL). The organic layer was dried over sodium sulfate, filtered, concentrated under reduced pressure and purified by silica gel chromatography (Gradient: 0% to 80% EtOAc in heptane) to provide the neutral product as a solid (331 mg, 5%). $^1$H NMR (500 MHz, $CDCl_3$) δ 3.90 (s, 2H), 6.63 (d, J=8.5 Hz, 1H), 7.14-7.24 (m, 4H), 7.31 (dd, J=7.6, 7.6 Hz, 2H), 7.81 (br s, 1H).

5-Benzyl-2-nitrobenzoic acid (76) To a solution of sodium perborate (1.170 g, 7.52 mmol) heated in acetic acid at 85° C. was added 2-amino-5-benzylbenzoic acid (75) (342 mg, 1.50 mmol). The reaction was stirred at reflux until LCMS data indicated that the reaction was complete. The reaction mixture was poured into water and extracted with EtOAc (3×50 mL), and the combined organic layers were dried over sodium sulfate and filtered. Purification using silica gel chromatography (Gradient: 0% to 100% EtOAc in heptane) afforded the desired product as a solid (177 mg, 46%). LCMS m/z 256.0 (M−1). $^1$H NMR (500 MHz, CDCl$_3$) δ 4.10 (s, 2H), 7.19 (br d, J=7.3 Hz, 2H), 7.26-7.30 (m, 1H), 7.35 (br dd, J=8, 7 Hz, 2H), 7.45 (br dd, J=8.3, 2.0 Hz, 1H), 7.67 (d, J=2.0 Hz, 1H), 7.82 (d, J=8.5 Hz, 1H).

(5-Benzyl-2-nitrophenyl)methanol (77) To a solution of 5-benzyl-2-nitrobenzoic acid (76) (145 mg, 0.56 mmol) in THF was added borane-THF complex (as a solution in THF, 4 equivalents) drop-wise. The reaction was refluxed for 2 h, then was quenched with aqueous ammonium chloride solution. After addition of EtOAc, the mixture was washed with water (3×50 mL) and saturated aqueous sodium chloride solution (3×50 mL), then dried over sodium sulfate and filtered. Purification via chromatography on silica gel (Gradient: 0% to 80% EtOAc in heptane) provided the product as a solid (105 mg, 77%). LCMS m/z 242.1 (M−1). $^1$H NMR (400 MHz, CDCl$_3$) δ 4.07 (s, 2H), 4.94 (s, 2H), 7.17-7.20 (m, 2H), 7.22-7.27 (m, 2H), 7.29-7.34 (m, 2H), 7.59 (br s, 1H), 8.04 (d, J=8.4 Hz, 1H).

4-Benzyl-2-(bromomethyl)-1-nitrobenzene (78) To a solution of (5-benzyl-2-nitrophenyl)methanol (77) (103 mg, 0.42 mmol) in dichloromethane was added triphenylphosphine (224 mg, 0.85 mmol) and carbon tetrabromide (286 mg, 0.85 mmol) and the reaction was allowed to stir at RT for 2 h. After removal of volatiles in vacuo, the residue was taken in EtOAc (50 mL), washed with water (3×100 mL) and with saturated aqueous sodium chloride solution (3×100 mL). After concentration under reduced pressure, purification was effected via silica gel chromatography (Gradient: 0% to 80% EtOAc in heptane) to provide the product as a solid (125 mg, 96%). $^1$H NMR (500 MHz, CDCl$_3$) δ 4.06 (s, 2H), 4.81 (s, 2H), 7.16-7.20 (m, 2H), 7.25-7.30 (m, 2H), 7.32-7.38 (m, 3H), 8.00 (d, J=8.3 Hz, 1H).

tert-Butyl 3-benzyl-N-(diphenylmethylene)-6-nitro-L-phenylalaninate (79) 4-Benzyl-2-(bromomethyl)-1-nitrobenzene (78) (130 mg, 0.42 mmol), tert-butyl N-(diphenylmethylene)glycinate (56) (85 mg, 0.28 mmol) and O-allyl-N-(9-anthracenylmethyl)cinchonidinium bromide (18.8 mg, 0.028 mmol) were mixed in a dry vial in dichloromethane and cooled to −30° C. Cesium hydroxide (71.4 mg, 0.42 mmol) was added after the reaction temperature in the vial reached -30° C. The reaction was allowed to stir at −30° C. for 18 h, at which time it was concentrated under reduced pressure, taken up in EtOAc (100 mL), washed with water (3×100 mL) and saturated aqueous sodium chloride solution (3×100 mL), then concentrated in vacuo. Purification by silica gel chromatography (Gradient: 0% to 80% EtOAc in heptane) provided the product as an oil (153 mg, 100%). LCMS m/z 521.3 (M+1). $^1$H NMR (500 MHz, CDCl$_3$) δ 1.45 (s, 9H), 3.35 (dd, J=13.1, 9.6 Hz, 1H), 3.72 (dd, J=13.2, 3.8 Hz, 1H), 3.88 (s, 2H), 4.33 (dd, J=9.6, 3.7 Hz, 1H), 6.55 (br m, 2H), 6.97-7.00 (m, 2H), 7.10-7.17 (m, 4H), 7.22-7.26 (m, 3H), 7.30-7.36 (m, 3H), 7.39-7.43 (m, 1H), 7.60 (br d, J=7 Hz, 2H), 7.82 (d, J=8.4 Hz, 1H).

tert-Butyl {(3S)-6-benzyl-1-[(tert-butoxycarbonyl)oxy]-2-oxo-1,2,3,4-tetrahydroquinolin-3-yl}carbamate (81) To a solution of tert-butyl 3-benzyl-N-(diphenylmethylene)-6-nitro-L-phenylalaninate (79) (150 mg, 0.288 mmol) in dichloromethane was added trifluoroacetic acid in equal volume at 0° C., and the reaction was allowed to stir at RT for 18 h. Solvents were removed under reduced pressure, and the residue was taken in water (50 mL), and washed with EtOAc (3×50 mL). The aqueous layer was concentrated under reduced pressure to provide 3-benzyl-6-nitro-L-phenylalaninine (80) as a solid (70.2 mg, 59%). LCMS m/z 301.0 (M+1). This crude product (70.2 mg, 0.234 mmol) was dissolved in a 1:1 mixture of THF and MeOH and treated with sodium acetate (325 mg, 2.34 mmol) and tin(II) chloride dihydrate (269 mg, 1.17 mmol) and stirred for 4 h at 0° C. To the reaction mixture was added triethylamine (0.33 mL, 2.4 mmol) and (BOC)$_2$O (132 mg, 0.585 mmol), and the reaction was allowed to warm to RT and stir for 18 h. The reaction mixture was filtered, and the filtrate was washed with water (3×100 mL), washed with saturated aqueous sodium chloride solution, dried over sodium sulfate, filtered, and concentrated in vacuo. Purification via silica gel chromatography (Gradient: 0% to 80% EtOAc in heptane) yielded the product as a solid (40 mg, 36%). $^1$H NMR (500 MHz, CDCl$_3$) δ 1.47 (br s, 9H), 1.56 (br s, 9H), 2.86-3.00 (m, 1H), 3.33-3.43 (m, 1H), 3.94 (s, 2H), 4.47-4.55 (m, 1H), 5.57 (br s, 1H), 6.9-7.1 (v br s, 1H), 7.04 (s, 1H), 7.11 (br d, J=8 Hz, 1H), 7.18 (d, J=7.6 Hz, 2H), 7.21-7.25 (m, 1H), 7.31 (dd, J=7.8, 7.3 Hz, 2H).

(3S)-3-Amino-6-benzyl-1-hydroxy-3,4-dihydroquinolin-2(1H)-one, trifluoroacetic acid salt (82) tert-Butyl {(3S)-6-benzyl-1-[(tert-butoxycarbonyl)oxy]-2-oxo-1,2,3,4-tetrahydroquinolin-3-yl}carbamate (81) (40 mg, 0.085 mmol) was dissolved in a 1:1 mixture of dichloromethane and trifluoroacetic acid and stirred at RT for 18 h. Removal of solvents under reduced pressure afforded the product as a solid (19 mg, 58%). LCMS m/z 269.0 (M+1). $^1$H NMR (500 MHz, CD$_3$OD) δ 3.12 (dd, half of ABX pattern, J=14.6, 14.4 Hz, 1H), 3.20 (dd, half of ABX pattern, J=14.8, 6.5 Hz, 1H), 3.95 (s, 2H), 4.29 (dd, J=14.5, 6.5 Hz, 1H), 7.12 (br s, 1H), 7.15-7.28 (m, 6H), 7.31 (d, J=8.0 Hz, 1H).

Example 69

Synthesis of 3-amino-6-(2-chlorophenoxy)-1-hydroxy-3,4-dihydroquinolin-2(1H)-one, hydrochloride salt (84)

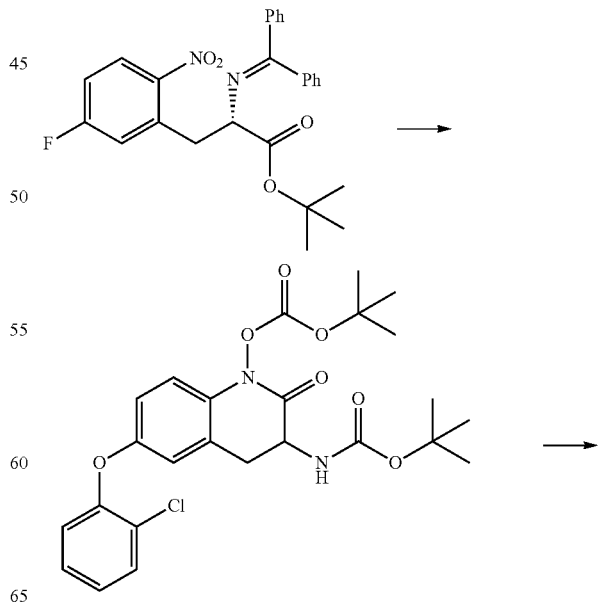

83

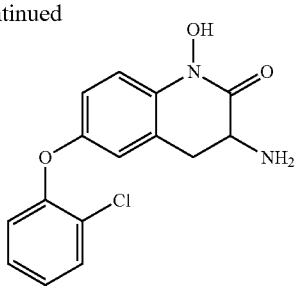

84 tert-Butyl {1-[(tert-butoxycarbonyl)oxy]-6-(2-chlorophenoxy)-2-oxo-1,2,3,4-tetrahydroquinolin-3-yl}carbamate (83) A mixture of tert-butyl N-(diphenylmethylene)-3-fluoro-6-nitro-L-phenylalaninate (which can be prepared according to the general method described in Example 12) (148 mg, 0.33 mmol), 2-chlorophenol (51 mg, 0.40 mmol), and Cs₂CO₃ (160 mg, 0.50 mmol) in anhydrous MeCN (5 mL) under N₂ was heated to 70° C. for 20 h. The reaction mixture was cooled to RT and concentrated in vacuo. The resulting residue was dissolved in EtOAc (20 mL) and water (20 mL), and the separated aqueous phase was washed with EtOAc (20 mL). The combined organic fractions were washed with saturated aqueous sodium chloride solution (20 mL), dried over Na₂SO₄, filtered, and concentrated in vacuo to yield tert-butyl 3-(2-chlorophenoxy)-N-(diphenylmethylene)-6-nitrophenylalaninate as a brown oil (180 mg). This residue was dissolved in a solution of HCl in dioxane (4 M, 10 mL), and the resulting solution was heated to 100° C. for 1 h. The reaction mixture was concentrated in vacuo to yield 3-(2-chlorophenoxy)-6-nitrophenylalanine (79 mg) as a solid. This product was converted to the title compound following the general procedure described in Example 9. The product was obtained as a gum (51 mg, 48%). LCMS m/z 505.6 (M+1). ¹H NMR (400 MHz, CDCl₃) δ 1.46 (s, 9H), 1.56 (br s, 9H), 2.94 (br dd, J=14, 14 Hz, 1H), 3.37 (v br d, J=15 Hz, 1H), 4.48-4.58 (m, 1H), 5.60 (br s, 1H), 6.79 (br s, 1H), 6.88-6.93 (m, 1H), 6.9-7.1 (v br s, 1H), 7.01 (br d, J=8 Hz, 1H), 7.13 (br dd, J=8, 8 Hz, 1H), 7.26 (br dd, J=8, 8 Hz, 1H), 7.47 (br d, J=8 Hz, 1H).

3-Amino-6-(2-chlorophenoxy)-1-hydroxy-3,4-dihydroquinolin-2(1H)-one, hydrochloride salt (84) tert-Butyl {1-[(tert-butoxycarbonyl)oxy]-6-(2-chlorophenoxy)-2-oxo-1,2,3,4-tetrahydroquinolin-3-yl}carbamate (83) was added to a solution of HCl in dioxane (4 M, 10 mL), and the reaction mixture was stirred at RT for 16 h. The reaction mixture was concentrated in vacuo. The resulting white solid was washed with Et₂O, filtered, and dried under vacuum at 45° C. to afford the crude product as a solid (31 mg). This product was slurried with CH₂Cl₂ (1 mL), filtered, washed with CH₂Cl₂, and dried under vacuum at 45° C. to yield the title compound as a white solid (16 mg, 46%). LCMS m/z 305.4 (M+1). ¹H NMR (400 MHz, CD₃OD) δ 3.10-3.25 (m, 2H), 4.35 (dd, J=14.1, 6.7 Hz, 1H), 6.92-6.95 (m, 2H), 7.06 (dd, J=8.1, 1.4 Hz, 1H), 7.19 (ddd, J=7.8, 7.8, 1.5 Hz, 1H), 7.32 (ddd, J=7.7, 7.7, 1.6 Hz, 1H), 7.38 (br d, J=8 Hz, 1H), 7.52 (dd, J=8.0, 1.4 Hz, 1H).

Example 70

Synthesis of 3-{[(3S)-3-amino-1-hydroxy-2-oxo-1,2,3,4-tetrahydroquinolin-6-yl]oxy}benzonitrile, hydrochloride salt (89)

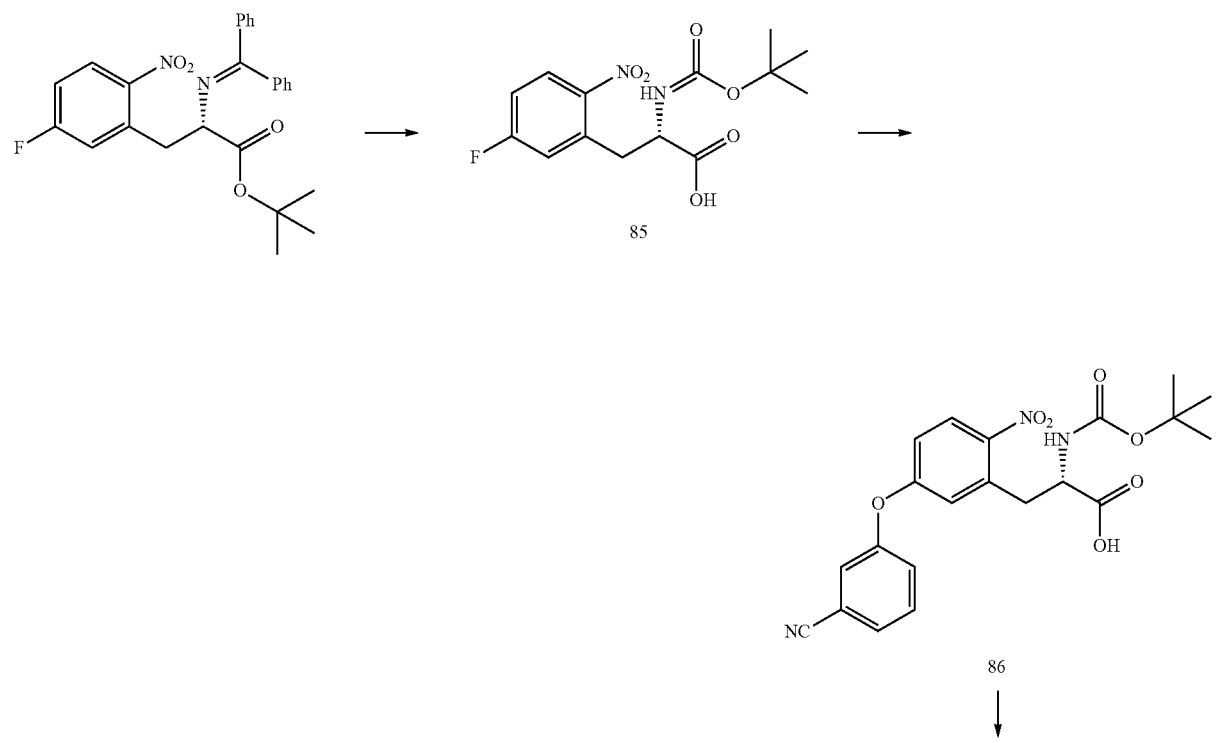

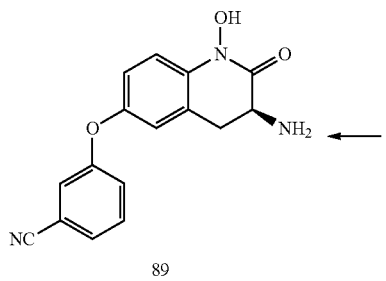 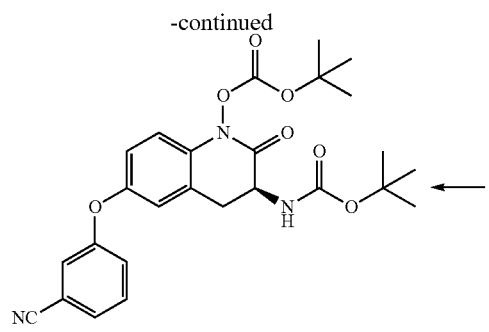 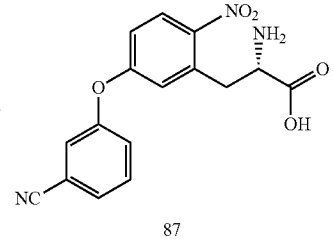

N-(tert-Butoxycarbonyl)-3-fluoro-6-nitro-L-phenylalanine (85) Concentrated HCl (7.5 mL) was added to a solution of tert-butyl N-(diphenylmethylene)-3-fluoro-6-nitro-L-phenylalaninate (8.1 g, 18.0 mmol) in MeCN (100 mL) at RT. The reaction mixture was heated to 50° C. and maintained at this temperature for 3 h. The reaction mixture was cooled to RT and concentrated in vacuo to provide a solid. The solid was slurried with EtOAc (200 mL), collected by filtration, washed sequentially with EtOAc and Et$_2$O, and dried under vacuum at 45° C. for 70 h. The resulting white solid was suspended in water (100 mL), and triethylamine (10.1 mL, 72.0 mmol) and BOC$_2$O (4.81 g, 21.6 mmol) were added at RT. The reaction mixture was maintained at RT with stirring for 16 h. The reaction mixture was acidified to pH 5 with 10% aqueous citric acid and washed with EtOAc (2×100 mL). The separated organic phase was washed with water (75 mL), dried over Na$_2$SO$_4$, filtered, and concentrated in vacuo to yield the title compound as a white waxy solid (4.6 g, 77% over two steps). LCMS m/z 327.0 (M−1).

N-(tert-Butoxycarbonyl)-3-(3-cyanophenoxy)-6-nitro-L-phenylalanine (86) A mixture of N-(tert-butoxycarbonyl)-3-fluoro-6-nitro-L-phenylalanine (85) (1.6 g, 4.8 mmol), 3-cyanophenol (1.7 g, 14.5 mmol), and cesium carbonate (4.7 g, 14.5 mmol) in anhydrous MeCN was heated to 75° C. for 22 h. The reaction mixture was cooled to RT and concentrated. The resulting residue was suspended in water (40 mL) and 1 N aqueous HCl was added at 0° C. to adjust the pH to ~4-5. The aqueous mixture was extracted with EtOAc (2×50 mL), and the combined organic phases were dried over Na$_2$SO$_4$, filtered, and concentrated in vacuo. Purification of the crude residue by silica gel chromatography (Eluant: EtOAc) provided a brown oil that was resubjected to column chromatography (Gradient: 0% to 50% EtOAc in hexanes) to afford the title compound as a white solid (1.6 g, 79%). LCMS m/z 426.1 (M−1).

3-(3-Cyanophenoxy)-6-nitro-L-phenylalanine (87) N-(tert-Butoxycarbonyl)-3-(3-cyanophenoxy)-6-nitro-L-phenylalanine (86) (1.6 g, 3.8 mmol) was dissolved in a solution of HCl in dioxane (4 N, 70 mL). After 1.5 h, the reaction mixture was diluted with Et$_2$O (200 mL) and filtered. The solid was washed with Et$_2$O and dried at 50° C. under vacuum to afford the title compound as a white solid (1.3 g, 97%). LCMS m/z 328.1 (M+1). $^1$H NMR (400 MHz, CD$_3$OD) δ 3.41 (dd, J=13.8, 7.5 Hz, 1H), 3.66 (dd, J=13.8, 7.4 Hz, 1H), 4.34 (t, J=7.4 Hz, 1H), 7.12-7.15 (m, 2H), 7.43-7.49 (m, 1H), 7.52-7.54 (m, 1H), 7.63-7.68 (m, 2H), 8.22-8.25 (m, 1H).

tert-Butyl [(3S)-1-[(tert-butoxycarbonyl)oxy]-6-(3-cyanophenoxy)-2-oxo-1,2,3,4-tetrahydroquinolin-3-yl]carbonate (88) Sodium acetate trihydrate (4.9 g, 36.3 mmol) was added to a 0° C. solution of 3-(3-cyanophenoxy)-6-nitro-L-phenylalanine (87) (1.3 g, 3.6 mmol) in THF (50 mL) and MeOH (50 mL). The mixture was stirred until all of the salts dissolved, and tin(II) chloride dihydrate (4.2 g, 18.1 mmol) was added. The reaction suspension was stirred at 0° C. for 6 h. Triethylamine (5.1 mL, 36.3 mmol) and BOC$_2$O (1.9 g, 8.7 mmol) were added and the mixture was allowed to stir for 18 h at RT. The reaction mixture was concentrated in vacuo, and the resulting residue was slurried in EtOAc. Insoluble solids were filtered off and washed with EtOAc, and the combined EtOAc fractions were washed with water and concentrated in vacuo. The resulting residue was purified by silica gel chromatography (Gradient: 0% to 50% EtOAc in heptane) to afford the title compound as a white solid (1.1 g, 61%). LCMS m/z 496.2 (M+1). $^1$H NMR (400 MHz, CDCl$_3$) δ 1.47 (s, 9H), 1.58 (br s, 9H), 2.98 (br dd, J=14, 14 Hz, 1H), 3.41 (v br d, J=14 Hz, 1H), 4.51-4.60 (m, 1H), 5.59 (br s, 1H), 6.91 (br s, 1H), 6.97 (br dd, J=8.5, 2.6 Hz, 1H), 7.0-7.2 (v br s, 1H), 7.19-7.25 (m, 2H), 7.38-7.47 (m, 2H).

3-{[(3S)-3-Amino-1-hydroxy-2-oxo-1,2,3,4-tetrahydroquinolin-6-yl]oxy}benzonitrile, hydrochloride salt (89) tert-Butyl [(3S)-1-[(ted-butoxycarbonyl)oxy]-6-(3-cyanophenoxy)-2-oxo-1,2,3,4-tetrahydroquinolin-3-yl]carbamate (88) was dissolved in a solution of HCl in dioxane (4 N, 70 mL). After 41 h, the reaction mixture was concentrated to a volume of 10 mL, and the resulting white solid was collected by filtration. The solid was washed with dioxane (3×10 mL) and Et$_2$O (3×10 mL) and dried under vacuum at 45° C. for 3 h. The solid was washed again with ether (3×10 mL) and dried under vacuum at 50° C. for 2 h. The washing (ether) and drying procedure was repeated three times in order to remove all residual dioxane, affording the title compound as a white solid (610 mg, 84%); LCMS m/z 296.0 (M+1). $^1$H NMR (400 MHz, CD$_3$OD) δ 3.18 (dd, half of ABX pattern, J=14.8, 14.4 Hz, 1H), 3.26 (dd, half of ABX pattern, J=15.0, 6.7 Hz, 1H), 4.38 (dd, J=14.4, 6.7 Hz, 1H), 7.07-7.12 (m, 2H), 7.28-7.29 (m, 1H), 7.31 (ddd, J=8.2, 2.5, 1.1 Hz, 1H), 7.46 (d, J=8.6 Hz, 1H), 7.46-7.49 (m, 1H), 7.54 (br dd, J=8, 8 Hz, 1H).

Example 71

Synthesis of (3S)-3-amino-1-hydroxy-6-phenoxy-3,4-dihydroquinolin-2(1H)-one, hydrochloride salt (93)

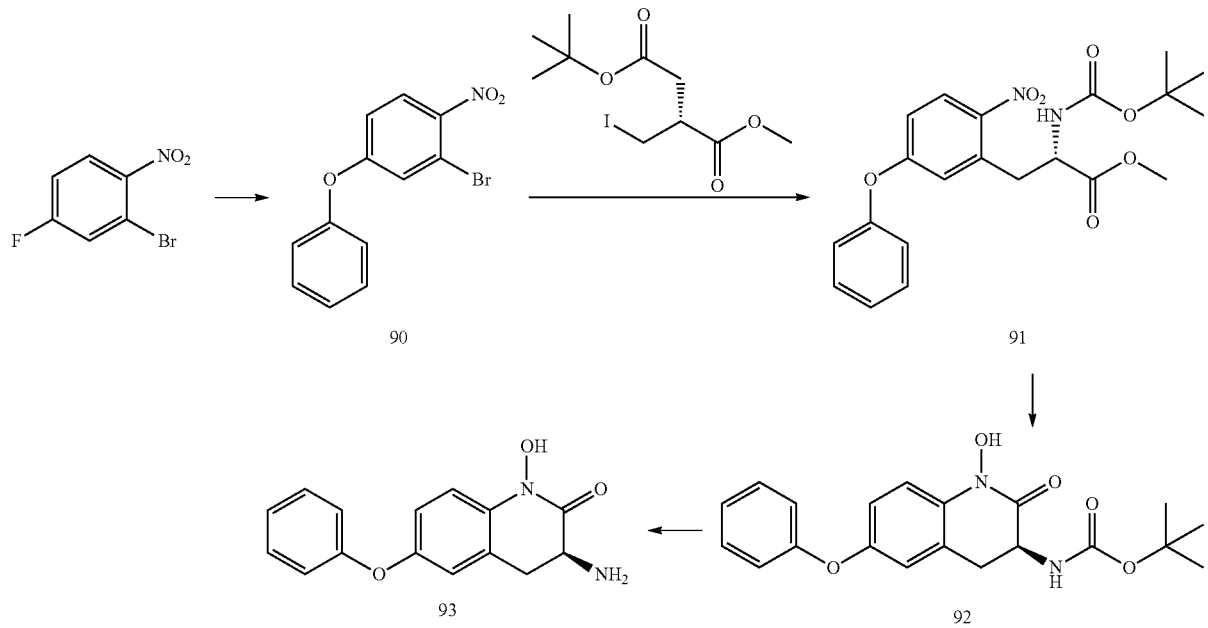

2-Bromo-1-nitro-4-phenoxybenzene (90) Phenol (11.1 g, 118 mmol) was added to a suspension of $Cs_2CO_3$ (46.2 g, 142 mmol) in MeCN (295 mL). The resulting solution was stirred at RT for 10 min, then 2-bromo-4-fluoronitrobenzene (26.0 g, 118 mmol) was added, and the reaction mixture was heated to 50° C. for 65 h. The reaction mixture was cooled to RT and filtered to remove $Cs_2CO_3$. The filtrate was concentrated in vacuo, and the resulting residue was dissolved in EtOAc (150 mL) and washed with aqueous sodium hydroxide solution (1 N, 250 mL), water (2×250 mL), and saturated aqueous sodium chloride solution (250 mL). The separated organic phase was dried over $Na_2SO_4$, filtered, and concentrated in vacuo. Purification by silica gel chromatography (Eluant: heptane) provided the title compound as a pale yellow oil (32.7 g, 94%). $^1$H NMR (400 MHz, $CDCl_3$) δ 6.97 (dd, J=9.1, 2.6 Hz, 1H), 7.08-7.12 (m, 2H), 7.26-7.31 (m, 2H), 7.43-7.49 (m, 2H), 7.95 (d, J=9.1 Hz, 1H).

Methyl N-(tert-butoxycarbonyl)-2-nitro-5-phenoxy-L-phenylalaninate (91) Freshly distilled DMF (45 mL) was added to Zn powder (20.0 g, 306 mmol) under $N_2$. Trimethylsilyl chloride (8.0 mL, ~0.2 eq.) was added at RT and the resulting suspension was stirred vigorously for 35 min. The resulting pale orange supernatant was removed via syringe. The activated Zn was washed with DMF (2×30 mL). After removal of the DMF, the activated zinc was dried under vacuum using a heat gun. Methyl N-(tert-butoxycarbonyl)-3-iodo-L-alaninate (37.0 g, 112 mmol) was freshly recrystallized from petroleum ether, dried in vacuo, and dissolved in freshly distilled DMF (93 mL), and the solution was added to the activated zinc at 0° C. After 5 min, the cooling bath was removed. The reaction mixture was stirred for 20 min in a RT water bath, at which time TLC analysis indicated disappearance of the starting iodide. The grayish supernatant was transferred via syringe into a dry flask under $N_2$, and the remaining zinc metal was washed with DMF (20 mL). To the flask containing the combined DMF fractions was added sequentially a solution of 2-bromo-1-nitro-4-phenoxybenzene (90) (30.0 g, 102 mmol) in DMF (18 mL), $Pd(OAc)_2$ (1.1 g, 5.1 mmol), then dicyclohexylphosphino-2',4',6'-triisopropyl-1,1'-biphenyl (4.9 g, 10.2 mmol). The resulting brown solution was stirred at RT, and the solution turned red within 1 h. The reaction mixture was maintained at RT for 16 h. The reaction mixture was poured into EtOAc (400 mL), and the resulting suspension was filtered through Celite. The filtrate was washed with water (2×400 mL) and saturated aqueous sodium chloride solution (400 mL), and the separated aqueous phase was washed with EtOAc (2×150 mL). The combined organic extracts were dried over $Na_2SO_4$, filtered, and concentrated in vacuo. The crude residue was purified by silica gel chromatography (Gradient: 0% to 25% EtOAc in heptane) to provide the title compound as a pale yellow solid (27.9 g, 66%). LCMS m/z 415.1 (M−1). $^1$H NMR (500 MHz, $CDCl_3$) δ 1.38 (s, 9H), 3.21 (dd, J=13, 9 Hz, 1H), 3.57 (dd, J=13.3, 5.2 Hz, 1H), 3.73 (s, 3H), 4.65-4.72 (m, 1H), 5.17 (br d, J=8 Hz, 1H), 6.87-6.92 (m, 2H), 7.07-7.10 (m, 2H), 7.24-7.27 (m, 1H), 7.44 (dd, J=7.9, 7.9 Hz, 2H), 8.03 (d, J=8.8 Hz, 1H).

tert-Butyl [(3S)-1-hydroxy-2-oxo-6-phenoxy-1,2,3,4-tetrahydroquinolin-3-yl]carbamate (92) In three equal batches, methyl N-(tert-butoxycarbonyl)-2-nitro-5-phenoxy-L-phenylalaninate (91) (9.33 g, 22.3 mmol) was dissolved in pyridine (250 mL) in a Parr bottle and Pt/C (5% w/w dry catalyst, 4.4 g, 1.1 mmol) was added. The reaction mixture was placed under $H_2$ atmosphere (30 psi) and shaken for 3 h. The combined reaction mixtures were filtered through Celite with EtOAc washing. The filtrate was concentrated in vacuo and the crude residue was purified by silica gel chromatography (Gradient: 20% to 50% EtOAc in heptane) to provide the title compound as a solid (19.2 g, 77%). LCMS m/z 369.1 (M−1). $^1$H NMR (400 MHz, CD$_3$OD) δ 1.47 (s, 9H), 2.96-3.06 (m, 2H), 4.39 (dd, J=12, 8 Hz, 1H), 6.89-6.99 (m, 4H), 7.09 (tt, J=7.4, 1.1 Hz, 1H), 7.31-7.37 (m, 3H).

(3S)-3-Amino-1-hydroxy-6-phenoxy-3,4-dihydroquinolin-2(1H)-one, hydrochloride salt (93) In two equal batches, tert-butyl [(3S)-1-hydroxy-2-oxo-6-phenoxy-1,2,3,4-tetrahydroquinolin-3-yl]carbamate (92) (8.6 g, 23.2 mmol) was added to a 0° C. solution of HCl in dioxane (4 N, 100 mL) with stirring. After 5 min, the ice bath was removed and the reaction mixture was maintained at RT for 1 h. Et$_2$O (800 mL) was added, the batches were combined, and precipitate was collected by filtration. The precipitate was washed with Et$_2$O and residual solvent was removed under vacuum. The resulting pale pink solid was slurried in cold MeOH (100 mL) and filtered, and the resulting solid was washed with Et$_2$O. The solid was dried under vacuum at 45° C. for 45 h to yield the title compound as a white solid (13.1 g, 92%). LCMS m/z 271.4 (M+1). $^1$H NMR (400 MHz, CD$_3$OD) δ 3.16 (br dd, J=14.8, 14.4 Hz, 1H), 3.23 (dd, J=15.0, 6.8 Hz, 1H), 4.35 (dd, J=14.2, 6.7 Hz, 1H), 6.97-7.02 (m, 4H), 7.13 (tt, J=7.4, 1.1 Hz, 1H), 7.33-7.40 (m, 3H).

Example 72

Synthesis of (3S)-3-amino-1-[(dimethylcarbamoyl)oxy]-6-phenoxy-3,4-dihydroquinolin-2(1H)-one (94)

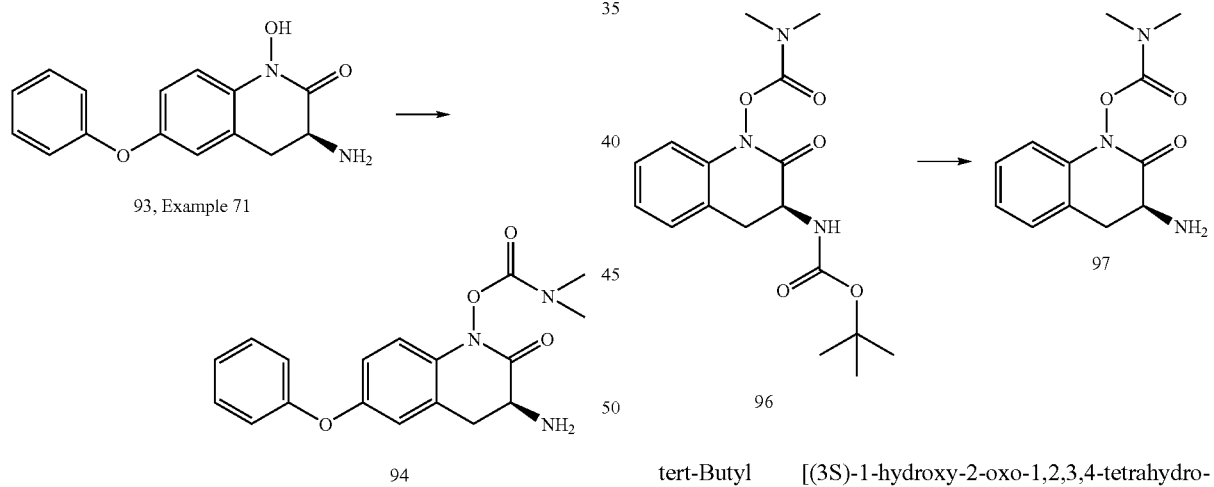

Dimethylcarbamyl chloride (37 μL, 0.39 mmol) was added to a solution of (3S)-3-amino-1-hydroxy-6-phenoxy-3,4-dihydroquinolin-2(1H)-one, hydrochloride salt (93, Example 71) (100 mg, 0.33 mmol) in pyridine (2 mL). The reaction mixture was maintained at RT for 1.5 h, then concentrated in vacuo; the resulting residue was diluted with EtOAc (20 mL) and water (10 mL). The separated organic phase was washed with water (10 mL), dried over Mg$_2$SO$_4$, filtered, and concentrated in vacuo to provide the title compound as an oil (72 mg, 65%). LCMS m/z 253.0 [(M-dimethyl carbamic acid)+1]. $^1$H NMR (400 MHz, CD$_3$OD) δ 2.94-3.02 (m, 1H), 3.02 (br s, 3H), 3.08 (dd, half of ABX pattern, J=15.5, 6.4 Hz, 1H), 3.17 (br s, 3H), 3.78 (dd, J=13.3, 6.3 Hz, 1H), 6.90-7.00 (m, 5H), 7.11 (ddt, J=7.7, 7.1, 1.1 Hz, 1H), 7.32-7.37 (m, 2H).

Example 73

Synthesis of (3S)-3-amino-1-[(dimethylcarbamoyl)oxy]-3,4-dihydroquinolin-2(1H)-one, hydrochloride salt (97)

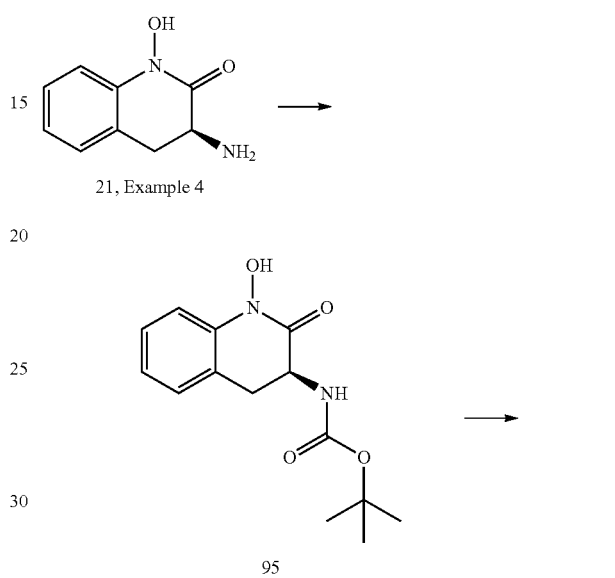

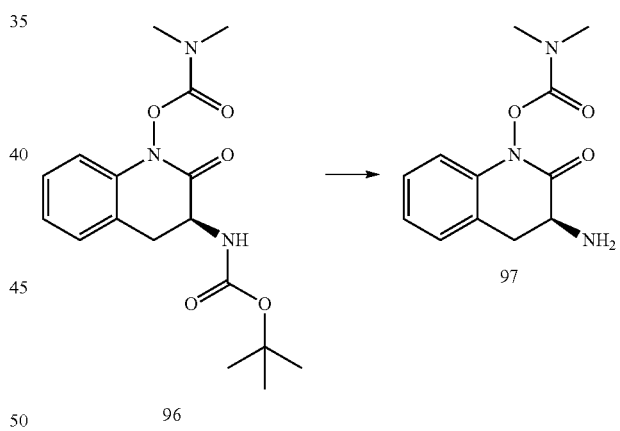

tert-Butyl [(3S)-1-hydroxy-2-oxo-1,2,3,4-tetrahydroquinolin-3-yl]carbamate (95) (3S)-3-Amino-1-hydroxy-3,4-dihydroquinolin-2(1H)-one (21, Example 4) (1.023 g, 5.742 mmol) was suspended in THF (16 mL) and water (16 mL). After addition of sodium carbonate (1.21 g, 14.4 mmol) and BOC$_2$O (2.76 g, 12.6 mmol), the reaction was allowed to stir for 18 h at RT. BOC$_2$O (0.69 g, 3.2 mmol) was again added to the reaction; after 1 h, the mixture was partitioned between EtOAc (20 mL) and water (10 mL), and the aqueous layer was extracted with EtOAc (3×15 mL). The combined organic layers were dried over sodium sulfate, filtered and concentrated in vacuo. The resulting yellow oil was dissolved in THF (18 mL), treated with water (18 mL) and acetic acid (1.3 mL, 23 mmol) and heated to 50° C. for 66 h. After cooling to RT, the reaction mixture was diluted with water and extracted with EtOAc. The combined organic layers were washed with water and saturated aqueous sodium chloride solution, then dried over magnesium sulfate, filtered and concentrated under reduced pressure. The product was obtained as a light pink solid (1.00 g, 63%). LCMS m/z 277.5 (M−1). $^1$H NMR (400 MHz, CDCl$_3$) δ 1.47 (s, 9H), 2.90 (br dd, J=15, 14 Hz, 1H), 3.35-3.46 (m, 1H), 4.46-4.57 (m, 1H), 5.47 (br s, 1H), 7.09 (br dd, J=7, 7 Hz, 1H), 7.20 (br d, J=7.4 Hz, 1H), 7.30-7.39 (m, 2H), 8.85 (br s, 1H).

tert-Butyl {(3S)-1-[(dimethylcarbamoyl)oxy]-2-oxo-1,2,3,4-tetrahydroquinolin-3-yl}carbamate (96) A solution of tert-butyl [(3S)-1-hydroxy-2-oxo-1,2,3,4-tetrahydroquinolin-3-yl]carbamate (95) (201.3 mg, 0.723 mmol) in acetone (2 mL) was treated with potassium carbonate (150 mg, 1.08 mmol) and dimethylcarbamyl chloride (98%, 0.102 mL, 1.09 mmol). The reaction was stirred at 70° C. for 42 h, then cooled and concentrated in vacuo. The residue was partitioned between EtOAc (5 mL), and water (5 mL), and the aqueous layer was extracted with EtOAc (3×5 mL). The combined organic layers were washed with water (5 mL), dried over sodium sulfate, filtered and concentrated in vacuo. Purification by chromatography on silica gel (Gradient: 0% to 45% EtOAc in heptane) provided the product (112.6 mg, 45%). APCI m/z 372.0 (M+Na). $^1$H NMR (400 MHz, CDCl$_3$) δ 1.48 (s, 9H), 2.96-3.06 (v br m, 1H), 3.03 (br s, 3H), 3.18 (br s, 3H), 3.38-3.47 (m, 1H), 4.53-4.62 (m, 1H), 5.54 (br s, 1H), 6.93-7.03 (v br s, 1H), 7.08 (br dd, J=7.6, 7.6 Hz, 1H), 7.21-7.29 (m, 2H).

(3S)-3-Amino-1-[(dimethylcarbamoyl)oxy]-3,4-dihydroquinolin-2(1H)-one, hydrochloride salt (97) tert-Butyl {(3S)-1-[(dimethylcarbamoyl)oxy]-2-oxo-1,2,3,4-tetrahydroquinolin-3-yl}carbamate (96) was deprotected using the conditions described for synthesis of 3-{[(3S)-3-amino-1-hydroxy-2-oxo-1,2,3,4-tetrahydroquinolin-6-yl]oxy}benzonitrile, hydrochloride salt (89) in Example 70. The product was obtained as a solid, which by NMR contained residual 1,4-dioxane (107.0 mg, assumed quantitative). LCMS m/z 161.3 [(M−dimethylcarbamic acid)+1]. $^1$H NMR (400 MHz, CD$_3$OD) δ 3.03 (br s, 3H), 3.19 (br s, 3H), 3.57-3.60, 3.64-3.69 and 3.72-3.76 (multiplets, total 2H), 4.45-4.51 (m, 1H), 7.10 (v br s, 1H), 7.19 (ddd, J=7.5, 7.5, 1.0 Hz, 1H), 7.35-7.41 (m, 2H).

Example 74

Synthesis of (3S)-3-amino-1-hydroxy-8-(morpholin-4-ylmethyl)-3,4-dihydroquinolin-2(1H)-one, trifluoroacetic acid salt (104)

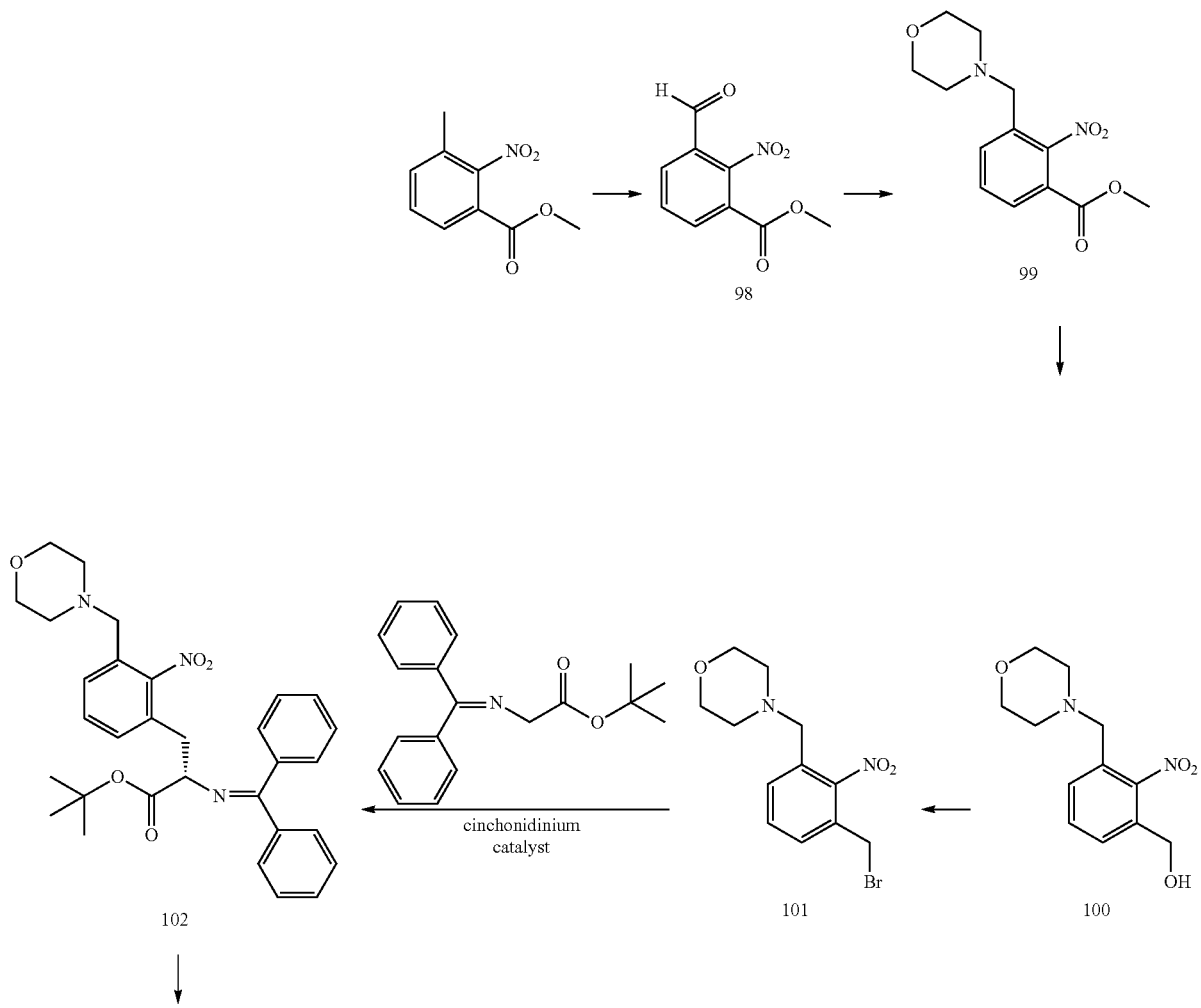

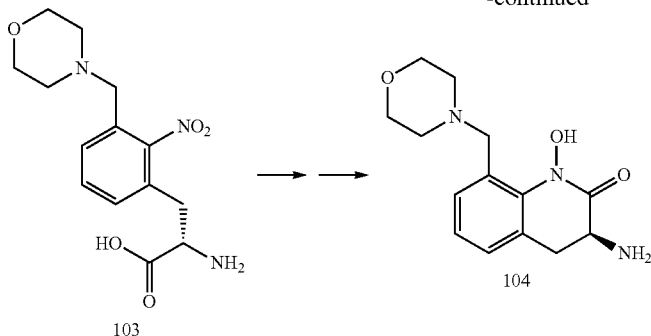

Methyl 3-formyl-2-nitrobenzoate (98) N,N-Dimethylformamide dimethyl acetal (10 g, 84 mmol) and methyl 3-methyl-2-nitrobenzoate (8.0 g, 41 mmol) were combined and heated to 120° C. for 42 h. After cooling, the mixture was concentrated under reduced pressure to provide methyl 3-[(E)-2-(dimethylamino)vinyl]-2-nitrobenzoate (9.0 g, 88%), which was dissolved in a 1:1 mixture of water and THF. After addition of sodium periodate (99%, 23.3 g, 108 mmol), the reaction was allowed to stir for 18 h, then was filtered. The filtrate was washed with water and with saturated aqueous sodium chloride solution, then dried over sodium sulfate. Filtration and removal of solvent under reduced pressure provided a residue, which was purified using silica gel chromatography (Gradient: 0% to 80% EtOAc in heptane) to provide the product as a solid (2.2 g, 29%). $^1$H NMR (500 MHz, CDCl$_3$) δ 3.96 (s, 3H), 7.78 (ddd, J=7.8, 7.8, 0.6 Hz, 1H), 8.19 (dd, J=7.8, 1.5 Hz, 1H), 8.29 (dd, J=7.8, 1.6 Hz, 1H), 9.99 (d, J=0.5 Hz, 1H).

Methyl 3-(morpholin-4-ylmethyl)-2-nitrobenzoate (99) Morpholine (1.03 mL, 11.6 mmol) and a few drops of acetic acid were added to a solution of methyl 3-formyl-2-nitrobenzoate (98) (1.34 g, 6.41 mmol) in 1,2-dichloroethane, and the mixture was stirred for 4 h. Sodium triacetoxyborohydride (5.72 g, 25.6 mmol) was added, and the reaction was allowed to stir for 18 h at RT. Solvents were removed in vacuo, and the residue was partitioned between EtOAc and water. The organic layer was washed with water and with saturated aqueous sodium chloride solution, and concentrated under reduced pressure to provide the product as a gum (1.4 g, 78%). LCMS m/z 280.9 (M+1). $^1$H NMR (500 MHz, CDCl$_3$) δ 2.39-2.43 (m, 4H), 3.56 (s, 2H), 3.64-3.68 (m, 4H), 3.90 (s, 3H), 7.53 (dd, J=7.8, 7.7 Hz, 1H), 7.73 (br d, J=7.7 Hz, 1H), 7.90 (dd, J=7.8, 1.3 Hz, 1H).

[3-(Morpholin-4-ylmethyl)-2-nitrophenyl]methanol (100) A solution of methyl 3-(morpholin-4-ylmethyl)-2-nitrobenzoate (99) (1.6 g, 5.7 mmol) in THF was added to a 0° C. suspension of lithium borohydride (691 mg, 28.5 mmol) in THF, followed by sufficient MeOH to provide a 1:6 ratio with the THF. The reaction was allowed to warm to RT and stir for 18 h, at which time it was quenched with aqueous ammonium chloride solution and extracted with EtOAc. The combined organic layers were washed with water and with saturated aqueous sodium chloride solution, then concentrated in vacuo. Silica gel chromatography (0% to 80% EtOAc in heptane) provided the product as a gum (1.3 g, 90%). LCMS m/z 253.0 (M+1). $^1$H NMR (500 MHz, CDCl$_3$) δ 2.38-2.41 (m, 4H), 3.62 (s, 2H), 3.62-3.66 (m, 4H), 4.68 (s, 2H), 7.40 (br d, J=7.3 Hz, 1H), 7.46 (dd, J=7.7, 7.6 Hz, 1H), 7.52 (br d, J=7.6 Hz, 1H).

4-[3-(Bromomethyl)-2-nitrobenzyl]morpholine (101) [3-(Morpholin-4-ylmethyl)-2-nitrophenyl]nethanol (100) was converted to the title product using the method described for bromination of (5-benzyl-2-nitrophenyl)methanol (77) in Example 68. The product was obtained as a gum (3.33 mmol, 68%). LCMS m/z 316.9 (M+1). $^1$H NMR (500 MHz, CDCl$_3$) δ 2.38-2.42 (m, 4H), 3.60 (s, 2H), 3.63-3.66 (m, 4H), 4.50 (s, 2H), 7.42-7.48 (m, 3H).

tert-Butyl N-(diphenylmethylene)-3-(morpholin-4-ylmethyl)-2-nitro-L-phenylalaninate (102) 4-[3-(Bromomethyl)-2-nitrobenzyl]morpholine (101) was converted to the product using the method for preparation of tert-butyl N-(diphenylmethylene)-2-methoxy-6-nitro-L-phenylalaninate (58) described in Example 12. The product was obtained as a thick semi-solid (1.12 g, 78%). LCMS m/z 530.3 (M+1). $^1$H NMR (500 MHz, CDCl$_3$) δ 1.44 (s, 9H), 2.30-2.38 (m, 4H), 3.18-3.26 (m, 2H), 3.41 (d, J=14.8 Hz, 1H), 3.56 (d, J=13.7 Hz, 1H), 3.58-3.66 (m, 4H), 4.22 (dd, J=8.5, 4.8 Hz, 1H), 6.70 (br d, J=6.8 Hz, 2H), 7.23-7.41 (m, 9H), 7.58-7.62 (m, 2H).

3-(Morpholin-4-ylmethyl)-2-nitro-L-phenylalanine (103) Deprotection of tert-butyl N-(diphenylmethylene)-3-(morpholin-4-ylmethyl)-2-nitro-L-phenylalaninate (102) was effected in the same way as that described for tert-butyl 3-benzyl-N-(diphenylmethylene)-6-nitro-L-phenylalaninate (79) in Example 68. The product was obtained as a solid (620 mg, 95%). LCMS m/z 310.0 (M+1).

(3S)-3-Amino-1-hydroxy-8-(morpholin-4-ylmethyl)-3,4-dihydroquinolin-2(1H)-one, trifluoroacetic acid salt (104) 3-(Morpholin-4-ylmethyl)-2-nitro-L-phenylalanine (103) was converted to the title product using the methods described for transformation of 2-amino-3-(5-chloro-3-methyl-2-nitrophenyl)propanoic acid, hydrochloride salt (40) to 3-amino-6-chloro-1-hydroxy-8-methyl-3,4-dihydroquinolin-2(1H)-one (42) in Example 8. In this case, the product did not require chromatographic purification. The product was obtained as a gum (5 mg, 19% over 2 steps). LCMS m/z 278.1 (M+1). $^1$H NMR (500 MHz, CD$_3$OD) δ 3.22 (br dd, half of ABX pattern, J=15, 14 Hz, 1H), 3.28 (dd, half of ABX pattern, J=14.9, 6.1 Hz, 1H, assumed; partially obscured by solvent peak), 3.32-3.46 (br s, 4H), 3.78-4.04 (br s, 4H), 4.36 (dd, J=14.4, 6.4 Hz, 1H), 4.67 (AB quartet, $J_{AB}$=13.2 Hz, $\Delta_{AB}$=72.3 Hz, 2H), 7.26 (dd, J=7.8, 7.6 Hz, 1H), 7.45-7.49 (m, 2H).

Example 75

Synthesis of (3S)-3-amino-6-benzyl-1-hydroxy-7-methoxy-3,4-dihydroquinolin-2(1H)-one, hydrochloride salt (109)

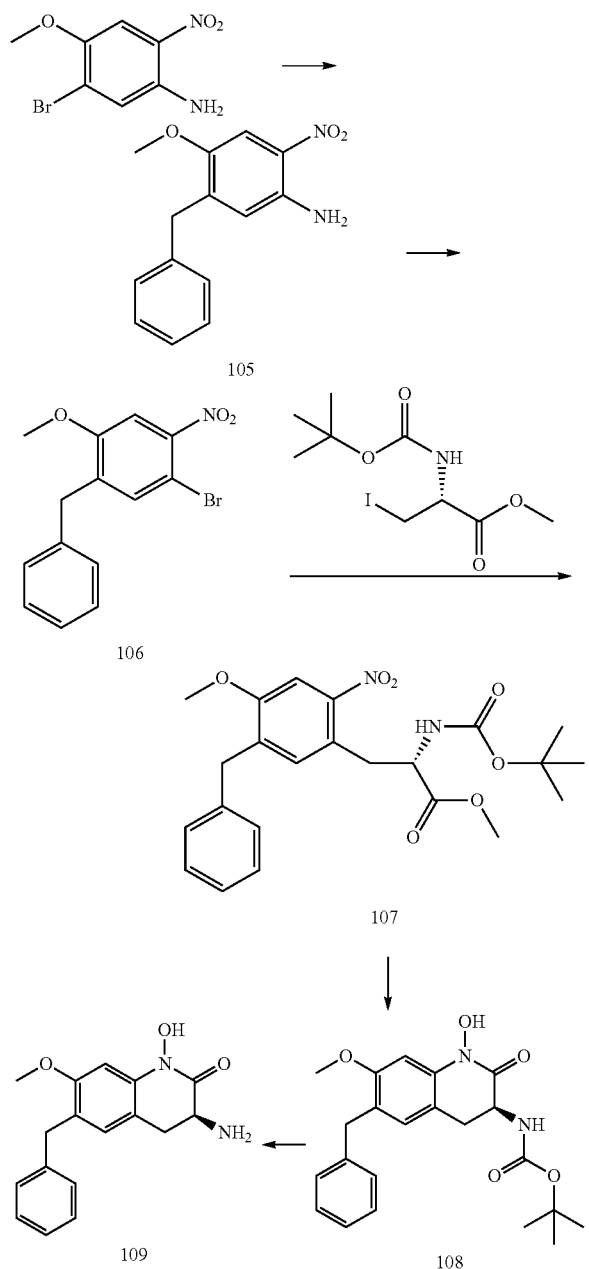

5-Benzyl-4-methoxy-2-nitroaniline (105) Benzylzinc chloride (0.5 M solution in THF, 10.1 mL, 5.05 mmol) was added to a suspension of 5-bromo-4-methoxy-2-nitroaniline (see L. A. Hasvold et al., *Bioorg. Med. Chem. Lett.* 2008, 18, 2311-2315) (1.26 g, 5.10 mmol), palladium(II) acetate (47.1 mg, 0.210 mmol) and 2-dicyclohexylphosphino-2',6'-dimethoxybiphenyl (172 mg, 0.420 mmol) in THF (4.2 mL) that had been stirred for 5 min. The resulting solution was stirred for 18 h at RT. After addition of saturated aqueous ammonium chloride solution (20 mL), the mixture was extracted with EtOAc (3×3 mL), and the combined organic layers were dried over sodium sulfate, filtered and concentrated in vacuo. Silica gel chromatography (Gradient: 0% to 50% EtOAc in heptane) provided the product as an orange solid (940 mg, 71%). $^1$H NMR (500 MHz, CDCl$_3$) δ 3.83 (s, 3H), 3.93 (s, 2H), 5.84 (br s, 2H), 6.42 (s, 1H), 7.20 (br d, J=7.4 Hz, 2H), 7.23-7.27 (m, 1H), 7.32 (br dd, J=7.6, 7.1 Hz, 2H), 7.52 (s, 1H).

1-Benzyl-5-bromo-2-methoxy-4-nitrobenzene (106) tert-Butyl nitrite (557 mg, 5.40 mmol) was added to a solution of copper(II) bromide (1.77 g, 7.92 mmol) in MeCN (8 mL) and the mixture was heated to 60° C. A solution of 5-benzyl-4-methoxy-2-nitroaniline (105) (930 mg, 3.60 mmol) in MeCN (12 mL) was added drop-wise, and the reaction was stirred for 10 min. It was then poured into aqueous hydrochloric acid (2 N, 100 mL) and extracted with EtOAc (2×100 mL). The combined organic layers were washed with saturated aqueous sodium chloride solution (200 mL), dried over sodium sulfate, filtered and concentrated in vacuo. Purification via silica gel chromatography (Eluant: hexanes) provided the product as a white solid (1.06 g of roughly 60% purity as assessed by $^1$H NMR, estimated yield 55%). $^1$H NMR (500 MHz, CDCl$_3$) δ 3.90 (s, 3H), 3.98 (s, 2H), 7.19 (br d, J=8 Hz, 2H), 7.23-7.27 (m, 1H), 7.32 (br dd, J=7.5, 7.5 Hz, 2H), 7.37 (s, 1H), 7.41 (s, 1H).

Methyl 3-benzyl-N-(tert-butoxycarbonyl)-O-methyl-6-nitro-L-tyrosinate (107) 1-Benzyl-5-bromo-2-methoxy-4-nitrobenzene (106) was converted to the product using the method described for conversion of 3-bromo-2-nitro-5-phenoxypyridine (64) to methyl N-(tert-butoxycarbonyl)-3-(2-nitro-5-phenoxypyridin-3-yl)-L-alaninate (65) in Example 66. The product was obtained as a gum (368 mg, 44%). LCMS m/z 445.0 (M+1). $^1$H NMR (500 MHz, CDCl$_3$) δ 1.38 (br s, 9H), 3.18 (dd, J=13.5, 8.0 Hz, 1H), 3.43 (dd, J=13.7, 5.6 Hz, 1H), 3.65 (s, 3H), 3.88 (br s, 3H), 3.98 (br s, 2H), 4.59-4.65 (m, 1H), 5.12 (br d, J=8.2 Hz, 1H), 7.02 (br s, 1H), 7.18 (br d, J=8 Hz, 2H), 7.20-7.24 (m, 1H), 7.29 (br dd, J=7.6, 7.2 Hz, 2H), 7.49 (br s, 1H).

tert-Butyl [(3S)-6-benzyl-1-hydroxy-7-methoxy-2-oxo-1,2,3,4-tetrahydroquinolin-3-yl]carbamate (108) Using the method described for preparation of tert-butyl [(3S)-1-hydroxy-2-oxo-6-(phenylsulfonyl)-1,2,3,4-tetrahydroquinolin-3-yl]carbamate (71) from methyl N-(tert-butoxycarbonyl)-2-nitro-5-(phenylsulfonyl)-L-phenylalaninate (70) in Example 67, methyl 3-benzyl-N-(tert-butoxycarbonyl)-O-methyl-6-nitro-L-tyrosinate (107) was converted to the product, which was obtained as a light purple solid (86 mg, 27%). LCMS m/z 399.1 (M+1). $^1$H NMR (500 MHz, CDCl$_3$) δ 1.45 (s, 9H), 2.75 (br dd, J=15, 14 Hz, 1H), 3.21-3.29 (m, 1H), 3.87 (s, 3H), 3.92 (AB quartet, $J_{AB}$=15.3 Hz, $\Delta_{AB}$=10.6 Hz, 2H), 4.42-4.51 (m, 1H), 5.42 (br s, 1H), 6.85 (s, 1H), 6.91 (s, 1H), 7.18-7.22 (m, 3H), 7.27-7.31 (m, 2H), 8.79 (br s, 1H).

(3S)-3-Amino-6-benzyl-1-hydroxy-7-methoxy-3,4-dihydroquinolin-2(1H-one, hydrochloride salt (109) The free base of the title product was synthesized from tert-butyl [(3S)-6-benzyl-1-hydroxy-7-methoxy-2-oxo-1,2,3,4-tetrahydroquinolin-3-yl]carbamate (108) using the deprotection procedure employed in the final step of the synthesis of (3S)-3-amino-1-hydroxy-6-phenoxy-3,4-dihydro-1,8-naphthyridin-2(1H)-one (67) in Example 66. Preparation of the hydrochloride salt was carried out by mixing the free base of the product with dichloromethane (2 mL) and adding MeOH (2 drops). To this solution was added a solution of hydrogen chloride (2 N in diethyl ether, 3 mL); solvents were removed under reduced pressure to yield the title product as a solid (60 mg, 85%). Characterization data was obtained on the neutral compound. LCMS m/z 299.0 (M+1). $^1$H NMR (500 MHz, CDCl$_3$) δ 2.58-2.91 (br m, 2H), 3.45 (br s, 2H), 3.4-3.69 (br m, 1H), 3.82 (br s, 3H), 6.68-6.81 (br m, 2H), 7.13-7.20 (m, 3H), 7.22-7.26 (m, 2H).

Example 76
Synthesis of (3S)-3-amino-1-hydroxy-6-{[methyl(phenyl)amino]methyl}-3,4-dihydroquinolin-2(1H)-one (116)
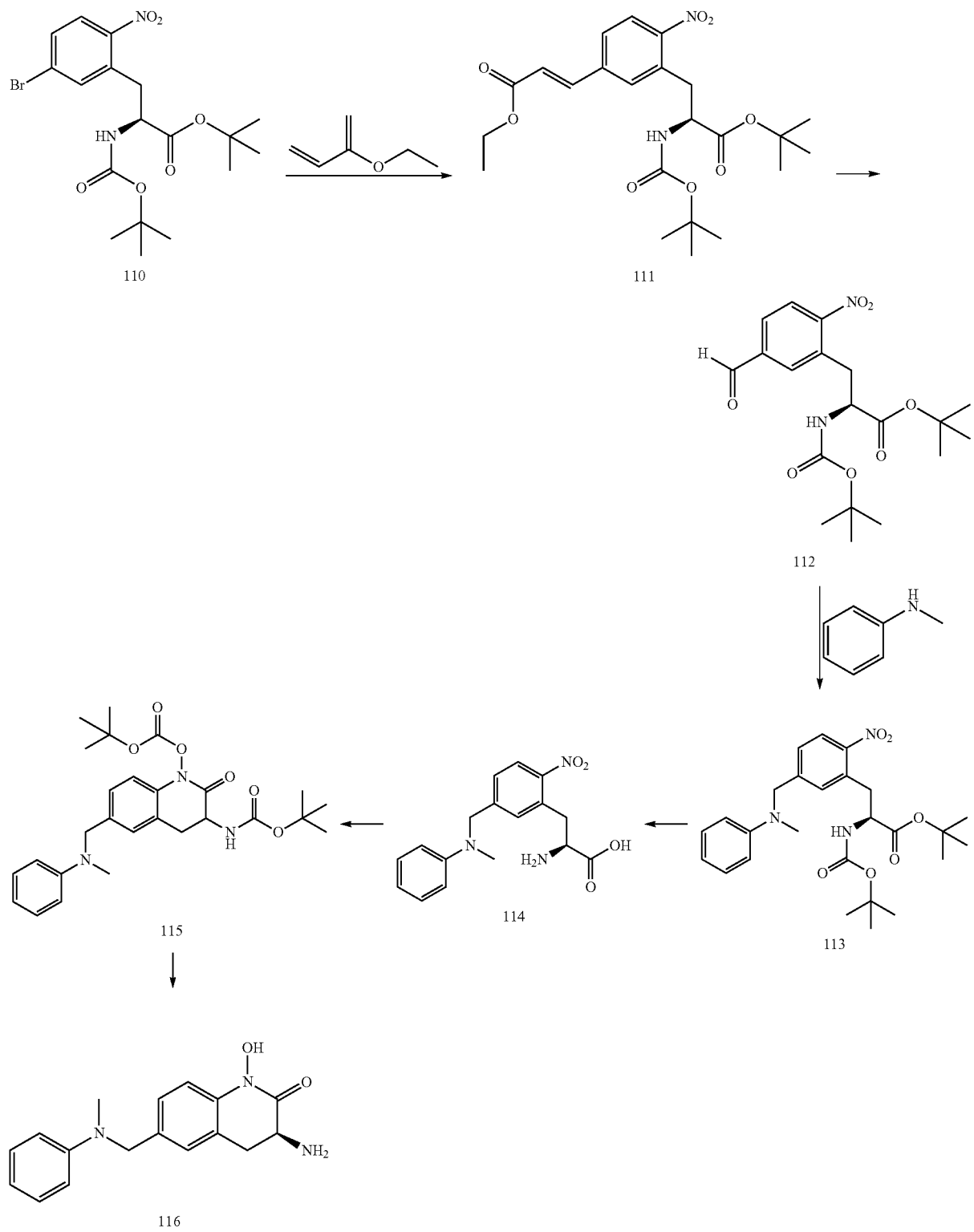

tert-Butyl N-(tert-butoxycarbonyl)-3-[(1E)-3-ethoxy-3-oxoprop-1-en-1-yl]-6-nitro-L-phenylalaninate (111) Tetrkis(triphenylphosphine)palladium(0) (1.0 g) was added to a mixture of tert-butyl 3-bromo-N-(tert-butoxycarbonyl)-6-nitro-L-phenylalaninate (110) (prepared from 4-bromo-2-(bromomethyl)-1-nitrobenzene using the method described for preparation of tert-butyl N-(diphenylmethylene)-2-methoxy-6-nitro-L-phenylalaninate (58) in Example 12, followed by removal of the diphenylmethylene group with 1 N aqueous citric acid, then by reprotection of the amino group through reaction with $BOC_2O$ and triethylamine in dichloromethane; the dibrominated starting material was derived from 5-bromo-2-nitrobenzoic acid using chemistry analogous to that employed in the conversion of 5-benzyl-2-nitrobenzoic acid (76) to 4-benzyl-2-(bromomethyl)-1-nitrobenzene (78) in Example 68) (10 g, 22.5 mmol), ethyl acrylate (2.25 g, 22.5 mmol) and triethylamine (8.0 g, 79 mmol) in DMF (150 mL), and the reaction was stirred at 90° C. for 18 h. The reaction mixture was diluted with water (750 mL) and extracted with EtOAc (4×300 mL). The combined organic layers were dried over sodium sulfate, filtered and concentrated in vacuo. Purification by silica gel chromatography (Eluant: 20:1 petroleum ether: EtOAc) provided the product (4.0 g, 38%). LCMS m/z * (M+1). $^1$H NMR (400 MHz, $CDCl_3$) δ 1.34 (br s, 9H), 1.36 (t, J=7.2 Hz, 3H), 1.43 (s, 9H), 3.18 (dd, J=14, 9 Hz, 1H), 3.56 (dd, J=14, 5 Hz, 1H), 4.30 (q, J=7.1 Hz, 2H), 4.55-4.63 (m, 1H), 5.18 (d, J=8 Hz, 1H), 6.54 (d, J=15.9 Hz, 1H), 7.50-7.55 (m, 2H), 7.65 (d, J=16.1 Hz, 1H), 8.00 (br d, J=9 Hz, 1H).

tert-Butyl N-(tert-butoxycarbonyl)-3-formyl-6-nitro-L-phenylalaninate (112) Ozone was bubbled into a −78° C. solution of tert-butyl N-(tert-butoxycarbonyl)-3-[(1E)-3-ethoxy-3-oxoprop-1-en-1-yl]-6-nitro-L-phenylalaninate (111) (8.0 g, 17 mmol) in dichloromethane (400 mL) until a blue color appeared, and TLC analysis indicated consumption of the starting material. Nitrogen was then bubbled through the reaction for 30 min, during which time the solution became yellow. Triphenylphosphine (4.51 g, 17 mmol) was added, and the mixture was stirred at RT for 18 h. The reaction mixture was washed with water (3×150 mL), dried over sodium sulfate, filtered and concentrated in vacuo. Purification by silica gel chromatography (Eluant: 20:1 petroleum ether: EtOAc), followed by chiral HPLC, provided the product (7.09 g, assumed quantitative). LCMS m/z * (M+1). $^1$H NMR (400 MHz, $CDCl_3$) δ 1.33 (s, 9H), 1.45 (s, 9H), 3.20 (dd, J=14, 9 Hz, 1H), 3.61 (dd, J=14, 5 Hz, 1H), 4.56-4.63 (m, 1H), 5.18 (br d, J=8 Hz, 1H), 7.89-7.94 (m, 2H), 8.06 (d, J=8 Hz, 1H), 10.09 (s, 1H).

tert-Butyl N-(tert-butoxycarbonyl)-3-{[methyl(phenyl)amino]methyl}-6-nitro-L-phenylalaninate (113) To a solution of tert-butyl N-(tert-butoxycarbonyl)-3-formyl-6-nitro-L-phenylalaninate (112) (1.0 g, 2.5 mmol) in 1,2-dichloroethane (15 mL) was added N-methylaniline (0.39 mL, 3.5 mmol) and a few drops (0.1 mL) of acetic acid, and the reaction was allowed to stir for 4 h at RT. Sodium triacetoxyborohydride (95%, 2.26 g, 10.1 mmol) was added to the reaction mixture, and the reaction was allowed to stir overnight at RT. The reaction was concentrated under reduced pressure, taken up in EtOAc (10 mL), and washed with water (1×10 mL) and saturated aqueous sodium chloride solution (1×10 mL). Silica gel chromatography (Gradient: 0% to 80% EtOAc in heptane) provided the product as a gum (900 mg, 70%). LCMS m/z 486.1 (M+1). $^1$H NMR (500 MHz, $CDCl_3$) δ 1.37 (br s, 9H), 1.43 (s, 9H), 3.05 (s, 3H), 3.21 (dd, J=13, 9 Hz, 1H), 3.49 (dd, J=13.7, 5.4 Hz, 1H), 4.52-4.57 (m, 3H), 5.15 (br d, J=8 Hz, 1H), 6.73-6.86 (m, 3H), 7.23-7.32 (m, 4H), 7.92 (d, J=8 Hz, 1H).

3-{[Methyl(phenyl)amino]methyl}-6-nitro-L-phenylalanine (114) tert-Butyl N-(tert-butoxycarbonyl)-3-{[methyl(phenyl)amino]methyl}-6-nitro-L-phenylalaninate (113) (900 mg, 1.8 mmol) was dissolved in a 1:1 mixture of TFA and DCM (12 mL) and stirred overnight at RT. After solvents were removed under reduced pressure, the reaction was taken up in EtOAc (50 mL) and washed with aqueous NaOH (1 N, 2×10 mL). The organic layer was dried over sodium sulfate, filtered, and concentrated under reduced pressure to provide the product as a gum (540 mg, 89%). LCMS m/z 330.0 (M+1). $^1$H NMR (500 MHz, $CD_3OD$) δ 3.07 (s, 3H), 3.38 (dd, J=13.9, 7.4 Hz, 1H), 3.61 (dd, J=13.9, 7.4 Hz, 1H), 4.29 (dd, J=7.4, 7.4 Hz, 1H), 4.65 (s, 2H), 6.71-6.75 (m, 1H), 6.78 (br d, J=8 Hz, 2H), 7.17-7.21 (m, 2H), 7.38-7.40 (m, 1H), 7.42 (br d, J=8.3 Hz, 1H), 8.08 (d, J=8.3 Hz, 1H).

tert-Butyl [(3S)-1-[(tert-butoxycarbonyl)oxy]-6-{[methyl(phenyl)amino]methyl}-2-oxo-1,2,3,4-tetrahydroquinolin-3-yl]carbamate (115) Sodium acetate trihydrate (414 mg, 3.04 mmol) and tin(II) chloride dihydrate (98%, 350 mg, 1.52 mmol) were added to a 0° C. solution of 3-{[methyl(phenyl)amino]methyl}-6-nitro-L-phenylalanine (114) (100 mg, 0.30 mmol) in a 1:1 mixture of THF/MeOH (8 mL). The reaction was allowed to stir at 0° C. until LCMS analysis showed conversion to the cyclized product. LCMS m/z 298.0 (M+1). Triethylamine (0.43 mL, 3.04 mmol) and $BOC_2O$ (97%, 171 mg, 0.76 mmol) were added to the reaction, which was then allowed to warm to RT and stir for 18 h. The reaction was filtered through Celite, and the filter pad was washed with MeOH (10 mL). The combined filtrates were washed with water (3×30 mL) and saturated aqueous sodium chloride solution (30 mL), dried over sodium sulfate and concentrated under reduced pressure to provide the crude product as an off-white solid (22 mg, 14%). The product was used in the next step without additional purification. LCMS m/z 498.1 (M+1).

(3S)-3-Amino-1-hydroxy-6-{[methyl(phenyl)amino]methyl}-3,4-dihydroquinolin-2(1H)-one (116) tert-Butyl [(3S)-1-[(tert-butoxycarbonyl)oxy]-6-{[methyl(phenyl)amino]methyl}-2-oxo-1,2,3,4-tetrahydroquinolin-3-yl]carbamate (115) (22 mg, 0.044 mmol) was dissolved in a 1:1 mixture of TFA/dichloromethane (4 mL) and stirred for 18 h at RT. The reaction was concentrated in vacuo, treated with aqueous NaOH (1 N, 5 mL) until the pH reached approximately 7, and extracted with EtOAc (20 mL). The organic layer was concentrated under reduced pressure, and the residue was adsorbed on silica gel (2 gm) and chromatographed (Gradient; 0% to 20% [10% ammonium hydroxide/MeOH] in dichloromethane), to provide the product as an off-white solid (6.5 mg, 50%). LCMS m/z 298.0 (M+1). $^1$H NMR (500 MHz, $CD_3OD$) δ 2.90-2.98 (m, 1H), 3.00 (br s, 3H), 3.05-3.11 (m, 1H), 3.85-3.91 (m, 1H), 4.50 (br s, 2H), 6.62-6.67 (m, 1H), 6.72-6.77 (m, 2H), 7.10-7.22 (m, 4H), 7.26-7.31 (m, 1H).

Examples 14-37 and Examples 77-130

The structures of Examples 14-37 and Examples 77-130 are shown in Table 1, which also gives characterization data and preparative information for these Examples. Each of these Examples was prepared in a similar manner to the Example or Method (see Methods below) referenced in the third column ("Method of Preparation") of Table 1.

TABLE 1

| Ex. No. | Structure and IUPAC Name | Method of Prep | ¹H NMR$^a$; Mass spectrum$^b$ |
|---|---|---|---|
| 14 | 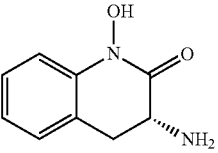<br>(3R)-3-amino-1-hydroxy-3,4-dihydroquinolin-2(1H)-one | Ex. 4 | 2.92 (m, 1H), 3.11 (dd, J=15.1, 6.2 Hz, 1H), 3.76 (dd, J=13.9, 6.1 Hz, 1H) 7.07 (ddd, J=7.2, 7.2, 1.7 Hz, 1H) 7.24 (br d, J=7.4 Hz, 1H) 7.29-7.36 (m, 2H); APCl, 179.2 (M + 1). |
| 15 | 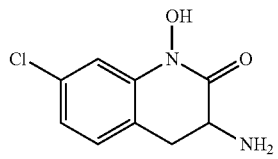<br>3-amino-7-chloro-1-hydroxy-3,4-dihydroquinolin-2(1H)-one | Ex. 2 | 2.84 (m, 1H), 3.09 (dd, J=15.3, 6.1 Hz, 1H), 3.66 (dd, J=13.6, 6.3 Hz, 1H), 7.05 (dd, J=8.0, 2.1 Hz, 1H), 7.21 (br d, J=8 Hz, 1H), 7.31 (d, J=2.1 Hz, 1H); 213.1 (M + 1). |
| 16 | 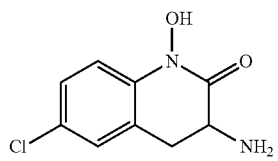<br>3-amino-6-chloro-1-hydroxy-3,4-dihydroquinolin-2(1H)-one | Ex. 2 | 2.87 (m, 1H), 3.08 (dd, J=15.6, 6.1 Hz, 1H), 3.67 (dd, J=13.6, 6.2 Hz, 1H), 7.27 (m, 1H), 7.30 (s, 2H); 213.1 (M + 1). |
| 17 | 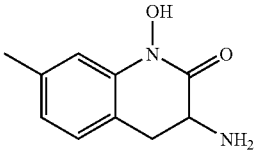<br>3-amino-1-hydroxy-7-methyl-3,4-dihydroquinolin-2(1H)-one | Ex. 2$^1$ | 2.34 (s, 3H), 2.81 (br dd, J=14, 14 Hz, 1H), 3.03 (dd, J=15.1, 6.2 Hz, 1H), 3.62 (dd, J=13.5, 6.2 Hz, 1H), 6.88 (br d, J=7.6 Hz, 1H), 7.10 (d, J=7.5 Hz, 1H), 7.16 (br s, 1H); 193.1 (M + 1). |
| 18 | 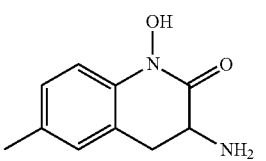<br>3-amino-1-hydroxy-6-methyl-3,4-dihydroquinolin-2(1H)-one | Ex. 2 | 2.35 (s, 3H), 2.94 (br dd, J=15, 14 Hz, 1H), 3.11 (dd, J=15.0, 6.3 Hz, 1H), 3.90 (dd, J=14.0, 6.3 Hz, 1H), 6.91 (br d, J=7.6 Hz, 1H), 7.13 (d, J=7.6 Hz, 1H), 7.19 (br s, 1H); 193.2 (M + 1). |
| 19 | 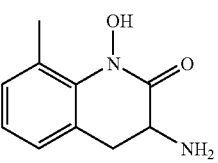<br>3-amino-1-hydroxy-8-methyl-3,4-dihydroquinolin-2(1H)-one, hydrochloride salt | Ex. 8 | ¹H NMR (500 MHz, CD$_3$OD) δ 2.49 (s, 3H), 3.07 (d, J=9.7 Hz, 2H), 4.06 (br dd, J=10, 10 Hz, 1H), 7.05 (dd, J=7.5, 7.5 Hz, 1H), 7.11 (d, J=7 Hz, 1H), 7.16 (d, J=7.5 Hz, 1H); 193.1 (M + 1). |

TABLE 1-continued

| Ex. No. | Structure and IUPAC Name | Method of Prep | $^1$H NMR$^a$; Mass spectrum$^b$ |
|---|---|---|---|
| 20 | 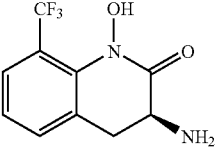<br>(3S)-3-amino-1-hydroxy-8-(trifluoromethyl)-3,4-dihydroquinolin-2(1H)-one, hydrochloride salt | Ex. 12$^{2,3}$ | $^1$H NMR (400 MHz, DMSO-d$_6$) δ 2.90 (dd, J=15, 15 Hz, 1H), 3.08 (dd, J=15.5, 5.6 Hz, 1H), 3.86 (dd, J=14.0, 5.6 Hz, 1H), 4.86 (v br s, 3H), 7.24 (dd, J=7.8, 7.8 Hz, 1H), 7.57 (d, J=7.4 Hz, 1H), 7.66 (d, J=7.8 Hz, 1H), 10.71 (v br s, 1H); 246.9 (M + 1). |
| 21 | 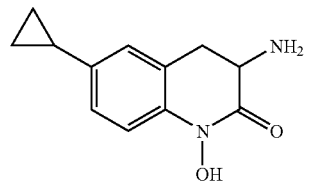<br>3-amino-6-cyclopropyl-1-hydroxy-3,4-dihydroquinolin-2(1H)-one, hydrochloride salt | Ex. 12$^4$ | $^1$H NMR (500 MHz, CD$_3$OD) δ ppm 0.66 (m, 2H), 0.96 (m, 2H), 1.90 (m, 1H), 3.14 (dd, J=14.7, 14.7 Hz, 1H), 3.25 (dd, J=14.9, 6.2 Hz, 1H), 4.30 (dd, J=14.7, 6.2 Hz, 1H), 7.02 (br s, 1H), 7.09 (br d, J=8.2 Hz, 1H), 7.26 (d, J=8.3 Hz, 1H); 219.0 (M + 1). |
| 22 | 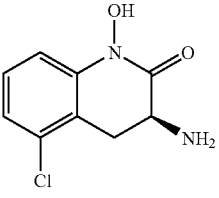<br>(3S)-3-amino-5-chloro-1-hydroxy-3,4-dihydroquinolin-2(1H)-one, hydrochloride salt | Ex. 12 | $^1$H NMR (400 MHz, DMSO-d$_6$) δ ppm 2.98 (dd, J=15, 15 Hz, 1H), 3.53 (dd, J=15.5, 6.7 Hz, 1H), 4.50 (dd, J=14.5, 6.6 Hz, 1H), 7.25 (dd, J=8.0, 1.1 Hz, 1H), 7.28 (dd, J=8.2, 1.1 Hz, 1H), 7.39 (br dd, J=8, 8 Hz, 1H), 8.63 (br s, 3H), 11.02 (s, 1H); 212.9 (M + 1). |
| 23 | 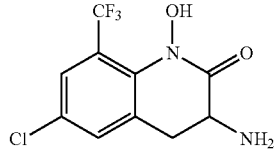<br>3-amino-6-chloro-1-hydroxy-8-(trifluoromethyl)-3,4-dihydroquinolin-2(1H)-one | Ex. 8$^5$ | $^1$H NMR (500 MHz, CD$_3$OD) δ ppm 2.94 (dd, J=15, 15 Hz, 1H), 3.09 (dd, J=15.6, 5.6 Hz, 1H), 3.77 (dd, J=14.2, 5.6 Hz, 1H), 7.57 (br s, 1H), 7.66 (d, J=2.3 Hz, 1H); 280.9 (M + 1). |
| 24 | 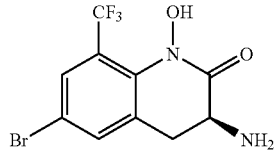<br>(3S)-3-amino-6-bromo-1-hydroxy-8-(trifluoromethyl)-3,4-dihydroquinolin-2(1H)-one, hydrochloride salt | Ex. 12$^{2,6}$ | 3.2-3.3 (m, 2H, assumed, partially obscured by solvent), 4.43 (dd, J=14.4, 6.3 Hz, 1H), 7.80 (br s, 1H), 7.89 (br d, J=2 Hz, 1H); 326.8 (M + 1). |

TABLE 1-continued

| Ex. No. | Structure and IUPAC Name | Method of Prep | $^1$H NMR$^a$; Mass spectrum$^b$ |
|---|---|---|---|
| 25 | (3S)-3-amino-1-hydroxy-7-isopropoxy-3,4-dihydroquinolin-2(1H)-one, hydrochloride salt | Ex. 12$^7$ | 1.32 (d, J=6.0 Hz, 6H), 3.06 (ddd, J=14.6, 14.6, 1.1 Hz, 1H), 3.19 (dd, J=14.6, 6.5 Hz, 1H), 4.29 (dd, J=14.6, 6.5 Hz, 1H), 4.61 (septet, J=6.0 Hz, 1H), 6.67 (dd, J=8.3, 2.5 Hz, 1H), 6.93 (d, J=2.4 Hz, 1H), 7.18 (br d, J=8.3 Hz, 1H); 237.2 (M + 1). |
| 26 | 3-amino-7-ethyl-1-hydroxy-3,4-dihydroquinolin-2(1H)-one, hydrochloride salt | Ex. 12$^8$ | 1.24 (t, J=7.6 Hz, 3H), 2.67 (q, J=7.6 Hz, 2H), 3.11 (dd, J=14.6, 14.6 Hz, 1H), 3.2 (m, 1H), 4.30 (dd, J=14.6, 6.0 Hz, 1H), 6.99 (dd, J=7.7, 1.5 Hz, 1H), 7.20 (d, J=7.7 Hz, 1H), 7.26 (d, J=1.4 Hz, 1H); 207.0 (M + 1). |
| 27 | (3S)-3-amino-5-fluoro-1-hydroxy-3,4-dihydroquinolin-2(1H)-one, hydrochloride salt | Ex. 12 | $^1$H NMR (400 MHz, DMSO-d$_6$) δ 2.94 (dd, J=14.7, 14.7 Hz, 1H), 3.42 (dd, J=15.1, 6.5 Hz, 1H), 4.47 (dd, J=14.2, 6.5 Hz, 1H), 7.00 (br dd, J=8.7, 8.7 Hz, 1H), 7.13 (d, J=8.2 Hz, 1H), 7.39 (ddd, J=8.2, 8.2, 6.3 Hz, 1H), 8.76 (br s, 3H), 11.02 (s, 1H); APCl, 196.9 (M + 1). |
| 28 | (3S)-3-amino-1-hydroxy-8-(trifluoromethyl)-6-[4-(trifluoromethyl)phenyl]-3,4-dihydroquinolin-2(1H)-one | Ex. 24$^9$ | 3.00 (dd, J=14.9, 14.9 Hz, 1H), 3.20 (dd, J=15.5, 5.7 Hz, 1H), 3.77 (dd, J=14.3, 5.7 Hz, 1H), 7.78 (br d, J=8.3 Hz, 2H), 7.85-7.88 (m, 3H), 7.95 (d, J=2 Hz, 1H); 391.0 (M + 1). |
| 29 | 3-amino-1-hydroxy-7-methoxy-3,4-dihydroquinolin-2(1H)-one, hydrochloride salt | Ex. 12 | 3.07 (dd, J=14.6, 14.6 Hz, 1H), 3.20 (dd, J=14.6, 6.5 Hz, 1H), 3.81 (s, 3H), 4.29 (dd, J=14.6, 6.4 Hz, 1H), 6.70 (dd, J=8.3, 2.4 Hz, 1H), 6.96 (d, J=2.3 Hz, 1H), 7.20 (d, J=8.5 Hz, 1H). |

TABLE 1-continued

| Ex. No. | Structure and IUPAC Name | Method of Prep | $^1$H NMR[a]; Mass spectrum[b] |
|---|---|---|---|
| 30 | 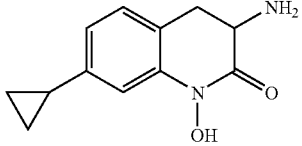<br>3-amino-7-cyclopropyl-1-hydroxy-3,4-dihydroquinolin-2(1H)-one, hydrochloride salt | Ex. 12[4] | $^1$H NMR (500 MHz, CD$_3$OD) δ 0.67-0.70 (m, 2H), 0.98-1.02 (m, 2H), 1.95 (tt, J=8.4, 5.0 Hz, 1H), 3.10 (ddd, J=14.6, 14.6, 0.9 Hz, 1H), 3.21 (dd, J=14.7, 6.4 Hz, 1H), 4.29 (dd, J=14.6, 6.5 Hz, 1H), 6.86 (dd, J=7.8, 1.7 Hz, 1H), 7.11 (d, J=1.7 Hz, 1H), 7.16 (br d, J=7.8 Hz, 1H); 219.0 (M + 1). |
| 31 | 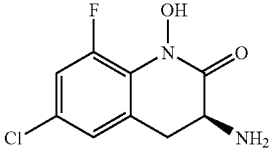<br>(3S)-3-amino-6-chloro-8-fluoro-1-hydroxy-3,4-dihydroquinolin-2(1H)-one, hydrochloride salt | Ex. 12[2,3] | $^1$H NMR (500 MHz, CD$_3$OD) δ 3.18-3.26 (m, 2H), 4.39 (dd, J=13.1, 7.5 Hz, 1H), 7.22 (m, 1H), 7.30 (dd, J=11.8, 2.2 Hz, 1H); 230.9 (M + 1). |
| 32 | 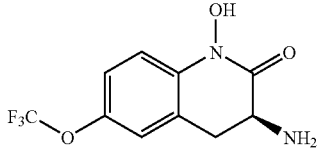<br>(3S)-3-amino-1-hydroxy-6-(trifluoromethoxy)-3,4-dihydroquinolin-2(1H)-one, hydrochloride salt | Ex. 12[10] | 3.20 (dd, J=14.9, 14.9 Hz, 1H) 3.33 (m, 1H, assumed, partially obscured by solvent), 4.40 (dd, J=14.7, 6.5 Hz, 1H), 7.30-7.33 (m, 2H), 7.47 (d, J=8.6 Hz, 1H); 261.0 (M − 1). |
| 33 | 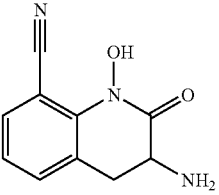<br>3-amino-1-hydroxy-2-oxo-1,2,3,4-tetrahydroquinoline-8-carbonitrile, hydrochloride salt | Ex. 1[11] | $^1$H NMR (400 MHz, DMSO-d$_6$) δ 3.16 (dd, J=15, 15 Hz, 1H), 3.27 (dd, J=15, 6 Hz, 1H), 4.47 (dd, J=14.6, 6.3 Hz, 1H), 7.23 (dd, J=7.6, 7.6 Hz, 1H), 7.65 (d, J=7.3 Hz, 1H), 7.74 (d, J=7.7 Hz, 1H), 8.76 (br s, 3H), 11.5 (v br s, 1H); 204.4 (M + 1). |
| 34 | 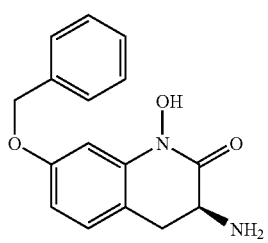<br>(3S)-3-amino-7-(benzyloxy)-1-hydroxy-3,4-dihydroquinolin-2(1H)-one, hydrochloride salt | Ex. 12[7] | $^1$H NMR (400 MHz, DMSO-d$_6$) δ 2.99 (dd, J=14.8, 14.8 Hz, 1H), 3.13 (dd, J=15.0, 6.5 Hz, 1H), 4.33 (dd, J=14.4, 6.5 Hz, 1H), 5.12 (s, 2H), 6.74 (dd, J=8.3, 2.5 Hz, 1H), 6.90 (d, J=2.5 Hz, 1H), 7.22 (br d, J=8.1 Hz, 1H), 7.33 (m, 1H), 7.37-7.46 (m, 4H), 8.57 (br s, 3H), 10.9 (v br s, 1H); 285.1 (M + 1). |
| 35 | 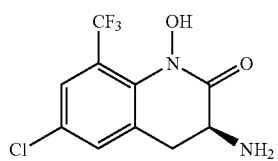<br>(3S)-3-amino-6-chloro-1-hydroxy-8-(trifluoromethyl)-3,4-dihydroquinolin-2(1H)-one, hydrochloride salt | Ex. 12[2] | $^1$H NMR (500 MHz, CD$_3$OD) δ 3.22 (dd, J=15.1, 14.5 Hz, 1H), 3.28 (dd, J=15.1, 6.2 Hz, 1H), 4.41 (dd, J=14.4, 6.2 Hz, 1H), 7.66 (br s, 1H), 7.76 (d, J=2.3 Hz, 1H); 280.9 (M + 1). |

TABLE 1-continued

| Ex. No. | Structure and IUPAC Name | Method of Prep | $^1$H NMR$^a$; Mass spectrum$^b$ |
|---|---|---|---|
| 36 | 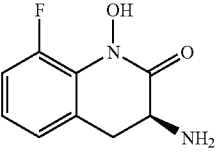<br>(3S)-3-amino-8-fluoro-1-hydroxy-3,4-dihydroquinolin-2(1H)-one | Ex. 12[12] | $^1$H NMR (400 MHz, DMSO-d$_6$) δ 2.09 (br s, 2H), 2.78 (dd, J=15, 14 Hz, 1H), 2.96 (dd, J=15.4, 5.8 Hz, 1H), 3.56 (dd, J=13.4, 5.6 Hz, 1H), 7.02-7.14 (m, 3H), 10.42 (br s, 1H); 196.9 (M + 1). |
| 37 | 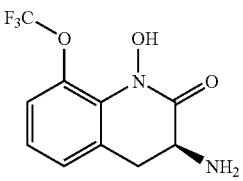<br>(3S)-3-amino-1-hydroxy-8-(trifluoromethoxy)-3,4-dihydroquinolin-2(1H)-one, hydrochloride salt | Ex. 12[3] | $^1$H NMR (400 MHz, DMSO-d$_6$) δ 3.10-3.22 (m, 2H), 4.46 (dd, J=13, 7 Hz, 1H), 7.25 (dd, J=8.2, 7.7 Hz, 1H), 7.36 (br d, J=8 Hz, 1H), 7.41 (br d, J=7.7 Hz, 1H), 8.58 (br s, 3H), 10.91 (s, 1H); 263.4 (M + 1). |
| 77 | 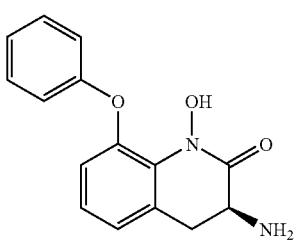<br>(3S)-3-amino-1-hydroxy-8-phenoxy-3,4-dihydroquinolin-2(1H)-one, hydrochloride salt | Method A[14] | $^1$H NMR (400 MHz, DMSO-d$_6$) δ 3.12-3.25 (m, 2H), 4.42 (dd, J=13.4, 6.9 Hz, 1H), 6.91-6.96 (m, 3H), 7.07 (br t, J=7.4 Hz, 1H), 7.13-7.20 (m, 2H), 7.34 (dd, J=8.7, 7.4 Hz, 2H), 8.75 (br s, 3H), 10.57 (s, 1H); 270.9 (M + 1); |
| 78 | 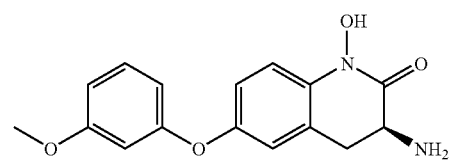<br>(3S)-3-amino-1-hydroxy-6-(3-methoxyphenoxy)-3,4-dihydroquinolin-2(1H)-one, hydrochloride salt | Ex. 70 | 3.15 (dd, half of ABX pattern, J=14.9, 14.1 Hz, 1H), 3.23 (dd, half of ABX pattern, J=15.0, 6.8 Hz, 1H), 3.77 (s, 3H), 4.35 (dd, J=14.3, 6.8 Hz, 1H), 6.53-6.56 (m, 2H), 6.70 (ddd, J=8.3, 2.3, 0.7 Hz, 1H), 6.98 (br d, J=2.5 Hz, 1H), 7.02 (br dd, J=8.8, 2.6 Hz, 1H), 7.25 (dd, J=8.6, 8.5 Hz, 1H), 7.39 (d, J=8.8 Hz, 1H); 301.1 (M + 1). |
| 79 | 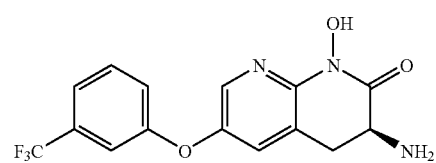<br>(3S)-3-amino-1-hydroxy-6-[3-(trifluoromethyl)phenoxy]-3,4-dihydro-1,8-naphthyridin-2(1H)-one, hydrochloride salt | Ex. 66 | 3.18-3.3 (m, 1H), 3.36-3.45 (m, 1H), 4.49-4.59 (m, 1H), 7.32-7.38 (m, 2H), 7.51 (br d, J=8 Hz, 1H), 7.62 (br dd, J=8, 8 Hz, 1H), 7.73 (br s, 1H), 8.15 (br s, 1H); 340.0 (M + 1). |

TABLE 1-continued

| Ex. No. | Structure and IUPAC Name | Method of Prep | ¹H NMR$^a$; Mass spectrum$^b$ |
|---|---|---|---|
| 80 | (3S)-3-amino-1-hydroxy-6-(3-methoxyphenoxy)-3,4-dihydro-1,8-naphthyridin-2(1H)-one, hydrochloride salt | Ex. 66 | 2.99 (br dd, J=15, 14 Hz, 1H), 3.19 (br dd, J=15, 6 Hz, 1H), 3.78 (s, 3H), 4.02 (br dd, J=14, 6 Hz, 1H), 6.57-6.62 (m, 2H), 6.75 (dd, J=8.3, 2.0 Hz, 1H), 7.28 (dd, J=8.2, 8.1 Hz, 1H), 7.45 (br s, 1H), 8.00 (br d, J=2 Hz, 1H); 302.0 (M + 1). |
| 81 | (3S)-3-amino-1-hydroxy-3,4,8,9-tetrahydrofuro[2,3-h]quinolin-2(1H)-one | Ex. 71[15] | ¹H NMR (500 MHz, CD₃OD) δ 3.03 (br dd, J=14, 14 Hz, 1H), 3.13 (br dd, J=14, 5 Hz, 1H), 3.39 (ddd, J=16.4, 10.0, 6.8 Hz, 1H), 3.55-3.63 (m, 1H), 4.16-4.23 (m, 1H), 4.47-4.53 (m, 1H), 4.54-4.60 (m, 1H), 6.50 (d, J=7.9 Hz, 1H), 7.01 (d, J=7.8 Hz, 1H). |
| 82 | 2-[(3-amino-1-hydroxy-2-oxo-1,2,3,4-tetrahydroquinolin-6-yl)oxy]benzonitrile, hydrochloride salt | Ex. 69 | 3.18 (dd, J=14.7, 14.4 Hz, 1H), 3.25-3.3 (m, 1H, assumed; partially obscured by solvent peak), 4.39 (dd, J=14.4, 6.5 Hz, 1H), 6.99 (d, J=8.4 Hz, 1H), 7.11-7.15 (m, 2H), 7.27 (ddd, J=7.6, 7.6, 0.8 Hz, 1H), 7.47 (d, J=9.5 Hz, 1H), 7.59-7.65 (m, 1H), 7.77 (dd, J=7.8, 1.6 Hz, 1H); 296.1 (M + 1). |
| 83 | (3S)-3-amino-1-hydroxy-7-methoxy-6-[3-(trifluoromethyl)benzyl]-3,4-dihydroquinolin-2(1H)-one, hydrochloride salt | Ex. 75[16] | ¹H NMR (500 MHz, CD₃OD) δ 3.07 (dd, J=14.6, 14.6 Hz, 1H), 3.18 (dd, J=14.8, 6.5 Hz, 1H), 3.85 (s, 3H), 4.00 (AB quartet, J$_{AB}$=14.8 Hz, Δ$_{AB}$=13.4 Hz, 2H), 4.30 (dd, J=14.6, 6.5 Hz, 1H), 7.03 (s, 1H), 7.10 (s, 1H), 7.41-7.48 (m, 4H); 367.1 (M + 1). |
| 84 | 3-amino-1-hydroxy-6-[(6-hydroxypyridin-3-yl)oxy]-3,4-dihydroquinolin-2(1H)-one, hydrochloride salt | Ex. 69 | 3.17 (dd, J=14.8, 14.8 Hz, 1H), 3.24-3.3 (m, 1H, assumed; partially obscured by solvent peak), 4.36 (dd, J=14.6, 6.4 Hz, 1H), 7.01 (d, J=9.6 Hz, 1H), 7.07-7.11 (m, 2H), 7.42 (d, J=9.7 Hz, 1H), 7.72 (br d, J=3.0 Hz, 1H), 7.87 (dd, J=9.7, 2.9 Hz, 1H); 288.1 (M + 1). |

TABLE 1-continued

| Ex. No. | Structure and IUPAC Name | Method of Prep | $^1$H NMR$^a$; Mass spectrum$^b$ |
|---|---|---|---|
| 85 | 3-amino-6-(2,4-difluorophenoxy)-1-hydroxy-3,4-dihydroquinolin-2(1H)-one, hydrochloride salt | Ex. 69 | 3.14 (br dd, half of ABX pattern, J=14.6, 14.6 Hz, 1H), 3.22 (dd, half of ABX pattern, J=15.1, 6.8 Hz, 1H), 4.34 (dd, J=14.3, 6.7 Hz, 1H), 6.93-7.03 (m, 3H), 7.12-7.22 (m, 2H), 7.37 (d, J=9.8 Hz, 1H); 307.0 (M + 1). |
| 86 | 3-amino-6-fluoro-1-hydroxy-8-phenoxy-3,4-dihydroquinolin-2(1H)-one | Method A$^{17}$ | $^1$H NMR (400 MHz, DMSO-d$_6$) δ 10.63 (s, 1H), 8.74 (s, 3H), 7.37 (m, 2H), 7.18 (d, J=6.4 Hz, 1H), 7.12 (m, 1H), 6.98 (d, J=7.6 Hz, 2H), 6.83 (m, 1H), 4.43 (m, 1H), 3.17 (m, 2H); 289.3 (M + 1). |
| 87 | 3-amino-1-hydroxy-6-[(2-methylpyridin-3-yl)oxy]-3,4-dihydroquinolin-2(1H)-one, hydrochloride salt | Ex. 69 | 2.81 (s, 3H), 3.21 (br dd, J=14.8, 14.6 Hz, 1H), 3.34 (dd, J=15.1, 6.5 Hz, 1H, assumed; partially obscured by solvent peak), 4.42 (dd, J=14.6, 6.4 Hz, 1H), 7.22-7.26 (m, 2H), 7.52 (d, J=8.3 Hz, 1H), 7.82 (dd, J=8.6, 5.8 Hz, 1H), 7.91 (dd, J=8.6, 1.2 Hz, 1H), 8.44 (dd, J=5.8, 1.3 Hz, 1H); 286.1 (M + 1). |
| 88 | 3-amino-1-hydroxy-6-[(6-methylpyridin-3-yl)oxy]-3,4-dihydroquinolin-2(1H)-one, hydrochloride salt | Ex. 69 | 2.76 (s, 3H), 3.21 (br dd, J=14.8, 14.6 Hz, 1H), 3.34 (dd, J=15.0, 6.4 Hz, 1H, assumed; partially obscured by solvent peak), 4.41 (dd, J=14.7, 6.5 Hz, 1H), 7.22-7.26 (m, 2H), 7.51 (d, J=8.5 Hz, 1H), 7.88 (d, J=9.0 Hz, 1H), 8.12 (dd, J=9.0, 2.7 Hz, 1H), 8.49 (d, J=2.8 Hz, 1H); 286.1 (M + 1). |
| 89 | 3-amino-6-(2,5-difluorophenoxy)-1-hydroxy-3,4-dihydroquinolin-2(1H)-one, dihydrochloride salt | Ex. 69 | 3.16 (br dd, half of ABX pattern, J=15.0, 14.4 Hz, 1H), 3.25 (dd, half of ABX pattern, J=15.1, 6.6 Hz, 1H), 4.36 (dd, J=14.4, 6.6 Hz, 1H), 6.86 (ddd, J=9.1, 6.5, 3.0 Hz, 1H), 6.90-6.97 (m, 1H), 7.02-7.06 (m, 2H), 7.27 (ddd, J=10.2, 9.1, 5.2 Hz, 1H), 7.41 (br d, J=8 Hz, 1H); 307.1 (M + 1). |

TABLE 1-continued

| Ex. No. | Structure and IUPAC Name | Method of Prep | $^1$H NMR$^a$; Mass spectrum$^b$ |
|---|---|---|---|
| 90 | (3S)-3-amino-1-hydroxy-8-[2-(trifluoromethyl)pyridin-3-yl]-3,4-dihydroquinolin-2(1H)-one, hydrochloride salt | Method A$^{18}$ | 3.24 (br dd, J=14.7, 14.7 Hz, 1H), 3.3-3.36 (m, 1H, assumed; partially obscured by solvent peak), 4.50 (dd, J=14.4, 6.2 Hz, 1H), 7.31 (dd, J=7.6, 7.6 Hz, 1H), 7.43-7.47 (m, 2H), 7.74 (d, J=8.0 Hz, 1H), 7.77 (d, J=7.8 Hz, 1H), 8.07 (dd, J=7.9, 7.8 Hz, 1H); 324.5 (M + 1). |
| 91 | 3-amino-1-hydroxy-6-(4-methoxyphenoxy)-3,4-dihydroquinolin-2(1H)-one, hydrochloride salt | Ex. 69 | 2.87 (dd, half of ABX pattern, J=15, 14 Hz, 1H), 3.02 (dd, half of ABX pattern, J=15.3, 6.1 Hz, 1H), 3.71 (dd, J=13.5, 6.5 Hz, 1H), 3.79 (s, 3H), 6.82-6.88 (m, 2H), 6.90-6.96 (m, 4H), 7.28 (d, J=8.6 Hz, 1H).$^{13}$ 299.1 (M − 1). |
| 92 | 3-amino-1-hydroxy-6-(pyridin-2-yloxy)-3,4-dihydroquinolin-2(1H)-one, hydrochloride salt | Ex. 69 | 3.21 (br d, J=15, 15 Hz, 1H), 3.26-3.3 (m, 1H, assumed; partially obscured by solvent peak), 4.40 (dd, J=15, 6 Hz, 1H), 7.10 (d, J=8.2 Hz, 1H), 7.21-7.25 (m, 2H), 7.29-7.34 (m, 1H), 7.49 (d, J=9 Hz, 1H), 8.04-8.09 (m, 1H), 8.26 (d, J=5 Hz, 1H); 272.4 (M + 1). |
| 93 | 3-amino-1-hydroxy-6-[3-(trifluoromethyl)phenoxy]-3,4-dihydroquinolin-2(1H)-one, hydrochloride salt | Ex. 69 | 3.17 (dd, half of ABX pattern, J=15, 15 Hz, 1H), 3.25 (dd, half of ABX pattern, J=15, 7 Hz, 1H), 4.38 (dd, J=14, 7 Hz, 1H), 7.06-7.12 (m, 2H), 7.21-7.26 (m, 2H), 7.40-7.47 (m, 2H), 7.56 (dd, J=8, 8 Hz, 1H); 339.5 (M + 1). |
| 94 | 3-amino-1-hydroxy-6-[3-(trifluoromethoxy)phenoxy]-3,4-dihydroquinolin-2(1H)-one, hydrochloride salt | Ex. 69 | 3.18 (dd, half of ABX pattern, J=14.8, 14.8 Hz, 1H), 3.27 (dd, half of ABX pattern, J=15.0, 6.7 Hz, 1H), 4.38 (dd, J=14.4, 6.7 Hz, 1H), 6.87 (br s, 1H), 6.98 (ddd, J=8.3, 2.3 0.8 Hz, 1H), 7.01-7.11 (m, 3H), 7.41-7.47 (m, 2H); 355.5 (M + 1). |

TABLE 1-continued

| Ex. No. | Structure and IUPAC Name | Method of Prep | $^1$H NMR$^a$; Mass spectrum$^b$ |
|---|---|---|---|
| 95 | 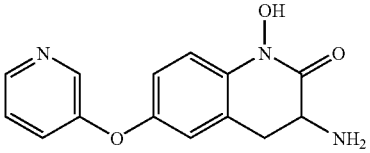<br>3-amino-1-hydroxy-6-(pyridin-3-yloxy)-3,4-dihydroquinolin-2(1H)-one, hydrochloride salt | Ex. 69 | 3.23 (dd, half of ABX pattern, J=14.8, 14.8 Hz, 1H), 3.35 (dd, half of ABX pattern, J=15.2, 6.5 Hz, 1H), 4.43 (dd, J=14.5, 6.4 Hz, 1H), 7.26-7.29 (m, 2H), 7.51-7.54 (m, 1H), 8.05 (dd, J=8.8, 5.5 Hz, 1H), 8.21 (ddd, J=8.9, 2.7, 1.1 Hz, 1H), 8.61 (br d, J=5.6 Hz, 1H), 8.68 (d, J=2.8 Hz, 1H); 272.5 (M + 1). |
| 96 | 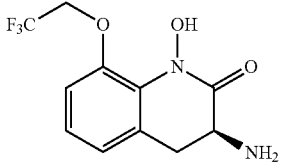<br>(3S)-3-amino-1-hydroxy-8-(2,2,2-trifluoroethoxy)-3,4-dihydroquinolin-2(1H)-one, hydrochloride salt | Method A$^{19}$ | 3.16-3.21 (m, 2H), 4.31 (dd, J=12.3, 8.0 Hz, 1H), 4.56-4.63 (m, 2H), 7.04-7.07 (m, 1H), 7.15-7.23 (m, 2H); 277.4 (M + 1). |
| 97 | 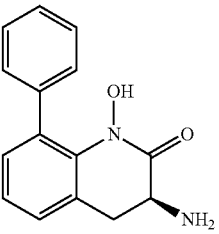<br>(3S)-3-amino-1-hydroxy-8-phenyl-3,4-dihydroquinolin-2(1H)-one, hydrochloride salt | Ex. 90 | 3.18-3.36 (m, 2H, assumed; partially obscured by solvent peak), 4.48 (dd, J=14, 6 Hz, 1H), 7.20-7.27 (m, 2H), 7.28-7.39 (m, 6H); 253.0 (M − 1). |
| 98 | 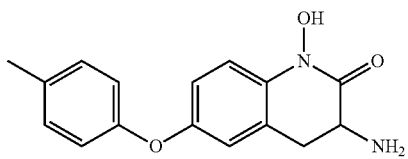<br>3-amino-1-hydroxy-6-(4-methylphenoxy)-3,4-dihydroquinolin-2(1H)-one, hydrochloride salt | Ex. 69 | 2.32 (s, 3H), 3.09-3.23 (m, 2H), 4.34 (dd, J=14.0, 7.0 Hz, 1H), 6.89 (d, J=8.5 Hz, 2H), 6.92-6.99 (m, 2H), 7.18 (d, J=8.3 Hz, 2H), 7.36 (d, J=8.8 Hz, 1H); 285.5 (M + 1). |
| 99 | 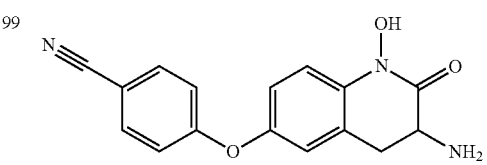<br>4-[(3-amino-1-hydroxy-2-oxo-1,2,3,4-tetrahydroquinolin-6-yl)oxy]benzonitrile, hydrochloride salt | Ex. 69 | 3.14-3.29 (m, 2H), 4.39 (dd, J=14.4, 6.7 Hz, 1H), 7.09 (d, J=9.0 Hz, 2H), 7.10-7.16 (m, 2H), 7.47 (d, J=8.7 Hz, 1H), 7.72 (d, J=9.0 Hz, 2H); 296.4 (M + 1). |

TABLE 1-continued

| Ex. No. | Structure and IUPAC Name | Method of Prep | $^1$H NMR$^a$; Mass spectrum$^b$ |
|---|---|---|---|
| 100 | 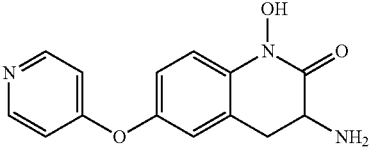<br>3-amino-1-hydroxy-6-(pyridin-4-yloxy)-3,4-dihydroquinolin-2(1H)-one, hydrochloride salt | Ex. 69 | 3.25-3.34 (m, 1H, assumed; partially obscured by solvent peak), 3.48 (dd, J=15.2, 6.4 Hz, 1H), 4.49 (dd, J=14.8, 6.5 Hz, 1H), 7.41 (d, J=7.6 Hz, 2H), 7.65 (d, J=8.6 Hz, 1H), 7.71-7.76 (m, 2H), 8.81 (d, J=7.5 Hz, 2H); APCI m/z 272.1 (M + 1). |
| 101 | 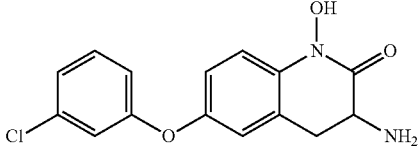<br>3-amino-6-(3-chlorophenoxy)-1-hydroxy-3,4-dihydroquinolin-2(1H)-one, hydrochloride salt | Ex. 69 | 3.17 (br dd, half of ABX pattern, J=15, 14 Hz, 1H), 3.25 (dd, half of ABX pattern, J=15.0, 6.7 Hz, 1H), 4.37 (dd, J=14.3, 6.7 Hz, 1H), 6.93 (ddd, J=8.2, 2.3, 0.8 Hz, 1H), 6.97 (br dd, J=2, 2 Hz, 1H), 7.03-7.09 (m, 2H), 7.12 (ddd, J=8.1, 1.9, 0.8 Hz, 1H), 7.34 (dd, J=8.1, 8.1 Hz, 1H), 7.43 (d, J=8.7 Hz, 1H); 305.4 (M + 1). |
| 102 | 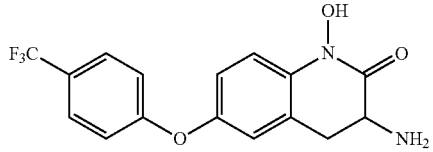<br>3-amino-1-hydroxy-6-[4-(trifluoromethyl)phenoxy]-3,4-dihydroquinolin-2(1H)-one, hydrochloride salt | Ex. 69 | 3.18 (br dd, half of ABX pattern, J=14.8, 14.6 Hz, 1H), 3.26 (dd, half of ABX pattern, J=15.0, 6.6 Hz, 1H), 4.38 (dd, J=14.4, 6.6 Hz, 1H), 7.08-7.14 (m, 4H), 7.46 (d, J=8.7 Hz, 1H), 7.66 (br d, J=8.8 Hz, 2H); 339.5 (M + 1). |
| 103 | 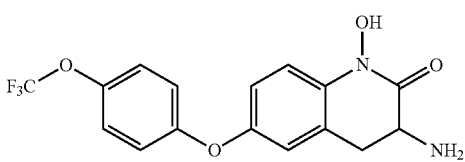<br>3-amino-1-hydroxy-6-[4-(trifluoromethoxy)phenoxy]-3,4-dihydroquinolin-2(1H)-one, hydrochloride salt | Ex. 69 | 3.16 (br dd, half of ABX pattern, J=15, 15 Hz, 1H), 3.23 (dd, half of ABX pattern, J=15, 7 Hz, 1H), 4.36 (dd, J=14.3, 6.8 Hz, 1H), 7.02-7.10 (m, 2H), 7.06 (d, J=9.2 Hz, 2H), 7.28 (br d, J=9 Hz, 2H) 7.42 (d, J=8.9 Hz, 1H); 355.4 (M + 1). |
| 104 | 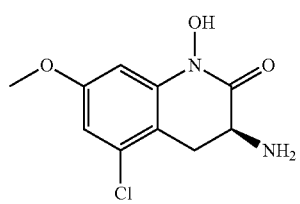<br>(3S)-3-amino-5-chloro-1-hydroxy-7-methoxy-3,4-dihydroquinolin-2(1H)-one, hydrochloride salt | Ex. 12[20] | 2.90 (dd, J=14.8, 14.8 Hz, 1H), 3.62 (dd, J=15.0, 6.6 Hz, 1H), 3.83 (s, 3H), 4.36 (dd, J=14.5, 6.6 Hz, 1H), 6.83 (d, J=2.4 Hz, 1H), 6.95 (d, J=2.4 Hz, 1H); 241.1 (M − 1). |

TABLE 1-continued

| Ex. No. | Structure and IUPAC Name | Method of Prep | $^1$H NMR$^a$; Mass spectrum$^b$ |
|---|---|---|---|
| 105 | 3-amino-6-(4-chlorophenoxy)-1-hydroxy-3,4-dihydroquinolin-2(1H)-one, hydrochloride salt | Ex. 69 | 3.15 (br dd, half of ABX pattern, J=15, 14 Hz, 1H), 3.23 (dd, half of ABX pattern, J=15.0, 6.8 Hz, 1H), 4.35 (dd, J=14.2, 6.8 Hz, 1H), 6.98 (d, J=8.9 Hz, 2H), 6.99-7.01 (m, 1H), 7.04 (br dd, J=8.8, 2.7 Hz, 1H), 7.35 (d, J=9.0 Hz, 2H), 7.41 (d, J=8.7 Hz, 1H); 305.4 (M + 1). |
| 106 | 3-amino-6-(3-fluorophenoxy)-1-hydroxy-3,4-dihydroquinolin-2(1H)-one, hydrochloride salt | Ex. 69 | 3.17 (br dd, half of ABX pattern, J=15, 15 Hz, 1H), 3.26 (dd, half of ABX pattern, J=15.1, 6.7 Hz, 1H), 4.37 (dd, J=14.4, 6.7 Hz, 1H), 6.72 (ddd, J=10.4, 2.4, 2.4 Hz, 1H), 6.80 (br dd, J=8.3, 2.2 Hz, 1H), 6.86 (dddd, J=8.4, 8.4, 2.4, 0.5 Hz, 1H), 7.04 (br d, J=2 Hz, 1H), 7.07 (br dd, J=8.8, 2.6 Hz, 1H), 7.35 (ddd, J=8.3, 8.3, 6.7 Hz, 1H), 7.43 (d, J=8.7 Hz, 1H); 289.5 (M + 1). |
| 107 | 3-amino-6-(2-fluorophenoxy)-1-hydroxy-3,4-dihydroquinolin-2(1H)-one, hydrochloride salt | Ex. 69 | 3.14 (br dd, half of ABX pattern, J=15, 14 Hz, 1H), 3.21 (dd, half of ABX pattern, J=14.9, 6.8 Hz, 1H), 4.34 (dd, J=14.2, 6.8 Hz, 1H), 6.94-6.98 (m, 2H), 7.10-7.28 (m, 4H), 7.36-7.39 (m, 1H); 289.4 (M + 1). |
| 108 | 3-amino-6-(4-fluorophenoxy)-1-hydroxy-3,4-dihydroquinolin-2(1H)-one, hydrochloride salt | Ex. 69 | 3.14 (br dd, half of ABX pattern, J=15, 14 Hz, 1H), 3.21 (dd, half of ABX pattern, J=15, 7 Hz, 1H), 4.34 (dd, J=14.2, 6.8 Hz, 1H), 6.95-6.97 (m, 1H), 6.98-7.04 (m, 3H), 7.11 (dd, J=9.1, 8.2 Hz, 2H), 7.38 (d, J=8.8 Hz, 1H); 289.5 (M + 1). |
| 109 | (3S)-3-amino-8-chloro-5-fluoro-1-hydroxy-3,4-dihydroquinolin-2(1H)-one, hydrochloride salt | Ex. 12[21] | 2.99 (dd, J=14.9, 14.9 Hz, 1H), 3.44-3.50 (m, 1H), 4.41 (dd, J=14.6, 5.8 Hz, 1H), 7.04 (dd, J=8.9, 8.4 Hz, 1H), 7.45 (ddd, J=9.1, 5.5, 0.8 Hz, 1H); 231.3, 233.3 (M + 1). |

TABLE 1-continued

| Ex. No. | Structure and IUPAC Name | Method of Prep | $^1$H NMR$^a$; Mass spectrum$^b$ |
|---|---|---|---|
| 110 | (3S)-3-amino-8-ethyl-1-hydroxy-3,4-dihydroquinolin-2(1H)-one, hydrochloride salt | Method A[22] | $^1$H NMR (400 MHz, CD$_3$OD) δ 7.15 (m, 1H), 7.04 (m, 2H), 4.17 (m, 1H), 3.05 (m, 2H), 2.81 (m, 2H), 1.16 (t, J=7.2 Hz, 3H); 207.0 (M + 1). |
| 111 | (3S)-3-amino-5-fluoro-1-hydroxy-6-phenoxy-3,4-dihydroquinolin-2(1H)-one, hydrochloride salt | Ex. 12[23] | $^1$H NMR (400 MHz, DMSO-d$_6$) δ 3.03 (br dd, J=15, 15 Hz, 1H), 3.46 (dd, J=15.2, 6.6 Hz, 1H), 4.48 (dd, J=14.2, 6.4 Hz, 1H), 6.96-7.00 (m, 2H), 7.10-7.14 (m, 2H), 7.19 (dd, J=8.8, 8.4 Hz, 1H), 7.37 (dd, J=8.8, 7.4 Hz, 2H), 8.82 (br s, 3H), 11.08 (br s, 1H); 289.4 (M + 1). |
| 112 | (3S)-3-amino-1-hydroxy-6-(tetrahydro-2H-pyran-4-yl)-3,4-dihydroquinolin-2(1H)-one | Ex. 12[24] | 1.72-1.83 (m, 4H), 2.73-2.82 (m, 1H), 2.86 (br dd, J=15, 14 Hz, 1H), 3.07 (dd, J=15.2, 6.0 Hz, 1H), 3.52-3.59 (m, 2H), 3.63 (dd, J=13.5, 6.1 Hz, 1H), 4.01-4.06 (m, 2H), 7.13 (br s, 1H), 7.19 (br dd, J=8.4, 1.8 Hz, 1H), 7.27 (d, J=8.4 Hz, 1H); 263.0 (M + 1). |
| 113 | (3S)-3-amino-6,8-dichloro-1-hydroxy-3,4-dihydroquinolin-2(1H)-one, hydrochloride salt | Ex. 12[25] | $^1$H NMR (400 MHz, DMSO-d$_6$) δ 11.0 (s, 1H), 8.98 (s, 3H), 7.55 (d, J=2.4 Hz, 1H), 7.50 (d, J=2.0 Hz, 1H), 4.37 (m, 1H), 3.16-3.27 (m, 2H); 246.9, 248.9 (M + 1). |
| 114 | (3S)-3-amino-5,6-difluoro-1-hydroxy-3,4-dihydroquinolin-2(1H)-one, hydrochloride salt | Ex. 12[26] | 2.99 (br dd, J=15, 15 Hz, 1H), 3.57 (dd, J=15.3, 6.6 Hz, 1H), 4.42 (dd, J=14.5, 6.6 Hz, 1H), 7.21 (ddd, J=9.2, 4.1, 1.7 Hz, 1H), 7.31 (br ddd, J=9, 9, 9 Hz, 1H); 215.1 (M + 1). |

TABLE 1-continued

| Ex. No. | Structure and IUPAC Name | Method of Prep | ¹H NMR[a]; Mass spectrum[b] |
|---|---|---|---|
| 115 | 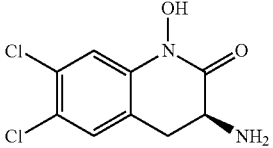<br>(3S)-3-amino-6,7-dichloro-1-hydroxy-3,4-dihydroquinolin-2(1H)-one, hydrochloride salt | Ex. 12[27] | ¹H NMR (400 MHz, DMSO-d$_6$) δ 11.20 (s, 1H), 8.78 (s, 3H), 7.71 (s, 1H), 7.40 (s, 1H), 4.44 (dd, J=14.4, 6.4 Hz, 1H), 3.28 (dd, J=15.6, 6.4 Hz, 1H), 3.13 (m, 1H); 247.2 (M + 1). |
| 116 | 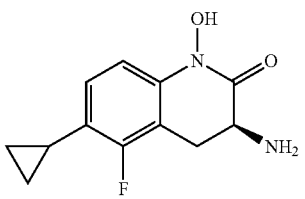<br>(3S)-3-amino-6-cyclopropyl-5-fluoro-1-hydroxy-3,4-dihydroquinolin-2(1H)-one, hydrochloride salt | Ex. 12[28] | 0.68-0.73 (m, 2H), 0.96-1.01 (m, 2H), 2.01-2.08 (m, 1H), 2.94 (dd, J=14.9, 14.9 Hz, 1H), 3.56 (dd, J=15.2, 6.7 Hz, 1H), 4.37 (dd, J=14.6, 6.6 Hz, 1H), 6.99 (dd, J=8.2, 8.1 Hz, 1H), 7.12 (d, J=8.7 Hz, 1H); 237.4 (M + 1). |
| 117 | 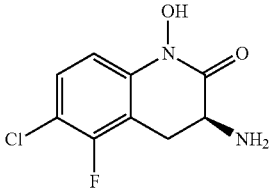<br>(3S)-3-amino-6-chloro-5-fluoro-1-hydroxy-3,4-dihydroquinolin-2(1H)-one, hydrochloride salt | Ex. 12[29] | 2.99 (br dd, J=15.2, 14.6 Hz, 1H), 3.56 (dd, J=15.2, 6.7 Hz, 1H), 4.42 (dd, J=14.5, 6.6 Hz, 1H), 7.23 (dd, J=8.9, 1.5 Hz, 1H), 7.49 (ddd, J=8.8, 7.9, 1.0 Hz, 1H); 229.1 (M − 1). |
| 118 | 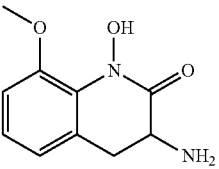<br>3-amino-1-hydroxy-8-methoxy-3,4-dihydroquinolin-2(1H)-one, hydrochloride salt | Method A[30] | 3.13 (dd, half of ABX pattern, J=14.8, 6.2 Hz, 1H), 3.20 (br dd, half of ABX pattern, J=15, 14 Hz, 1H), 3.90 (s, 3H), 4.26 (dd, J=14.0, 6.2 Hz, 1H), 6.91 (br d, J=7.4 Hz, 1H), 7.08 (br d, J=8.4 Hz, 1H), 7.20 (dd, J=8.3, 7.6 Hz, 1H); 209.0 (M + 1). |
| 119 | 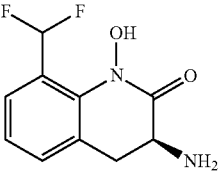<br>(3S)-3-amino-8-(difluoromethyl)-1-hydroxy-3,4-dihydroquinolin-2(1H)-one, trifluoroacetic acid salt | Ex. 12[31,32] | ¹H NMR (500 MHz, CD$_3$OD) δ 3.21 (br dd, half of ABX pattern, J=15, 14 Hz, 1H), 3.27 (dd, half of ABX pattern, J=14.9, 6.2 Hz, 1H), 4.36 (dd, J=14.4, 6.2 Hz, 1H), 7.28 (dd, J=7.8, 7.8 Hz, 1H), 7.44 (t, J=55.7 Hz, 1H), 7.46 (br d, J=7.3 Hz, 1H), 7.69 (br d, J=8.0 Hz, 1H); 229.0 (M + 1). |

TABLE 1-continued

| Ex. No. | Structure and IUPAC Name | Method of Prep | $^1$H NMR$^a$; Mass spectrum$^b$ |
|---|---|---|---|
| 120 | (3S)-3-amino-6,8-difluoro-1-hydroxy-3,4-dihydroquinolin-2(1H)-one, hydrochloride salt | Ex. 12$^{33,34}$ | $^1$H NMR (500 MHz, CD$_3$OD) δ 3.19-3.29 (m, 2H), 4.39 (dd, J=13.0, 7.6 Hz, 1H), 7.01 (br d, J= 8 Hz, 1H), 7.07 (ddd, J=12.0, 8.9, 2.7 Hz, 1H); 215.0 (M + 1). |
| 121 | (3S)-3-amino-1-[(diethylcarbamoyl)oxy]-6-phenoxy-3,4-dihydroquinolin-2(1H)-one | Ex. 72 | 1.16-1.24 (m, 3H), 1.34 (br t, J=6.8 Hz, 3H), 2.99 (br dd, half of ABX pattern, J=15, 14 Hz, 1H), 3.08 (dd, half of ABX pattern, J=15.3, 6.3 Hz, 1H), 3.35-3.44 (m, 2H), 3.49-3.58 (m, 2H), 3.75-3.82 (m, 1H), 6.91-7.00 (m, 5H), 7.11 (br t, J=7.4 Hz, 1H), 7.35 (dd, J=8.4, 7.6 Hz, 2H); 370.1 (M + 1). |
| 122 | (3S)-3-amino-6-phenoxy-1-[(piperidin-1-ylcarbonyl)oxy]-3,4-dihydroquinolin-2(1H)-one | Ex. 72 | 1.61-1.75 (m, 6H), 2.98 (br dd, half of ABX pattern, J=15, 14 Hz, 1H), 3.08 (dd, half of ABX pattern, J=15.5, 6.2 Hz, 1H), 3.44-3.57 (br s, 2H), 3.63-3.73 (br s, 2H), 3.78 (dd, J=13.2, 6.4 Hz, 1H), 6.90-6.97 (m, 3H), 6.98 (dd, J=8.7, 1.0 Hz, 2H), 7.11 (tt, J=7.4, 1.0 Hz, 1H), 7.35 (dd, J=8.6, 7.5 Hz, 2H); 382.4 (M + 1). |
| 123 | (3S)-3-amino-6-phenoxy-1-[(pyrrolidin-1-ylcarbonyl)oxy]-3,4-dihydroquinolin-2(1H)-one | Ex. 72 | 1.92-2.07 (m, 4H), 2.99 (br dd, half of ABX pattern, J=15, 14 Hz, 1H), 3.08 (dd, half of ABX pattern, J=15.4, 6.3 Hz, 1H), 3.43-3.50 (m, 2H), 3.62-3.68 (m, 2H), 3.80 (dd, J=13.3, 6.4 Hz, 1H), 6.90-7.03 (m, 5H), 7.11 (tt, J=7.4, 1.0 Hz, 1H), 7.35 (dd, J=8.6, 7.4 Hz, 2H); 253.4 [(M − pyrrolidine-1-carboxylic acid)] + 1]. |

TABLE 1-continued

| Ex. No. | Structure and IUPAC Name | Method of Prep | $^1$H NMR$^a$; Mass spectrum$^b$ |
|---|---|---|---|
| 124 | (3S)-3-amino-6-(4-chlorophenoxy)-1-hydroxy-3,4-dihydro-1,8-naphthyridin-2(1H)-one, hydrochloride salt | Ex. 66$^2$ | 3.18 (br dd, J=15, 15 Hz, 1H), 3.3-3.37 (m, 1H, assumed; partially obscured by solvent peak), 4.48 (dd, J=14.6, 6.5 Hz, 1H), 7.06 (d, J=8.9 Hz, 2H), 7.40 (d, J=9.0 Hz, 2H), 7.55 (br s, 1H), 8.08 (br s, 1H); 305.9 (M + 1). |
| 125 | (3S)-3-amino-1-hydroxy-7-methoxy-6-(3-methoxybenzyl)-3,4-dihydroquinolin-2(1H)-one, hydrochloride salt | Ex. 75 | $^1$H NMR (500 MHz, CD$_3$OD ) δ 2.75 (br dd, J=14, 14 Hz, 1H), 2.95 (dd, J=15.0, 6.3 Hz, 1H), 3.61 (dd, J=13.5, 6.3 Hz, 1H), 3.74 (s, 3H), 3.83 (s, 3H), 3.86 (AB quartet, J$_{AB}$=14.8 Hz, Δ $_{AB}$=12.6 Hz, 2H), 6.70-6.77 (m, 3H), 6.93 (s, 1H), 6.96 (s, 1H), 7.14 (dd, J=7.8, 7.7 Hz, 1H).$^{13}$ 329.0 (M + 1); |
| 126 | 3-{[(3S)-3-amino-1-hydroxy-7-methoxy-2-oxo-1,2,3,4-tetrahydroquinolin-6-yl]methyl}benzonitrile, hydrochloride salt | Ex. 66 | $^1$H NMR (500 MHz, CD$_3$OD ) δ 2.78 (br dd, J=15, 14 Hz, 1H), 3.00 (dd, J=15.1, 6.1 Hz, 1H), 3.64 (dd, J=13.6, 6.3 Hz, 1H), 3.82 (s, 3H), 3.95 (AB quartet, J$_{AB}$=14.9 Hz, Δ $_{AB}$=12.2 Hz, 2H), 6.98 (s, 1H), 7.04 (s, 1H), 7.42 (dd, J=8.3, 8.0 Hz, 1H), 7.50-7.53 (m, 3H).$^{13}$ 324.0 (M + 1); |
| 127 | (3S)-3-amino-6-benzyl-1-hydroxy-3,4-dihydro-1,8-naphthyridin-2(1H)-one, hydrochloride salt | Ex. 75$^{35}$ | $^1$H NMR (500 MHz, CD$_3$OD ) δ 2.83 (br dd, J=15.4, 13.7 Hz, 1H), 3.07 (dd, J=15.6, 6.2 Hz, 1H), 3.69 (dd, J=13.5, 6.2 Hz, 1H), 3.96 (s, 2H), 7.18-7.24 (m, 3H), 7.27-7.31 (m, 2H), 7.52 (br s, 1H), 8.11 (br s, 1H); 270.0 (M + 1). |

TABLE 1-continued

| Ex. No. | Structure and IUPAC Name | Method of Prep | $^1$H NMR$^a$; Mass spectrum$^b$ |
|---|---|---|---|
| 128 | 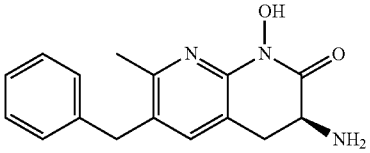(3S)-3-amino-6-benzyl-1-hydroxy-7-methyl-3,4-dihydro-1,8-naphthyridin-2(1H)-one, hydrochloride salt | Ex. 127 | $^1$H NMR (500 MHz, CD$_3$OD) δ 2.42 (s, 3H), 2.84 (br dd, J=15, 14 Hz, 1H), 3.06 (dd, J=15.4, 6.2 Hz, 1H), 3.78 (dd, J=13.7, 6.2 Hz, 1H), 3.99 (s, 2H), 7.14 (br d, J=8 Hz, 2H), 7.19 (br t, J=7.4 Hz, 1H), 7.28 (br dd, J=8, 7 Hz, 2H), 7.41 (s, 1H).[13] 284.0 (M + 1). |
| 129 | 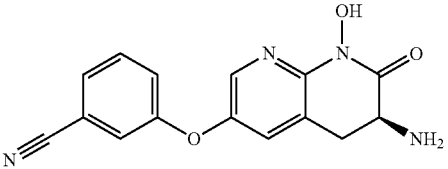3-{[(6S)-amino-8-hydroxy-7-oxo-5,6,7,8-tetrahydro-1,8-naphthyridin-3-yl]oxy}benzonitrile, hydrochloride salt | Ex. 66 | 3.20 (br dd, J=15, 15 Hz, 1H), 3.33-3.39 (m, 1H), 4.49 (dd, J=14.4, 6.4 Hz, 1H), 7.37-7.42 (m, 2H), 7.51-7.62 (m, 3H), 8.14 (br d, J=2 Hz, 1H); 296.9 (M + 1). |
| 130 | 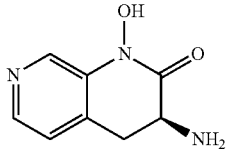(3S)-3-amino-1-hydroxy-3,4-dihydro-1,7-naphthyridin-2(1H)-one, hydrochloride salt | Ex. 66[36] | 3.53 (dd, J=16, 15 Hz, 1H), 3.73 (dd, J=16.4, 6.2 Hz, 1H), 4.65 (dd, J=14.3, 6.5 Hz, 1H), 8.04 (d, J=5.5 Hz, 1H), 8.59 (br d, J=5.5 Hz, 1H), 8.78 (br s, 1 H); 180.0 (M + 1). |

$^a$$^1$H NMR: 400 MHz, CD$_3$OD (unless otherwise indicated): observed peaks, δ (ppm).
$^b$Mass spectrum: LCMS, observed ion m/z (unless otherwise indicated).
[1] The benzyl bromide was prepared from (4-methyl-2-nitrophenyl)methanol via treatment with NBS and triphenylphosphine.
[2] In this case, the SnCl$_2$ reaction was carried out at 60° C.
[3] The benzyl bromide reagent was derived from the appropriate 2-aminobenzoic acid via sodium perborate oxidation (see A. McKillop and J. A. Tarbin, Tetrahedron 1987, 43, 1753-1758), followed by borane reduction of the carboxylic acid and bromination using PBr$_3$.
[4] The benzyl bromide was prepared via palladium-mediated reaction of cyclopropylboronic acid with the appropriate brominated methyl 2-nitrobenzoate, followed by ester reduction with lithium borohydride/zinc chloride. Bromination was effected with triphenylphosphine and carbon tetrabromide.
[5] The benzyl bromide was prepared via NCS chlorination of the appropriate 2-aminobenzoic acid, followed by treatment as in footnote 3.
[6] The benzyl bromide was prepared via NBS bromination of the appropriate 2-aminobenzoic acid, followed by treatment as in footnote 3.
[7] Ethyl 4-hydroxy-2-nitrobenzoate was alkylated with the appropriate alkyl or benzyl halide. Ester hydrolysis and reduction with borane was followed by PBr$_3$ bromination of the resulting alcohol.
[8] A Suzuki reaction with ethylboronic acid was carried out on methyl 4-bromo-2-nitrobenzoate; the ester was reduced with lithium borohydride and converted to the bromide.
[9] The BOC precursor to Ex. 24 was subjected to a Suzuki reaction with [4-(trifluoromethyl)phenyl]boronic acid, followed by deprotection.
[10] 2-Amino-5-(trifluoromethoxy)benzoic acid was converted to the ester, then oxidized to the nitro compound with mCPBA. Lithium borohydride reduction followed by PBr$_3$ treatment provided the benzyl bromide.
[11] The benzyl bromide reagent was derived from 3-methyl-2-nitrobenzoic acid via conversion of the acid to a nitrile, followed by bromination with NBS.
[12] See Example 3 for general approach to benzyl bromide preparation.
[13] Data was obtained on the neutral material.
[14] Synthesized from 2-amino-3-fluorobenzoic acid; the phenoxy group was introduced using cesium carbonate as base, just prior to formation of the 2,2,2-trifluoroethyl ester.
[15] 2,3-Dihydro-1-benzofuran-4-amine was converted to 5-bromo-4-nitro-2,3-dihydro-1-benzofuran by treatment with NBS followed by sodium perborate oxidation.
[16] Preparation of intermediate 4-methoxy-2-nitro-5-[3-(trifluoromethyl)benzyl]aniline began with the reaction of 3-(trifluoromethyl) benzaldehyde with 2-methoxyphenylmagnesium bromide. After palladium-catalyzed hydrogenolysis of the resulting secondary alcohol, nitration provided 1-methoxy-4-nitro-2-[3-(trifluoromethyl)benzyl]benzene. Raney nickel reduction, followed by acetylation of the new amino group, gave N-{4-methoxy-3-[3-(trifluoromethyl)benzyl]phenyl}acetamide, which was nitrated to provide N-{4-methoxy-2-nitro-5-[3-(trifluoromethyl)benzyl]phenyl}acetamide. Hydrolysis of the acetamide moiety afforded the requisite intermediate.
[17] The requisite substrate for cyclization was prepared from 3,5-difluorobenzoic acid: nitration, followed by borane reduction of the carboxylic acid and bromination with carbon tetrabromide and triphenylphosphine, provided 1-(bromomethyl)-3,5-difluoro-2-nitrobenzene. This was reacted with tert-butyl N-(diphenylmethylene)glycinate (56) and cesium hydroxide, followed by fluoride displacement with phenol, using cesium carbonate as base, to generate tert-butyl N-(diphenylmethylene)-3-fluoro-6-nitro-5-phenoxyphenylalaninate.
[18] The cyclization precursor was synthesized from 1-bromo-3-methyl-2-nitrobenzene, via bromination with NBS followed by conversion to tert-butyl 3-bromo-N-(diphenylmethylene)-2-nitro-L-phenylalaninate using the procedure described in Example 12. A Suzuki reaction with the appropriate boronic acid, catalyzed by [1,1'-bis(diphenylphosphino)ferrocene]dichloropalladium(II)-dichloromethane complex in the presence of cesium fluoride, provided the requisite intermediate.
[19] Methyl 3-hydroxy-2-nitrobenzoate was converted to intermediate methyl 2-nitro-3-(2,2,2-trifluoroethoxy)benzoate using the method described by F. J. Lopez et al., Bioorg. Med. Chem. Lett. 2003, 13, 1873-1878.

TABLE 1-continued

| Ex. No. | Structure and IUPAC Name | Method of Prep | $^1$H NMR$^a$; Mass spectrum$^b$ |
| --- | --- | --- | --- |

[20] 2-Chloro-4-methoxy-6-nitrobenzoic acid was synthesized using a modification of the method reported by M. Kitagawa et al., Chem. Pharm. Bull. 1991, 39, 2400-2407. Conversion to the allyl ester was effected using allyl bromide and potassium carbonate, and the ester was reduced to the primary alcohol with lithium borohydride. Phosphorus tribromide reaction then afforded the requisite intermediate 2-(bromomethyl)-1-chloro-5-methoxy-3-nitrobenzene.

[21] 2-Amino-6-fluorobenzoic acid was chlorinated with NCS to provide 2-amino-3-chloro-6-fluorobenzoic acid, which was converted to the appropriate benzyl bromide using the chemistry described within the preparation of tert-butyl N-(diphenylmethylene)-2-nitro-3-(trifluoromethoxy)-L-phenylalaninate (118) in Method A.

[22] 2-Amino-3-bromobenzoic acid was subjected to oxidation with sodium perborate followed by ester formation to provide methyl 3-bromo-2-nitrobenzoate. This was reacted with ethylboronic acid in a Suzuki reaction, followed by lithium borohydride reduction of the ester to afford (3-ethyl-2-nitrophenyl)methanol. Conversion to the requisite bromide was effected with triphenylphosphine and carbon tetrabromide.

[23] 2-(Bromomethyl)-3-fluoro-1-nitro-4-phenoxybenzene was prepared from (6-amino-2,3-difluorophenyl)methanol via mCPBA oxidation of the amino group, followed by displacement of fluoride by phenoxide and conversion of the primary alcohol to a bromide by reaction with triphenylphosphine and carbon tetrabromide.

[24] A Suzuki reaction between 5-bromo-2-nitrobenzaldehyde and 4-(4,4,5,5-tetramethyl-1,3,2-dioxaborolan-2-yl)-3,6-dihydro-2H-pyran (which can be prepared using chemistry described by M. V. Patel et al., J. Med. Chem. 2006, 49, 7450-7465) provided 5-(3,6-dihydro-2H-pyran-4-yl)-2-nitrobenzaldehyde. Conversion of the aldehyde to the requisite primary bromide was carried out via sodium borohydride reduction followed by reaction with phosphorus tribromide. The cyclization step in this case was carried out by hydrogenation over platinum on carbon; this also reduced the double bond of the dihydropyran ring.

[25] 2-Amino-3,5-dichlorobenzoic acid was oxidized to the nitro analogue by reaction with hydrogen peroxide, then converted to the corresponding methyl ester. Sodium borohydride reduction to the primary alcohol, followed by reaction with triphenylphosphine and carbon tetrabromide, provided 1-(bromomethyl)-3,5-dichloro-2-nitrobenzene. In this case, the $SnCl_2$ cyclization was carried out at 30-35° C.

[26] The requisite benzyl bromide can be prepared in a manner similar to that described in footnote 22, except that the Suzuki reaction is not carried out.

[27] 4-(Bromomethyl)-1,2-dichlorobenzene was converted to 1-(bromomethyl)-4,5-dichloro-2-nitrobenzene by reaction with nitronium tetrafluoroborate.

[28] Bromination of 2-amino-6-fluorobenzoic acid with NBS provided 6-amino-3-bromo-2-fluorobenzoic acid, which was converted to methyl 3-cyclopropyl-2-fluoro-6-nitrobenzoate in a manner analogous to that described in footnote 22. Ester hydrolysis, followed by borane reduction and conversion of the resulting primary alcohol to a bromide with triphenylphosphine and carbon tetrabromide, provided 2-(bromomethyl)-4-cyclopropyl-3-fluoro-1-nitrobenzene.

[29] Chlorination of 2-amino-6-fluorobenzoic acid with NCS provided 6-amino-3-chloro-2-fluorobenzoic acid, which was subjected to sodium perborate oxidation, followed by borane reduction of the carboxylic acid and phosphorus tribromide-mediated conversion to 2-(bromomethyl)-4-chloro-3-fluoro-1-nitrobenzene.

[30] The benzyl bromide alkylation partner was prepared by NBS bromination of the corresponding methylbenzene derivative. The alkylation in this case was carried out with sodium hydride, without a chiral catalyst.

[31] Methyl 3-formyl-2-nitrobenzoate (98) was converted to methyl 3-(difluoromethyl)-2-nitrobenzoate with (diethylamino)sulfur trifluoride. Ester reduction with lithium borohydride, followed by reaction with phosphorus tribromide, afforded 1-(bromomethyl)-3-(difluoromethyl)-2-nitrobenzene.

[32] In this case, the $SnCl_2$ reaction was carried out at reflux.

[33] Nitration of 3,5-difluorobenzoic acid provided 3,5-difluoro-2-nitrobenzoic acid, which was reduced with borane and then reacted with phosphorus tribromide to afford 1-(bromomethyl)-3,5-difluoro-2-nitrobenzene.

[34] In this case, the $SnCl_2$ reaction was carried out at RT.

[35] Palladium(II) acetate/2-dicyclohexylphosphino-2',6'-dimethoxybiphenyl-mediated reaction of benzylzinc bromide with 5-bromopyridin-2-amine, followed by bromination with bromine, provided 5-benzyl-3-bromopyridin-2-amine. Oxidation to 5-benzyl-3-bromo-2-nitropyridine was carried using the procedure of K. Krohn et al., J. Prakt. Chemie 1997, 339, 335-339.

[36] 4-Chloro-3-nitropyridine was converted to 4-iodo-3-nitropyridine with sodium iodide and acetone.

Examples 38-65

Synthesis of 3-amino-7-aryl/heteroaryl-1-hydroxy-3,4-dihydroquinolin-2(1H)-ones, trifluoroacetate salt

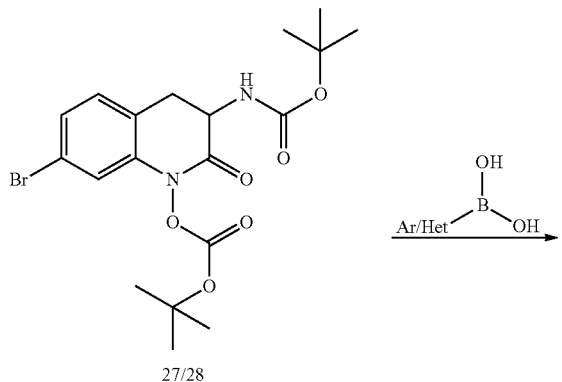

27/28

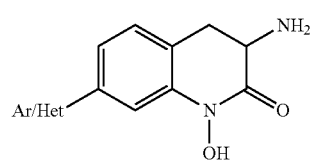

The boronic acid (0.112 mmol) was treated with biphenyl-2-yl(di-tert-butyl)phosphine (0.45 mg, 0.0015 mmol), Pd(II) (OAc)$_2$ (0.2 mg, 0.0009 mmol), and KF (13 mg, 0.225 mmol) in a nitrogen box, and the reaction vial was evacuated and filled with nitrogen twice. A solution of tert-butyl {7-bromo-1-[(tert-butoxycarbonyl)oxy]-2-oxo-1,2,3,4-tetrahydroquinolin-3-yl}carbamate (27/28) (34.3 mg, 0.075 mmol) in dry, degassed THF (0.8 mL) was added via syringe, and the reaction vial was evacuated and filled with nitrogen twice, then shaken at 60° C. for 18 h. The reaction was concentrated, then partitioned between water (1.5 mL) and EtOAc (2.5 mL), vortexed, and the aqueous layer was extracted twice with EtOAc. The organic extracts were dried by passage through a solid phase extraction (SPE) cartridge charged with sodium sulfate, then concentrated in vacuo. The residue was mixed with a solution of TFA in DCM (1:1, 1 mL), and shaken at RT for 3 h. Removal of solvent provided a residue, which was dissolved in MeOH/dichloroethane (1:1, 2.5 mL), vortexed, and loaded onto an SCX SPE column (Silicycle, 6 mL, 1 g). The product was rinsed with MeOH, then eluted with a 1N solution of NEt$_3$ in MeOH (7.5 mL). After concentration in vacuo, the product was dissolved in DMSO (1 mL) and purified by preparative HPLC (Column: Waters Sunfire C$_{18}$, 19×50 mm, 5 μm; Gradient: 95:5 to 5:95 water (containing 0.05% TFA): MeCN (containing 0.05% TFA) over 6 min; flow rate: 25 mL/min).

The structures of Examples 38-65 are shown in Table 2, which also shows characterization data for Examples 38-65.

TABLE 2

[Core structure: 3-amino-1-hydroxy-3,4-dihydroquinolin-2(1H)-one with R substituent at 7-position]

| Ex. No. | R | IUPAC Name | HPLC Retention Time (min.)[a] | MW[b] | MS[c] |
|---|---|---|---|---|---|
| 38 | 3-(trifluoromethoxy)phenyl | 3-amino-1-hydroxy-7-[3-(trifluoromethoxy)phenyl]-3,4-dihydroquinolin-2(1H)-one, trifluoroacetate salt | 2.03 | 338.09 | 339.0 |
| 39 | 4-methylphenyl | 3-amino-1-hydroxy-7-(4-methylphenyl)-3,4-dihydroquinolin-2(1H)-one, trifluoroacetate salt | 1.84 | 268.12 | 269.1 |
| 40 | 2,3-difluorophenyl | 3-amino-7-(2,3-difluorophenyl)-1-hydroxy-3,4-dihydroquinolin-2(1H)-one, trifluoroacetate salt | 1.77 | 290.09 | 291.0 |
| 41 | 2-(trifluoromethoxy)phenyl | 3-amino-1-hydroxy-7-[2-(trifluoromethoxy)phenyl]-3,4-dihydroquinolin-2(1H)-one, trifluoroacetate salt | 1.93 | 338.09 | 339.0 |
| 42 | phenyl | 3-amino-1-hydroxy-7-phenyl-3,4-dihydroquinolin-2(1H)-one, trifluoroacetate salt | 1.68 | 254.11 | 255.0 |
| 43 | 2,5-dichlorophenyl | 3-amino-7-(2,5-dichlorophenyl)-1-hydroxy-3,4-dihydroquinolin-2(1H)-one, trifluoroacetate salt | 1.97 | 322.03 | 322.9 |
| 44 | 3,4-difluorophenyl | 3-amino-7-(3,4-difluorophenyl)-1-hydroxy-3,4-dihydroquinolin-2(1H)-one, trifluoroacetate salt | 1.82 | 290.09 | 291.0 |
| 45 | 2-chlorophenyl | 3-amino-7-(2-chlorophenyl)-1-hydroxy-3,4-dihydroquinolin-2(1H)-one, trifluoroacetate salt | 1.79 | 288.07 | 289.0 |

TABLE 2-continued

| Ex. No. | R | IUPAC Name | HPLC Retention Time (min.)[a] | MW[b] | MS[c] |
|---|---|---|---|---|---|
| 46 | 3-(trifluoromethyl)phenyl (F$_3$C-) | 3-amino-1-hydroxy-7-[3-(trifluoromethyl)phenyl]-3,4-dihydroquinolin-2(1H)-one, trifluoroacetate salt | 1.97 | 322.29 | 323.0 |
| 47 | 2,3-dimethylphenyl | 3-amino-7-(2,3-dimethylphenyl)-1-hydroxy-3,4-dihydroquinolin-2(1H)-one, trifluoroacetate salt | 1.93 | 282.14 | 283.1 |
| 48 | 6-(dimethylamino)pyridin-3-yl | 3-amino-7-[6-(dimethylamino)pyridin-3-yl]-1-hydroxy-3,4-dihydroquinolin-2(1H)-one, trifluoroacetate salt | 2.02 | 298.14 | 299.1 |
| 49 | 3-fluoro-4-methoxyphenyl | 3-amino-7-(3-fluoro-4-methoxyphenyl)-1-hydroxy-3,4-dihydroquinolin-2(1H)-one, trifluoroacetate salt | 1.68 | 302.11 | 303.0 |
| 50 | 2,5-difluorophenyl | 3-amino-7-(2,5-difluorophenyl)-1-hydroxy-3,4-dihydroquinolin-2(1H)-one, trifluoroacetate salt | 1.77 | 290.09 | 291.0 |
| 51 | 2-furyl | 3-amino-7-(2-furyl)-1-hydroxy-3,4-dihydroquinolin-2(1H)-one, trifluoroacetate salt | 1.49 | 244.08 | 245.1 |
| 52 | 3-chlorophenyl | 3-amino-7-(3-chlorophenyl)-1-hydroxy-3,4-dihydroquinolin-2(1H)-one, trifluoroacetate salt | 1.88 | 288.07 | 289.0 |
| 53 | 4-(trifluoromethyl)phenyl | 3-amino-1-hydroxy-7-[4-(trifluoromethyl)phenyl]-3,4-dihydroquinolin-2(1H)-one, trifluoroacetate salt | 2.01 | 322.09 | 323.0 |

TABLE 2-continued

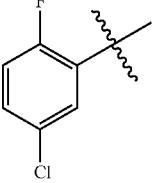

| Ex. No. | R | IUPAC Name | HPLC Retention Time (min.)[a] | MW[b] | MS[c] |
|---|---|---|---|---|---|
| 54 | 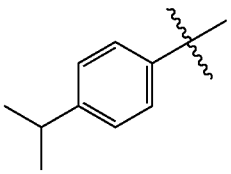 | 3-amino-7-(5-chloro-2-fluorophenyl)-1-hydroxy-3,4-dihydroquinolin-2(1H)-one, trifluoroacetate salt | 1.88 | 306.06 | 307.0 |
| 55 | 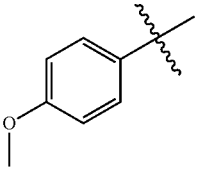 | 3-amino-1-hydroxy-7-(4-isopropylphenyl)-3,4-dihydroquinolin-2(1H)-one, trifluoroacetate salt | 2.12 | 296.15 | 297.0 |
| 56 | 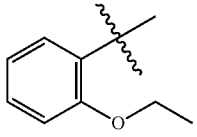 | 3-amino-1-hydroxy-7-(4-methoxyphenyl)-3,4-dihydroquinolin-2(1H)-one, trifluoroacetate salt | 1.69 | 284.12 | 285.0 |
| 57 | 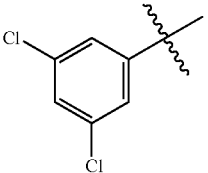 | 3-amino-7-(2-ethoxyphenyl)-1-hydroxy-3,4-dihydroquinolin-2(1H)-one, trifluoroacetate salt | 1.84 | 298.13 | 299.1 |
| 58 | 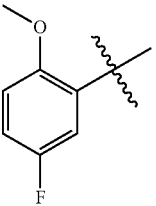 | 3-amino-7-(3,5-dichlorophenyl)-1-hydroxy-3,4-dihydroquinolin-2(1H)-one, trifluoroacetate salt | 2.06 | 322.03 | 322.9 |
| 59 | 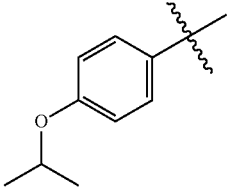 | 3-amino-7-(5-fluoro-2-methoxyphenyl)-1-hydroxy-3,4-dihydroquinolin-2(1H)-one, trifluoroacetate salt | 1.74 | 302.11 | 303.0 |
| 60 |  | 3-amino-1-hydroxy-7-(4-isopropoxyphenyl)-3,4-dihydroquinolin-2(1H)-one, trifluoroacetate salt | 1.97 | 312.15 | 313.0 |

TABLE 2-continued

[Structure: 7-R-substituted 3-amino-1-hydroxy-3,4-dihydroquinolin-2(1H)-one core]

| Ex. No. | R | IUPAC Name | HPLC Retention Time (min.)[a] | MW[b] | MS[c] |
|---|---|---|---|---|---|
| 61 | 4-(trifluoromethoxy)phenyl (F$_3$C-O-C$_6$H$_4$-) | 3-amino-1-hydroxy-7-[4-(trifluoromethoxy)phenyl]-3,4-dihydroquinolin-2(1H)-one, trifluoroacetate salt | 2.07 | 338.09 | 339.0 |
| 62 | 2-cyanophenyl | 2-(3-amino-1-hydroxy-2-oxo-1,2,3,4-tetrahydroquinolin-7-yl)benzonitrile, trifluoroacetate salt | 1.59 | 279.1 | 280.0 |
| 63 | 3-methylphenyl | 3-amino-1-hydroxy-7-(3-methylphenyl)-3,4-dihydroquinolin-2(1H)-one, trifluoroacetate salt | 1.85 | 268.12 | 269.1 |
| 64 | 4-methoxy-3-methylphenyl | 3-amino-1-hydroxy-7-(4-methoxy-3-methylphenyl)-3,4-dihydroquinolin-2(1H)-one, trifluoroacetate salt | 1.88 | 298.13 | 299.0 |
| 65 | 2,3-dihydro-1-benzofuran-5-yl | 3-amino-7-(2,3-dihydro-1-benzofuran-5-yl)-1-hydroxy-3,4-dihydroquinolin-2(1H)-one, trifluoroacetate salt | 1.68 | 296.12 | 297.0 |

[a] HPLC Method: Column: Waters Sunfire C$_{18}$; 3.5 μm, 4.6 × 50 mm; Mobile phase A: 0.05% TFA in water; Mobile phase B: 0.05% TFA in MeCN; Flow rate 2.0 mL/min.

Gradient:

| 0 minutes | 5% B |
| 4 minutes | 95% B |
| 4-5.5 minutes | 100% B |

[b] Calculated Exact Molecular Weight.

[c] Mass spectrum: observed ion m/z (M + 1).

Method A: Trifluoroethyl Ester Synthesis and Cyclization

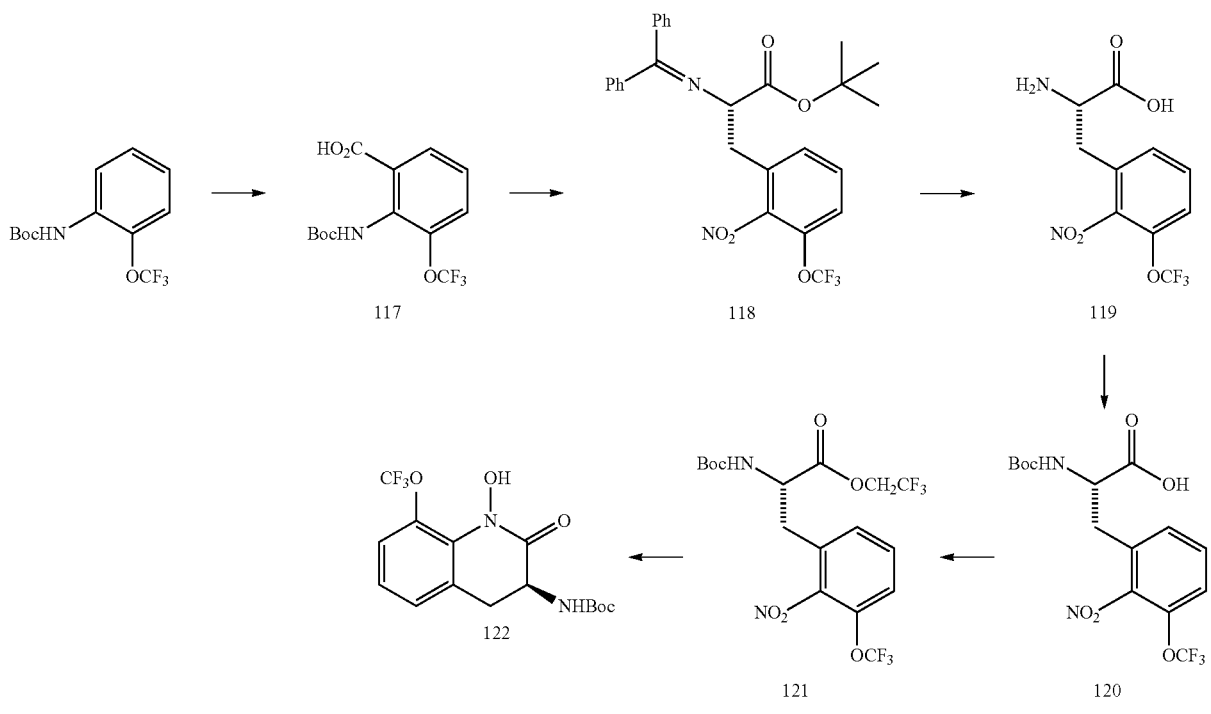

2-[(tert-Butoxycarbonyl)amino]-3-(trifluoromethoxy)benzoic acid (117) A solution of tert-butyl [2-(trifluoromethoxy)phenyl]carbamate (139 g, 0.50 mol) in dry THF (900 mL) was cooled to −78° C. A tert-BuLi solution (1.6 M in pentane, 800 mL, 1.28 mol) was added drop-wise. After completion of the addition, the mixture was stirred at −50° C. for 1 h. The clear solution was added to solid carbon dioxide, and the mixture was left overnight. Water (900 mL) was added and the layers were separated. The aqueous layer was extracted with $Et_2O$ (500 mL) followed by acidification to pH 1 with aqueous 1 N HCl. The mixture was extracted with $Et_2O$ (2×500 mL), and the combined extracts were dried over $Na_2SO_4$, filtered and concentrated in vacuo. Trituration with pentane yielded the title compound as a white solid (128 g, 79%). $^1$H NMR (300 MHz, $CDCl_3$) δ 1.51 (s, 9H), 7.26 (dd, J=8.1, 8.1 Hz, 1H), 7.47-7.53 (m, 1H), 7.74 (br s, 1H), 7.93 (dd, J=7.9, 1.5 Hz, 1H).

tert-Butyl N-(diphenylmethylene)-2-nitro-3-(trifluoromethoxy)-L-phenylalaninate (118) Trifluoroacetic acid (6 mL, 80 mmol) was added to a solution of 2-[(tert-butoxycarbonyl)amino]-3-(trifluoromethoxy)benzoic acid (117) (7.254 g, 22.58 mmol) in dichloromethane (40 mL). The mixture was stirred at RT for 2 h. The volatiles were removed in vacuo to provide 2-amino-3-(trifluoromethoxy)benzoic acid, which was dissolved in trifluoroacetic acid (30 mL). After addition of $NaBO_3.4H_2O$ (18.3 g, 113 mmol), the mixture was stirred and heated at reflux for 18 h. The reaction mixture was cooled to RT, poured into water and extracted with $Et_2O$. The combined extracts were dried, filtered and concentrated in vacuo to yield 2-nitro-3-(trifluoromethoxy)benzoic acid, which was then dissolved in THF (8.5 mL) and cooled to 0° C. Sodium borohydride (99%, 2.40 g, 62.8 mmol) was added in two portions; after gas evolution had subsided, boron trifluoride dimethyl etherate (98%, 5.89 mL, 62.9 mmol) was added drop-wise at 0° C., and the reaction mixture was stirred for 30 min at 0° C. The reaction was allowed to warm to RT over 18 h, then recooled in an ice bath and treated with saturated aqueous ammonium chloride solution until no additional gas evolution was observed. The mixture was partitioned between EtOAc (30 mL) and water (10 mL), and the aqueous layer was extracted with EtOAc (3×20 mL). The combined organic layers were washed with saturated aqueous sodium chloride solution, dried over sodium sulfate, filtered and concentrated in vacuo to provide [2-nitro-3-(trifluoromethoxy)phenyl]methanol. This crude residue was dissolved in $Et_2O$ (150 mL). The mixture was cooled to 0° C. and phosphorus tribromide (97%, 3.68 mL, 37.9 mmol) was added. The mixture was allowed to warm to RT over 18 h, then poured onto ice water. The layers were separated and the aqueous layer was extracted with $Et_2O$. The combined extracts were washed with water, dried, filtered and concentrated in vacuo to yielding 1-(bromomethyl)-2-nitro-3-(trifluoromethoxy)benzene. This crude residue was converted to the title compound using the general procedure outlined in Example 12 to afford the product as a yellow oil (3.67 g, 32%). LCMS m/z 515.5 (M+1). $^1$H NMR (400 MHz, $CDCl_3$) δ 1.44 (s, 9H), 3.20-3.31 (m, 2H), 4.23 (dd, J=8.2, 5.1 Hz, 1H), 6.68 (br d, J=7.2 Hz, 2H), 7.25-7.43 (m, 9H), 7.59-7.62 (m, 2H).

2-Nitro-3-(trifluoromethoxy)-L-phenylalanine, hydrochloride salt (119) Trifluoroacetic acid (30 mL) was added to a solution of tert-butyl N-(diphenylmethylene)-2-nitro-3-(trifluoromethoxy)-L-phenylalaninate (118) (3.661 g, 7.116 mmol) in dichloromethane (10 mL), and the reaction was allowed to stir for 18 h. Volatiles were removed in vacuo, and the residue was diluted with concentrated HCl (12 mL) and washed with EtOAc (10 mL). The EtOAc layer was extracted with water (5×10 mL), and the combined aqueous layers were concentrated in vacuo to give the product as a solid (2.163 g, 92%). LCMS m/z 295.4 (M+1). $^1$H NMR (400 MHz, $CD_3OD$) δ 3.20 (dd, half of ABX pattern, J=14.8, 7.6 Hz, 1H), 3.34 (dd, half of ABX pattern, J=14.7, 7.3 Hz, 1H, assumed; partially obscured by solvent peak), 4.28 (dd, J=7.5, 7.5 Hz, 1H), 7.56-7.62 (m, 2H), 7.72 (dd, J=8.4, 7.9 Hz, 1H).

2,2,2-Trifluoroethyl N-(tert-butoxycarbonyl)-2-nitro-3-(trifluoromethoxy)-L-phenylalaninate (121) 2-Nitro-3-(trifluoromethoxy)-L-phenylalanine, hydrochloride salt (119) (250.6 mg, 0.758 mmol) was suspended in dioxane (3.5 mL)/water (3.5 mL) and the mixture was cooled to 0° C. Triethylamine (0.368 mL, 2.65 mmol) was added, resulting in a solution. BOC$_2$O (199 mg, 0.910 mmol) was added and the mixture was stirred at 0° C. for 15 min, then allowed to warm to RT. After 2 h at RT, most of the dioxane was removed by evaporation under reduced pressure, and saturated aqueous ammonium chloride solution was added until the pH was lowered to ~3. The mixture was diluted with EtOAc (10 mL), and the aqueous layer was extracted with EtOAc (3×15 mL). The combined extracts were dried over sodium sulfate, filtered and evaporated in vacuo to give N-(tert-butoxycarbonyl)-2-nitro-3-(trifluoromethoxy)phenylalanine (120), which was dissolved in dichloromethane (7 mL). 1-[3-(Dimethylamino)propyl]-3-ethylcarbodiimide hydrochloride (98%, 0.195 mL, 0.874 mmol), N,N-dimethylpyridin-4-amine (97%, 45.7 mg, 0.363 mmol) and 2,2,2-trifluoroethanol (99%, 0.106 mL, 1.46 mmol) were added and the resulting mixture was stirred for 18 h at RT. The reaction mixture was washed with saturated aqueous sodium chloride solution, and the aqueous layer was extracted with dichloromethane (3×5 mL). The combined organic layers were dried, filtered and concentrated in vacuo. Purification using silica gel chromatography (Gradient: 0% to 30% EtOAc in heptane) provided the product as a white solid (170.3 mg, 47% over 2 steps). LCMS m/z 475.4 (M−1). $^1$H NMR (400 MHz, DMSO-d$_6$) δ 1.33 (s, 9H), 3.01-3.12 (m, 2H), 4.32-4.39 (m, 1H), 4.69-4.79 (m, 2H), 7.57-7.66 (m, 3H), 7.74 (dd, J=8.2, 8.2 Hz, 1H).

tert-Butyl [(3S)-1-hydroxy-2-oxo-8-(trifluoromethoxy)-1,2,3,4-tetrahydroquinolin-3-yl]carbamate (122) Platinum black (68.6 mg, 0.351 mmol) was added to a solution of 2,2,2-trifluoroethyl N-(tert-butoxycarbonyl)-2-nitro-3-(trifluoromethoxy)-L-phenylalaninate (121) (167.3 mg, 0.351 mmol) in pyridine (20 mL). The mixture was shaken on a Parr shaker at 30 psi hydrogen for 3 h, at which time the reaction was filtered through Celite and the filtrate was concentrated in vacuo. Purification via silica gel chromatography (Gradient: 0% to 45% EtOAc in heptane) afforded the product (79.7 mg, 63%). LCMS m/z 361.5 (M−1). $^1$H NMR (400 MHz, CDCl$_3$) δ 1.45 (s, 9H), 2.91 (br dd, J=14.7, 14.7 Hz, 1H), 3.34 (br dd, J=15, 5 Hz, 1H), 4.44-4.55 (m, 1H), 5.66 (br d, J=4.5 Hz, 1H), 7.12-7.17 (m, 2H), 7.22-7.26 (m, 1H).

Method B: Preparation of 6-substituted (3S)-3-amino-1-hydroxy-3,4-dihydroquinolin-2(1H)-ones

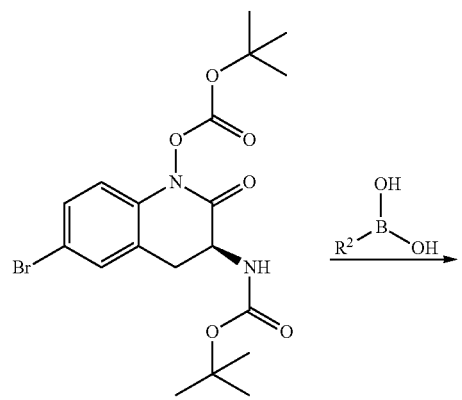

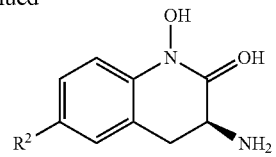

The appropriate boronic acid (0.112 mmol) was reacted with tert-butyl {(3S)-6-bromo-1-[(tert-butoxycarbonyl)oxy]-2-oxo-1,2,3,4-tetrahydroquinolin-3-yl}carbamate as described for the preparation of Examples 38-65. tert-Butyl {(3S)-6-bromo-1-[(tert-butoxycarbonyl)oxy]-2-oxo-1,2,3,4-tetrahydroquinolin-3-yl}carbamate was prepared from 4-bromo-2-(bromomethyl)-1-nitrobenzene using the method described in Example 12. The title products were purified by reversed-phase preparative HPLC (Column: Waters Sunfire C$_{18}$ 19×100, 5 μm; Mobile phase A: 0.05% TFA in water (v/v); Mobile phase B: 0.05% TFA in MeCN (v/v); Gradient: 5% B to 100% B).

Method C: Preparation of 6-aryloxy and 6-heteroaryloxy (3S)-3-amino-1-hydroxy-3,4-dihydroquinolin-2(1H)-ones

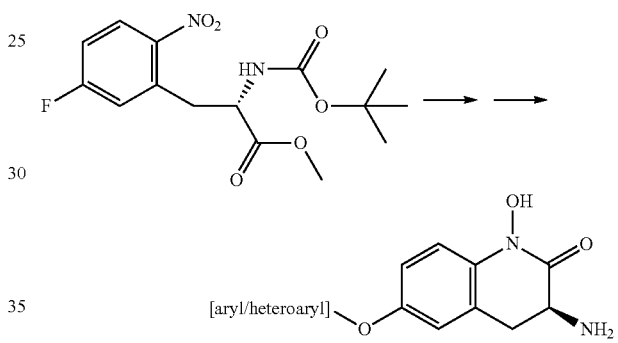

The requisite phenol or hydroxy-substituted heteroaryl (0.225 mmol) was dissolved in THF (0.2 mL), treated with a solution of potassium tert-butoxide in THF (1 N, 0.225 mL, 0.225 mmol), and shaken at RT for approximately 10 min. A solution of methyl N-(tert-butoxycarbonyl)-3-fluoro-6-nitro-L-phenylalaninate (51 mg, 0.15 mmol) (prepared from 2-bromo-4-fluoro-1-nitrobenzene using the method described for conversion of 3-bromo-2-nitro-5-phenoxypyridine (64) to methyl N-(tert-butoxycarbonyl)-3-(2-nitro-5-phenoxypyridin-3-yl)-L-alaninate (65) in Example 66) in THF (0.3 mL) was added, and the reaction was shaken at 60° C. for 17 h. It was then partitioned between water (1.5 mL) and EtOAc (2.5 mL) with vortexing. The organic layer was dried by passage through an SPE cartridge packed with sodium sulfate. The extraction was repeated twice, then solvent was removed from the combined organic layers. This material was mixed with 50% trifluoroacetic acid in dichloromethane (1 mL), and the reaction was shaken at RT for 4 h. After removal of solvent, the residue was treated with a solution of tin(II) chloride (45 mg, 0.2 mmol) in EtOH (0.5 mL). This was shaken at RT for 3 h, then subjected to partitioning, drying and repeated extraction as described above. Centrifugation was required in some cases to break up emulsions. The solvent was removed, and the residue was dissolved in DMSO (1 mL) and filtered through a Waters Oasis® filter plate, then purified by reversed-phase HPLC using one of the following methods: 1) Column: Waters Sunfire C$_{18}$ 19×100 mm, 5 μm; Mobile phase A: 0.05% TFA in water (v/v); Mobile phase B: 0.05% TFA in MeCN (v/v); Gradient: 5% B to 100% B, linear; 2) Column: Waters XBridge C$_{18}$ 19×100 mm, μm; Mobile phase A: 0.03% NH₄OH in water (v/v); Mobile phase B: 0.03% NH₄OH in MeCN (v/v); Gradient: 5% B to 100% B, linear.

Examples 131-171 were prepared using these Methods; characterization data for these Examples is provided in Tables 3 and 4.

TABLE 3

| Ex # | R | IUPAC Name | Meth Of Prep | HPLC Ret'n Time (min) | MW[3] | MS[4] |
|---|---|---|---|---|---|---|
| 131 | 3-(trifluoromethoxy)phenyl | (3S)-3-amino-1-hydroxy-6-[3-(trifluoromethoxy)phenyl]-3,4-dihydroquinolin-2(1H)-one, trifluoroacetate salt | B | 0.81[1] | 338.09 | 417.4[5] |
| 132 | 2-(trifluoromethoxy)phenyl | (3S)-3-amino-1-hydroxy-6-[2-(trifluoromethoxy)phenyl]-3,4-dihydroquinolin-2(1H)-one, trifluoroacetate salt | B | 0.77[1] | 338.09 | 339.5 |
| 133 | 2,5-difluorophenyl | (3S)-3-amino-6-(2,5-difluorophenyl)-1-hydroxy-3,4-dihydroquinolin-2(1H)-one, trifluoroacetate salt | B | 0.67[1] | 290.09 | 369.3[5] |
| 134 | 4-methoxy-3-methylphenyl | (3S)-3-amino-1-hydroxy-6-(4-methoxy-3-methylphenyl)-3,4-dihydroquinolin-2(1H)-one, trifluoroacetate salt | B | 0.73[1] | 298.13 | 377.5 |
| 135 | 2-methylphenyl | (3S)-3-amino-1-hydroxy-6-(2-methylphenyl)-3,4-dihydroquinolin-2(1H)-one, trifluoroacetate salt | B | 0.71[1] | 268.12 | 347.4[5] |
| 136 | 2-fluorophenyl | (3S)-3-amino-6-(2-fluorophenyl)-1-hydroxy-3,4-dihydroquinolin-2(1H)-one, trifluoroacetate salt | B | 0.65[1] | 272.10 | 351.4[5] |
| 137 | 4-methoxy-2-methylphenyl | (3S)-3-amino-1-hydroxy-6-(4-methoxy-2-methylphenyl)-3,4-dihydroquinolin-2(1H)-one, trifluoroacetate salt | B | 0.70[1] | 298.13 | 377.4[5] |

TABLE 3-continued

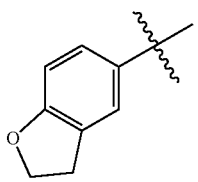

| Ex # | R | IUPAC Name | Meth Of Prep | HPLC Ret'n Time (min) | MW[3] | MS[4] |
|---|---|---|---|---|---|---|
| 138 | 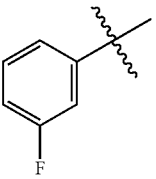 | (3S)-3-amino-6-(2,3-dihydro-1-benzofuran-5-yl)-1-hydroxy-3,4-dihydroquinolin-2(1H)-one, trifluoroacetate salt | B | 0.64[1] | 296.12 | 375.4[5] |
| 139 | 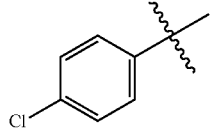 | (3S)-3-amino-6-(3-fluorophenyl)-1-hydroxy-3,4-dihydroquinolin-2(1H)-one, trifluoroacetate salt | B | 0.66[1] | 272.10 | 351.4[5] |
| 140 | 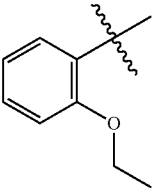 | (3S)-3-amino-6-(4-chlorophenyl)-1-hydroxy-3,4-dihydroquinolin-2(1H)-one, trifluoroacetate salt | B | 0.74[1] | 288.07 | 367.3[5] |
| 141 | 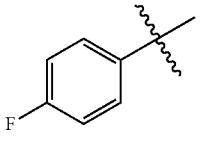 | (3S)-3-amino-6-(2-ethoxyphenyl)-1-hydroxy-3,4-dihydroquinolin-2(1H)-one, trifluoroacetate salt | B | 0.65[1] | 298.13 | 377.5[5] |
| 142 | 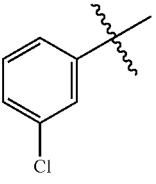 | (3S)-3-amino-6-(4-fluorophenyl)-1-hydroxy-3,4-dihydroquinolin-2(1H)-one, trifluoroacetate salt | B | 0.66[1] | 272.10 | 351.3[5] |
| 143 | 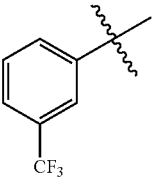 | (3S)-3-amino-6-(3-chlorophenyl)-1-hydroxy-3,4-dihydroquinolin-2(1H)-one, trifluoroacetate salt | B | 0.73[1] | 288.07 | 367.4[5] |
| 144 |  | (3S)-3-amino-1-hydroxy-6-[3-(trifluoromethyl)phenyl]-3,4-dihydroquinolin-2(1H)-one, trifluoroacetate salt | B | 0.78[1] | 322.09 | 401.4[5] |

TABLE 3-continued

| Ex # | R | IUPAC Name | Meth Of Prep | HPLC Ret'n Time (min) | MW[3] | MS[4] |
|---|---|---|---|---|---|---|
| 145 | 2,3-dichlorophenyl | (3S)-3-amino-6-(2,3-dichlorophenyl)-1-hydroxy-3,4-dihydroquinolin-2(1H)-one, trifluoroacetate salt | B | 0.78[1] | 322.03 | 401.4[5] |
| 146 | 3-methylphenyl | (3S)-3-amino-1-hydroxy-6-(3-methylphenyl)-3,4-dihydroquinolin-2(1H)-one, trifluoroacetate salt | B | 0.65[1] | 268.12 | 347.5[5] |
| 147 | 2,4-difluorophenyl | (3S)-3-amino-6-(2,4-difluorophenyl)-1-hydroxy-3,4-dihydroquinolin-2(1H)-one, trifluoroacetate salt | B | 0.68[1] | 290.09 | 369.4[5] |
| 148 | 2,6-difluorophenyl | (3S)-3-amino-6-(2,6-difluorophenyl)-1-hydroxy-3,4-dihydroquinolin-2(1H)-one, trifluoroacetate salt | B | 0.65[1] | 290.09 | 291.4 |
| 149 | 2-ethylphenyl | (3S)-3-amino-6-(2-ethylphenyl)-1-hydroxy-3,4-dihydroquinolin-2(1H)-one, trifluoroacetate salt | B | 0.76[1] | 282.14 | 361.4[5] |
| 150 | phenyl | (3S)-3-amino-1-hydroxy-6-phenyl-3,4-dihydroquinolin-2(1H)-one, trifluoroacetate salt | B | 0.64[1] | 254.11 | 333.3[5] |
| 151 | 2-methoxypyridin-3-yl | (3S)-3-amino-1-hydroxy-6-(2-methoxypyridin-3-yl)-3,4-dihydroquinolin-2(1H)-one, trifluoroacetate salt | B | 0.54[1] | 285.11 | 364.4[5] |
| 152 | 2-chloro-5-fluorophenyl | (3S)-3-amino-6-(2-chloro-5-fluorophenyl)-1-hydroxy-3,4-dihydroquinolin-2(1H)-one, trifluoroacetate salt | B | 0.72[1] | 306.06 | 385.4[5] |

TABLE 3-continued

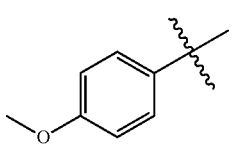

| Ex # | R | IUPAC Name | Meth Of Prep | HPLC Ret'n Time (min) | MW[3] | MS[4] |
|---|---|---|---|---|---|---|
| 153 | 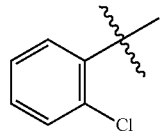 | (3S)-3-amino-1-hydroxy-6-(4-methoxyphenyl)-3,4-dihydroquinolin-2(1H)-one, trifluoroacetate salt | B | 0.64[1] | 284.12 | 363.6[5] |
| 154 | 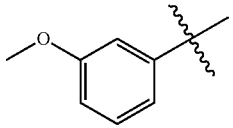 | (3S)-3-amino-6-(2-chlorophenyl)-1-hydroxy-3,4-dihydroquinolin-2(1H)-one, trifluoroacetate salt | B | 0.70[1] | 288.07 | 367.1[5] |
| 155 | 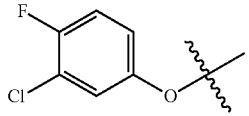 | (3S)-3-amino-1-hydroxy-6-(3-methoxyphenyl)-3,4-dihydroquinolin-2(1H)-one, trifluoroacetate salt | B | 0.65[1] | 284.12 | 363.4[5] |
| 156 | 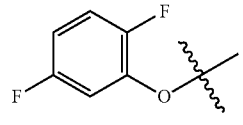 | (3S)-3-amino-6-(3-chloro-4-fluorophenoxy)-1-hydroxy-3,4-dihydroquinolin-2(1H)-one, trifluoroacetate salt | C | 2.28[2] | 322.05 | 323.1 |
| 157 | 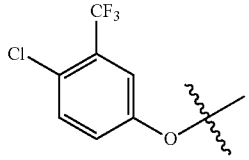 | (3S)-3-amino-6-(2,5-difluorophenoxy)-1-hydroxy-3,4-dihydroquinolin-2(1H)-one, trifluoroacetate salt | C | 2.11[2] | 306.08 | 307.1 |
| 158 | 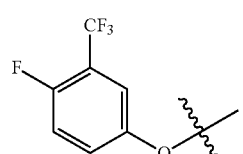 | (3S)-3-amino-6-[4-chloro-3-(trifluoromethyl)phenoxy]-1-hydroxy-3,4-dihydroquinolin-2(1H)-one, trifluoroacetate salt | C | 2.50[2] | 372.05 | 373.0 |
| 159 | 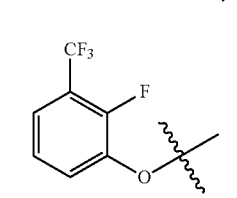 | (3S)-3-amino-6-[4-fluoro-3-(trifluoromethyl)phenoxy]-1-hydroxy-3,4-dihydroquinolin-2(1H)-one, trifluoroacetate salt | C | 2.39[2] | 356.08 | 357.1 |
| 160 |  | (3S)-3-amino-6-[2-fluoro-3-(trifluoromethyl)phenoxy]-1-hydroxy-3,4-dihydroquinolin-2(1H)-one, trifluoroacetate salt | C | 2.37[2] | 356.08 | 357.0 |

TABLE 3-continued

[Structure: 1-hydroxy-3,4-dihydroquinolin-2(1H)-one core with R group at 6-position and NH2 at 3-position (S configuration)]

| Ex # | R | IUPAC Name | Meth Of Prep | HPLC Ret'n Time (min) | MW³ | MS⁴ |
|---|---|---|---|---|---|---|
| 161 | 2-chloro-4-fluorophenoxy | (3S)-3-amino-6-(2-chloro-4-fluorophenoxy)-1-hydroxy-3,4-dihydroquinolin-2(1H)-one, trifluoroacetate salt | C | 2.22² | 322.05 | 323.1 |
| 162 | 3,4-difluorophenoxy | (3S)-3-amino-6-(3,4-difluorophenoxy)-1-hydroxy-3,4-dihydroquinolin-2(1H)-one, trifluoroacetate salt | C | 2.18² | 306.08 | 307.1 |
| 163 | 3,4-dichlorophenoxy | (3S)-3-amino-6-(3,4-dichlorophenoxy)-1-hydroxy-3,4-dihydroquinolin-2(1H)-one, trifluoroacetate salt | C | 2.41² | 338.02 | 339.0 |
| 164 | 4-cyano-3-(trifluoromethyl)phenoxy | 4-{[(3S)-3-amino-1-hydroxy-2-oxo-1,2,3,4-tetrahydroquinolin-6-yl]oxy}-2-(trifluoromethyl)benzonitrile, trifluoroacetate salt | C | 2.27² | 363.08 | 364.0 |
| 165 | 5-fluoro-2-methylphenoxy | (3S)-3-amino-6-(5-fluoro-2-methylphenoxy)-1-hydroxy-3,4-dihydroquinolin-2(1H)-one, trifluoroacetate salt | C | 2.23² | 302.11 | 303.1 |
| 166 | 3-fluoro-5-(trifluoromethyl)phenoxy | (3S)-3-amino-6-[3-fluoro-5-(trifluoromethyl)phenoxy]-1-hydroxy-3,4-dihydroquinolin-2(1H)-one, trifluoroacetate salt | C | 2.41² | 356.08 | 357.1 |
| 167 | 4-chloro-3-fluorophenoxy | (3S)-3-amino-6-(4-chloro-3-fluorophenoxy)-1-hydroxy-3,4-dihydroquinolin-2(1H)-one, trifluoroacetate salt | C | 2.29² | 322.05 | 323.1 |

TABLE 3-continued

| Ex # | R | IUPAC Name | Meth Of Prep | HPLC Ret'n Time (min) | MW[3] | MS[4] |
|---|---|---|---|---|---|---|
| 168 | (3-chloro-5-fluorophenoxy) | (3S)-3-amino-6-(3-chloro-5-fluorophenoxy)-1-hydroxy-3,4-dihydroquinolin-2(1H)-one, trifluoroacetate salt | C | 2.27[2] | 322.05 | 323.1 |
| 169 | 3-(trifluoromethoxy)phenoxy | (3S)-3-amino-1-hydroxy-6-[3-(trifluoromethoxy)phenoxy]-3,4-dihydroquinolin-2(1H)-one, trifluoroacetate salt | C | 2.35[2] | 354.08 | 355.1 |
| 170 | (5-chloropyridin-3-yl)oxy | (3S)-3-amino-6-[(5-chloropyridin-3-yl)oxy]-1-hydroxy-3,4-dihydroquinolin-2(1H)-one, ammonium salt | C | 1.83[2] | 305.06 | 306.0, 308.0 |

[1]HPLC method: Column: Waters Acquity HSS T3; 1.8 μm, 2.1 × 50 mm; Mobile phase A: 0.05% TFA in water (v/v); Mobile phase B: 0.05% TFA in MeCN (v/v); Gradient: 5% B to 98% B, linear over 1.8 min, hold at 95% B to 2.0 min; Flow rate 1.3 mL/min.
[2]HPLC method: Column: Waters Atlantis dC$_{18}$; 5 μm, 4.6 × 50 mm; Mobile phase A: 0.05% TFA in water (v/v); Mobile phase B: 0.05% TFA in MeCN (v/v); Gradient: 5% B to 95% B, linear over 4.0 min, hold at 95% B to 5.0 min; Flow rate 2.0 mL/min.
[3]Calculated Exact Molecular Weight.
[4]Mass spectrum: observed ion m/z (M + 1).
[5][(M + DMSO) + 1]

TABLE 4

| Ex. No. | R[2] | IUPAC Name | Method of Prep | HPLC Ret'n Time (min) | MW[3] | MS[4] |
|---|---|---|---|---|---|---|
| 171 | (6-methoxypyridin-3-yl)oxy | 3-amino-1-hydroxy-6-[(6-methoxypyridin-3-yl)oxy]-3,4-dihydroquinolin-2(1H)-one, ammonium salt | Ex. 69[1] | 1.80[2] | 301.11 | 302.2 |

[1]Purification of this compound was carried out using reversed-phase HPLC (Column: Waters XBridge C$_{18}$, 5 μm; Mobile phase A: 0.03% NH$_4$OH in water (v/v); Mobile phase B: 0.03% NH$_4$OH in MeCN (v/v); Gradient: 10% to 100% B.
[2]HPLC method: Column: Waters Atlantis dC$_{18}$; 5 μm, 4.6 × 50 mm; Mobile phase A: 0.05% TFA in water (v/v); Mobile phase B: 0.05% TFA in MeCN (v/v); Gradient: 5% B to 95% B, linear over 4.0 min, hold at 95% B to 5.0 min; Flow rate 2.0 mL/min.
[3]Calculated Exact Molecular Weight.
[4]Mass spectrum: observed ion m/z (M + 1).

The compounds shown in Table X, below, and their pharmaceutically acceptable salts may be prepared according to the procedures described herein, making non-critical changes well known to those of ordinary skill in organic synthesis.

TABLE X

| Ex. No. | IUPAC Name |
|---|---|
| 172 | (3S)-3-amino-6-(2,3-dihydro-1H-inden-4-yloxy)-1-hydroxy-3,4-dihydro-1,8-naphthyridin-2(1H)-one |
| 173 | 2-{[(6S)-6-amino-8-hydroxy-7-oxo-5,6,7,8-tetrahydro-1,8-naphthyridin-3-yl]oxy}-5-methoxybenzonitrile |
| 174 | (3S)-3-amino-1-hydroxy-6-(2-methoxyphenoxy)-3,4-dihydro-1,8-naphthyridin-2(1H)-one |
| 175 | (3S)-3-amino-1-hydroxy-6-(4-methoxyphenoxy)-3,4-dihydro-1,8-naphthyridin-2(1H)-one |
| 176 | (3S)-3-amino-6-(3,4-dichlorophenoxy)-1-hydroxy-3,4-dihydro-1,8-naphthyridin-2(1H)-one |
| 177 | (3S)-3-amino-6-(2-fluorophenoxy)-1-hydroxy-3,4-dihydro-1,8-naphthyridin-2(1H)-one |
| 178 | (3S)-3-amino-6-(3-chloro-5-fluorophenoxy)-1-hydroxy-3,4-dihydro-1,8-naphthyridin-2(1H)-one |
| 179 | (3S)-3-amino-6-(4-fluoro-2-methoxyphenoxy)-1-hydroxy-3,4-dihydro-1,8-naphthyridin-2(1H)-one |
| 180 | (3S)-3-amino-6-(3-chlorophenoxy)-1-hydroxy-3,4-dihydro-1,8-naphthyridin-2(1H)-one |
| 181 | (3S)-3-amino-1-hydroxy-6-phenoxy-3,4-dihydro-1,8-naphthyridin-2(1H)-one |
| 182 | (3S)-3-amino-6-(5-fluoro-2-methylphenoxy)-1-hydroxy-3,4-dihydro-1,8-naphthyridin-2(1H)-one |
| 183 | (3S)-3-amino-1-hydroxy-6-[2-(methylsulfonyl)phenoxy]-3,4-dihydro-1,8-naphthyridin-2(1H)-one |
| 184 | 2-{[(6S)-6-amino-8-hydroxy-7-oxo-5,6,7,8-tetrahydro-1,8-naphthyridin-3-yl]oxy}benzonitrile |
| 185 | 3-{[(6S)-6-amino-8-hydroxy-7-oxo-5,6,7,8-tetrahydro-1,8-naphthyridin-3-yl]oxy}benzonitrile |
| 186 | 4-{[(6S)-6-amino-8-hydroxy-7-oxo-5,6,7,8-tetrahydro-1,8-naphthyridin-3-yl]oxy}benzonitrile |
| 187 | (3S)-3-amino-6-(2,3-dihydro-1H-inden-5-yloxy)-1-hydroxy-3,4-dihydro-1,8-naphthyridin-2(1H)-one |
| 188 | (3S)-3-amino-6-(4-chlorophenoxy)-1-hydroxy-3,4-dihydro-1,8-naphthyridin-2(1H)-one |
| 189 | (3S)-3-amino-1-hydroxy-6-[3-(trifluoromethyl)phenoxy]-3,4-dihydro-1,8-naphthyridin-2(1H)-one |
| 190 | (3S)-3-amino-6-(3-ethylphenoxy)-1-hydroxy-3,4-dihydro-1,8-naphthyridin-2(1H)-one |
| 191 | (3S)-3-amino-6-(2-chlorophenoxy)-1-hydroxy-3,4-dihydro-1,8-naphthyridin-2(1H)-one |
| 192 | (3S)-3-amino-6-(2,3-dimethylphenoxy)-1-hydroxy-3,4-dihydro-1,8-naphthyridin-2(1H)-one |
| 193 | (3S)-3-amino-6-(2-fluoro-5-methylphenoxy)-1-hydroxy-3,4-dihydro-1,8-naphthyridin-2(1H)-one |
| 194 | (3S)-3-amino-6-(4-chloro-2-methylphenoxy)-1-hydroxy-3,4-dihydro-1,8-naphthyridin-2(1H)-one |
| 195 | (3S)-3-amino-6-(2-chloro-4-methylphenoxy)-1-hydroxy-3,4-dihydro-1,8-naphthyridin-2(1H)-one |
| 196 | (3S)-3-amino-6-(3,5-difluorophenoxy)-1-hydroxy-3,4-dihydro-1,8-naphthyridin-2(1H)-one |
| 197 | 5-{[(6S)-6-amino-8-hydroxy-7-oxo-5,6,7,8-tetrahydro-1,8-naphthyridin-3-yl]oxy}-2-fluorobenzonitrile |
| 198 | (3S)-3-amino-1-hydroxy-6-[2-(trifluoromethyl)phenoxy]-3,4-dihydro-1,8-naphthyridin-2(1H)-one |
| 199 | (3S)-3-amino-6-(2-chloro-4-fluorophenoxy)-1-hydroxy-3,4-dihydro-1,8-naphthyridin-2(1H)-one |
| 200 | (3S)-3-amino-6-(3-chloro-4-fluorophenoxy)-1-hydroxy-3,4-dihydro-1,8-naphthyridin-2(1H)-one |
| 201 | (3S)-3-amino-6-(3,4-difluorophenoxy)-1-hydroxy-3,4-dihydro-1,8-naphthyridin-2(1H)-one |
| 202 | (3S)-3-amino-6-(2,6-difluorophenoxy)-1-hydroxy-3,4-dihydro-1,8-naphthyridin-2(1H)-one |
| 203 | (3S)-3-amino-6-(4-fluoro-2-methylphenoxy)-1-hydroxy-3,4-dihydro-1,8-naphthyridin-2(1H)-one |
| 204 | 3-amino-6-(4-chloro-3-fluorophenoxy)-1-hydroxy-3,4-dihydro-1,8-naphthyridin-2(1H)-one |
| 205 | 3-amino-6-(2,3-difluorophenoxy)-1-hydroxy-3,4-dihydro-1,8-naphthyridin-2(1H)-one |
| 206 | 3-amino-6-(2-cyclopropyl-4-fluorophenoxy)-1-hydroxy-3,4-dihydro-1,8-naphthyridin-2(1H)-one |
| 207 | 2-{[(6S)-6-amino-8-hydroxy-7-oxo-5,6,7,8-tetrahydro-1,8-naphthyridin-3-yl]oxy}-5-fluorobenzonitrile |
| 208 | 4-{[(6S)-6-amino-8-hydroxy-7-oxo-5,6,7,8-tetrahydro-1,8-naphthyridin-3-yl]oxy}-3-fluorobenzonitrile |
| 209 | 4-{[(6S)-6-amino-8-hydroxy-7-oxo-5,6,7,8-tetrahydro-1,8-naphthyridin-3-yl]oxy}-2-chlorobenzonitrile |
| 210 | (3S)-3-amino-6-(2-chloro-6-fluorophenoxy)-1-hydroxy-3,4-dihydro-1,8-naphthyridin-2(1H)-one |
| 211 | (3S)-3-amino-6-(3-chloro-2-fluorophenoxy)-1-hydroxy-3,4-dihydro-1,8-naphthyridin-2(1H)-one |
| 212 | (3S)-3-amino-1-hydroxy-6-[2-(tetrahydrofuran-2-yl)phenoxy]-3,4-dihydro-1,8-naphthyridin-2(1H)-one |

TABLE X-continued

| Ex. No. | IUPAC Name |
|---|---|
| 213 | (3S)-3-amino-6-(anilinomethyl)-1-hydroxy-3,4-dihydroquinolin-2(1H)-one |
| 214 | (3S)-3-amino-1-hydroxy-6-[(tetrahydro-2H-pyran-4-ylamino)methyl]-3,4-dihydroquinolin-2(1H)-one |
| 215 | (3S)-3-amino-1-hydroxy-6-(morpholin-4-ylmethyl)-3,4-dihydroquinolin-2(1H)-one |
| 216 | (3S)-3-amino-1-hydroxy-6-(piperidin-1-ylmethyl)-3,4-dihydroquinolin-2(1H)-one |
| 217 | (3S)-3-amino-1-hydroxy-6-{[(1-methyl-1H-pyrazol-5-yl)amino]methyl}-3,4-dihydroquinolin-2(1H)-one |
| 218 | (3S)-3-amino-1-hydroxy-6-{[methyl(phenyl)amino]methyl}-3,4-dihydroquinolin-2(1H)-one |
| 219 | (3S)-3-amino-1-hydroxy-6-{[methyl(pyridin-2-yl)amino]methyl}-3,4-dihydroquinolin-2(1H)-one |
| 220 | (3S)-3-amino-1-hydroxy-6-{[methyl(4-methylpyrimidin-2-yl)amino]methyl}-3,4-dihydroquinolin-2(1H)-one |
| 221 | (3S)-3-amino-1-hydroxy-6-({methyl[3-(trifluoromethoxy)phenyl]amino}methyl)-3,4-dihydroquinolin-2(1H)-one |
| 222 | 3-[{[(3S)-3-amino-1-hydroxy-2-oxo-1,2,3,4-tetrahydroquinolin-6-yl]methyl}(methyl)amino]-1H-pyrazole-4-carbonitrile |
| 223 | (3S)-3-amino-1-hydroxy-6-{[methyl(3-methylisoxazol-5-yl)amino]methyl}-3,4-dihydroquinolin-2(1H)-one |
| 224 | (3S)-3-amino-1-hydroxy-6-({methyl[3-(trifluoromethyl)phenyl]amino}methyl)-3,4-dihydroquinolin-2(1H)-one |
| 225 | (3S)-3-amino-6-{[cyclobutyl(methyl)amino]methyl}-1-hydroxy-3,4-dihydroquinolin-2(1H)-one |
| 226 | 2-[{[(3S)-3-amino-1-hydroxy-2-oxo-1,2,3,4-tetrahydroquinolin-6-yl]methyl}(methyl)amino]benzonitrile |
| 227 | (3S)-3-amino-1-hydroxy-6-{[methyl(6-methylpyridin-3-yl)amino]methyl}-3,4-dihydroquinolin-2(1H)-one |
| 228 | (3S)-3-amino-6-{[(1,3-dimethyl-1H-pyrazol-5-yl)(methyl)amino]methyl}-1-hydroxy-3,4-dihydroquinolin-2(1H)-one |
| 229 | (3S)-3-amino-1-hydroxy-6-({methyl[2-(trifluoromethoxy)phenyl]amino}methyl)-3,4-dihydroquinolin-2(1H)-one |
| 230 | (3S)-3-amino-1-hydroxy-6-({methyl[4-(trifluoromethoxy)phenyl]amino}methyl)-3,4-dihydroquinolin-2(1H)-one |
| 231 | 4-[{[(3S)-3-amino-1-hydroxy-2-oxo-1,2,3,4-tetrahydroquinolin-6-yl]methyl}(methyl)amino]benzonitrile |
| 232 | (3S)-3-amino-1-hydroxy-6-{[methyl(1-methyl-1H-pyrazol-3-yl)amino]methyl}-3,4-dihydroquinolin-2(1H)-one |
| 233 | 2-[{[(3S)-3-amino-1-hydroxy-2-oxo-1,2,3,4-tetrahydroquinolin-6-yl]methyl}(methyl)amino]-4-chlorobenzonitrile |
| 234 | (3S)-3-amino-1-hydroxy-6-{[methyl(pyridazin-3-yl)amino]methyl}-3,4-dihydroquinolin-2(1H)-one |
| 235 | (3S)-3-amino-1-hydroxy-6-{[isoxazol-3-yl(methyl)amino]methyl}-3,4-dihydroquinolin-2(1H)-one |
| 236 | (3S)-3-amino-1-hydroxy-6-{[(2-methoxyphenyl)(methyl)amino]methyl}-3,4-dihydroquinolin-2(1H)-one |
| 237 | (3S)-3-amino-6-{[(3-chlorophenyl)(methyl)amino]methyl}-1-hydroxy-3,4-dihydroquinolin-2(1H)-one |
| 238 | (3S)-3-amino-6-{[(2,6-difluorophenyl)(methyl)amino]methyl}-1-hydroxy-3,4-dihydroquinolin-2(1H)-one |
| 239 | 3-[{[(3S)-3-amino-1-hydroxy-2-oxo-1,2,3,4-tetrahydroquinolin-6-yl]methyl}(methyl)amino]benzonitrile |
| 240 | (3S)-3-amino-6-{[(3,5-difluorophenyl)(methyl)amino]methyl}-1-hydroxy-3,4-dihydroquinolin-2(1H)-one |
| 241 | (3S)-3-amino-1-hydroxy-6-{[methyl(5-methylpyridin-2-yl)amino]methyl}-3,4-dihydroquinolin-2(1H)-one |
| 242 | (3S)-3-amino-1-hydroxy-6-{[(4-methoxyphenyl)(methyl)amino]methyl}-3,4-dihydroquinolin-2(1H)-one |
| 243 | (3S)-3-amino-1-hydroxy-6-{[methyl(6-methylpyridin-2-yl)amino]methyl}-3,4-dihydroquinolin-2(1H)-one |
| 244 | (3S)-3-amino-6-{[(4-chlorophenyl)(methyl)amino]methyl}-1-hydroxy-3,4-dihydroquinolin-2(1H)-one |
| 245 | (3S)-3-amino-6-{[(2-chlorophenyl)(methyl)amino]methyl}-1-hydroxy-3,4-dihydroquinolin-2(1H)-one |
| 246 | (3S)-3-amino-1-hydroxy-6-{[methyl(3-methylpyridin-2-yl)amino]methyl}-3,4-dihydroquinolin-2(1H)-one |
| 247 | (3S)-3-amino-6-{[(3,4-dichlorophenyl)(methyl)amino]methyl}-1-hydroxy-3,4-dihydroquinolin-2(1H)-one |
| 248 | (3S)-3-amino-6-{[(4-fluorophenyl)(methyl)amino]methyl}-1-hydroxy-3,4-dihydroquinolin-2(1H)-one |
| 249 | (3S)-3-amino-6-{[(3-chloro-4-fluorophenyl)(methyl)amino]methyl}-1-hydroxy-3,4-dihydroquinolin-2(1H)-one |
| 250 | (3S)-3-amino-6-{[(4-chloro-2-fluorophenyl)(methyl)amino]methyl}-1-hydroxy-3,4-dihydroquinolin-2(1H)-one |
| 251 | (3S)-3-amino-6-{[(3-chloro-2-fluorophenyl)(methyl)amino]methyl}-1-hydroxy-3,4-dihydroquinolin-2(1H)-one |
| 252 | (3S)-3-amino-6-{[(3-fluorophenyl)(methyl)amino]methyl}-1-hydroxy-3,4-dihydroquinolin-2(1H)-one |

TABLE X-continued

| Ex. No. | IUPAC Name |
|---|---|
| 253 | (3S)-3-amino-1-hydroxy-6-{[isoxazol-4-yl(methyl)amino]methyl}-3,4-dihydroquinolin-2(1H)-one |
| 254 | (3S)-3-amino-1-hydroxy-6-{[methyl(5-methylpyrimidin-2-yl)amino]methyl}-3,4-dihydroquinolin-2(1H)-one |
| 255 | (3S)-3-amino-6-{[(2,3-difluorophenyl)(methyl)amino]methyl}-1-hydroxy-3,4-dihydroquinolin-2(1H)-one |
| 256 | (3S)-3-amino-6-{[(2-chloro-4-fluorophenyl)(methyl)amino]methyl}-1-hydroxy-3,4-dihydroquinolin-2(1H)-one |
| 257 | (3S)-3-amino-1-hydroxy-6-({methyl[2-(trifluoromethyl)phenyl]amino}methyl)-3,4-dihydroquinolin-2(1H)-one |
| 258 | (3S)-3-amino-6-{[(2-chloro-5-fluorophenyl)(methyl)amino]methyl}-1-hydroxy-3,4-dihydroquinolin-2(1H)-one |
| 259 | (3S)-3-amino-1-hydroxy-6-{[methyl(1-methyl-1H-pyrazol-5-yl)amino]methyl}-3,4-dihydroquinolin-2(1H)-one |
| 260 | 3-amino-6-(1,3-benzoxazol-2-yloxy)-1-hydroxy-3,4-dihydroquinolin-2(1H)-one |
| 261 | 3-amino-1-hydroxy-6-[(5-methoxy-1,3-benzoxazol-2-yl)oxy]-3,4-dihydroquinolin-2(1H)-one |
| 262 | 6-[(3-amino-1-hydroxy-2-oxo-1,2,3,4-tetrahydroquinolin-6-yl)oxy]-2-methylnicotinonitrile |
| 263 | 2-[(3-amino-1-hydroxy-2-oxo-1,2,3,4-tetrahydroquinolin-6-yl)oxy]-4-methylnicotinonitrile |
| 264 | 3-amino-1-hydroxy-6-(quinoxalin-2-yloxy)-3,4-dihydroquinolin-2(1H)-one |
| 265 | 2-[(3-amino-1-hydroxy-2-oxo-1,2,3,4-tetrahydroquinolin-6-yl)oxy]-6-methylnicotinonitrile |
| 266 | 3-amino-1-hydroxy-6-(1H-pyrazolo[3,4-d]pyrimidin-4-yloxy)-3,4-dihydroquinolin-2(1H)-one |
| 267 | 3-amino-1-hydroxy-6-(quinazolin-4-yloxy)-3,4-dihydroquinolin-2(1H)-one |
| 268 | 3-amino-6-[(3-chloropyridin-2-yl)oxy]-1-hydroxy-3,4-dihydroquinolin-2(1H)-one |
| 269 | methyl 6-[(3-amino-1-hydroxy-2-oxo-1,2,3,4-tetrahydroquinolin-6-yl)oxy]nicotinate |
| 270 | 3-amino-1-hydroxy-6-(pyrimidin-4-yloxy)-3,4-dihydroquinolin-2(1H)-one |
| 271 | 3-amino-1-hydroxy-6-[(6-methylpyrimidin-4-yl)oxy]-3,4-dihydroquinolin-2(1H)-one |
| 272 | 3-amino-1-hydroxy-6-[(4-methylpyrimidin-2-yl)oxy]-3,4-dihydroquinolin-2(1H)-one |
| 273 | 3-amino-6-[(6-ethylpyrimidin-4-yl)oxy]-1-hydroxy-3,4-dihydroquinolin-2(1H)-one |
| 274 | 3-amino-6-[(5-chloro-6-ethylpyrimidin-4-yl)oxy]-1-hydroxy-3,4-dihydroquinolin-2(1H)-one |
| 275 | 2-[(3-amino-1-hydroxy-2-oxo-1,2,3,4-tetrahydroquinolin-6-yl)oxy]-4,6-dimethylnicotinonitrile |
| 276 | 3-amino-1-hydroxy-6-{[4-(trifluoromethyl)pyrimidin-2-yl]oxy}-3,4-dihydroquinolin-2(1H)-one |
| 277 | 3-amino-1-hydroxy-6-(quinazolin-2-yloxy)-3,4-dihydroquinolin-2(1H)-one |
| 278 | 3-amino-1-hydroxy-6-[(2-methylpyrazolo[1,5-a]pyrimidin-5-yl)oxy]-3,4-dihydroquinolin-2(1H)-one |
| 279 | 3-amino-1-hydroxy-6-[(5-methyl-7H-pyrrolo[2,3-d]pyrimidin-4-yl)oxy]-3,4-dihydroquinolin-2(1H)-one |
| 280 | 3-amino-1-hydroxy-6-(7H-pyrrolo[2,3-d]pyrimidin-4-yloxy)-3,4-dihydroquinolin-2(1H)-one |
| 281 | 3-amino-1-hydroxy-6-(pyrazolo[1,5-a]pyrimidin-7-yloxy)-3,4-dihydroquinolin-2(1H)-one |
| 282 | 3-amino-1-hydroxy-6-[(9-methyl-9H-purin-6-yl)oxy]-3,4-dihydroquinolin-2(1H)-one |
| 283 | 3-amino-6-[(2,6-dimethyl pyrimidin-4-yl)oxy]-1-hydroxy-3,4-dihydroquinolin-2(1H)-one |
| 284 | 3-amino-6-[(4,6-dimethyl pyrimidin-2-yl)oxy]-1-hydroxy-3,4-dihydroquinolin-2(1H)-one |
| 285 | 3-amino-1-hydroxy-6-[(3-methylquinoxalin-2-yl)oxy]-3,4-dihydroquinolin-2(1H)-one |
| 286 | 3-amino-1-hydroxy-6-{[3-(trifluoromethyl)pyridin-2-yl]oxy}-3,4-dihydroquinolin-2(1H)-one |
| 287 | 3-amino-6-[(3,5-dichloropyridin-2-yl)oxy]-1-hydroxy-3,4-dihydroquinolin-2(1H)-one |
| 288 | 3-amino-6-[(5-fluoropyrimidin-2-yl)oxy]-1-hydroxy-3,4-dihydroquinolin-2(1H)-one |
| 289 | 3-amino-1-hydroxy-6-(pyrido[2,3-d]pyrimidin-4-yloxy)-3,4-dihydroquinolin-2(1H)-one |
| 290 | 3-amino-6-[(5-fluoropyridin-2-yl)oxy]-1-hydroxy-3,4-dihydroquinolin-2(1H)-one |
| 291 | 3-amino-6-[(7-fluoroquinazolin-4-yl)oxy]-1-hydroxy-3,4-dihydroquinolin-2(1H)-one |
| 292 | 3-amino-6-[(8-fluoroquinazolin-4-yl)oxy]-1-hydroxy-3,4-dihydroquinolin-2(1H)-one |
| 293 | 3-amino-6-[(7-fluoroquinazolin-2-yl)oxy]-1-hydroxy-3,4-dihydroquinolin-2(1H)-one |
| 294 | 3-amino-6-[(5-ethylpyrimidin-2-yl)oxy]-1-hydroxy-3,4-dihydroquinolin-2(1H)-one |
| 295 | 3-amino-1-hydroxy-6-(pyrido[2,3-d]pyrimidin-2-yloxy)-3,4-dihydroquinolin-2(1H)-one |
| 296 | 3-amino-6-[(5-chloropyrimidin-2-yl)oxy]-1-hydroxy-3,4-dihydroquinolin-2(1H)-one |
| 297 | 3-amino-1-hydroxy-6-[(3-methylisoxazolo[4,5-d]pyrimidin-7-yl)oxy]-3,4-dihydroquinolin-2(1H)-one |
| 298 | 3-amino-1-hydroxy-6-[(6-methyl[1,2,4]triazolo[1,5-a]pyrimidin-7-yl)oxy]-3,4-dihydroquinolin-2(1H)-one |
| 299 | 3-amino-1-hydroxy-6-[(5-methylpyrimidin-4-yl)oxy]-3,4-dihydroquinolin-2(1H)-one |
| 300 | 3-amino-6-[(5-ethylpyrimidin-4-yl)oxy]-1-hydroxy-3,4-dihydroquinolin-2(1H)-one |
| 301 | 3-amino-6-[(5-fluoro-2-methylpyrimidin-4-yl)oxy]-1-hydroxy-3,4-dihydroquinolin-2(1H)-one |
| 302 | 3-amino-6-[(2-ethyl-5-fluoropyrimidin-4-yl)oxy]-1-hydroxy-3,4-dihydroquinolin-2(1H)-one |
| 303 | 3-amino-1-hydroxy-6-(imidazo[1,2-a]pyridin-5-yloxy)-3,4-dihydroquinolin-2(1H)-one |
| 304 | 4-[(3-amino-1-hydroxy-2-oxo-1,2,3,4-tetrahydroquinolin-6-yl)oxy]quinoline-6-carbonitrile |
| 305 | 3-amino-1-hydroxy-6-(imidazo[1,2-b]pyridazin-3-yloxy)-3,4-dihydroquinolin-2(1H)-one |
| 306 | 3-amino-1-hydroxy-6-(pyrazin-2-yloxy)-3,4-dihydroquinolin-2(1H)-one |
| 307 | 3-amino-6-[(3,6-dimethylpyrazin-2-yl)oxy]-1-hydroxy-3,4-dihydroquinolin-2(1H)-one |
| 308 | 3-amino-1-hydroxy-6-[(1-methyl-1H-benzimidazol-2-yl)oxy]-3,4-dihydroquinolin-2(1H)-one |
| 309 | 3-amino-1-hydroxy-6-[(2-methylpyridin-4-yl)oxy]-3,4-dihydroquinolin-2(1H)-one |
| 310 | 3-amino-1-hydroxy-6-(1H-1,2,4-triazol-3-yloxy)-3,4-dihydroquinolin-2(1H)-one |

TABLE X-continued

| Ex. No. | IUPAC Name |
|---|---|
| 311 | 3-amino-6-[(1,3-dimethyl-1H-pyrazol-5-yl)oxy]-1-hydroxy-3,4-dihydroquinolin-2(1H)-one |
| 312 | 3-amino-6-(6,7-dihydro-5H-cyclopenta[b]pyridin-2-yloxy)-1-hydroxy-3,4-dihydroquinolin-2(1H)-one |
| 313 | 3-amino-1-hydroxy-6-[(3-isopropylpyrazin-2-yl)oxy]-3,4-dihydroquinolin-2(1H)-one |
| 314 | 3-amino-1-hydroxy-6-(6H-pyrrolo[2,3-c]pyridin-7-yloxy)-3,4-dihydroquinolin-2(1H)-one |
| 315 | 3-amino-6-[(5-cyclopropylpyridin-2-yl)oxy]-1-hydroxy-3,4-dihydroquinolin-2(1H)-one |
| 316 | 3-amino-1-hydroxy-6-{[3-(trifluoromethyl)pyridin-4-yl]oxy}-3,4-dihydroquinolin-2(1H)-one |
| 317 | 3-amino-1-hydroxy-6-[(3-methyl-1H-1,2,4-triazol-5-yl)oxy]-3,4-dihydroquinolin-2(1H)-one |
| 318 | (3S)-3-amino-1-hydroxy-7-(2-methoxyethoxy)-3,4-dihydroquinolin-2(1H)-one |
| 319 | (3S)-3-amino-1-hydroxy-7-(oxetan-3-yloxy)-3,4-dihydroquinolin-2(1H)-one |
| 320 | (3S)-3-amino-1-hydroxy-7-(tetrahydro-2H-pyran-4-yloxy)-3,4-dihydroquinolin-2(1H)-one |
| 321 | (3S)-3-amino-1-hydroxy-7-[(3R)-tetrahydrofuran-3-yloxy]-3,4-dihydroquinolin-2(1H)-one |
| 322 | (3S)-3-amino-1-hydroxy-7-[(3S)-tetrahydrofuran-3-yloxy]-3,4-dihydroquinolin-2(1H)-one |
| 323 | (3S)-3-amino-7-(cyclopentyloxy)-1-hydroxy-3,4-dihydroquinolin-2(1H)-one |
| 324 | (3S)-3-amino-7-(cyclopropyloxy)-1-hydroxy-3,4-dihydroquinolin-2(1H)-one |
| 325 | (3S)-3-amino-1-hydroxy-7-{[(1R)-1-methylpropyl]oxy}-3,4-dihydroquinolin-2(1H)-one |
| 326 | (3S)-3-amino-1-hydroxy-7-{[(1S)-1-methylpropyl]oxy}-3,4-dihydroquinolin-2(1H)-one |
| 327 | (3S)-3-amino-7-(cyclohexyloxy)-1-hydroxy-3,4-dihydroquinolin-2(1H)-one |
| 328 | (3S)-3-amino-7-(difluoromethoxy)-1-hydroxy-3,4-dihydroquinolin-2(1H)-one |
| 329 | (3S)-3-amino-7-(cyclobutyloxy)-1-hydroxy-3,4-dihydroquinolin-2(1H)-one |
| 330 | (3S)-3-amino-7-(cyclopropyloxy)-1-hydroxy-3,4-dihydroquinolin-2(1H)-one |
| 331 | (7S)-7-amino-2-benzyl-5-hydroxy-7,8-dihydropyrido[3,2-d]pyrimidin-6(5H)-one |
| 332 | (7S)-7-amino-5-hydroxy-2-phenoxy-7,8-dihydropyrido[3,2-d]pyrimidin-6(5H)-one |
| 333 | (7S)-7-amino-5-hydroxy-2-phenoxy-7,8-dihydropyrido[2,3-b]pyrazin-6(5H)-one |
| 334 | (7S)-7-amino-2-benzyl-5-hydroxy-7,8-dihydropyrido[2,3-b]pyrazin-6(5H)-one |
| 335 | (3S)-3-amino-6-benzyl-8-fluoro-1-hydroxy-3,4-dihydroquinolin-2(1H)-one |
| 336 | (3S)-3-amino-1-hydroxy-6-(phenylsulfonyl)-3,4-dihydro-1,8-naphthyridin-2(1H)-one |
| 337 | (3S)-3-amino-7-cyclobutyl-1-hydroxy-3,4-dihydroquinolin-2(1H)-one |
| 338 | (3S)-3-amino-1-hydroxy-2-oxo-1,2,3,4-tetrahydroquinoline-6-carbonitrile |
| 339 | (3S)-3-amino-6-cyclobutyl-1-hydroxy-3,4-dihydroquinolin-2(1H)-one |
| 340 | (3S)-3-amino-6-cyclopentyl-1-hydroxy-3,4-dihydroquinolin-2(1H)-one |
| 341 | (3S)-3-amino-1-hydroxy-7-(methylsulfonyl)-3,4-dihydroquinolin-2(1H)-one |
| 342 | (3S)-3-amino-1-hydroxy-6-(methylsulfonyl)-3,4-dihydroquinolin-2(1H)-one |
| 343 | (3S)-3-amino-1-hydroxy-7-(trifluoromethyl)-3,4-dihydro-1,8-naphthyridin-2(1H)-one |
| 344 | (3S)-3-amino-1-hydroxy-7-methyl-3,4-dihydro-1,8-naphthyridin-2(1H)-one |
| 345 | (3S)-3-amino-7-cyclopropyl-1-hydroxy-3,4-dihydro-1,8-naphthyridin-2(1H)-one |
| 346 | (3S)-3-amino-7-cyclobutyl-1-hydroxy-3,4-dihydro-1,8-naphthyridin-2(1H)-one |
| 347 | (3S)-3-amino-1-hydroxy-6-(trifluoromethyl)-3,4-dihydro-1,8-naphthyridin-2(1H)-one |
| 348 | (3S)-3-amino-6-chloro-1-hydroxy-3,4-dihydro-1,8-naphthyridin-2(1H)-one |
| 349 | (3S)-3-amino-1-hydroxy-6-methyl-3,4-dihydro-1,8-naphthyridin-2(1H)-one |
| 350 | (3S)-3-amino-6-cyclopropyl-1-hydroxy-3,4-dihydro-1,8-naphthyridin-2(1H)-one |
| 351 | (3S)-3-amino-6-cyclobutyl-1-hydroxy-3,4-dihydro-1,8-naphthyridin-2(1H)-one |
| 352 | (3S)-3-amino-1-hydroxy-7-(trifluoromethoxy)-3,4-dihydro-1,8-naphthyridin-2(1H)-one |
| 353 | (3S)-3-amino-7-(trifluoromethyl)l-1-hydroxy-3,4-dihydroquinolin-2(1H)-one |

The compounds shown in Table Y, below, and their pharmaceutically acceptable salts may be prepared according to the procedures described herein, making non-critical changes well known to those of ordinary skill in organic synthesis.

TABLE Y

| Ex. No. | IUPAC Name |
|---|---|
| 354 | (3S)-3-amino-1-[(methylcarbamoyl)oxy]-6-phenoxy-3,4-dihydroquinolin-2(1H)-one |
| 355 | (3S)-3-amino-1-[(ethylcarbamoyl)oxy]-6-phenoxy-3,4-dihydroquinolin-2(1H)-one |
| 356 | (3S)-3-amino-1-[(isopropylcarbamoyl)oxy]-6-phenoxy-3,4-dihydroquinolin-2(1H)-one |
| 357 | (3S)-3-amino-1-[(cyclopropylcarbamoyl)oxy]-6-phenoxy-3,4-dihydroquinolin-2(1H)-one |
| 358 | (3S)-3-amino-1-[(tert-butylcarbamoyl)oxy]-6-phenoxy-3,4-dihydroquinolin-2(1H)-one |
| 359 | (3S)-3-amino-1-[(morpholin-4-ylcarbonyl)oxy]-6-phenoxy-3,4-dihydroquinolin-2(1H)-one |
| 360 | (3S)-3-amino-1-{[(4-methylpiperazin-1-yl)carbonyl]oxy}-6-phenoxy-3,4-dihydroquinolin-2(1H)-one |
| 361 | (3S)-3-amino-1-[(dimethylcarbamoyl)oxy]-7-isopropoxy-3,4-dihydroquinolin-2(1H)-one |
| 362 | (3S)-3-amino-1-[(dimethylcarbamoyl)oxy]-7-(trifluoromethoxy)-3,4-dihydroquinolin-2(1H)-one |
| 363 | (3S)-3-amino-6-benzyl-1-[(dimethylcarbamoyl)oxy]-7-methoxy-3,4-dihydroquinolin-2(1H)-one |
| 364 | 3-({(3S)-3-amino-1-[(dimethylcarbamoyl)oxy]-7-methoxy-2-oxo-1,2,3,4-tetrahydroquinolin-6-yl}methyl)benzonitrile |
| 365 | (3S)-3-amino-6-benzyl-1-[(dimethylcarbamoyl)oxy]-7-methyl-3,4-dihydro-1,8-naphthyridin-2(1H)-one |

The compounds shown in Table Z, below, and their pharmaceutically acceptable salts, were prepared as described below.

TABLE Z

| Ex. No. | IUPAC Name | Synthesis |
|---|---|---|
| 366 | (3S)-3-amino-1-(benzyloxy)-3,4-dihydroquinolin-2(1H)-one | Synthesized by treatment of tert-butyl [(3S)-1-hydroxy-2-oxo-1,2,3,4-tetrahydroquinolin-3-yl]carbamate (95) with benzyl alcohol, di-tert-butyl azodicarboxylate, and triphenylphosphine in $CHCl_3$ at 50° C., followed by treatment of the resultant crude product with TFA. |
| 367 | (3S)-3-amino-1-(pyridin-2-ylmethoxy)-3,4-dihydroquinolin-2(1H)-one | Synthesized similarly to Example 366, using pyridin-2-yl methanol. |
| 368 | (3S)-3-amino-1-[(2,2-dimethylpropanoyl)oxy]-3,4-dihydroquinolin-2(1H)-one | Synthesized similarly to Example 73 by reaction of (95) with trimethylacetyl chloride and triethylamine in acetonitrile and subsequent BOC removal using TFA in dichloromethane. |
| 369 | (3S)-3-amino-1-[(5-methyl-2-oxo-1,3-dioxol-4-yl)methoxy]-3,4-dihydroquinolin-2(1H)-one | Synthesized similarly to Examples 366 and 368 using 4-hydroxymethyl-5-methyl-[1,3]dioxol-2-one. |

KAT II Inhibition Spectra Assay

Formation of kynurenic acid (KYNA) is indirectly assessed by a decrease in light absorbance at 370 nm (OD370) as the L-kynurenine (KYN) substrate is converted by the human KAT II (hKAT II) enzyme into KYNA. An inhibitor would therefore inhibit the decrease in OD370.

The protocol was performed by placing the following reagents into a Costar 384 well black plate (30 µL total assay volume/well):

10 µL of 3× concentrated compound;

10 µL of 3× concentrated substrate mix (BGG (Sigma G-5009); 3 mM L-Kynurenine in 150 mM Tris Acetate (Sigma K3750); 3 mM α-ketoglutaric acid in 150 mM Tris Acetate (Sigma K2010); and 210 µM pyridoxal 5-phosphate (PLP) in 150 mM Tris Acetate (Sigma 9255)); and 10 µL of 3× concentrated enzyme (15 nM enzyme in 150 mM Tris Acetate with 0.3% bovine serum).

Plates were sealed and incubated at 37° C. for 15-20 h before reading OD370 on a SpectraMax Plus plate reader. $IC_{50}$s were generated by comparing the efficacy of compounds across a concentration range to inhibit a reduction in the OD370 value relative to assay wells with DMSO added in place of concentrated compound. Biological data for the Examples may be found in Tables 5 and 6.

TABLE 5

| Ex. No. | KATII $IC_{50}$ (nM) |
|---|---|
| 1 | 52.7* |
| 2 | 23.4 |
| 3 | 204* |
| 4 | 37.5† |
| 5 | 131* |
| 6 | 25.4* |
| 7 | 3280 |
| 8 | 608* |
| 9 | 2230* |
| 10 | 73.7* |
| 11 | 121 |
| 12 | 379 |
| 13 | 57.3 |
| 14 | 270* |
| 15 | 11.1 |
| 16 | 22.7 |

TABLE 5-continued

| Ex. No. | KATII $IC_{50}$ (nM) |
|---|---|
| 17 | 95.1 |
| 18 | 139* |
| 19 | 3040* |
| 20 | 127 |
| 21 | 46.2 |
| 22 | 45.2 |
| 23 | 65.3* |
| 24 | 50 |
| 25 | 48.4 |
| 26 | 88* |
| 27 | 51.9 |
| 28 | 1330 |
| 29 | 10.5 |
| 30 | 23.7 |
| 31 | 49.7 |
| 32 | 35.9 |
| 33 | 33 |
| 34 | 35.6 |
| 35 | 49.2* |
| 36 | 79.3 |
| 37 | 34.1 |
| 38 | 133 |
| 39 | 136 |
| 40 | 122 |
| 41 | 257 |
| 42 | 101 |
| 43 | 133 |
| 44 | 118 |
| 45 | 235 |
| 46 | 128 |
| 47 | 118 |
| 48 | 523 |
| 49 | 105 |
| 50 | 103 |
| 51 | 101 |
| 52 | 139 |
| 53 | 206 |
| 54 | 137 |
| 55 | 141 |
| 56 | 91.1 |
| 57 | 102 |
| 58 | 174 |
| 59 | 156 |
| 60 | 161 |
| 61 | 162 |
| 62 | 135 |

TABLE 5-continued

| Ex. No. | KATII IC$_{50}$ (nM) |
| --- | --- |
| 63 | 113 |
| 64 | 141 |
| 65 | 155 |

*IC$_{50}$ value represents the geometric mean of 2-9 IC$_{50}$ determinations.
†IC$_{50}$ value represents the geometric mean of 74 IC$_{50}$ determinations.

TABLE 6

| Ex. No. | KATII IC$_{50}$ (nM) |
| --- | --- |
| 66 | 23.1* |
| 67 | 42.1* |
| 68 | 42.7* |
| 69 | 43.3* |
| 70 | 24.6* |
| 71 | 22.7† |
| 72 | N/A |
| 73 | 1090 |
| 74 | 151* |
| 75 | 35.2 |
| 76 | 34.6 |
| 77 | 80.1 |
| 78 | 17.3* |
| 79 | 29.5* |
| 80 | 31.1* |
| 81 | 212* |
| 82 | 41.1* |
| 83 | 39.7* |
| 84 | 41.1* |
| 85 | 39.9* |
| 86 | 65.0* |
| 87 | 40.9* |
| 88 | 20.9* |
| 89 | 36.4* |
| 90 | 355* |
| 91 | 36.2 |
| 92 | 51.3* |
| 93 | 35.6* |
| 94 | 43.9* |
| 95 | 35.9* |
| 96 | 49.6* |
| 97 | 313* |
| 98 | 31.9* |
| 99 | 19.8* |
| 100 | 103* |
| 101 | 39.7* |
| 102 | 68.6* |
| 103 | 77.5* |
| 104 | 307* |
| 105 | 68.1* |
| 106 | 49.2* |
| 107 | 56.7* |
| 108 | 70.1* |
| 109 | 288* |
| 110 | 983* |
| 111 | 45.2* |
| 112 | 49.3* |
| 113 | 301* |
| 114 | 37.0* |
| 115 | 52.7* |
| 116 | 51.9* |
| 117 | 53.7* |
| 118 | 1270* |
| 119 | 41.1* |
| 120 | 61.9* |
| 121 | N/A |
| 122 | N/A |
| 123 | N/A |
| 124 | 35.1 |
| 125 | 17.2 |
| 126 | 30.9 |
| 127 | 28.2 |
| 128 | 25.5* |
| 129 | 49.1 |
| 130 | 1570 |
| 131 | 246 |
| 132 | 121 |
| 133 | 86.6* |
| 134 | 199 |
| 135 | 116 |
| 136 | 129 |
| 137 | 69.0 |
| 138 | 156 |
| 139 | 66.1 |
| 140 | 252 |
| 141 | 283 |
| 142 | 102* |
| 143 | 96.0 |
| 144 | 145 |
| 145 | 179 |
| 146 | 78.6 |
| 147 | 75.6 |
| 148 | 76.1 |
| 149 | 118 |
| 150 | 96.7* |
| 151 | 63.6* |
| 152 | 94.0 |
| 153 | 162 |
| 154 | 96.5 |
| 155 | 136* |
| 156 | 86.7* |
| 157 | 68.5* |
| 158 | 126* |
| 159 | 109* |
| 160 | 101* |
| 161 | 54.0* |
| 162 | 46.7* |
| 163 | 60.0* |
| 164 | 42.2* |
| 165 | 96.6* |
| 166 | 128* |
| 167 | 105† |
| 168 | 54.3* |
| 169 | 123* |
| 170 | 28.9* |
| 171 | 42.8 |

*IC$_{50}$ value represents the geometric mean of 2-3 IC$_{50}$ determinations.
†IC$_{50}$ value represents the geometric mean of 4-9 IC$_{50}$ determinations.

Prodrug In Vivo Data

Dogs

Test substances (Examples 4 and 71-73) were administered by oral gavage to groups of two dogs. Example 71 was also administered intravenously. The characteristics of the test animals are given in Table 7.

TABLE 7

| Characteristics of experimental dogs used in study | |
| --- | --- |
| Species | Dog |
| Type | Beagle |
| Number and sex | 2 males |
| Approximate age | 4-6 years |
| Approx. Body weight | 9-12 kg at start of treatment |
| Source | Marshall Farms |

Blood samples were taken at various times after administration and submitted to analysis for the parent drug (Example 71) and pro-drug (Examples 72 and 73) using an LC-MS-MS assay. Pharmacokinetic parameters derived from the plasma analytical data were determined using Watson LIMS 7.2.003 (Thermo Fisher Scientific, Waltham, Mass.). The results are given in FIG. 1 and Tables 8, 9, 10, and 11.

TABLE 8

Pharmacokinetics of Example 71 in dogs after oral administration of Example 71 (2 mg/kg active)

| Parameter | Subject: Dog 1 | Subject: Dog 2 | Mean |
|---|---|---|---|
| $C_{max}$ (ng/mL) | 25.4 | 15.4 | 20.4 |
| $T_{max}$ (h) | 0.25 | 0.25 | 0.25 |
| $T_{1/2}$ (h) | 0.439 | 0.299 | 0.369 |
| AUC (ng · h/mL) | 10.3 | 12.2 | 11.3 |
| AUC Extrap (ng · h/mL) | 10.7 | 12.5 | 11.6 |
| % AUC Extrap | 3.44 | 2.35 | 2.9 |
| F (%)[a] | 1.0 | 1.3 | 1.2 |

[a] calculated using AUC of 247 ng · h/mL, exposure of Example 71 in dogs following intravenous administration of Example 71 at 0.5 mg/kg.

TABLE 9

Pharmacokinetics of Example 71 in dogs after oral administration of Example 72 (1 mg/kg active)

| Parameter | Subject: Dog 1 | Subject: Dog 2 | Mean |
|---|---|---|---|
| $C_{max}$ (ng/mL) | 12.5 | 17.2 | 14.9 |
| $T_{max}$ (h) | 0.5 | 1.0 | 0.75 |
| $T_{1/2}$ (h) | 1.60 | 1.58 | 1.59 |
| AUC (ng · h/mL) | 30.0 | 46.3 | 38.2 |
| AUC Extrap (ng · h/mL) | 31.5 | 49.0 | 40.3 |
| % AUC Extrap | 4.80 | 5.48 | 5.14 |
| F (%)[a] | 6.4 | 9.9 | 8.1 |

[a] calculated using AUC of 247 ng · h/mL, exposure of Example 71 in dogs following intravenous administration of Example 71 at 0.5 mg/kg.

TABLE 10

Pharmacokinetics of Example 72 in dogs after oral administration of Example 72 (1 mg/kg active)

| Parameter | Subject: Dog 1 | Subject: Dog 2 | Mean |
|---|---|---|---|
| $C_{max}$ (ng/mL) | 142 | 248 | 195 |
| $T_{max}$ (h) | 0.5 | 1 | 0.75 |
| $T_{1/2}$ (h) | 2.31 | 1.94 | 2.13 |
| AUC (ng · h/mL) | 402 | 721 | 562 |
| AUC Extrap (ng · h/mL) | 455 | 790 | 623 |
| % AUC Extrap | 11.7 | 8.77 | 10.2 |
| F (%)[a] | 38 | 54 | 46 |

[a] calculated using AUC of 497 ng · h/mL, exposure of Example 72 in dogs following intravenous administration of Example 72 at 0.47 mg/kg.

TABLE 11

Pharmacokinetics of Example 4 and 73 in dogs (n = 2) after oral administration

| Ex. No. | Dose (Ex. 4 eq) (mg/kg) | AUC/dose (ng · h/mL) | AUC increase vs. oral administration of Ex. 4 | $T_{1/2}$ (h) |
|---|---|---|---|---|
| 4 | 1 | 27.9 | 1.0 | 0.5 |
| 73 | 1 | 1130 | 41 | 2.7 |

Monkeys

Test substances (Examples 4 and 71-73) were administered by oral gavage to groups of two monkeys. The characteristics of the test animals are given in Table 12.

TABLE 12

Characteristics of experimental monkeys used in study

| Species | Monkey |
|---|---|
| Type | Cynomolgus |
| Number and sex | 2 males |
| Approximate age | 3 years |
| Approx. Body weight | 3.5-8.1 kg at start of treatment |
| Source | Charles River Labs-BRF |

Figure 2:
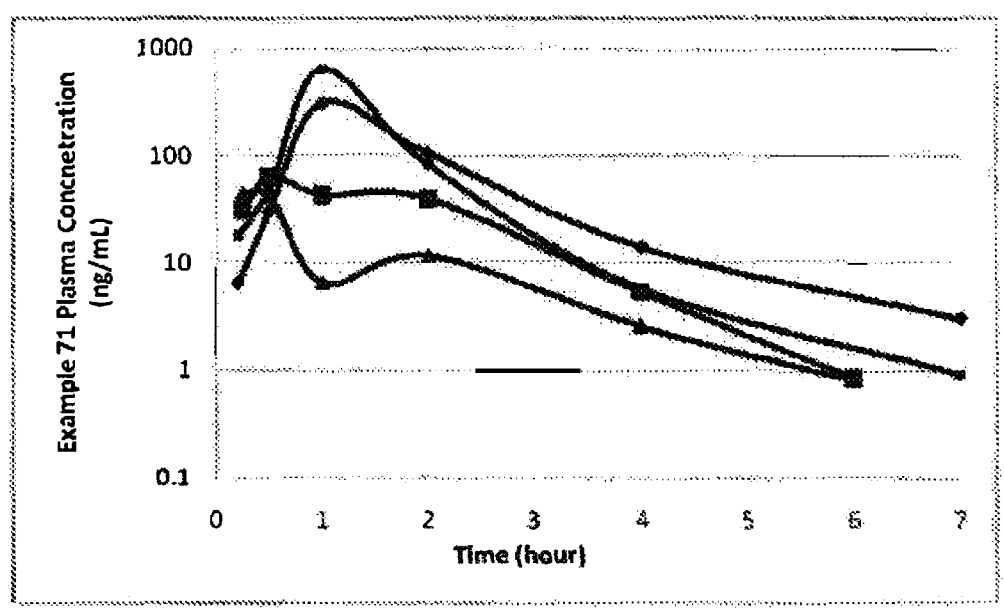
FIG. 2 describes in vivo plasma exposure of Example 71 in monkeys following oral dosing of Example 71 at 3 mg/kg or Example 72 at a dose equivalent to 3 mg/kg Example 71. The line indicated by "-♦-" represents plasma exposure of Example 71 following oral administration of Example 72 to subject 1. The line indicated by "-■-" represents plasma exposure of Example 71 following oral administration of Example 72 to subject 2. The line indicated by "-▲-" represents plasma exposure of Example 71 following oral administration of Example 71 to subject 3. The line indicated by "-■-" represents plasma exposure of Example 71 following oral administration of Example 71 to subject 4.

Blood samples were taken at various times after administration and submitted to analysis for the parent drug (Example 4 and Example 71) and pro-drug (Examples 72 and 73) using an LC-MS-MS assay. Plasma levels of Example 72 were below the limit of quantitation at all time points. Pharmacokinetic parameters derived from the plasma analytical data were determined using Watson LIMS 7.2.003 (Thermo Fisher Scientific, Waltham, Mass.). The results are given in FIG. 2 and Tables 13, 14, and 15.

TABLE 13

Pharmacokinetics of Example 71 in monkeys after oral administration of Example 71 (3 mg/kg active)

| Parameter | Subject: Monkey 1 | Subject: Monkey 2 | Mean |
|---|---|---|---|
| $C_{max}$ (ng/mL) | 44 | 62.8 | 53.4 |
| $T_{max}$ (h) | 0.25 | 0.5 | 0.38 |
| $T_{1/2}$ (h) | 1.04 | 0.724 | 0.882 |
| AUC (ng · h/mL) | 55.5 | 134 | 94.8 |
| AUC Extrap (ng · h/mL) | 56.7 | 134 | 95.4 |
| % AUC Extrap | 2.19 | 0.366 | 1.28 |
| F (%)[a] | 2.2 | 4.2 | 3.2 |

[a] calculated using AUC of 476 ng · h/mL, plasma exposure of Example 71 in monkeys following intravenous administration of Example 71 at 0.5 mg/kg.

TABLE 14

Pharmacokinetics of Example 71 in monkeys after oral administration of Example 72 (3 mg/kg active)

| Parameter | Subject: Monkey 1 | Subject: Monkey 2 | Mean |
|---|---|---|---|
| $C_{max}$ (ng/mL) | 306 | 635 | 471 |
| $T_{max}$ (h) | 1 | 1 | 1 |
| $T_{1/2}$ (h) | 1.00 | 0.794 | 0.896 |
| AUC (ng · h/mL) | 440 | 636 | 538 |
| AUC Extrap (ng · h/mL) | 444 | 637 | 541 |
| % AUC Extrap | 0.95 | 0.189 | 0.569 |
| F (%)[a] | 16 | 22 | 19 |

[a] calculated using AUC of 476 ng · h/mL, plasma exposure of Example 71 in monkeys following intravenous administration of Example 71 at 0.5 mg/kg.

TABLE 15

Pharmacokinetics of Example 4 in monkeys after oral administration of Example 4 (10 mg/kg active)

| Parameter | Subject: Monkey 1 | Subject: Monkey 2 | Subject: Monkey 3 | Subject: Monkey 4 | Mean |
|---|---|---|---|---|---|
| $C_{max}$ (ng/mL) | 200 | 340 | 206 | 133 | 220 |
| $T_{max}$ (h) | 1.0 | 0.25 | 0.5 | 1.0 | 0.69 |
| $T_{1/2}$ (h) | 0.78 | 0.82 | 0.68 | 0.63 | 0.73 |
| AUC (ng · h/mL) | 184 | 239 | 141 | 159 | 181 |
| AUC Extrap (ng · h/mL) | 188 | 247 | 144 | 163 | 186 |
| % AUC Extrap | 2.28 | 3.05 | 1.96 | 2.56 | 2.46 |
| F (%)[a] | 2.1 | 2.8 | 1.6 | 1.8 | 2.1 |

[a] calculated using AUC of 265 ng · h/mL, plasma exposure of Example 4 in monkeys following intravenous administration of Example 4 at 0.3 mg/kg.

TABLE 16

Pharmacokinetics of Example 4 in monkeys after oral administration of Example 73 (10 mg/kg active)

| Parameter | Subject: Monkey 1 | Subject: Monkey 2 | Mean |
|---|---|---|---|
| $C_{max}$ (ng/mL) | 2340 | 1910 | 2130 |
| $T_{max}$ (h) | 1.0 | 1.0 | 1.0 |
| $T_{1/2}$ (h) | 1.0 | 1.04 | 0.94 |
| AUC (ng · h/mL) | 4450 | 3650 | 4050 |
| AUC Extrap (ng · h/mL) | 4470 | 3690 | 4080 |
| % AUC Extrap | 0.432 | 0.95 | 0.691 |
| F (%)[a] | 50.6 | 41.8 | 46 |

[a]calculated using AUC of 265 ng · h/mL, plasma exposure of Example 4 in monkeys following intravenous administration of Example 4 at 0.3 mg/kg.

Rats

Test substances (Examples 4, 73, and 366-369) were administered by oral gavage to groups of three rats. The characteristics of the test animals are given in Table 17.

TABLE 17

Characteristics of experimental monkeys used in study

| | |
|---|---|
| Species | Rat |
| Type | Wistar-Han |
| Number and sex | 3 males |
| Approximate age | 7-9 weeks |
| Approx. Body weight | 220-240 g |
| Source | Charles River Labs-BRF |

Blood samples were taken at various times after administration and analyzed for the parent drug (Example 4) and prodrugs (Examples 73 and 366-369) using an LC-MS-MS assay. Pharmacokinetic parameters derived from the plasma analytical data were determined using Watson LIMS version 7.2.003 (Thermo Fisher Scientific, Waltham, Mass.). The results are given in Table 18.

TABLE 18

Pharmacokinetics of Example 4 in rats after oral administration of prodrugs

| Ex. No. | Dose (Ex. 4 eq) (mg/kg) | AUC/dose (ng · h/mL) | AUC increase vs. oral administration of Ex. 4 | $T_{1/2}$ (h) |
|---|---|---|---|---|
| 4 | 10 | 18 | 1.0 | 2.48 |
| 73 | 1 | 425.0 | 24.0 | 1.04 |
| 366 | 10 | 2.9 | 0.2 | 1.09 |
| 367 | 7 | 3.3 | 0.2 | 0.45 |
| 368 | 2 | 13.8 | 0.8 | 0.25 |
| 369 | 6 | 7.7 | 0.4 | 0.66 |

When introducing elements of the present invention or the exemplary embodiment(s) thereof, the articles "a," "an," "the" and "said" are intended to mean that there are one or more of the elements. The terms "comprising," "including" and "having" are intended to be inclusive and mean that there may be additional elements other than the listed elements. Although this invention has been described with respect to specific embodiments, the details of these embodiments are not to be construed as limitations to the invention, the scope of which is defined by the appended claims.

The invention claimed is:

1. A compound of Formula X-I:

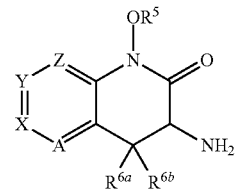

wherein:
A is $CR^1$;
X is $CR^2$;
Y is $CR^3$;
Z is $CR^4$;
$R^1$ is H, halo, alkyl, alkoxy, or cyclopropyl;
$R^2$, $R^3$, and $R^4$ are independently H, halo, alkyl, aryl, aralkyl, heteroaryl, alkoxy, cycloalkyloxy, alkoxyaryl, aryloxy, aralkyloxy, heterocycloalkyloxy, heteroaryloxy, cycloalkyl, alkylaryloxy, alkylheterocycloalkyl, alkylheteroaryloxy, heterocycloalkyl, CN, $CH_2NR^7R^8$, $NR^7R^8$, $C(=O)NR^7R^8$, $SO_2NR^7R^8$, $SO_2R^{7a}$, $NR^7SO_2R^{7a}$, or $NR^7C(=O)R^{7a}$, wherein each of said alkyl, aryl, aralkyl, heteroaryl, alkoxy, cycloalkyloxy, alkoxyaryl, aryloxy, aralkyloxy, heterocycloalkyloxy, heteroaryloxy, cycloalkyl, alkylaryloxy, alkylheterocycloalkyl, alkylheteroaryloxy, and heterocycloalkyl may be substituted with one or more substituents selected from hydroxy, amino, halo, alkyl, haloalkyl, CN, alkoxy, haloalkoxy, alkylamino, and aminoalkyl;
$R^5$ is $C(=O)R^9$, $C(=O)OR^9$, $C(=O)NR^{9a}R^{9b}$, or $(CH_2)R^{10}$;
$R^{6a}$ and $R^{6b}$ are independently H, methyl, halomethyl, fluoro, or methoxy;
each $R^7$ and $R^8$ is independently H, alkyl, haloalkyl, aryl, or heteroaryl;
each $R^{7a}$ is independently alkyl, haloalkyl, aryl, or heteroaryl;
$R^9$ is alkyl, aryl, heteroaryl, or cycloalkyl, wherein each of said alkyl, aryl, heteroaryl, and cycloalkyl may be substituted with one or more substituents selected from hydroxy, amino, halo, alkoxy, and aminoalkyl;
each $R^{9a}$ and $R^{9b}$ is independently H, alkyl, aryl, heteroaryl, or cycloalkyl, wherein each of said alkyl, aryl, heteroaryl, and cycloalkyl may be substituted with one or more substituents selected from hydroxy, amino, halo, alkoxy, and aminoalkyl, or, $R^{9a}$ and $R^{9b}$, together with the nitrogen atom to which they are attached, form a 5- or 6-membered N-containing heterocyclic ring;
$R^{10}$ is

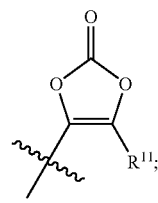

$R^{11}$ is H, alkyl, aryl, heteroaryl, or cycloalkyl, wherein each of said alkyl, aryl, heteroaryl, and cycloalkyl may be substituted with one or more substituents selected from hydroxy, amino, halo, alkoxy, and aminoalkyl;
or a pharmaceutically acceptable salt thereof.

2. A compound according to claim 1 wherein $R^5$ is $C(=O)R^9$, $C(=O)NR^{9a}R^{9b}$, or $(CH_2)R^{10}$; or a pharmaceutically acceptable salt thereof.

3. A compound of Formula X-I:

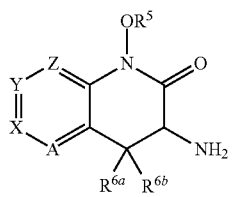

X-I wherein:
A is $CR^1$;
X is $CR^2$;
Y is $CR^3$;
Z is $CR^4$;
$R^1$ is H;
$R^2$ is arylalkyl that is benzyl, aryloxy that is phenoxy, or heteroaryloxy, wherein each of said aryl or heteroaryl may be substituted with one or more substituents selected from hydroxy, amino, halo, alkyl, haloalkyl, CN, alkoxy, haloalkoxy, alkylamino, and aminoalkyl;
$R^3$ is H or alkoxy where said alkoxy may be substituted with one or more halo; and
$R^4$ is H;
$R^5$ is H, $C(=O)R^9$, $C(=O)OR^9$, $C(=O)NR^{9a}R^{9b}$, or $(CH_2)R^{10}$;
$R^{6a}$ and $R^{6b}$ are independently H, methyl, halomethyl, fluoro, or methoxy;
each $R^7$ and $R^8$ is independently H, alkyl, haloalkyl, aryl, or heteroaryl;
each $R^{7a}$ is independently alkyl, haloalkyl, aryl, or heteroaryl;
$R^9$ is alkyl, aryl, heteroaryl, or cycloalkyl, wherein each of said alkyl, aryl, heteroaryl, and cycloalkyl may be substituted with one or more substituents selected from hydroxy, amino, halo, alkoxy, and aminoalkyl;
each $R^{9a}$ and $R^{9b}$ is independently H, alkyl, aryl, heteroaryl, or cycloalkyl, wherein each of said alkyl, aryl, heteroaryl, and cycloalkyl may be substituted with one or more substituents selected from hydroxy, amino, halo, alkoxy, and aminoalkyl, or, $R^{9a}$ and $R^{9b}$, together with the nitrogen atom to which they are attached, form a 5- or 6-membered N-containing heterocyclic ring;
$R^{10}$ is

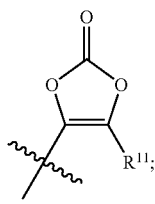

$R^{11}$ is H, alkyl, aryl, heteroaryl, or cycloalkyl, wherein each of said alkyl, aryl, heteroaryl, and cycloalkyl may be substituted with one or more substituents selected from hydroxy, amino, halo, alkoxy, and aminoalkyl;
or a pharmaceutically acceptable salt thereof.

4. A compound according to claim 3 wherein $R^2$ is benzyl, or a pharmaceutically acceptable salt thereof.

5. A compound according to claim 4 wherein $R^3$ is H, or a pharmaceutically acceptable salt thereof.

6. A compound according to claim 2 wherein $R^5$ is $C(=O)NR^{9a}R^{9b}$, or a pharmaceutically acceptable salt thereof.

7. A compound according to claim 6 wherein $R^5$ is

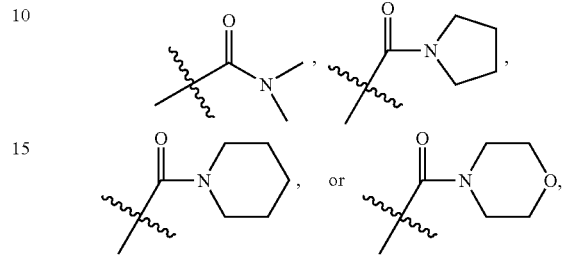

or a pharmaceutically acceptable salt thereof.

8. A pharmaceutical composition comprising a compound according to claim 1, or a pharmaceutically acceptable salt thereof, and a pharmaceutically acceptable carrier.

9. A compound selected from:
(3S)-3-amino-1-hydroxy-8-(trifluoromethyl)-3,4-dihydroquinolin-2(1H)-one;
3-amino-6-cyclopropyl-1-hydroxy-3,4-dihydroquinolin-2(1H)-one;
3-amino-7-cyclopropyl-1-hydroxy-3,4-dihydroquinolin-2(1H)-one;
(3S)-3-amino-1-hydroxy-6-(trifluoromethoxy)-3,4-dihydroquinolin-2(1H)-one;
3-amino-1-hydroxy-2-oxo-1,2,3,4-tetrahydroquinoline-8-carbonitrile;
(3S)-3-amino-1-hydroxy-8-(trifluoromethoxy)-3,4-dihydroquinolin-2(1H)-one;
(3S)-3-amino-1-hydroxy-6-phenoxy-3,4-dihydroquinolin-2(1H)-one;
(3S)-3-amino-1-[(dimethylcarbamoyl)oxy]-6-phenoxy-3,4-dihydroquinolin-2(1H)-one;
(3S)-3-amino-1-[(dimethylcarbamoyl)oxy]-3,4-dihydroquinolin-2(1H)-one;
(3S)-3-amino-6-benzyl-1-hydroxy-7-methoxy-3,4-dihydroquinolin-2(1H)-one;
(3S)-3-amino-1-hydroxy-8-(2,2,2-trifluoroethoxy)-3,4-dihydroquinolin-2(1H)-one;
(3S)-3-amino-8-(difluoromethyl)-1-hydroxy-3,4-dihydroquinolin-2(1H)-one;
3-{[(3S)-3-amino-1-hydroxy-7-methoxy-2-oxo-1,2,3,4-tetrahydroquinolin-6-yl]methyl}benzonitrile;
or a pharmaceutically acceptable salt thereof.

10. A compound that is (3S)-3-amino-1-hydroxy-7-(2-methoxyethoxy)-3,4-dihydroquinolin-2(1H)-one, or a pharmaceutically acceptable salt thereof.

11. A pharmaceutical composition comprising a compound according to claim 9, or a pharmaceutically acceptable salt thereof, and a pharmaceutically acceptable carrier.

12. A pharmaceutical composition comprising the compound according to claim 10, or a pharmaceutically acceptable salt thereof, and a pharmaceutically acceptable carrier.

13. A pharmaceutical composition comprising the compound according to claim 3, or a pharmaceutically acceptable salt thereof, and a pharmaceutically acceptable carrier.

* * * * *